US007041643B2

(12) United States Patent
Bertin et al.

(10) Patent No.: US 7,041,643 B2
(45) Date of Patent: May 9, 2006

(54) MOLECULES OF THE PYRIN/NBS/LRR PROTEIN FAMILY AND USES THEREOF

(75) Inventors: John Bertin, Watertown, MA (US); Weiye Wang, Plainsboro, NJ (US); Maria Blatcher, Moorestown, NJ (US)

(73) Assignees: Millennium Pharmaceuticals, Inc., Cambridge, MA (US); Wyeth, Madison, NJ (US)

( * ) Notice: Subject to any disclaimer, the term of this patent is extended or adjusted under 35 U.S.C. 154(b) by 448 days.

(21) Appl. No.: 10/124,498

(22) Filed: Apr. 17, 2002

(65) Prior Publication Data

US 2003/0017983 A1 Jan. 23, 2003

Related U.S. Application Data

(63) Continuation-in-part of application No. 10/066,521, filed on Jan. 31, 2002.

(60) Provisional application No. 60/318,645, filed on Sep. 10, 2001, provisional application No. 60/265,231, filed on Jan. 31, 2001.

(51) Int. Cl.
*A61K 38/00* (2006.01)
*C07K 1/00* (2006.01)
*C07K 14/00* (2006.01)

(52) U.S. Cl. .................... 514/12; 514/12; 530/350
(58) Field of Classification Search ................ 530/350, 530/387.1; 514/12
See application file for complete search history.

(56) References Cited

U.S. PATENT DOCUMENTS

2003/0027757 A1 2/2003 Bertin et al.

FOREIGN PATENT DOCUMENTS

| EP | 1 285 964 | 2/2003 |
|---|---|---|
| WO | WO 01/61005 | 8/2001 |
| WO | WO 01/75067 | 10/2001 |
| WO | WO 01/92527 | 12/2001 |
| WO | WO 02/14500 | 2/2002 |
| WO | WO 02/32955 | 4/2002 |
| WO | WO 200232955 A1 * | 4/2002 |
| WO | WO 02/40668 | 5/2002 |
| WO | WO 02/48362 | 6/2002 |
| WO | WO 200248362 A2 * | 6/2002 |

OTHER PUBLICATIONS

Kobe et al. (Curr. Opin. Struct. Biol. 2001; 11:725-732).*
Bowie et al (Science, 1990, 257:1306-1310).*
Burgess et al (J of Cell Bio. 111:2129-2138, 1990).*
Scott et al (Nature Genetics, 1999, 21:440-443).*
Bertin et al., "The pyrin domain: A novel motif found in apoptosis and inflammation proteins", Cell Death Differentiation, Edward Arnold, Oxford, Great Britian, 12(7):1273-1274 (2000).
Dias Neta et al., "IL2-UT0074-040900-153-G02 UT0074 homo sapiens cDNA, mRNA sequence", Database accession No. BF380801.
DOE Joint Genome Institute, GenBank Accession No. AC012310 (2001).
Martinon et al., GenBank Accession No. AF442488 (2001).
Masumoto et al., "Pyrin N-terminal homology domain- and caspase recruitment domain-dependent oligmerization of ASC", Biochemical and Biophysical Research Communications, Academic Press Inc., Orlando, Fl, USA, 280(3):652-655 (2001).
Strausberg, GenBank Accession No. BE278926 (2000).
Zhao et al., "CITBI-E1-2565K18.TF CITBI-E1 homo sapiens genomic clone 2565K18, genomic survey sequence", Database Accession No. AQ424752 XP002269231.
Eck et al. (Gene-Based Therpay, In: The Pharmacological Basis of Therapeutics, Goodman and Gillman, Eds, 1996, pp. 77-101.

(Continued)

*Primary Examiner*—Jeffrey Siew
*Assistant Examiner*—Brandon Fetterolf
(74) *Attorney, Agent, or Firm*—Fish & Richardson P.C.

(57) ABSTRACT

Novel PYRIN-2, PYRIN-3, PYRIN-5, PYRIN-6, PYRIN-7, PYRIN-8, PYRIN-10, and PYRIN-11 polypeptides, proteins, and nucleic acid molecules are disclosed. In addition to isolated PYRIN-2, PYRIN-3, PYRIN-5, PYRIN-6, PYRIN-7, PYRIN-8, PYRIN-10, and PYRIN-11 proteins, the invention further provides PYRIN-2, PYRIN-3, PYRIN-5, PYRIN-6, PYRIN-7, PYRIN-8, PYRIN-10, and PYRIN-11 fusion proteins, antigenic peptides and anti-PYRIN-2, -PYRIN-3, -PYRIN-5, -PYRIN-6, -PYRIN-7, -PYRIN-8, -PYRIN-10, and -PYRIN-11 antibodies. The invention also provides PYRIN-2, PYRIN-3, PYRIN-5, PYRIN-6, PYRIN-7, PYRIN-8, PYRIN-10, and PYRIN-11 nucleic acid molecules, recombinant expression vectors containing a nucleic acid molecule of the invention, host cells into which the expression vectors have been introduced and non-human transgenic animals in which a PYRIN-2, PYRIN-3, PYRIN-5, PYRIN-6, PYRIN-7, PYRIN-8, PYRIN-10, or PYRIN-11 gene has been introduced or disrupted. Diagnostic, screening and therapeutic methods utilizing compositions of the invention are also provided.

12 Claims, 45 Drawing Sheets

OTHER PUBLICATIONS

Houdebine, Journal of Biotechnology, 1994, vol. 34, pp. 269-287.
Orkin, "Report and Recommendation of the Panel to Assess the NIH Investment in Research on Gene Therapy."
Tong et al., "A Human Homologue of Mouse Mater, A maternal Effect Gene Essential for Early Embryonic Development," Human Reproduction 17(4):903-911, 2002.
Verma et al., Nature, 1997, vol. 389, pp. 239-242.

* cited by examiner

| | |
|---|---|
| atg gca gaa tct ttt ttt tcg gat ttt ggc ttg ttg tgg tat ctg aag<br>Met Ala Glu Ser Phe Phe Ser Asp Phe Gly Leu Leu Trp Tyr Leu Lys<br>1               5                    10                  15 | 48 |
| gag ctc aga aag gaa gag ttt tgg aaa ttt aag gag ctc ctc aaa caa<br>Glu Leu Arg Lys Glu Glu Phe Trp Lys Phe Lys Glu Leu Leu Lys Gln<br>            20                  25                  30 | 96 |
| cct ttg gag aaa ttt gaa ctc aag cca atc ccc tgg gct gag ctg aag<br>Pro Leu Glu Lys Phe Glu Leu Lys Pro Ile Pro Trp Ala Glu Leu Lys<br>        35                  40                  45 | 144 |
| aag gcc tcc aaa gaa gat gta gca aag ctg ctg gac aaa cat tac cca<br>Lys Ala Ser Lys Glu Asp Val Ala Lys Leu Leu Asp Lys His Tyr Pro<br>    50                  55                  60 | 192 |
| gga aag cag gca tgg gag gta aca ctg aac ctg ttt cta cag atc aat<br>Gly Lys Gln Ala Trp Glu Val Thr Leu Asn Leu Phe Leu Gln Ile Asn<br>65                  70                  75                  80 | 240 |
| agg aaa gat ctc tgg aca aag gct cag gaa gag atg aga aat aag cta<br>Arg Lys Asp Leu Trp Thr Lys Ala Gln Glu Glu Met Arg Asn Lys Leu<br>            85                  90                  95 | 288 |
| aac cca tac aga aag cat atg aag gaa aca ttt caa ctc ata tgg gag<br>Asn Pro Tyr Arg Lys His Met Lys Glu Thr Phe Gln Leu Ile Trp Glu<br>        100                 105                 110 | 336 |
| aag gaa acc tgt ctt cac gtc cct gag cat ttc tac aaa gaa acc atg<br>Lys Glu Thr Cys Leu His Val Pro Glu His Phe Tyr Lys Glu Thr Met<br>    115                 120                 125 | 384 |
| aaa aat gag tat aaa gaa ttg aat gac gca tat act gct gcg gct aga<br>Lys Asn Glu Tyr Lys Glu Leu Asn Asp Ala Tyr Thr Ala Ala Ala Arg<br>130                 135                 140 | 432 |
| cga cac act gtg gtc ctg gaa ggt cct gat gga att gga aaa aca acc<br>Arg His Thr Val Val Leu Glu Gly Pro Asp Gly Ile Gly Lys Thr Thr<br>145                 150                 155                 160 | 480 |
| ctt tta aga aaa gtg atg ttg gac tgg gca gag gga aac tta tgg aag<br>Leu Leu Arg Lys Val Met Leu Asp Trp Ala Glu Gly Asn Leu Trp Lys<br>            165                 170                 175 | 528 |
| gac agt tac aat gag aag ctc gtc tac tgg cgg gag ctt tgc tca atg<br>Asp Ser Tyr Asn Glu Lys Leu Val Tyr Trp Arg Glu Leu Cys Ser Met<br>        180                 185                 190 | 576 |
| ttc att acc aac aag aac ttc cag att tta gac atg gaa aat acc agc<br>Phe Ile Thr Asn Lys Asn Phe Gln Ile Leu Asp Met Glu Asn Thr Ser<br>    195                 200                 205 | 624 |

Fig. 1A

```
ctc gat gat ccc tcc ctg gcg att ctt tgc aaa gcg ctg gct cag cct        672
Leu Asp Asp Pro Ser Leu Ala Ile Leu Cys Lys Ala Leu Ala Gln Pro
    210                 215                 220 gtt tgt aaa ctc cga aaa ctc ata ttt act tct gtg tac ttt gga cat        720
Val Cys Lys Leu Arg Lys Leu Ile Phe Thr Ser Val Tyr Phe Gly His
225                 230                 235                 240 gat tca gaa tta ttt aag gca gtt ctt cac aac cct cat ctg aaa ctt        768
Asp Ser Glu Leu Phe Lys Ala Val Leu His Asn Pro His Leu Lys Leu
                245                 250                 255 ctg agc ctg tac ggc act agc ctc tcc cag tct gac atc aga cac ctg        816
Leu Ser Leu Tyr Gly Thr Ser Leu Ser Gln Ser Asp Ile Arg His Leu
            260                 265                 270 tgt gag acg ctg aaa cat cca atg tgc aag ata gaa gag ctg ata ctg        864
Cys Glu Thr Leu Lys His Pro Met Cys Lys Ile Glu Glu Leu Ile Leu
        275                 280                 285 gga aag tgt gac atc tcc agt gaa gtt tgt gaa gac atc gcc tcc gtc        912
Gly Lys Cys Asp Ile Ser Ser Glu Val Cys Glu Asp Ile Ala Ser Val
    290                 295                 300 ctg gcc tgc aac agc aag ctg aaa cac ctc tcc ttg gta gaa aat ccc        960
Leu Ala Cys Asn Ser Lys Leu Lys His Leu Ser Leu Val Glu Asn Pro
305                 310                 315                 320 ttg agg gac gaa gga atg acg ttg ctg tgt gaa gcc ctg aag cac tca       1008
Leu Arg Asp Glu Gly Met Thr Leu Leu Cys Glu Ala Leu Lys His Ser
                325                 330                 335 cac tgt gcc ctg gag agg ctg atg ttg atg ggc tgt ttc ctt act tcc       1056
His Cys Ala Leu Glu Arg Leu Met Leu Met Gly Cys Phe Leu Thr Ser
            340                 345                 350 gat tcc tgt aag gac att gct gct gtt ctt att tgc aat ggg aaa ctg       1104
Asp Ser Cys Lys Asp Ile Ala Ala Val Leu Ile Cys Asn Gly Lys Leu
        355                 360                 365 aag acc ctg aaa ctt ggg cat aat gaa ata gga gac act ggt gtc aga       1152
Lys Thr Leu Lys Leu Gly His Asn Glu Ile Gly Asp Thr Gly Val Arg
    370                 375                 380 cag tta tgt gca gct ttg cag cat cct cac tgt aaa tta gag tgt ctc       1200
Gln Leu Cys Ala Ala Leu Gln His Pro His Cys Lys Leu Glu Cys Leu
385                 390                 395                 400 ggg ctg caa acg tgt ccg atc acc cgt gcc tgc tgc gac gac atc gcc       1248
Gly Leu Gln Thr Cys Pro Ile Thr Arg Ala Cys Cys Asp Asp Ile Ala
                405                 410                 415
```

Fig. 1B

```
gca gca ctc atc gcc tgc aaa aca ctg agg agc ctg aac ctc gac tgg         1296
Ala Ala Leu Ile Ala Cys Lys Thr Leu Arg Ser Leu Asn Leu Asp Trp
            420                 425                 430 att gcc ttg gat gct gat gca gtg gtg gtg ctg tgt gag gca ttg agc         1344
Ile Ala Leu Asp Ala Asp Ala Val Val Val Leu Cys Glu Ala Leu Ser
            435                 440                 445 cac ccg gac tgt gcc ctg cag atg ctg ggg ctg cac aaa tct ggc ttt         1392
His Pro Asp Cys Ala Leu Gln Met Leu Gly Leu His Lys Ser Gly Phe
        450                 455                 460 gat gaa gaa act cag aag atc ctg atg tct gtg gaa gaa aaa att ccc         1440
Asp Glu Glu Thr Gln Lys Ile Leu Met Ser Val Glu Glu Lys Ile Pro
465                 470                 475                 480 cat ctg acc att tca cat gga cct tgg att gac gag gaa tac aag atc         1488
His Leu Thr Ile Ser His Gly Pro Trp Ile Asp Glu Glu Tyr Lys Ile
                    485                 490                 495 agg ggt gtg ctc ctc tga                                                 1506
Arg Gly Val Leu Leu  *
            500
```

Fig. 1C

```
atg gca gcc tct ttc ttc tct gat ttt ggt ctt atg tgg tat ctg gag        48
Met Ala Ala Ser Phe Phe Ser Asp Phe Gly Leu Met Trp Tyr Leu Glu
 1               5                  10                  15 gag ctc aaa aag gag gag ttc agg aaa ttt aaa gaa cat ctc aag caa        96
Glu Leu Lys Lys Glu Glu Phe Arg Lys Phe Lys Glu His Leu Lys Gln
                20                  25                  30 atg act ttg cag ctt gaa ctc aag cag att ccc tgg act gag gtc aaa       144
Met Thr Leu Gln Leu Glu Leu Lys Gln Ile Pro Trp Thr Glu Val Lys
            35                  40                  45 aaa gca tcc cgg gaa gaa ctt gca aac ctc ttg atc aag cac tat gaa       192
Lys Ala Ser Arg Glu Glu Leu Ala Asn Leu Leu Ile Lys His Tyr Glu
        50                  55                  60 gaa caa caa gct tgg aac ata acc tta aga atc ttt caa aag atg gat       240
Glu Gln Gln Ala Trp Asn Ile Thr Leu Arg Ile Phe Gln Lys Met Asp
 65                  70                  75                  80 aga aag gat ctc tgc atg aag gtc atg agg gag aga aca ggt gag gga       288
Arg Lys Asp Leu Cys Met Lys Val Met Arg Glu Arg Thr Gly Glu Gly
                85                  90                  95 gtc tgg gaa ggg gga agc ctt ctt ata atg agg act atg tcc taa           333
Val Trp Glu Gly Gly Ser Leu Leu Ile Met Arg Thr Met Ser  *
                100                 105                 110
```

Fig. 2

```
atg gaa gga gac aaa tcg ctc acc ttt tcc agc tac ggg ctg caa tgg    48
Met Glu Gly Asp Lys Ser Leu Thr Phe Ser Ser Tyr Gly Leu Gln Trp
 1               5                  10                  15 tgt ctc tat gag cta gac aag gaa gaa ttt cag aca ttc aag gaa tta    96
Cys Leu Tyr Glu Leu Asp Lys Glu Glu Phe Gln Thr Phe Lys Glu Leu
             20                  25                  30 cta aag aag aaa tct tca gaa tcg acc aca tgc tct att cca cag ttt   144
Leu Lys Lys Lys Ser Ser Glu Ser Thr Thr Cys Ser Ile Pro Gln Phe
         35                  40                  45 gaa atc gag aat gcc aac gtg gaa tgt ctg gca ctc ctc ttg cat gag   192
Glu Ile Glu Asn Ala Asn Val Glu Cys Leu Ala Leu Leu Leu His Glu
     50                  55                  60 tat tat gga gca tcg ctg gcc tgg gct acg tcc att agc atc ttt gaa   240
Tyr Tyr Gly Ala Ser Leu Ala Trp Ala Thr Ser Ile Ser Ile Phe Glu
 65                  70                  75                  80 aac atg aac ctg cga acc ctc tcg gag aag gca cgg gat gac atg aaa   288
Asn Met Asn Leu Arg Thr Leu Ser Glu Lys Ala Arg Asp Asp Met Lys
             85                  90                  95 aaa att tca caa gct atg gaa caa gaa ggt gcc aca gca gca gag aca   336
Lys Ile Ser Gln Ala Met Glu Gln Glu Gly Ala Thr Ala Ala Glu Thr
         100                 105                 110 gaa gaa caa gaa att tca caa gct atg gaa caa gaa ggt gcc aca gca   384
Glu Glu Gln Glu Ile Ser Gln Ala Met Glu Gln Glu Gly Ala Thr Ala
     115                 120                 125 gca gag aca gaa gaa caa gga cat gga ggt gac aca tgg gac tac aag   432
Ala Glu Thr Glu Glu Gln Gly His Gly Gly Asp Thr Trp Asp Tyr Lys
 130                 135                 140 agt cac gtg atg acc aaa ttc gct gag gag gag gat gta cgt cgt agt   480
Ser His Val Met Thr Lys Phe Ala Glu Glu Glu Asp Val Arg Arg Ser
145                 150                 155                 160 ttt gaa aac act gct gct gac tgg ccg gaa atg caa acg ttg gct ggt   528
Phe Glu Asn Thr Ala Ala Asp Trp Pro Glu Met Gln Thr Leu Ala Gly
             165                 170                 175 gct ttt gat tca gac cgg tgg ggc ttc cgg cct cgc acg gtg gtt ctg   576
Ala Phe Asp Ser Asp Arg Trp Gly Phe Arg Pro Arg Thr Val Val Leu
         180                 185                 190 cac gga aag tca gga att ggg aaa tcg gct cta gcc aga agg atc gtg   624
His Gly Lys Ser Gly Ile Gly Lys Ser Ala Leu Ala Arg Arg Ile Val
     195                 200                 205
```

Fig. 3A

```
ctg tgc tgg gcg caa ggt gga ctc tac cag gga atg ttc tcc tac gtc      672
Leu Cys Trp Ala Gln Gly Gly Leu Tyr Gln Gly Met Phe Ser Tyr Val
    210                 215                 220 ttc ttc ctc ccc gtt aga gag atg cag cgg aag aag gag agc agt gtc      720
Phe Phe Leu Pro Val Arg Glu Met Gln Arg Lys Lys Glu Ser Ser Val
225                 230                 235                 240 aca gag ttc atc tcc agg gag tgg cca gac tcc cag gct ccg gtg acg      768
Thr Glu Phe Ile Ser Arg Glu Trp Pro Asp Ser Gln Ala Pro Val Thr
                245                 250                 255 gag atc atg tcc cga cca gaa agg ctg ttg ttc atc att gac ggt ttc      816
Glu Ile Met Ser Arg Pro Glu Arg Leu Leu Phe Ile Ile Asp Gly Phe
            260                 265                 270 gat gac ctg ggc tct gtc ctc aac aat gac aca aag ctc tgc aaa gac      864
Asp Asp Leu Gly Ser Val Leu Asn Asn Asp Thr Lys Leu Cys Lys Asp
        275                 280                 285 tgg gct gag aag cag cct ccg ttc acc ctc ata cgc agt ctg ctg agg      912
Trp Ala Glu Lys Gln Pro Pro Phe Thr Leu Ile Arg Ser Leu Leu Arg
    290                 295                 300 aag gtc ctg ctc cct gag tcc ttc ctg atc gtc acc gtc aga gac gtg      960
Lys Val Leu Leu Pro Glu Ser Phe Leu Ile Val Thr Val Arg Asp Val
305                 310                 315                 320 ggc aca gag aag ctc aag tca gag gtc gtg tct ccc cgt tac ctg tta     1008
Gly Thr Glu Lys Leu Lys Ser Glu Val Val Ser Pro Arg Tyr Leu Leu
                325                 330                 335 gtt aga gga atc tcc ggg gaa caa aga atc cac ttg ctc ctt gag cgc     1056
Val Arg Gly Ile Ser Gly Glu Gln Arg Ile His Leu Leu Leu Glu Arg
            340                 345                 350 ggg att ggt gag cat cag aag aca caa ggg ttg cgt gcg atc atg aac     1104
Gly Ile Gly Glu His Gln Lys Thr Gln Gly Leu Arg Ala Ile Met Asn
        355                 360                 365 aac cgt gag ctg ctc gac cag tgc cag gtg ccc gcc gtg ggc tct ctc     1152
Asn Arg Glu Leu Leu Asp Gln Cys Gln Val Pro Ala Val Gly Ser Leu
    370                 375                 380 atc tgc gtg gcc ctg cag ctg cag gac gtg gtg ggg gag agc gtc gcc     1200
Ile Cys Val Ala Leu Gln Leu Gln Asp Val Val Gly Glu Ser Val Ala
385                 390                 395                 400 ccc ttc aac caa acg ctc aca ggc ctg cac gcc gct ttt gtg ttt cat     1248
Pro Phe Asn Gln Thr Leu Thr Gly Leu His Ala Ala Phe Val Phe His
                405                 410                 415
```

Fig. 3B

```
cag ctc acc cct cga ggc gtg gtc cgg cgc tgt ctc aat ctg gag gaa    1296
Gln Leu Thr Pro Arg Gly Val Val Arg Arg Cys Leu Asn Leu Glu Glu
            420             425             430 aga gtt gtc ctg aag cgc ttc tgc cgt atg gct gtg gag gga gtg tgg    1344
Arg Val Val Leu Lys Arg Phe Cys Arg Met Ala Val Glu Gly Val Trp
            435             440             445 aat agg aag tca gtg ttt gat ggt gac gac ctc atg gtt caa gga ctc    1392
Asn Arg Lys Ser Val Phe Asp Gly Asp Asp Leu Met Val Gln Gly Leu
            450             455             460 ggg gag tct gag ctc cgt gct ctg ttt cac atg aac atc ctt ctc cca    1440
Gly Glu Ser Glu Leu Arg Ala Leu Phe His Met Asn Ile Leu Leu Pro
465             470             475             480 gac agc cac tgt gag gag tac tac acc ttc ttc cac ctc agt ctc cag    1488
Asp Ser His Cys Glu Glu Tyr Tyr Thr Phe Phe His Leu Ser Leu Gln
                485             490             495 gac ttc tgt gcc gcc ttg tac tac gtg tta gag ggc ctg gaa atc gag    1536
Asp Phe Cys Ala Ala Leu Tyr Tyr Val Leu Glu Gly Leu Glu Ile Glu
            500             505             510 cca gct ctc tgc cct ctg tac gtt gag aag aca aag agg tcc atg gag    1584
Pro Ala Leu Cys Pro Leu Tyr Val Glu Lys Thr Lys Arg Ser Met Glu
            515             520             525 ctt aaa cag gca ggc ttc cat atc cac tcg ctt tgg atg aag cgt ttc    1632
Leu Lys Gln Ala Gly Phe His Ile His Ser Leu Trp Met Lys Arg Phe
        530             535             540 ttg ttt ggc ctc gtg agc gaa gac gta agg agg cca ctg gag gtc ctg    1680
Leu Phe Gly Leu Val Ser Glu Asp Val Arg Arg Pro Leu Glu Val Leu
545             550             555             560 ctg ggc tgt ccc gtt ccc ctg ggg gtg aag cag aag ctt ctg cac tgg    1728
Leu Gly Cys Pro Val Pro Leu Gly Val Lys Gln Lys Leu Leu His Trp
                565             570             575 gtc tct ctg ttg ggt cag cag cct aat gcc acc acc cca gga gac acc    1776
Val Ser Leu Leu Gly Gln Gln Pro Asn Ala Thr Thr Pro Gly Asp Thr
            580             585             590 ctg gac gcc ttc cac tgt ctt ttc gag act caa gac aaa gag ttt gtt    1824
Leu Asp Ala Phe His Cys Leu Phe Glu Thr Gln Asp Lys Glu Phe Val
            595             600             605 cgc ttg gca tta aac agc ttc caa gaa gtg tgg ctt ccg att aac cag    1872
Arg Leu Ala Leu Asn Ser Phe Gln Glu Val Trp Leu Pro Ile Asn Gln
        610             615             620
```

Fig. 3C

```
aac ctg gac ttg ata gca tct tcc ttc tgc ctc cag cac tgt ccg tat    1920
Asn Leu Asp Leu Ile Ala Ser Ser Phe Cys Leu Gln His Cys Pro Tyr
625                 630                 635                 640 ttg cgg aaa att cgg gtg gat gtc aaa ggg atc ttc cca aga gat gag    1968
Leu Arg Lys Ile Arg Val Asp Val Lys Gly Ile Phe Pro Arg Asp Glu
                645                 650                 655 tcc gct gag gca tgt cct gtg gtc cct cta tgg atg cgg gat aag acc    2016
Ser Ala Glu Ala Cys Pro Val Val Pro Leu Trp Met Arg Asp Lys Thr
            660                 665                 670 ctc att gag gag cag tgg gaa gat ttc tgc tcc atg ctt ggc acc cac    2064
Leu Ile Glu Glu Gln Trp Glu Asp Phe Cys Ser Met Leu Gly Thr His
        675                 680                 685 cca cac ctg cgg cag ctg gac ctg ggc agc agc atc ctg aca gag cgg    2112
Pro His Leu Arg Gln Leu Asp Leu Gly Ser Ser Ile Leu Thr Glu Arg
690                 695                 700 gcc atg aag acc ctg tgt gcc aag ctg agg cat ccc acc tgc aag ata    2160
Ala Met Lys Thr Leu Cys Ala Lys Leu Arg His Pro Thr Cys Lys Ile
705                 710                 715                 720 cag acc ctg atg ttt aga aat gca cag att acc cct ggt gtg cag cac    2208
Gln Thr Leu Met Phe Arg Asn Ala Gln Ile Thr Pro Gly Val Gln His
                725                 730                 735 ctc tgg aga atc gtc atg gcc aac cgt aac cta aga tcc ctc aac ttg    2256
Leu Trp Arg Ile Val Met Ala Asn Arg Asn Leu Arg Ser Leu Asn Leu
            740                 745                 750 gga ggc acc cac ctg aag gaa gag gat gta agg atg gcg tgt gaa gcc    2304
Gly Gly Thr His Leu Lys Glu Glu Asp Val Arg Met Ala Cys Glu Ala
        755                 760                 765 tta aaa cac cca aaa tgt ttg ttg gag tct ttg agg ctg gat tgc tgt    2352
Leu Lys His Pro Lys Cys Leu Leu Glu Ser Leu Arg Leu Asp Cys Cys
770                 775                 780 gga ttg acc cat gcc tgt tac ctg aag atc tcc caa atc ctt acg acc    2400
Gly Leu Thr His Ala Cys Tyr Leu Lys Ile Ser Gln Ile Leu Thr Thr
785                 790                 795                 800 tcc ccc agc ctg aaa tct ctg agc ctg gca gga aac aag gtg aca gac    2448
Ser Pro Ser Leu Lys Ser Leu Ser Leu Ala Gly Asn Lys Val Thr Asp
                805                 810                 815 cag gga gta atg cct ctc agt gat gcc ttg aga gtc tcc cag tgc gcc    2496
Gln Gly Val Met Pro Leu Ser Asp Ala Leu Arg Val Ser Gln Cys Ala
            820                 825                 830
```

Fig. 3D

```
ctg cag aag ctg ata ctg gag gac tgt ggc atc aca gcc acg ggt tgc    2544
Leu Gln Lys Leu Ile Leu Glu Asp Cys Gly Ile Thr Ala Thr Gly Cys
        835             840             845 cag agt ctg gcc tca gcc ctc gtc agc aac cgg agc ttg aca cac ctg    2592
Gln Ser Leu Ala Ser Ala Leu Val Ser Asn Arg Ser Leu Thr His Leu
    850             855             860 tgc cta tcc aac aac agc ctg ggg aac gaa ggt gta aat cta ctg tgt    2640
Cys Leu Ser Asn Asn Ser Leu Gly Asn Glu Gly Val Asn Leu Leu Cys
865             870             875             880 cga tcc atg agg ctt ccc cac tgt agt ctg cag agg ctg atg ctg aat    2688
Arg Ser Met Arg Leu Pro His Cys Ser Leu Gln Arg Leu Met Leu Asn
            885             890             895 cag tgc cac ctg gac acg gct ggc tgt ggt ttt ctt gca ctt gcg ctt    2736
Gln Cys His Leu Asp Thr Ala Gly Cys Gly Phe Leu Ala Leu Ala Leu
        900             905             910 atg ggt aac tca tgg ctg acg cac ctg agc ctt agc atg aac cct gtg    2784
Met Gly Asn Ser Trp Leu Thr His Leu Ser Leu Ser Met Asn Pro Val
            915             920             925 gaa gac aat ggc gtg aag ctt ctg tgc gag gtc atg aga gaa cca tct    2832
Glu Asp Asn Gly Val Lys Leu Leu Cys Glu Val Met Arg Glu Pro Ser
        930             935             940 tgt cat ctc cag gac ctg gag ttg gta aag tgt cat ctc acc gcc gcg    2880
Cys His Leu Gln Asp Leu Glu Leu Val Lys Cys His Leu Thr Ala Ala
945             950             955             960 tgc tgt gag agt ctg tcc tgt gtg atc tcg agg agc aga cac ctg aag    2928
Cys Cys Glu Ser Leu Ser Cys Val Ile Ser Arg Ser Arg His Leu Lys
            965             970             975 agc ctg gat ctc acg gac aat gcc ctg ggt gac ggt ggg gtt gct gcg    2976
Ser Leu Asp Leu Thr Asp Asn Ala Leu Gly Asp Gly Gly Val Ala Ala
        980             985             990 ctg tgc gag gga ctg aag caa aag aac agt gtt ctg acg aga ctc ggg    3024
Leu Cys Glu Gly Leu Lys Gln Lys Asn Ser Val Leu Thr Arg Leu Gly
            995             1000            1005 ttg aag gca tgt gga ctg act tct gat tgc tgt gag gca ctc tcc ttg    3072
Leu Lys Ala Cys Gly Leu Thr Ser Asp Cys Cys Glu Ala Leu Ser Leu
        1010            1015            1020 gcc ctt tcc tgc aac cgg cat ctg acc agt cta aac ctg gtg cag aat    3120
Ala Leu Ser Cys Asn Arg His Leu Thr Ser Leu Asn Leu Val Gln Asn
    1025            1030            1035            1040
```

Fig. 3E

```
aac ttc agt ccc aaa gga atg atg aag ctg tgt tcg gcc ttt gcc tgt    3168
Asn Phe Ser Pro Lys Gly Met Met Lys Leu Cys Ser Ala Phe Ala Cys
            1045                1050                1055 ccc acg tct aac tta cag ata att ggg ctg tgg aaa tgg cag tac cct    3216
Pro Thr Ser Asn Leu Gln Ile Ile Gly Leu Trp Lys Trp Gln Tyr Pro
            1060                1065                1070 gtg caa ata agg aag ctg ctg gag gaa gtg cag cta ctc aag ccc cga    3264
Val Gln Ile Arg Lys Leu Leu Glu Glu Val Gln Leu Leu Lys Pro Arg
            1075                1080                1085 gtc gta att gac ggt agt tgg cat tct ttt gat gaa gat gac cga cac    3312
Val Val Ile Asp Gly Ser Trp His Ser Phe Asp Glu Asp Asp Arg His
            1090                1095                1100 aaa ata gga ctt act ttc cgg ctc cct gaa agc cgg gca tgg cca tgt    3360
Lys Ile Gly Leu Thr Phe Arg Leu Pro Glu Ser Arg Ala Trp Pro Cys
1105                1110                1115                1120 gcc ttg ctg tgg ggg atg aac cca gag cag aag aag cgt gtg tcg ctt    3408
Ala Leu Leu Trp Gly Met Asn Pro Glu Gln Lys Lys Arg Val Ser Leu
            1125                1130                1135 ctg gct gga gac ttc aag agc agt aca cga ttt gcc aag tct ctc tgc    3456
Leu Ala Gly Asp Phe Lys Ser Ser Thr Arg Phe Ala Lys Ser Leu Cys
            1140                1145                1150 ctg gcc acg gca aat ggt gag tcc cag aga gtt gac aac gtg gag cag    3504
Leu Ala Thr Ala Asn Gly Glu Ser Gln Arg Val Asp Asn Val Glu Gln
            1155                1160                1165 agc tcc ccg caa ccc atg gca ggc acg gaa cac aaa caa gat aaa atg    3552
Ser Ser Pro Gln Pro Met Ala Gly Thr Glu His Lys Gln Asp Lys Met
            1170                1175                1180 ttg agt gtt gga tat tcc gga gcc tgg tct gaa act gct gag ctc gaa    3600
Leu Ser Val Gly Tyr Ser Gly Ala Trp Ser Glu Thr Ala Glu Leu Glu
1185                1190                1195                1200 ggg ctt gga tcc aac agt gct gat cat gac cac gga ggt atg gcc tgg    3648
Gly Leu Gly Ser Asn Ser Ala Asp His Asp His Gly Gly Met Ala Trp
            1205                1210                1215 tca cta ggg aga gag ctg agc tcg agg ggc ttg tgt cca aca gtg ctg    3696
Ser Leu Gly Arg Glu Leu Ser Ser Arg Gly Leu Cys Pro Thr Val Leu
            1220                1225                1230 atg acc aca gcg gtg tgt cct ggt cac tgg gag cgg ctg ggc tct agg    3744
Met Thr Thr Ala Val Cys Pro Gly His Trp Glu Arg Leu Gly Ser Arg
            1235                1240                1245
```

Fig. 3F

```
ggc tgg tgt ctt aac agt gct gat gac cac agc ggt gtg tcc tgg tca       3792
Gly Trp Cys Leu Asn Ser Ala Asp Asp His Ser Gly Val Ser Trp Ser
    1250                1255                1260 ctg gga gcg gct ggg ctc gag ggg ctt gtg tcc aac agt gct gat gac       3840
Leu Gly Ala Ala Gly Leu Glu Gly Leu Val Ser Asn Ser Ala Asp Asp
1265                1270                1275                1280 cac agc ggt gtg gcc tgg tca ctg gga gcg gct ggg ctc gag ggg ctt       3888
His Ser Gly Val Ala Trp Ser Leu Gly Ala Ala Gly Leu Glu Gly Leu
                1285                1290                1295 gtg tcc aac agt gct gat gac cac agc ggt gtg tcc tgg tca ctg gga       3936
Val Ser Asn Ser Ala Asp Asp His Ser Gly Val Ser Trp Ser Leu Gly
            1300                1305                1310 gcg gct ggg ctc gag ggg ctt gtg tcc aac agt gct gat gac cac agc       3984
Ala Ala Gly Leu Glu Gly Leu Val Ser Asn Ser Ala Asp Asp His Ser
        1315                1320                1325 ggt gtg tcc tgg tca ctg gga gcg gct ggg ctc gag ggg ctg gtg tct       4032
Gly Val Ser Trp Ser Leu Gly Ala Ala Gly Leu Glu Gly Leu Val Ser
    1330                1335                1340 taa                                                                    4035
 *
```

Fig. 3G

```
atg gca tct tct gca gag ctg gac ttc aac ctg cag gct ctt ctg gag      48
Met Ala Ser Ser Ala Glu Leu Asp Phe Asn Leu Gln Ala Leu Leu Glu
1               5                   10                  15 cag ctc agc cag gat gag ttg agc aag ttc aag tct ctg atc aga aca      96
Gln Leu Ser Gln Asp Glu Leu Ser Lys Phe Lys Ser Leu Ile Arg Thr
            20                  25                  30 atc tcc ctg gga aag gag cta cag acc gtc ccc cag aca gag gta gac     144
Ile Ser Leu Gly Lys Glu Leu Gln Thr Val Pro Gln Thr Glu Val Asp
        35                  40                  45 aag gct aat ggg aag caa ctg gta gaa atc ttc acc agc cac tcc tgc     192
Lys Ala Asn Gly Lys Gln Leu Val Glu Ile Phe Thr Ser His Ser Cys
    50                  55                  60 agc tac tgg gca ggg atg gca gcc atc cag gtc ttt gaa aag atg aat     240
Ser Tyr Trp Ala Gly Met Ala Ala Ile Gln Val Phe Glu Lys Met Asn
65                  70                  75                  80 cga acg cat ctg tct ggg aga gct gat gaa cac tgt gtg atg ccc cca     288
Arg Thr His Leu Ser Gly Arg Ala Asp Glu His Cys Val Met Pro Pro
                85                  90                  95 cct taa                                                              294
Pro *
```

Fig. 4

```
tccggttagg tatcaagctg tagctggtag gtaccagcac caccaaacag aagtgaacta      60
gtgaggtatg ggctaagaga gcccaaactt ggacctgtag agctgtcgga ccaggaaagg     120
ggatctgttt cgtctcagtc cccaggcttt gcttactggg ctcctggatc aagggagctt     180
gagttctcgc tgcctcacct ccagctcccc aagtctgaac tgtggtcact ggtcttctgg     240
tctggacttg atccttcccc cagatcacc atg gcc atg gcc aag gcc aga aag       293
                                 Met Ala Met Ala Lys Ala Arg Lys
                                  1               5 ccc cgg gag gca ttg ctc tgg gcc ttg agt gac ctt gag gag aac gat       341
Pro Arg Glu Ala Leu Leu Trp Ala Leu Ser Asp Leu Glu Glu Asn Asp
       10              15                  20 ttc aag aag tta aag ttc tac tta cgg gat atg acc ctg tct gag ggg       389
Phe Lys Lys Leu Lys Phe Tyr Leu Arg Asp Met Thr Leu Ser Glu Gly
 25              30                  35                  40 cca gcc ccc act ggc cag agg ggg agt ttg gag ggg                       425
Pro Ala Pro Thr Gly Gln Arg Gly Ser Leu Glu Gly
                 45                  50
```

Fig. 5

```
atg gcc atg gcc aag gcc aga aag ccc cgg gag gca ttg ctc tgg gcc    48
Met Ala Met Ala Lys Ala Arg Lys Pro Arg Glu Ala Leu Leu Trp Ala
 1           5                  10                  15 ttg agt gac ctt gag gag aac gat ttc aag aag tta aag ttc tac tta    96
Leu Ser Asp Leu Glu Glu Asn Asp Phe Lys Lys Leu Lys Phe Tyr Leu
            20                  25                  30 cgg gat atg acc ctg tct gag ggc cag ccc cca ctg gcc aga ggg gag   144
Arg Asp Met Thr Leu Ser Glu Gly Gln Pro Pro Leu Ala Arg Gly Glu
        35                  40                  45 ttg gag ggc ctg att ccg gtg gac ctg gca gaa tta ctg att tca aag   192
Leu Glu Gly Leu Ile Pro Val Asp Leu Ala Glu Leu Leu Ile Ser Lys
    50                  55                  60 tat gga gaa aag gag gct gtg aaa gtt gtc ctc aag ggc ttg aag gtc   240
Tyr Gly Glu Lys Glu Ala Val Lys Val Val Leu Lys Gly Leu Lys Val
65                  70                  75                  80 atg aac ctg ttg gaa ctt gtg gac cag ctc agc cat att tgt ctg cat   288
Met Asn Leu Leu Glu Leu Val Asp Gln Leu Ser His Ile Cys Leu His
                85                  90                  95 gat tac aga gaa gta tac cga gag cat gtg cgc tgc cta gag gaa tgg   336
Asp Tyr Arg Glu Val Tyr Arg Glu His Val Arg Cys Leu Glu Glu Trp
            100                 105                 110 cag gaa gca gga gtc aat ggc aga tac aac cag gtg ctc ctg gtg gcc   384
Gln Glu Ala Gly Val Asn Gly Arg Tyr Asn Gln Val Leu Leu Val Ala
        115                 120                 125 aag ccc agc tca gag agc cca gaa tca ctt gcc tgc ccc ttc ccg gag   432
Lys Pro Ser Ser Glu Ser Pro Glu Ser Leu Ala Cys Pro Phe Pro Glu
    130                 135                 140 cag gag ctg gag tct gtc acg gtg gag gct cta ttt gat tca ggg gaa   480
Gln Glu Leu Glu Ser Val Thr Val Glu Ala Leu Phe Asp Ser Gly Glu
145                 150                 155                 160 aag ccc tca ctg gcc cca tcc tta gtt gtg cta cag ggg tcg gct ggc   528
Lys Pro Ser Leu Ala Pro Ser Leu Val Val Leu Gln Gly Ser Ala Gly
                165                 170                 175 act gga aag aca act ctc gcc aga aaa atg gtg ttg gac tgg gcc acc   576
Thr Gly Lys Thr Thr Leu Ala Arg Lys Met Val Leu Asp Trp Ala Thr
            180                 185                 190 ggt act ctg tac cca ggc cgg ttt gat tat gtc ttt tat gta agc tgc   624
Gly Thr Leu Tyr Pro Gly Arg Phe Asp Tyr Val Phe Tyr Val Ser Cys
        195                 200                 205
```

Fig. 6A

| | | | | | | | | | | | | | | | |
|---|---|---|---|---|---|---|---|---|---|---|---|---|---|---|---|
| aaa | gaa | gtg | gtc | ctg | ctg | ctg | gag | agc | aaa | ctg | gag | cag | ctc | ctt | ttc | 672 |
| Lys | Glu | Val | Val | Leu | Leu | Leu | Glu | Ser | Lys | Leu | Glu | Gln | Leu | Leu | Phe |
| | 210 | | | | 215 | | | | | 220 | | | | | |

| tgg | tgc | tgc | ggg | gac | aat | caa | gcc | cct | gtc | aca | gag | att | ctg | agg | cag | 720 |
| Trp | Cys | Cys | Gly | Asp | Asn | Gln | Ala | Pro | Val | Thr | Glu | Ile | Leu | Arg | Gln |
| 225 | | | | | 230 | | | | | 235 | | | | | 240 |

| cca | gag | cgg | ctc | ctg | ttc | atc | ctg | gat | ggc | ttt | gat | gag | ctg | cag | agg | 768 |
| Pro | Glu | Arg | Leu | Leu | Phe | Ile | Leu | Asp | Gly | Phe | Asp | Glu | Leu | Gln | Arg |
| | | | | 245 | | | | | 250 | | | | | 255 | |

| ccc | ttt | gaa | gaa | aag | ttg | aag | aag | agg | ggt | ttg | agt | ccc | aag | gag | agc | 816 |
| Pro | Phe | Glu | Glu | Lys | Leu | Lys | Lys | Arg | Gly | Leu | Ser | Pro | Lys | Glu | Ser |
| | | | 260 | | | | | 265 | | | | | 270 | | |

| ctg | ctg | cac | ctt | cta | att | agg | aga | cat | aca | ctc | ccc | acg | tgc | tcc | ctt | 864 |
| Leu | Leu | His | Leu | Leu | Ile | Arg | Arg | His | Thr | Leu | Pro | Thr | Cys | Ser | Leu |
| | | | 275 | | | | | 280 | | | | | 285 | | |

| ctc | atc | acc | acc | cgg | ccc | ctg | gct | ttg | agg | aat | ctg | gag | ccc | ttg | ctg | 912 |
| Leu | Ile | Thr | Thr | Arg | Pro | Leu | Ala | Leu | Arg | Asn | Leu | Glu | Pro | Leu | Leu |
| | 290 | | | | | 295 | | | | | 300 | | | | |

| aaa | caa | gca | cgt | cat | gtc | cat | atc | cta | ggc | ttc | tct | gag | gag | gag | agg | 960 |
| Lys | Gln | Ala | Arg | His | Val | His | Ile | Leu | Gly | Phe | Ser | Glu | Glu | Glu | Arg |
| 305 | | | | | 310 | | | | | 315 | | | | | 320 |

| gcg | agg | tac | ttc | agc | tcc | tat | ttc | acg | gat | gag | aag | caa | gct | gac | cgt | 1008 |
| Ala | Arg | Tyr | Phe | Ser | Ser | Tyr | Phe | Thr | Asp | Glu | Lys | Gln | Ala | Asp | Arg |
| | | | | 325 | | | | | 330 | | | | | 335 | |

| gcc | ttc | gac | att | gta | cag | aaa | aat | gac | att | ctc | tac | aaa | gcg | tgt | cag | 1056 |
| Ala | Phe | Asp | Ile | Val | Gln | Lys | Asn | Asp | Ile | Leu | Tyr | Lys | Ala | Cys | Gln |
| | | | | 340 | | | | | 345 | | | | | 350 | |

| gtt | cca | ggc | att | tgc | tgg | gtg | gtc | tgc | tcc | tgg | ctg | cag | ggg | cag | atg | 1104 |
| Val | Pro | Gly | Ile | Cys | Trp | Val | Val | Cys | Ser | Trp | Leu | Gln | Gly | Gln | Met |
| | | 355 | | | | | 360 | | | | | 365 | | | |

| gag | aga | ggc | aaa | gtt | gtc | tta | gag | aca | cct | aga | aac | agc | act | gac | atc | 1152 |
| Glu | Arg | Gly | Lys | Val | Val | Leu | Glu | Thr | Pro | Arg | Asn | Ser | Thr | Asp | Ile |
| | | 370 | | | | | 375 | | | | | 380 | | | |

| ttc | atg | gct | tac | gtc | tcc | acc | ttt | ctg | ccg | ccc | gat | gat | gat | ggg | ggc | 1200 |
| Phe | Met | Ala | Tyr | Val | Ser | Thr | Phe | Leu | Pro | Pro | Asp | Asp | Asp | Gly | Gly |
| 385 | | | | | 390 | | | | | 395 | | | | | 400 |

| tgc | tcc | gag | ctt | tcc | cgg | cac | agg | gtc | ctg | agg | agt | ctg | tgc | tcc | cta | 1248 |
| Cys | Ser | Glu | Leu | Ser | Arg | His | Arg | Val | Leu | Arg | Ser | Leu | Cys | Ser | Leu |
| | | | | 405 | | | | | 410 | | | | | 415 | |

Fig. 6B

```
gca gct gaa ggg att cag cac cag agg ttc cta ttt gaa gaa gct gag    1296
Ala Ala Glu Gly Ile Gln His Gln Arg Phe Leu Phe Glu Glu Ala Glu
            420                 425                 430 ctc agg aaa cat aat tta gat ggc ccc agg ctt gcc gct ttc ctg agt    1344
Leu Arg Lys His Asn Leu Asp Gly Pro Arg Leu Ala Ala Phe Leu Ser
        435                 440                 445 agt aac gac tac caa ttg gga ctt gcc atc aag aag ttc tac agc ttc    1392
Ser Asn Asp Tyr Gln Leu Gly Leu Ala Ile Lys Lys Phe Tyr Ser Phe
    450                 455                 460 cgc cac atc agc ttc cag gac ttt ttt cat gcc atg tct tac ctg gtg    1440
Arg His Ile Ser Phe Gln Asp Phe Phe His Ala Met Ser Tyr Leu Val
465                 470                 475                 480 aaa gag gac caa agc cgg ctg ggg aag gag tcc cgc aga gaa gtg caa    1488
Lys Glu Asp Gln Ser Arg Leu Gly Lys Glu Ser Arg Arg Glu Val Gln
                485                 490                 495 agg ctg ctg gag gta aag gag cag gaa ggg aat gat gag atg acc ctc    1536
Arg Leu Leu Glu Val Lys Glu Gln Glu Gly Asn Asp Glu Met Thr Leu
            500                 505                 510 act atg cag ttt tta ctg gac atc tcg aaa aaa gac agc ttc tcg aac    1584
Thr Met Gln Phe Leu Leu Asp Ile Ser Lys Lys Asp Ser Phe Ser Asn
        515                 520                 525 ttg gag ctc aag ttc tgc ttc aga att tct ccc tgt tta gcg cag gat    1632
Leu Glu Leu Lys Phe Cys Phe Arg Ile Ser Pro Cys Leu Ala Gln Asp
    530                 535                 540 ctg aag cat ttt aaa gaa cag atg gaa tct atg aag cac aac agg acc    1680
Leu Lys His Phe Lys Glu Gln Met Glu Ser Met Lys His Asn Arg Thr
545                 550                 555                 560 tgg gat ttg gaa ttc tcc ctg tat gaa gct aaa ata aag aat ctg gta    1728
Trp Asp Leu Glu Phe Ser Leu Tyr Glu Ala Lys Ile Lys Asn Leu Val
                565                 570                 575 aaa ggt att cag atg aac aat gta tca ttc aag ata aaa cat tca aat    1776
Lys Gly Ile Gln Met Asn Asn Val Ser Phe Lys Ile Lys His Ser Asn
            580                 585                 590 gaa aag aaa tca cag agc cag aat tta ttt tct gtc aaa agc agc ttg    1824
Glu Lys Lys Ser Gln Ser Gln Asn Leu Phe Ser Val Lys Ser Ser Leu
        595                 600                 605 agt cat gga cct aag gag gag caa aaa tgt cct tct gtc cat gga cag    1872
Ser His Gly Pro Lys Glu Glu Gln Lys Cys Pro Ser Val His Gly Gln
    610                 615                 620
```

Fig. 6C

```
aag gag ggc aaa gat aat ata gca gga aca caa aag gaa gct tct act        1920
Lys Glu Gly Lys Asp Asn Ile Ala Gly Thr Gln Lys Glu Ala Ser Thr
625                 630                 635                 640 gga aaa ggc aga ggg aca gag gaa aca cca aaa aat act tac ata taa        1968
Gly Lys Gly Arg Gly Thr Glu Glu Thr Pro Lys Asn Thr Tyr Ile  *
                645                 650                 655
```

Fig. 6D

```
gcctgtgaat gatgcaatgg aaggtgtgct ggggtcgccc tgtgtcccgt gcataggagc    60
atctcagcct ccaggtcctc tcctttgggg cttacggcac cccc atg cta cga acc   116
                                                  Met Leu Arg Thr
                                                    1 gca ggc agg gac ggc ctc tgt cgc ctg tcc acc tac ttg gaa gaa ctc    164
Ala Gly Arg Asp Gly Leu Cys Arg Leu Ser Thr Tyr Leu Glu Glu Leu
 5                  10                  15                  20 gag gct gtg gaa ctg aag aag ttc aag tta tac ctg ggg acc gcg aca    212
Glu Ala Val Glu Leu Lys Lys Phe Lys Leu Tyr Leu Gly Thr Ala Thr
                25                  30                  35 gag ctg gga gaa ggc aag atc ccc tgg gga agc atg gag ata gcc ggt    260
Glu Leu Gly Glu Gly Lys Ile Pro Trp Gly Ser Met Glu Ile Ala Gly
                40                  45                  50 ccc ctg gaa atg gcc cag ctg ctc atc acc cac ttc ggg                299
Pro Leu Glu Met Ala Gln Leu Leu Ile Thr His Phe Gly
                55                  60                  65
```

Fig. 7

| | |
|---|---|
| atg cta cga acc gca ggc agg gac ggc ctc tgt cgc ctg tcc acc tac<br>Met Leu Arg Thr Ala Gly Arg Asp Gly Leu Cys Arg Leu Ser Thr Tyr<br>1                      5                          10                      15 | 48 |
| ttg gaa gaa ctc gag gct gtg gaa ctg aag aag ttc aag tta tac ctg<br>Leu Glu Glu Leu Glu Ala Val Glu Leu Lys Lys Phe Lys Leu Tyr Leu<br>                 20                          25                      30 | 96 |
| ggg acc gcg aca gag ctg gga gaa ggc aag atc ccc tgg gga agc atg<br>Gly Thr Ala Thr Glu Leu Gly Glu Gly Lys Ile Pro Trp Gly Ser Met<br>              35                          40                      45 | 144 |
| gag aag gcc ggt ccc ctg gaa atg gcc cag ctg ctc atc acc cac ttc<br>Glu Lys Ala Gly Pro Leu Glu Met Ala Gln Leu Leu Ile Thr His Phe<br>    50                          55                          60 | 192 |
| ggg cca gag gag gcc tgg agg ttg gct ctc agc acc ttt gag cgg ata<br>Gly Pro Glu Glu Ala Trp Arg Leu Ala Leu Ser Thr Phe Glu Arg Ile<br>65                      70                          75                      80 | 240 |
| aac agg aag gac ctg tgg gag aga gga cag aga gag gac ctg gtg agg<br>Asn Arg Lys Asp Leu Trp Glu Arg Gly Gln Arg Glu Asp Leu Val Arg<br>              85                          90                      95 | 288 |
| gat acc cca cct ggt ggc ccg tcc tca ctt ggg aac cag tca aca tgc<br>Asp Thr Pro Pro Gly Gly Pro Ser Ser Leu Gly Asn Gln Ser Thr Cys<br>                100                        105                    110 | 336 |
| ctt ctg gaa gtc tct ctt gtc act cca aga aaa gat ccc cag gaa acc<br>Leu Leu Glu Val Ser Leu Val Thr Pro Arg Lys Asp Pro Gln Glu Thr<br>            115                        120                      125 | 384 |
| tac agg gac tat gtc cgc agg aaa ttc cgg ctc atg gaa gac cgc aat<br>Tyr Arg Asp Tyr Val Arg Arg Lys Phe Arg Leu Met Glu Asp Arg Asn<br>    130                        135                      140 | 432 |
| gcg cgc cta ggg gaa tgt gtc aac ctc agc cac cgg tac acc cgg ctc<br>Ala Arg Leu Gly Glu Cys Val Asn Leu Ser His Arg Tyr Thr Arg Leu<br>145                      150                        155                    160 | 480 |
| ctg ctg gtg aag gag cac tca aac ccc atg cag gtc cag cag cag ctt<br>Leu Leu Val Lys Glu His Ser Asn Pro Met Gln Val Gln Gln Gln Leu<br>                165                        170                    175 | 528 |
| ctg gac aca ggc cgg gga cac gcg agg acc gtg gga cac cag gct agc<br>Leu Asp Thr Gly Arg Gly His Ala Arg Thr Val Gly His Gln Ala Ser<br>            180                        185                      190 | 576 |
| ccc atc aag ata gag acc ctc ttt gag cca gac gag gag cgc ccc gag<br>Pro Ile Lys Ile Glu Thr Leu Phe Glu Pro Asp Glu Glu Arg Pro Glu<br>              195                        200                    205 | 624 |

Fig. 8A

```
cca ccg cgc acc gtg gtc atg caa ggc gcg gca ggg ata ggc aag tcc    672
Pro Pro Arg Thr Val Val Met Gln Gly Ala Ala Gly Ile Gly Lys Ser
    210             215             220 atg ctg gca cac aag gtg atg ctg gac tgg gcg gac ggg aag ctc ttc    720
Met Leu Ala His Lys Val Met Leu Asp Trp Ala Asp Gly Lys Leu Phe
225             230             235             240 caa ggc aga ttt gat tat ctc ttc tac atc aac tgc agg gag atg aac    768
Gln Gly Arg Phe Asp Tyr Leu Phe Tyr Ile Asn Cys Arg Glu Met Asn
            245             250             255 cag agt gcc acg gaa tgc agc atg caa gac ctc atc ttc agc tgc tgg    816
Gln Ser Ala Thr Glu Cys Ser Met Gln Asp Leu Ile Phe Ser Cys Trp
        260             265             270 cct gag ccc agc gcg cct ctc cag gag ctc atc cga gtt ccc gag cgc    864
Pro Glu Pro Ser Ala Pro Leu Gln Glu Leu Ile Arg Val Pro Glu Arg
    275             280             285 ctc ctt ttc atc atc gac ggc ttc gat gag ctc aag cct tct ttc cac    912
Leu Leu Phe Ile Ile Asp Gly Phe Asp Glu Leu Lys Pro Ser Phe His
290             295             300 gat cct cag gga ccc tgg tgc ctc tgc tgg gag gag aaa cgg ccc acg    960
Asp Pro Gln Gly Pro Trp Cys Leu Cys Trp Glu Glu Lys Arg Pro Thr
305             310             315             320 gag ctg ctt ctt aac agc tta att cgg aag aag ctg ctc cct gag cta   1008
Glu Leu Leu Leu Asn Ser Leu Ile Arg Lys Lys Leu Leu Pro Glu Leu
            325             330             335 tct ttg ctc atc acc aca cgg ccc acg gct ttg gag aag ctc cac cgt   1056
Ser Leu Leu Ile Thr Thr Arg Pro Thr Ala Leu Glu Lys Leu His Arg
        340             345             350 ctg ctg gag cac ccc agg cat gtg gag atc ctg ggc ttc tct gag gca   1104
Leu Leu Glu His Pro Arg His Val Glu Ile Leu Gly Phe Ser Glu Ala
    355             360             365 gaa agg aag gaa tac ttc tac aag tat ttc cac aat gca gag cag gcg   1152
Glu Arg Lys Glu Tyr Phe Tyr Lys Tyr Phe His Asn Ala Glu Gln Ala
370             375             380 ggc caa gtc ttc aat tac gtg agg gac aac gag cct ctc ttc acc atg   1200
Gly Gln Val Phe Asn Tyr Val Arg Asp Asn Glu Pro Leu Phe Thr Met
385             390             395             400 tgc ttc gtc ccc ctg gtg tgc tgg gtg gtg tgt acc tgc ctc cag cag   1248
Cys Phe Val Pro Leu Val Cys Trp Val Val Cys Thr Cys Leu Gln Gln
            405             410             415
```

Fig. 8B

```
cag ctg gag ggt ggg ggg ctg ttg aga cag acg tcc agg acc acc act    1296
Gln Leu Glu Gly Gly Gly Leu Leu Arg Gln Thr Ser Arg Thr Thr Thr
            420                 425                 430 gca gtg tac atg ctc tac ctg ctg agt ctg atg caa ccc aag ccg ggg    1344
Ala Val Tyr Met Leu Tyr Leu Leu Ser Leu Met Gln Pro Lys Pro Gly
            435                 440                 445 gcc ccg cgc ctc cag ccc cca ccc aac cag aga ggg ttg tgc tcc ttg    1392
Ala Pro Arg Leu Gln Pro Pro Pro Asn Gln Arg Gly Leu Cys Ser Leu
            450                 455                 460 gcg gca gat ggg ctc tgg aat cag aaa atc cta ttt gag gag cag gac    1440
Ala Ala Asp Gly Leu Trp Asn Gln Lys Ile Leu Phe Glu Glu Gln Asp
465                 470                 475                 480 ctc cgg aag cac ggc cta gac ggg gaa gac gtc tct gcc ttc ctc aac    1488
Leu Arg Lys His Gly Leu Asp Gly Glu Asp Val Ser Ala Phe Leu Asn
            485                 490                 495 atg aac atc ttc cag aag gac atc aac tgt gag agg tac tac agc ttc    1536
Met Asn Ile Phe Gln Lys Asp Ile Asn Cys Glu Arg Tyr Tyr Ser Phe
            500                 505                 510 atc cac ttg agt ttc cag gaa ttc ttt gca gct atg tac tat atc ctg    1584
Ile His Leu Ser Phe Gln Glu Phe Phe Ala Ala Met Tyr Tyr Ile Leu
            515                 520                 525 gac gag ggg gag ggc ggg gca ggc cca gac cag gac gtg acc agg ctg    1632
Asp Glu Gly Glu Gly Gly Ala Gly Pro Asp Gln Asp Val Thr Arg Leu
            530                 535                 540 ttg acc gag tac gcg ttt tct gaa agg agc ttc ctg gca ctc acc agc    1680
Leu Thr Glu Tyr Ala Phe Ser Glu Arg Ser Phe Leu Ala Leu Thr Ser
545                 550                 555                 560 cgc ttc ctg ttt gga ctc ctg aac gag gag acc agg agc cac ctg gag    1728
Arg Phe Leu Phe Gly Leu Leu Asn Glu Glu Thr Arg Ser His Leu Glu
            565                 570                 575 aag agt ctc tgc tgg aag gtc tcg ccg cac atc aag atg gac ctg ttg    1776
Lys Ser Leu Cys Trp Lys Val Ser Pro His Ile Lys Met Asp Leu Leu
            580                 585                 590 cag tgg atc caa agc aaa gct cag agc gac ggc tcc acc ctg cag cag    1824
Gln Trp Ile Gln Ser Lys Ala Gln Ser Asp Gly Ser Thr Leu Gln Gln
            595                 600                 605 ggc tcc ttg gag ttc ttc agc tgc ttg tac gag atc cag gag gag gag    1872
Gly Ser Leu Glu Phe Phe Ser Cys Leu Tyr Glu Ile Gln Glu Glu Glu
            610                 615                 620
```

Fig. 8C

```
ttt atc cag cag gcc ctg agc cac ttc cag gtg atc gtg gtc agc aac    1920
Phe Ile Gln Gln Ala Leu Ser His Phe Gln Val Ile Val Val Ser Asn
625                 630                 635                 640 att gcc tcc aag atg gag cac atg gtc tcc tcg ttc tgt ctg aag cgc    1968
Ile Ala Ser Lys Met Glu His Met Val Ser Ser Phe Cys Leu Lys Arg
                645                 650                 655 tgc agg agc gcc cag gtg ctg cac ttg tat ggc gcc acc tac agc gcg    2016
Cys Arg Ser Ala Gln Val Leu His Leu Tyr Gly Ala Thr Tyr Ser Ala
            660                 665                 670 gac ggg gaa gac cgc gcg agg tgc tcc gca gga gcg cac acg ctg ttg    2064
Asp Gly Glu Asp Arg Ala Arg Cys Ser Ala Gly Ala His Thr Leu Leu
        675                 680                 685 gtg cag cta cca gag agg acc gtt ctg ctg gac gcc tac agt gaa cat    2112
Val Gln Leu Pro Glu Arg Thr Val Leu Leu Asp Ala Tyr Ser Glu His
    690                 695                 700 ctg gca gcg gcc ctg tgc acc aat cca aac ctg ata gag ctg tct ctg    2160
Leu Ala Ala Ala Leu Cys Thr Asn Pro Asn Leu Ile Glu Leu Ser Leu
705                 710                 715                 720 tac cga aat gcc ctg ggc agc cgg ggg gtg aag ctg ctc tgt caa gga    2208
Tyr Arg Asn Ala Leu Gly Ser Arg Gly Val Lys Leu Leu Cys Gln Gly
                725                 730                 735 ctc aga cac ccc aac tgc aaa ctt cag aac ctg agg ctg aag agg tgc    2256
Leu Arg His Pro Asn Cys Lys Leu Gln Asn Leu Arg Leu Lys Arg Cys
            740                 745                 750 cgc atc tcc agc tca gcc tgc gag gac ctc tct gca gct ctc ata gcc    2304
Arg Ile Ser Ser Ser Ala Cys Glu Asp Leu Ser Ala Ala Leu Ile Ala
        755                 760                 765 aat aag aat ttg aca agg atg gat ctc agt ggc aac ggc gtt gga ttc    2352
Asn Lys Asn Leu Thr Arg Met Asp Leu Ser Gly Asn Gly Val Gly Phe
    770                 775                 780 cca ggc atg atg ctg ctt tgc gag ggc ctg cgg cat ccc caa tgc agg    2400
Pro Gly Met Met Leu Leu Cys Glu Gly Leu Arg His Pro Gln Cys Arg
785                 790                 795                 800 ctg cag atg att cag ttg agg aag tgt cag ctg gag tcc ggg gct tgt    2448
Leu Gln Met Ile Gln Leu Arg Lys Cys Gln Leu Glu Ser Gly Ala Cys
                805                 810                 815 cag gag atg gct tct gtg ctt ggc acc aac cca cat ctg gtt gag ttg    2496
Gln Glu Met Ala Ser Val Leu Gly Thr Asn Pro His Leu Val Glu Leu
            820                 825                 830
```

Fig. 8D

```
gac ctg aca gga aat gca ctg gag gat ttg ggc ctg agg tta cta tgc    2544
Asp Leu Thr Gly Asn Ala Leu Glu Asp Leu Gly Leu Arg Leu Leu Cys
        835             840             845 cag gga ctg agg cac cca gtc tgc aga cta cgg act ttg tgg ctg aag    2592
Gln Gly Leu Arg His Pro Val Cys Arg Leu Arg Thr Leu Trp Leu Lys
    850             855             860 atc tgc cgc ctc act gct gct gcc tgt gac gag ctg gcc tca act ctc    2640
Ile Cys Arg Leu Thr Ala Ala Ala Cys Asp Glu Leu Ala Ser Thr Leu
865             870             875             880 agt gtg aac cag agc ctg aga gag ctg gac ctg agc ctg aat gag ctg    2688
Ser Val Asn Gln Ser Leu Arg Glu Leu Asp Leu Ser Leu Asn Glu Leu
                885             890             895 ggg gac ctc ggg gtg ctg ctg ctg tgt gag ggc ctc agg cat ccc acg    2736
Gly Asp Leu Gly Val Leu Leu Leu Cys Glu Gly Leu Arg His Pro Thr
            900             905             910 tgc aag ctc cag acc ctg cgg ttg ggc atc tgc cgg ctg ggc tct gcc    2784
Cys Lys Leu Gln Thr Leu Arg Leu Gly Ile Cys Arg Leu Gly Ser Ala
        915             920             925 gcc tgt gag ggt ctt tct gtg gtg ctc cag gcc aac cac aac ctc cgg    2832
Ala Cys Glu Gly Leu Ser Val Val Leu Gln Ala Asn His Asn Leu Arg
    930             935             940 gag ctg gac ttg agt ttc aac gac ctg gga gac tgg ggc ctg tgg ttg    2880
Glu Leu Asp Leu Ser Phe Asn Asp Leu Gly Asp Trp Gly Leu Trp Leu
945             950             955             960 ctg gct gag ggg ctg caa cat ccc gcc tgc aga ctc cag aaa ctg tgg    2928
Leu Ala Glu Gly Leu Gln His Pro Ala Cys Arg Leu Gln Lys Leu Trp
            965             970             975 ctg gat agc tgt ggc ctc aca gcc aag gct tgt gag aat ctt tac ttc    2976
Leu Asp Ser Cys Gly Leu Thr Ala Lys Ala Cys Glu Asn Leu Tyr Phe
        980             985             990 acc ctg ggg atc aac cag acc ttg acc gac ctt tac ctg acc aac aac    3024
Thr Leu Gly Ile Asn Gln Thr Leu Thr Asp Leu Tyr Leu Thr Asn Asn
    995             1000            1005 gcc cta ggg gac aca ggt gtc cga ctg ctt tgc aag cgg ctg agc cat    3072
Ala Leu Gly Asp Thr Gly Val Arg Leu Leu Cys Lys Arg Leu Ser His
1010            1015            1020 cct ggc tgc aaa ctc cga gtc ctc tgg tta ttt ggg atg gac ctg aat    3120
Pro Gly Cys Lys Leu Arg Val Leu Trp Leu Phe Gly Met Asp Leu Asn
1025            1030            1035            1040
```

Fig. 8E

```
aaa atg acc cac agt agg ttg gca gcg ctt cga gta aca aaa cct tat    3168
Lys Met Thr His Ser Arg Leu Ala Ala Leu Arg Val Thr Lys Pro Tyr
            1045                1050                1055 ttg gac att ggc tgc tga                                            3186
Leu Asp Ile Gly Cys  *
            1060
```

Fig. 8F

```
atg agt gac gtg aat cca ccc tct gac acc ccc att ccc ttt tca tcc    48
Met Ser Asp Val Asn Pro Pro Ser Asp Thr Pro Ile Pro Phe Ser Ser
1               5                   10                  15 tcc tcc act cac agt tct cat att ctg ccc tgg aca ttc tct tgc tac    96
Ser Ser Thr His Ser Ser His Ile Leu Pro Trp Thr Phe Ser Cys Tyr
            20                  25                  30 ccc ggc tcc cca tgt gaa aat ggg gtc atg ctg tac atg aga aac gtg   144
Pro Gly Ser Pro Cys Glu Asn Gly Val Met Leu Tyr Met Arg Asn Val
        35                  40                  45 agc cat gag gag cta caa cgg ttc aag cag ctc tta ctg act gag ctc   192
Ser His Glu Glu Leu Gln Arg Phe Lys Gln Leu Leu Leu Thr Glu Leu
    50                  55                  60 agt act ggc acc atg ccc atc acc tgg gac cag gtc gag aca gcc agc   240
Ser Thr Gly Thr Met Pro Ile Thr Trp Asp Gln Val Glu Thr Ala Ser
65                  70                  75                  80 tgg gca gag gtg gtt cat ctc ttg ata gag cgt ttc cct gga cga cgc   288
Trp Ala Glu Val Val His Leu Leu Ile Glu Arg Phe Pro Gly Arg Arg
                85                  90                  95 gct tgg gat gtg act tcg aac atc ttt gcc att atg aac tgt gat aaa   336
Ala Trp Asp Val Thr Ser Asn Ile Phe Ala Ile Met Asn Cys Asp Lys
            100                 105                 110 att ggg gtc ccg cag tta ttc tac tgt ctg cat gaa atc cgg gag gaa   384
Ile Gly Val Pro Gln Leu Phe Tyr Cys Leu His Glu Ile Arg Glu Glu
        115                 120                 125 gcc ttt gta agc caa gcc tta aat gat tat cat aaa gtt gtc ttg aga   432
Ala Phe Val Ser Gln Ala Leu Asn Asp Tyr His Lys Val Val Leu Arg
    130                 135                 140 att ggc aac aac aaa gaa gtt caa gtg tct gct ttt tgc ctg aag cgg   480
Ile Gly Asn Asn Lys Glu Val Gln Val Ser Ala Phe Cys Leu Lys Arg
145                 150                 155                 160 tgt caa tat ttg cat gag gtg gaa ctg acc gtc acc ctg aac ttc atg   528
Cys Gln Tyr Leu His Glu Val Glu Leu Thr Val Thr Leu Asn Phe Met
                165                 170                 175 aac gtg tgg aag ctc agc tcc agc tcc cat cct ggc tct gac cta agg   576
Asn Val Trp Lys Leu Ser Ser Ser Ser His Pro Gly Ser Asp Leu Arg
            180                 185                 190 cgt gtg aat agc acc atg ttg aac cag gac tta atc ggt gtt ttg acg   624
Arg Val Asn Ser Thr Met Leu Asn Gln Asp Leu Ile Gly Val Leu Thr
        195                 200                 205
```

Fig. 9A

```
ggg aac cag cat ctg aga tac ttg gaa ata caa cat gtg gaa gtg gag    672
Gly Asn Gln His Leu Arg Tyr Leu Glu Ile Gln His Val Glu Val Glu
    210             215             220 tcc aag gct gtg aag ctt cta tgc agg gcg ctg aga tcc ccc cgg tgc    720
Ser Lys Ala Val Lys Leu Leu Cys Arg Ala Leu Arg Ser Pro Arg Cys
225             230             235             240 cgt ctg cag tgt ctc agg ttg gaa gac tgc ttg gcc acc cct aga att    768
Arg Leu Gln Cys Leu Arg Leu Glu Asp Cys Leu Ala Thr Pro Arg Ile
            245             250             255 tgg act gat ctt ggc aat aat ctt caa ggt aac ggg cat cta aag act    816
Trp Thr Asp Leu Gly Asn Asn Leu Gln Gly Asn Gly His Leu Lys Thr
        260             265             270 ctc ata cta aga aaa aac tcc ctg gag aac tgt ggg gcg tat tac ctg    864
Leu Ile Leu Arg Lys Asn Ser Leu Glu Asn Cys Gly Ala Tyr Tyr Leu
        275             280             285 tct gtg gcc cag ctg gag agg ctg tcg cag agt aag atg ctg acc cac    912
Ser Val Ala Gln Leu Glu Arg Leu Ser Gln Ser Lys Met Leu Thr His
        290             295             300 ctg agc ttg gca gaa aac gcc ttg aaa gat gaa ggg gcc aag cat att    960
Leu Ser Leu Ala Glu Asn Ala Leu Lys Asp Glu Gly Ala Lys His Ile
305             310             315             320 tgg aat gcc ctg cca cac ctg aga tgt cct ctg cag agg ctg gta ctg   1008
Trp Asn Ala Leu Pro His Leu Arg Cys Pro Leu Gln Arg Leu Val Leu
            325             330             335 aga aag tgt gac ttg acc ttt aat tgc tgt cag gat atg atc tct gcg   1056
Arg Lys Cys Asp Leu Thr Phe Asn Cys Cys Gln Asp Met Ile Ser Ala
            340             345             350 ctc tgt aaa aat aaa acc ctg aaa agt ctt gac cta agt ttt aat agc   1104
Leu Cys Lys Asn Lys Thr Leu Lys Ser Leu Asp Leu Ser Phe Asn Ser
        355             360             365 ctg aag gat gat ggg gtg atc ctg ctg tgt gag gcc ctg aag aac cct   1152
Leu Lys Asp Asp Gly Val Ile Leu Leu Cys Glu Ala Leu Lys Asn Pro
        370             375             380 gac tgt aca tta cag atc ctg gag ctg gaa aac tgc ctg ttt acc tcc   1200
Asp Cys Thr Leu Gln Ile Leu Glu Leu Glu Asn Cys Leu Phe Thr Ser
385             390             395             400 atc tgc tgc cag gcc atg gct tcc atg ctc cgc aaa aac caa cat ctg   1248
Ile Cys Cys Gln Ala Met Ala Ser Met Leu Arg Lys Asn Gln His Leu
            405             410             415
```

Fig. 9B

```
aga cat ctg gac ttg agc aag aat gcg att gga gtc tat ggt att ctg      1296
Arg His Leu Asp Leu Ser Lys Asn Ala Ile Gly Val Tyr Gly Ile Leu
        420                 425                 430 acc ttg tgc gag gcc ttc tca agc caa aag aag aga gaa gag gtc att      1344
Thr Leu Cys Glu Ala Phe Ser Ser Gln Lys Lys Arg Glu Glu Val Ile
        435                 440                 445 ttc tgt att cct gcc tgg act cga ata act agc ttc tcc cca act cct      1392
Phe Cys Ile Pro Ala Trp Thr Arg Ile Thr Ser Phe Ser Pro Thr Pro
        450                 455                 460 cac cca ccc gac ttc acg gga aaa agt gac tgc cta tcc cag att aat      1440
His Pro Pro Asp Phe Thr Gly Lys Ser Asp Cys Leu Ser Gln Ile Asn
465                 470                 475                 480 cct tag                                                              1446
Pro *
```

Fig. 9C

```
atg gca gat tca tca tca tct tct ttc ttt cct gat ttt ggg ctg cta        48
Met Ala Asp Ser Ser Ser Ser Ser Phe Phe Pro Asp Phe Gly Leu Leu
1               5                   10                  15 ttg tat ttg gag gag cta aac aaa gag gaa tta aat aca ttc aag tta        96
Leu Tyr Leu Glu Glu Leu Asn Lys Glu Glu Leu Asn Thr Phe Lys Leu
            20                  25                  30 ttc cta aag gag acc atg gaa cct gag cat ggc ctg aca ccc tgg act       144
Phe Leu Lys Glu Thr Met Glu Pro Glu His Gly Leu Thr Pro Trp Thr
        35                  40                  45 gaa gtg aag aag gcc agg cgg gag gac ctg gcc aat ttg atg aag aaa       192
Glu Val Lys Lys Ala Arg Arg Glu Asp Leu Ala Asn Leu Met Lys Lys
    50                  55                  60 tat tat cca gga gag aaa gcc tgg agt gtg tct ctc aaa atc ttt ggc       240
Tyr Tyr Pro Gly Glu Lys Ala Trp Ser Val Ser Leu Lys Ile Phe Gly
65                  70                  75                  80 aag atg aac ctg aag gat ctg tgt gag aga gcg aaa gaa gag atc aac       288
Lys Met Asn Leu Lys Asp Leu Cys Glu Arg Ala Lys Glu Glu Ile Asn
            85                  90                  95 tgg tcg gcc cag act ata gga cca gat gat gcc aag gct gga gag aca       336
Trp Ser Ala Gln Thr Ile Gly Pro Asp Asp Ala Lys Ala Gly Glu Thr
        100                 105                 110 caa gaa gat cag gag gca gtg ctg ggt gat gga aca gaa tac aga aat       384
Gln Glu Asp Gln Glu Ala Val Leu Gly Asp Gly Thr Glu Tyr Arg Asn
    115                 120                 125 aga ata aag gaa aaa ttt tgc atc act tgg gac aag aag tct ttg gct       432
Arg Ile Lys Glu Lys Phe Cys Ile Thr Trp Asp Lys Lys Ser Leu Ala
130                 135                 140 gga aag cct gaa gat ttc cat cat gga att gca gag aaa gat aga aaa       480
Gly Lys Pro Glu Asp Phe His His Gly Ile Ala Glu Lys Asp Arg Lys
145                 150                 155                 160 ctg ttg gaa cac ttg ttt gat gtg gat gtc aaa acc ggt gca cag cca       528
Leu Leu Glu His Leu Phe Asp Val Asp Val Lys Thr Gly Ala Gln Pro
            165                 170                 175 cag atc gtg gtg ctt cag gga gct gct gga gtt ggg aaa aca acc ttg       576
Gln Ile Val Val Leu Gln Gly Ala Ala Gly Val Gly Lys Thr Thr Leu
        180                 185                 190 gtg aga aag gca atg tta gat tgg gca gag ggc agt ctc tac cag cag       624
Val Arg Lys Ala Met Leu Asp Trp Ala Glu Gly Ser Leu Tyr Gln Gln
    195                 200                 205
```

Fig. 10A

```
agg ttt aag tat gtt ttt tat ctc aat ggg aga gaa att aac cag ctg     672
Arg Phe Lys Tyr Val Phe Tyr Leu Asn Gly Arg Glu Ile Asn Gln Leu
    210             215             220 aaa gag aga agc ttt gct caa ttg ata tca aag gac tgg ccc agc aca     720
Lys Glu Arg Ser Phe Ala Gln Leu Ile Ser Lys Asp Trp Pro Ser Thr
225             230             235             240 gaa ggc ccc att gaa gaa atc atg tac cag cca agt agc ctc ttg ttt     768
Glu Gly Pro Ile Glu Glu Ile Met Tyr Gln Pro Ser Ser Leu Leu Phe
            245             250             255 att att gac agt ttc gat gaa ctg aac ttt gcc ttt gaa gaa cct gag     816
Ile Ile Asp Ser Phe Asp Glu Leu Asn Phe Ala Phe Glu Glu Pro Glu
                260             265             270 ttt gca ctg tgc gaa gac tgg acc caa gaa cac cca gtg tcc ttc ctc     864
Phe Ala Leu Cys Glu Asp Trp Thr Gln Glu His Pro Val Ser Phe Leu
        275             280             285 atg agt agt ttg ctg agg aaa gtg atg ctc cct gag gca tcc tta ttg     912
Met Ser Ser Leu Leu Arg Lys Val Met Leu Pro Glu Ala Ser Leu Leu
    290             295             300 gtg aca aca aga ctc aca act tct aag aga cta aag cag ttg ttg aag     960
Val Thr Thr Arg Leu Thr Thr Ser Lys Arg Leu Lys Gln Leu Leu Lys
305             310             315             320 aat cac cat tat gta gag cta cta gga atg tct gag gat gca aga gag    1008
Asn His His Tyr Val Glu Leu Leu Gly Met Ser Glu Asp Ala Arg Glu
            325             330             335 gag tat att tac cag ttt ttt gaa gat aag agg tgg gcc atg aaa gta    1056
Glu Tyr Ile Tyr Gln Phe Phe Glu Asp Lys Arg Trp Ala Met Lys Val
                340             345             350 ttc agt tca cta aaa agc aat gag atg ctg ttt agc atg tgc caa gtc    1104
Phe Ser Ser Leu Lys Ser Asn Glu Met Leu Phe Ser Met Cys Gln Val
        355             360             365 ccc cta gtg tgc tgg gcc gct tgt act tgt ctg aag cag caa atg gag    1152
Pro Leu Val Cys Trp Ala Ala Cys Thr Cys Leu Lys Gln Gln Met Glu
    370             375             380 aag ggt ggt gat gtc aca ttg acc tgc caa aca acc aca gct ctg ttt    1200
Lys Gly Gly Asp Val Thr Leu Thr Cys Gln Thr Thr Thr Ala Leu Phe
385             390             395             400 acc tgc tat att tct agc ttg ttc aca cca gta gat gga ggc tct cct    1248
Thr Cys Tyr Ile Ser Ser Leu Phe Thr Pro Val Asp Gly Gly Ser Pro
            405             410             415
```

Fig. 10B

```
agt cta ccc aac caa gcc cag ctg aga aga ctg tgc caa gtc gct gcc    1296
Ser Leu Pro Asn Gln Ala Gln Leu Arg Arg Leu Cys Gln Val Ala Ala
            420                 425                 430 aaa gga ata tgg act atg act tac gtg ttt tac aga gaa aat ctc aga    1344
Lys Gly Ile Trp Thr Met Thr Tyr Val Phe Tyr Arg Glu Asn Leu Arg
            435                 440                 445 agg ctt ggg tta act caa tct gat gtc tct agt ttt atg gac agc aat    1392
Arg Leu Gly Leu Thr Gln Ser Asp Val Ser Ser Phe Met Asp Ser Asn
    450                 455                 460 att att cag aag gac gca gag tat gaa aac tgc tat gtg ttc acc cac    1440
Ile Ile Gln Lys Asp Ala Glu Tyr Glu Asn Cys Tyr Val Phe Thr His
465                 470                 475                 480 ctt cat gtt cag gag ttt ttt gca gct atg ttc tat atg ttg aaa ggc    1488
Leu His Val Gln Glu Phe Phe Ala Ala Met Phe Tyr Met Leu Lys Gly
                485                 490                 495 agt tgg gaa gct ggg aac cct tcc tgc cag cct ttt gaa gat ttg aag    1536
Ser Trp Glu Ala Gly Asn Pro Ser Cys Gln Pro Phe Glu Asp Leu Lys
            500                 505                 510 tca tta ctt caa agc aca agt tat aaa gac ccc cat ttg aca cag atg    1584
Ser Leu Leu Gln Ser Thr Ser Tyr Lys Asp Pro His Leu Thr Gln Met
            515                 520                 525 aag tgc ttt ttg ttt ggc ctt ttg aat gaa gat cga gta aaa caa ctg    1632
Lys Cys Phe Leu Phe Gly Leu Leu Asn Glu Asp Arg Val Lys Gln Leu
    530                 535                 540 gag agg act ttt aac tgt aaa atg tca ctg aag ata aaa tca aag tta    1680
Glu Arg Thr Phe Asn Cys Lys Met Ser Leu Lys Ile Lys Ser Lys Leu
545                 550                 555                 560 ctt cag tgt atg gaa cac tgc cgg tgt ttg cgg acc atc agg ctg tct    1728
Leu Gln Cys Met Glu His Cys Arg Cys Leu Arg Thr Ile Arg Leu Ser
                565                 570                 575 gta act gtg gta ttt gag aag aag ata tta aaa aca agc ctc cca act    1776
Val Thr Val Val Phe Glu Lys Lys Ile Leu Lys Thr Ser Leu Pro Thr
            580                 585                 590 aac act tgg ttg aaa ttt atc act ttc cct gat ggt tgt cag gat atc    1824
Asn Thr Trp Leu Lys Phe Ile Thr Phe Pro Asp Gly Cys Gln Asp Ile
            595                 600                 605 tct act tct ttg att cat aac aag aat ctg atg cat ctt gac cta aaa    1872
Ser Thr Ser Leu Ile His Asn Lys Asn Leu Met His Leu Asp Leu Lys
    610                 615                 620
```

Fig. 10C

```
ggg agt gat ata ggg gat aat gga gta aag tca ttg tgt gaa gcc ttg      1920
Gly Ser Asp Ile Gly Asp Asn Gly Val Lys Ser Leu Cys Glu Ala Leu
625             630                 635                 640 aaa cac cca gag tgt aaa cta cag act ctc agc tta gaa agc tgt ggt      1968
Lys His Pro Glu Cys Lys Leu Gln Thr Leu Ser Leu Glu Ser Cys Gly
                645                 650                 655 ctc aca gag gct ggc tgt gag tat ctt tct ttg gct ctc atc agc aat      2016
Leu Thr Glu Ala Gly Cys Glu Tyr Leu Ser Leu Ala Leu Ile Ser Asn
            660                 665                 670 aaa aga ctg aca cat ttg tgc ttg gca gac aat gtc ttg ggt gat ggt      2064
Lys Arg Leu Thr His Leu Cys Leu Ala Asp Asn Val Leu Gly Asp Gly
        675                 680                 685 gga gta aag ctt atg agt gat gcc ctg caa cat gca caa tgt act ctg      2112
Gly Val Lys Leu Met Ser Asp Ala Leu Gln His Ala Gln Cys Thr Leu
    690                 695                 700 aag agc ctt gta ttg atg ggc tgt gtt ctc act aat gca tgt tgt ctg      2160
Lys Ser Leu Val Leu Met Gly Cys Val Leu Thr Asn Ala Cys Cys Leu
705                 710                 715                 720 gat ctg gct tct gtt att ttg aat aac cca aac ctg agg agc ctg gac      2208
Asp Leu Ala Ser Val Ile Leu Asn Asn Pro Asn Leu Arg Ser Leu Asp
                725                 730                 735 ctt ggg aac aac gat ttg cag gat gat gga gtg aaa att ctg tgt gat      2256
Leu Gly Asn Asn Asp Leu Gln Asp Asp Gly Val Lys Ile Leu Cys Asp
            740                 745                 750 gct ttg aga tat cca aac tgt aac att cag agg ctc ggg ttg gaa tac      2304
Ala Leu Arg Tyr Pro Asn Cys Asn Ile Gln Arg Leu Gly Leu Glu Tyr
        755                 760                 765 tgt ggt ttg aca tct ctc tgc tgt caa gat ctc tcc tct gct ctt atc      2352
Cys Gly Leu Thr Ser Leu Cys Cys Gln Asp Leu Ser Ser Ala Leu Ile
    770                 775                 780 tgc aac aaa aga ctg ata aaa atg aat ctg aca cag aat acc tta gga      2400
Cys Asn Lys Arg Leu Ile Lys Met Asn Leu Thr Gln Asn Thr Leu Gly
785                 790                 795                 800 tat gaa gga att gtg aag tta tat aaa gtc ttg aag tct cct aag tgt      2448
Tyr Glu Gly Ile Val Lys Leu Tyr Lys Val Leu Lys Ser Pro Lys Cys
                805                 810                 815 aaa cta caa gtt cta gga caa cag gat ttc caa gct gcc caa gga aaa      2496
Lys Leu Gln Val Leu Gly Gln Gln Asp Phe Gln Ala Ala Gln Gly Lys
            820                 825                 830
```

Fig. 10D

```
ctc caa caa agg agg cca ttg aag ccg tta aga ccg ggt cag gtg aac    2544
Leu Gln Gln Arg Arg Pro Leu Lys Pro Leu Arg Pro Gly Gln Val Asn
            835                 840                 845 agg aag tta aag act gaa aag gag aca caa aac tgc cga ctt tcc cga    2592
Arg Lys Leu Lys Thr Glu Lys Glu Thr Gln Asn Cys Arg Leu Ser Arg
    850                 855                 860 cgg cga att ggc cct ctg gaa aca gcc gac caa tca cag gca gca ggg    2640
Arg Arg Ile Gly Pro Leu Glu Thr Ala Asp Gln Ser Gln Ala Ala Gly
865                 870                 875                 880 gcg cgc cct gca gcg ggg ctc cgg ctg cgg ttc cgt gga ctc ggc gac    2688
Ala Arg Pro Ala Ala Gly Leu Arg Leu Arg Phe Arg Gly Leu Gly Asp
                885                 890                 895 tag                                                                2691
 *
```

Fig. 10E

```
ggcacgagga tttatttatt gttcctggtc actgtctctt tgaggattgg tatctctgct        60
ccagaaaag atg gca gcc tct ttc ttc tct gat ttt ggt ctt atg tgg tat       111
          Met Ala Ala Ser Phe Phe Ser Asp Phe Gly Leu Met Trp Tyr
            1               5                  10 ctg gag gag ctc aaa aag gag gag ttc agg aaa ttt aaa gaa cat ctc         159
Leu Glu Glu Leu Lys Lys Glu Glu Phe Arg Lys Phe Lys Glu His Leu
 15              20                  25                  30 aag caa atg act ttg cag ctt gaa ctc aag cag att ccc tgg act gag         207
Lys Gln Met Thr Leu Gln Leu Glu Leu Lys Gln Ile Pro Trp Thr Glu
             35                  40                  45 gtc aaa aaa gca tcc cgg gaa gaa ctt gca aac ctc ttg atc aag cac         255
Val Lys Lys Ala Ser Arg Glu Glu Leu Ala Asn Leu Leu Ile Lys His
                 50                  55                  60 tat gaa gaa caa caa gct tgg aac ata acc tta aga atc ttt caa aag         303
Tyr Glu Glu Gln Gln Ala Trp Asn Ile Thr Leu Arg Ile Phe Gln Lys
         65                  70                  75 atg gat aga aag gat ctc tgc atg aag gtc atg agg gag aga aca gga         351
Met Asp Arg Lys Asp Leu Cys Met Lys Val Met Arg Glu Arg Thr Gly
 80                  85                  90 tac aca aag acc tat caa gct cac gca aag cag aaa ttc agc cgc tta         399
Tyr Thr Lys Thr Tyr Gln Ala His Ala Lys Gln Lys Phe Ser Arg Leu
 95                 100                 105                 110 tgg tcc agc aag tct gtc act gag att cac cta tac ttt gag gag gaa         447
Trp Ser Ser Lys Ser Val Thr Glu Ile His Leu Tyr Phe Glu Glu Glu
                115                 120                 125 gtc aag caa gaa gaa tgt gac cat ttg gac cgc ctt ttt gct ccc aag         495
Val Lys Gln Glu Glu Cys Asp His Leu Asp Arg Leu Phe Ala Pro Lys
            130                 135                 140 gaa act ggg aaa cag cca cgt aca gtg att att caa gga cca caa gga         543
Glu Thr Gly Lys Gln Pro Arg Thr Val Ile Ile Gln Gly Pro Gln Gly
        145                 150                 155 att gga aaa acg aca ctc ctg atg aag ctg atg atg gcc tgg tcg gac         591
Ile Gly Lys Thr Thr Leu Leu Met Lys Leu Met Met Ala Trp Ser Asp
    160                 165                 170 aac aag atc ttt cgg gat agg ttc ctg tac acg ttc tat ttc tgc tgc         639
Asn Lys Ile Phe Arg Asp Arg Phe Leu Tyr Thr Phe Tyr Phe Cys Cys
175                 180                 185                 190
```

Fig. 11A

| | | |
|---|---|---|
| aga gaa ctg agg gag ttg ccg cca acg agt ttg gct gac ttg att tcc<br>Arg Glu Leu Arg Glu Leu Pro Pro Thr Ser Leu Ala Asp Leu Ile Ser<br>195                               200                     205 | | 687 |
| aga gag tgg cct gac ccc gct gct cct ata aca gag atc gtg tct caa<br>Arg Glu Trp Pro Asp Pro Ala Ala Pro Ile Thr Glu Ile Val Ser Gln<br>          210                        215                    220 | | 735 |
| ccg gag aga ctc ttg ttc gtc atc gac agc ttc gaa gag ctg cag ggc<br>Pro Glu Arg Leu Leu Phe Val Ile Asp Ser Phe Glu Glu Leu Gln Gly<br>        225                      230                    235 | | 783 |
| ggc ttg aac gaa ccc gat tcg gat ctg tgt ggt gac ttg atg gag aaa<br>Gly Leu Asn Glu Pro Asp Ser Asp Leu Cys Gly Asp Leu Met Glu Lys<br>240                              245                    250 | | 831 |
| cgg ccg gtg cag gtg ctt ctg agc agt ttg ctg agg aag aag atg ctc<br>Arg Pro Val Gln Val Leu Leu Ser Ser Leu Leu Arg Lys Lys Met Leu<br>255                            260                    265                    270 | | 879 |
| ccg gag gcc tcc ctg ctc atc gcc atc aaa ccc gtg tgc ccg aag gag<br>Pro Glu Ala Ser Leu Leu Ile Ala Ile Lys Pro Val Cys Pro Lys Glu<br>                275                      280                    285 | | 927 |
| ctc cgg gat cag gtg acg atc tca gaa atc tac cag ccc cgg gga ttc<br>Leu Arg Asp Gln Val Thr Ile Ser Glu Ile Tyr Gln Pro Arg Gly Phe<br>                    290                    295                    300 | | 975 |
| aac gag agt gat agg tta gtg tat ttc tgc tgt ttc ttc aaa gac ccg<br>Asn Glu Ser Asp Arg Leu Val Tyr Phe Cys Cys Phe Phe Lys Asp Pro<br>                305                      310                    315 | | 1023 |
| aaa aga gcc atg gaa gcc ttc aat ctt gta aga gaa agt gaa cag ctg<br>Lys Arg Ala Met Glu Ala Phe Asn Leu Val Arg Glu Ser Glu Gln Leu<br>320                              325                    330 | | 1071 |
| ttt tcc ata tgc caa atc ccg ctc ctc tgc tgg atc ctg tgt acc agt<br>Phe Ser Ile Cys Gln Ile Pro Leu Leu Cys Trp Ile Leu Cys Thr Ser<br>335                              340                    345                    350 | | 1119 |
| ctg aag caa gag atg cag aaa gga aaa gac ctg gcc ctg acc tgc cag<br>Leu Lys Gln Glu Met Gln Lys Gly Lys Asp Leu Ala Leu Thr Cys Gln<br>                    355                      360                    365 | | 1167 |
| agc act acc tct gtg tac tcc tct ttc gtc ttt aac ctg ttc aca cct<br>Ser Thr Thr Ser Val Tyr Ser Ser Phe Val Phe Asn Leu Phe Thr Pro<br>                370                      375                    380 | | 1215 |
| gag ggt gcc gag ggc ccg act ccg caa acc cag cac cag ctg aag gcc<br>Glu Gly Ala Glu Gly Pro Thr Pro Gln Thr Gln His Gln Leu Lys Ala<br>        385                      390                    395 | | 1263 |

Fig. 11B

```
ctg tgc tcc ctg gct gca gag ggt atg tgg aca gac aca ttt gag ttt    1311
Leu Cys Ser Leu Ala Ala Glu Gly Met Trp Thr Asp Thr Phe Glu Phe
        400                 405                 410 tgt gaa gac gac ctc cgg aga aat ggg gtt gtt gac gct gac atc cct    1359
Cys Glu Asp Asp Leu Arg Arg Asn Gly Val Val Asp Ala Asp Ile Pro
415                 420                 425                 430 gcg ctg ctg ggc acc aag ata ctt ctg aag tac ggg gag cgt gag agc    1407
Ala Leu Leu Gly Thr Lys Ile Leu Leu Lys Tyr Gly Glu Arg Glu Ser
                435                 440                 445 tcc tac gtg ttc ctc cac gtg tgt atc cag gag ttc tgt gcc gcc ttg    1455
Ser Tyr Val Phe Leu His Val Cys Ile Gln Glu Phe Cys Ala Ala Leu
        450                 455                 460 ttc tat ttg ctc aag agc cac ctt gat cat cct cac cca gct gtg aga    1503
Phe Tyr Leu Leu Lys Ser His Leu Asp His Pro His Pro Ala Val Arg
            465                 470                 475 tgt gta cag gaa ttg cta gtt gcc aat ttt gaa aaa gca agg aga gca    1551
Cys Val Gln Glu Leu Leu Val Ala Asn Phe Glu Lys Ala Arg Arg Ala
        480                 485                 490 cat tgg att ttt ttg ggg tgt ttt cta act ggc ctt tta aat aaa aag    1599
His Trp Ile Phe Leu Gly Cys Phe Leu Thr Gly Leu Leu Asn Lys Lys
495                 500                 505                 510 gaa caa gaa aaa ctg gat ccg ttt ttt ggc ttc caa ctg tcc caa gag    1647
Glu Gln Glu Lys Leu Asp Ala Phe Phe Gly Phe Gln Leu Ser Gln Glu
                515                 520                 525 ata aag cag caa att cac cag tgc ctg aag agc tta ggg gag cgt ggc    1695
Ile Lys Gln Gln Ile His Gln Cys Leu Lys Ser Leu Gly Glu Arg Gly
        530                 535                 540 aat cct cag gga cag gtg gat tcc ttg gcg ata ttt tac tgt ctc ttt    1743
Asn Pro Gln Gly Gln Val Asp Ser Leu Ala Ile Phe Tyr Cys Leu Phe
            545                 550                 555 gaa atg cag gat cct gcc ttt gtg aag cag gca gtg aac ctc ctc caa    1791
Glu Met Gln Asp Pro Ala Phe Val Lys Gln Ala Val Asn Leu Leu Gln
560                 565                 570 gaa gct aac ttt cat att att gac aac gtg gac ttg gtg gtt tct gcc    1839
Glu Ala Asn Phe His Ile Ile Asp Asn Val Asp Leu Val Val Ser Ala
575                 580                 585                 590 tac tgc tta aaa tac tgc tcc agc ttg agg aaa ctc tgt ttt tcc gtt    1887
Tyr Cys Leu Lys Tyr Cys Ser Ser Leu Arg Lys Leu Cys Phe Ser Val
                595                 600                 605
```

Fig. 11C

```
caa aat gtc ttt aag aaa gag gat gaa cac agc tct acg tcg gat tac    1935
Gln Asn Val Phe Lys Lys Glu Asp Glu His Ser Ser Thr Ser Asp Tyr
            610                 615                 620 agc ctc atc tgt tgg cat cac atc tgc tct gtg ctc acc acc agc ggg    1983
Ser Leu Ile Cys Trp His His Ile Cys Ser Val Leu Thr Thr Ser Gly
        625                 630                 635 cac ctc aga gag ctc cag gtg cag gac agc acc ctc agc gag tcg acc    2031
His Leu Arg Glu Leu Gln Val Gln Asp Ser Thr Leu Ser Glu Ser Thr
        640                 645                 650 ttt gtg acc tgg tgt aac cag ctg agg cat ccc agc tgt cgc ctt cag    2079
Phe Val Thr Trp Cys Asn Gln Leu Arg His Pro Ser Cys Arg Leu Gln
655                 660                 665                 670 aag ctt gga ata aat aac gtt tcc ttt tct ggc cag agt gtt ctg ctc    2127
Lys Leu Gly Ile Asn Asn Val Ser Phe Ser Gly Gln Ser Val Leu Leu
                675                 680                 685 ttt gag gtg ctc ttt tat cag cca gac ttg aaa tac ctg agc ttc acc    2175
Phe Glu Val Leu Phe Tyr Gln Pro Asp Leu Lys Tyr Leu Ser Phe Thr
            690                 695                 700 ctc acg aaa ctc tct cgt gat gac atc agg tcc ctc tgt gat gcc ttg    2223
Leu Thr Lys Leu Ser Arg Asp Asp Ile Arg Ser Leu Cys Asp Ala Leu
        705                 710                 715 aac tac cca gca ggc aac gtc aaa gag cta gcg ctg gta aat tgt cac    2271
Asn Tyr Pro Ala Gly Asn Val Lys Glu Leu Ala Leu Val Asn Cys His
        720                 725                 730 ctc tca ccc att gat tgt gaa gtc ctt gct ggc ctt cta acc aac aac    2319
Leu Ser Pro Ile Asp Cys Glu Val Leu Ala Gly Leu Leu Thr Asn Asn
735                 740                 745                 750 aag aag ctg acg tat ctg aat gta tcc tgc aac cag tta gac aca ggc    2367
Lys Lys Leu Thr Tyr Leu Asn Val Ser Cys Asn Gln Leu Asp Thr Gly
                755                 760                 765 gtg ccc ctt ttg tgt gaa gcc ctg tgc agc cca gac acg gtc ctg gta    2415
Val Pro Leu Leu Cys Glu Ala Leu Cys Ser Pro Asp Thr Val Leu Val
            770                 775                 780 tac ctg atg ttg gct ttc tgc cac ctc agc gag cag tgc tgc gaa tac    2463
Tyr Leu Met Leu Ala Phe Cys His Leu Ser Glu Gln Cys Cys Glu Tyr
        785                 790                 795 atc tct gaa atg ctt ctg cgt aac aag agc gtg cgc tat cta gac ctc    2511
Ile Ser Glu Met Leu Leu Arg Asn Lys Ser Val Arg Tyr Leu Asp Leu
800                 805                 810
```

Fig. 11D

```
agt gcc aat gtc ctg aag gac gaa gga ctg aaa act ctc tgc gag gcc    2559
Ser Ala Asn Val Leu Lys Asp Glu Gly Leu Lys Thr Leu Cys Glu Ala
815                 820                 825                 830 ttg aaa cat ccg gac tgc tgc ctg gat tca ctg tgt ttg gta aaa tgt    2607
Leu Lys His Pro Asp Cys Cys Leu Asp Ser Leu Cys Leu Val Lys Cys
                835                 840                 845 ttt atc act gct gct ggc tgt gaa gac ctc gcc tct gct ctc atc agc    2655
Phe Ile Thr Ala Ala Gly Cys Glu Asp Leu Ala Ser Ala Leu Ile Ser
            850                 855                 860 aat caa aac ctg aag att ctg caa att ggg tgc aat gaa atc gga gat    2703
Asn Gln Asn Leu Lys Ile Leu Gln Ile Gly Cys Asn Glu Ile Gly Asp
        865                 870                 875 gtg ggt gtg cag ctg ttg tgt cgg gct ctg acg cat acg gat tgc cgc    2751
Val Gly Val Gln Leu Leu Cys Arg Ala Leu Thr His Thr Asp Cys Arg
    880                 885                 890 tta gag att ctt ggg ttg gaa gaa tgt ggg tta acg agc acc tgc tgt    2799
Leu Glu Ile Leu Gly Leu Glu Glu Cys Gly Leu Thr Ser Thr Cys Cys
895                 900                 905                 910 aag gat ctc gcg tct gtt ctc acc tgc agt aag acc ctg cag cag ctc    2847
Lys Asp Leu Ala Ser Val Leu Thr Cys Ser Lys Thr Leu Gln Gln Leu
                915                 920                 925 aac ctg acc ttg aac acc ttg gac cac aca ggg gtg gtt gta ctc tgt    2895
Asn Leu Thr Leu Asn Thr Leu Asp His Thr Gly Val Val Val Leu Cys
            930                 935                 940 gag gcc ctg aga cac cca gag tgt gcc ctg cag gtg ctc ggg ctg aga    2943
Glu Ala Leu Arg His Pro Glu Cys Ala Leu Gln Val Leu Gly Leu Arg
        945                 950                 955 aaa act gat ttt gat gag gaa acc cag gca ctt ctg acg gct gag gaa    2991
Lys Thr Asp Phe Asp Glu Glu Thr Gln Ala Leu Leu Thr Ala Glu Glu
    960                 965                 970 gag aga aat cct aac ctg acc atc aca gat gac tgt gac aca atc aca    3039
Glu Arg Asn Pro Asn Leu Thr Ile Thr Asp Asp Cys Asp Thr Ile Thr
975                 980                 985                 990 agg gta gag atc tgattgcgag gaacctgggc tctgactcga acacctgcaa        3091
Arg Val Glu Ile aggacaggga ctgggaccgt tacttacatg acactgcacc caggagatac aaatcattga  3151
cactctgagt tgtgagattt ctggcacccc attcatagat ttgatatgat acacgtggtt  3211
tttatgtgct ctgtggcctt ggatgagtca ctgaaaggcc ttcatggtct ctcggtctca  3271
caaggacctc ttaaccctc aataaagtgt tacatttcta aacattggaa aaaaaaaaa  3331
aaaaaaaaaa aaaaaaaaaa aaaaaaaaaa aaaaaa                           3368
```

Fig. 11E

SEQUENCE LISTING

```
<160> NUMBER OF SEQ ID NOS: 25

<210> SEQ ID NO 1
<211> LENGTH: 1506
<212> TYPE: DNA
<213> ORGANISM: Homo sapiens
<220> FEATURE:
<221> NAME/KEY: CDS
<222> LOCATION: (1)...(1503)

<400> SEQUENCE: 1 atg gca gaa tct ttt ttt tcg gat ttt ggc ttg ttg tgg tat ctg aag        48
Met Ala Glu Ser Phe Phe Ser Asp Phe Gly Leu Leu Trp Tyr Leu Lys
1               5                   10                  15 gag ctc aga aag gaa gag ttt tgg aaa ttt aag gag ctc ctc aaa caa        96
Glu Leu Arg Lys Glu Glu Phe Trp Lys Phe Lys Glu Leu Leu Lys Gln
            20                  25                  30 cct ttg gag aaa ttt gaa ctc aag cca atc ccc tgg gct gag ctg aag       144
Pro Leu Glu Lys Phe Glu Leu Lys Pro Ile Pro Trp Ala Glu Leu Lys
        35                  40                  45 aag gcc tcc aaa gaa gat gta gca aag ctg ctg gac aaa cat tac cca       192
Lys Ala Ser Lys Glu Asp Val Ala Lys Leu Leu Asp Lys His Tyr Pro
    50                  55                  60 gga aag cag gca tgg gag gta aca ctg aac ctg ttt cta cag atc aat       240
Gly Lys Gln Ala Trp Glu Val Thr Leu Asn Leu Phe Leu Gln Ile Asn
65                  70                  75                  80 agg aaa gat ctc tgg aca aag gct cag gaa gag atg aga aat aag cta       288
Arg Lys Asp Leu Trp Thr Lys Ala Gln Glu Glu Met Arg Asn Lys Leu
                85                  90                  95 aac cca tac aga aag cat atg aag gaa aca ttt caa ctc ata tgg gag       336
Asn Pro Tyr Arg Lys His Met Lys Glu Thr Phe Gln Leu Ile Trp Glu
            100                 105                 110 aag gaa acc tgt ctt cac gtc cct gag cat ttc tac aaa gaa acc atg       384
```

```
                                   -continued

Lys Glu Thr Cys Leu His Val Pro Glu His Phe Tyr Lys Glu Thr Met
            115                 120                 125 aaa aat gag tat aaa gaa ttg aat gac gca tat act gct gcg gct aga      432
Lys Asn Glu Tyr Lys Glu Leu Asn Asp Ala Tyr Thr Ala Ala Ala Arg
130                 135                 140 cga cac act gtg gtc ctg gaa ggt cct gat gga att gga aaa aca acc      480
Arg His Thr Val Val Leu Glu Gly Pro Asp Gly Ile Gly Lys Thr Thr
145                 150                 155                 160 ctt tta aga aaa gtg atg ttg gac tgg gca gag gga aac tta tgg aag      528
Leu Leu Arg Lys Val Met Leu Asp Trp Ala Glu Gly Asn Leu Trp Lys
                165                 170                 175 gac agt tac aat gag aag ctc gtc tac tgg cgg gag ctt tgc tca atg      576
Asp Ser Tyr Asn Glu Lys Leu Val Tyr Trp Arg Glu Leu Cys Ser Met
            180                 185                 190 ttc att acc aac aag aac ttc cag att tta gac atg gaa aat acc agc      624
Phe Ile Thr Asn Lys Asn Phe Gln Ile Leu Asp Met Glu Asn Thr Ser
        195                 200                 205 ctc gat gat ccc tcc ctg gcg att ctt tgc aaa gcg ctg gct cag cct      672
Leu Asp Asp Pro Ser Leu Ala Ile Leu Cys Lys Ala Leu Ala Gln Pro
    210                 215                 220 gtt tgt aaa ctc cga aaa ctc ata ttt act tct gtg tac ttt gga cat      720
Val Cys Lys Leu Arg Lys Leu Ile Phe Thr Ser Val Tyr Phe Gly His
225                 230                 235                 240 gat tca gaa tta ttt aag gca gtt ctt cac aac cct cat ctg aaa ctt      768
Asp Ser Glu Leu Phe Lys Ala Val Leu His Asn Pro His Leu Lys Leu
                245                 250                 255 ctg agc ctg tac ggc act agc ctc tcc cag tct gac atc aga cac ctg      816
Leu Ser Leu Tyr Gly Thr Ser Leu Ser Gln Ser Asp Ile Arg His Leu
            260                 265                 270 tgt gag acg ctg aaa cat cca atg tgc aag ata gaa gag ctg ata ctg      864
Cys Glu Thr Leu Lys His Pro Met Cys Lys Ile Glu Glu Leu Ile Leu
        275                 280                 285 gga aag tgt gac atc tcc agt gaa gtt tgt gaa gac atc gcc tcc gtc      912
Gly Lys Cys Asp Ile Ser Ser Glu Val Cys Glu Asp Ile Ala Ser Val
    290                 295                 300 ctg gcc tgc aac agc aag ctg aaa cac ctc tcc ttg gta gaa aat ccc      960
Leu Ala Cys Asn Ser Lys Leu Lys His Leu Ser Leu Val Glu Asn Pro
305                 310                 315                 320 ttg agg gac gaa gga atg acg ttg ctg tgt gaa gcc ctg aag cac tca     1008
Leu Arg Asp Glu Gly Met Thr Leu Leu Cys Glu Ala Leu Lys His Ser
                325                 330                 335 cac tgt gcc ctg gag agg ctg atg ttg atg ggc tgt ttc ctt act tcc     1056
His Cys Ala Leu Glu Arg Leu Met Leu Met Gly Cys Phe Leu Thr Ser
            340                 345                 350 gat tcc tgt aag gac att gct gct gtt ctt att tgc aat ggg aaa ctg     1104
Asp Ser Cys Lys Asp Ile Ala Ala Val Leu Ile Cys Asn Gly Lys Leu
        355                 360                 365 aag acc ctg aaa ctt ggg cat aat gaa ata gga gac act ggt gtc aga     1152
Lys Thr Leu Lys Leu Gly His Asn Glu Ile Gly Asp Thr Gly Val Arg
    370                 375                 380 cag tta tgt gca gct ttg cag cat cct cac tgt aaa tta gag tgt ctc     1200
Gln Leu Cys Ala Ala Leu Gln His Pro His Cys Lys Leu Glu Cys Leu
385                 390                 395                 400 ggg ctg caa acg tgt ccg atc acc cgt gcc tgc tgc gac gac atc gcc     1248
Gly Leu Gln Thr Cys Pro Ile Thr Arg Ala Cys Cys Asp Asp Ile Ala
                405                 410                 415 gca gca ctc atc gcc tgc aaa aca ctg agg agc ctg aac ctc gac tgg     1296
Ala Ala Leu Ile Ala Cys Lys Thr Leu Arg Ser Leu Asn Leu Asp Trp
            420                 425                 430
```

```
att gcc ttg gat gct gat gca gtg gtg gtg ctg tgt gag gca ttg agc    1344
Ile Ala Leu Asp Ala Asp Ala Val Val Val Leu Cys Glu Ala Leu Ser
    435                 440                 445 cac ccg gac tgt gcc ctg cag atg ctg ggg ctg cac aaa tct ggc ttt    1392
His Pro Asp Cys Ala Leu Gln Met Leu Gly Leu His Lys Ser Gly Phe
450                 455                 460 gat gaa gaa act cag aag atc ctg atg tct gtg gaa gaa aaa att ccc    1440
Asp Glu Glu Thr Gln Lys Ile Leu Met Ser Val Glu Glu Lys Ile Pro
465                 470                 475                 480 cat ctg acc att tca cat gga cct tgg att gac gag gaa tac aag atc    1488
His Leu Thr Ile Ser His Gly Pro Trp Ile Asp Glu Glu Tyr Lys Ile
                485                 490                 495 agg ggt gtg ctc ctc tga                                            1506
Arg Gly Val Leu Leu
            500

<210> SEQ ID NO 2
<211> LENGTH: 501
<212> TYPE: PRT
<213> ORGANISM: Homo sapiens

<400> SEQUENCE: 2

Met Ala Glu Ser Phe Phe Ser Asp Phe Gly Leu Leu Trp Tyr Leu Lys
1               5                   10                  15

Glu Leu Arg Lys Glu Glu Phe Trp Lys Phe Lys Glu Leu Leu Lys Gln
            20                  25                  30

Pro Leu Glu Lys Phe Glu Leu Lys Pro Ile Pro Trp Ala Glu Leu Lys
        35                  40                  45

Lys Ala Ser Lys Glu Asp Val Ala Lys Leu Leu Asp Lys His Tyr Pro
    50                  55                  60

Gly Lys Gln Ala Trp Glu Val Thr Leu Asn Leu Phe Leu Gln Ile Asn
65                  70                  75                  80

Arg Lys Asp Leu Trp Thr Lys Ala Gln Glu Glu Met Arg Asn Lys Leu
                85                  90                  95

Asn Pro Tyr Arg Lys His Met Lys Glu Thr Phe Gln Leu Ile Trp Glu
            100                 105                 110

Lys Glu Thr Cys Leu His Val Pro Glu His Phe Tyr Lys Glu Thr Met
        115                 120                 125

Lys Asn Glu Tyr Lys Glu Leu Asn Asp Ala Tyr Thr Ala Ala Ala Arg
    130                 135                 140

Arg His Thr Val Val Leu Glu Gly Pro Asp Gly Ile Gly Lys Thr Thr
145                 150                 155                 160

Leu Leu Arg Lys Val Met Leu Asp Trp Ala Glu Gly Asn Leu Trp Lys
                165                 170                 175

Asp Ser Tyr Asn Glu Lys Leu Val Tyr Trp Arg Glu Leu Cys Ser Met
            180                 185                 190

Phe Ile Thr Asn Lys Asn Phe Gln Ile Leu Asp Met Glu Asn Thr Ser
        195                 200                 205

Leu Asp Asp Pro Ser Leu Ala Ile Leu Cys Lys Ala Leu Ala Gln Pro
    210                 215                 220

Val Cys Lys Leu Arg Lys Leu Ile Phe Thr Ser Val Tyr Phe Gly His
225                 230                 235                 240

Asp Ser Glu Leu Phe Lys Ala Val Leu His Asn Pro His Leu Lys Leu
                245                 250                 255

Leu Ser Leu Tyr Gly Thr Ser Leu Ser Gln Ser Asp Ile Arg His Leu
            260                 265                 270
```

-continued

```
Cys Glu Thr Leu Lys His Pro Met Cys Lys Ile Glu Glu Leu Ile Leu
        275                 280                 285

Gly Lys Cys Asp Ile Ser Ser Glu Val Cys Glu Asp Ile Ala Ser Val
        290                 295                 300

Leu Ala Cys Asn Ser Lys Leu Lys His Leu Ser Leu Val Glu Asn Pro
305                 310                 315                 320

Leu Arg Asp Glu Gly Met Thr Leu Leu Cys Glu Ala Leu Lys His Ser
                325                 330                 335

His Cys Ala Leu Glu Arg Leu Met Leu Met Gly Cys Phe Leu Thr Ser
        340                 345                 350

Asp Ser Cys Lys Asp Ile Ala Ala Val Leu Ile Cys Asn Gly Lys Leu
        355                 360                 365

Lys Thr Leu Lys Leu Gly His Asn Glu Ile Gly Asp Thr Gly Val Arg
        370                 375                 380

Gln Leu Cys Ala Ala Leu Gln His Pro His Cys Lys Leu Glu Cys Leu
385                 390                 395                 400

Gly Leu Gln Thr Cys Pro Ile Thr Arg Ala Cys Cys Asp Asp Ile Ala
                405                 410                 415

Ala Ala Leu Ile Ala Cys Lys Thr Leu Arg Ser Leu Asn Leu Asp Trp
        420                 425                 430

Ile Ala Leu Asp Ala Asp Ala Val Val Leu Cys Glu Ala Leu Ser
        435                 440                 445

His Pro Asp Cys Ala Leu Gln Met Leu Gly Leu His Lys Ser Gly Phe
        450                 455                 460

Asp Glu Glu Thr Gln Lys Ile Leu Met Ser Val Glu Lys Ile Pro
465                 470                 475                 480

His Leu Thr Ile Ser His Gly Pro Trp Ile Asp Glu Glu Tyr Lys Ile
                485                 490                 495

Arg Gly Val Leu Leu
            500

<210> SEQ ID NO 3
<211> LENGTH: 333
<212> TYPE: DNA
<213> ORGANISM: Homo sapiens
<220> FEATURE:
<221> NAME/KEY: CDS
<222> LOCATION: (1)...(330)

<400> SEQUENCE: 3 atg gca gcc tct ttc ttc tct gat ttt ggt ctt atg tgg tat ctg gag    48
Met Ala Ala Ser Phe Phe Ser Asp Phe Gly Leu Met Trp Tyr Leu Glu
1               5                   10                  15 gag ctc aaa aag gag gag ttc agg aaa ttt aaa gaa cat ctc aag caa    96
Glu Leu Lys Lys Glu Glu Phe Arg Lys Phe Lys Glu His Leu Lys Gln
                20                  25                  30 atg act ttg cag ctt gaa ctc aag cag att ccc tgg act gag gtc aaa   144
Met Thr Leu Gln Leu Glu Leu Lys Gln Ile Pro Trp Thr Glu Val Lys
            35                  40                  45 aaa gca tcc cgg gaa gaa ctt gca aac ctc ttg atc aag cac tat gaa   192
Lys Ala Ser Arg Glu Glu Leu Ala Asn Leu Leu Ile Lys His Tyr Glu
        50                  55                  60 gaa caa caa gct tgg aac ata acc tta aga atc ttt caa aag atg gat   240
Glu Gln Gln Ala Trp Asn Ile Thr Leu Arg Ile Phe Gln Lys Met Asp
65                  70                  75                  80 aga aag gat ctc tgc atg aag gtc atg agg gag aga aca ggt gag gga   288
Arg Lys Asp Leu Cys Met Lys Val Met Arg Glu Arg Thr Gly Glu Gly
                85                  90                  95
```

```
gtc tgg gaa ggg gga agc ctt ctt ata atg agg act atg tcc        330
Val Trp Glu Gly Gly Ser Leu Leu Ile Met Arg Thr Met Ser
            100                 105                 110 taa                                                            333
```

<210> SEQ ID NO 4
<211> LENGTH: 110
<212> TYPE: PRT
<213> ORGANISM: Homo sapiens

<400> SEQUENCE: 4

```
Met Ala Ala Ser Phe Phe Ser Asp Phe Gly Leu Met Trp Tyr Leu Glu
 1               5                  10                  15

Glu Leu Lys Lys Glu Glu Phe Arg Lys Phe Lys Glu His Leu Lys Gln
             20                  25                  30

Met Thr Leu Gln Leu Glu Leu Lys Gln Ile Pro Trp Thr Glu Val Lys
         35                  40                  45

Lys Ala Ser Arg Glu Glu Leu Ala Asn Leu Leu Ile Lys His Tyr Glu
     50                  55                  60

Glu Gln Gln Ala Trp Asn Ile Thr Leu Arg Ile Phe Gln Lys Met Asp
 65                  70                  75                  80

Arg Lys Asp Leu Cys Met Lys Val Met Arg Glu Arg Thr Gly Glu Gly
                 85                  90                  95

Val Trp Glu Gly Gly Ser Leu Leu Ile Met Arg Thr Met Ser
            100                 105                 110
```

<210> SEQ ID NO 5
<211> LENGTH: 4035
<212> TYPE: DNA
<213> ORGANISM: Homo sapiens
<220> FEATURE:
<221> NAME/KEY: CDS
<222> LOCATION: (1)...(4032)

<400> SEQUENCE: 5

```
atg gaa gga gac aaa tcg ctc acc ttt tcc agc tac ggg ctg caa tgg        48
Met Glu Gly Asp Lys Ser Leu Thr Phe Ser Ser Tyr Gly Leu Gln Trp
 1               5                  10                  15 tgt ctc tat gag cta gac aag gaa gaa ttt cag aca ttc aag gaa tta        96
Cys Leu Tyr Glu Leu Asp Lys Glu Glu Phe Gln Thr Phe Lys Glu Leu
             20                  25                  30 cta aag aag aaa tct tca gaa tcg acc aca tgc tct att cca cag ttt       144
Leu Lys Lys Lys Ser Ser Glu Ser Thr Thr Cys Ser Ile Pro Gln Phe
         35                  40                  45 gaa atc gag aat gcc aac gtg gaa tgt ctg gca ctc ctc ttg cat gag       192
Glu Ile Glu Asn Ala Asn Val Glu Cys Leu Ala Leu Leu Leu His Glu
     50                  55                  60 tat tat gga gca tcg ctg gcc tgg gct acg tcc att agc atc ttt gaa       240
Tyr Tyr Gly Ala Ser Leu Ala Trp Ala Thr Ser Ile Ser Ile Phe Glu
 65                  70                  75                  80 aac atg aac ctg cga acc ctc tcg gag aag gca cgg gat gac atg aaa       288
Asn Met Asn Leu Arg Thr Leu Ser Glu Lys Ala Arg Asp Asp Met Lys
                 85                  90                  95 aaa att tca caa gct atg gaa caa gaa ggt gcc aca gca gca gag aca       336
Lys Ile Ser Gln Ala Met Glu Gln Glu Gly Ala Thr Ala Ala Glu Thr
            100                 105                 110 gaa gaa caa gaa att tca caa gct atg gaa caa gaa ggt gcc aca gca       384
Glu Glu Gln Glu Ile Ser Gln Ala Met Glu Gln Glu Gly Ala Thr Ala
        115                 120                 125
```

```
gca gag aca gaa gaa caa gga cat gga ggt gac aca tgg gac tac aag    432
Ala Glu Thr Glu Glu Gln Gly His Gly Gly Asp Thr Trp Asp Tyr Lys
    130             135             140 agt cac gtg atg acc aaa ttc gct gag gag gag gat gta cgt cgt agt    480
Ser His Val Met Thr Lys Phe Ala Glu Glu Glu Asp Val Arg Arg Ser
145             150             155             160 ttt gaa aac act gct gct gac tgg ccg gaa atg caa acg ttg gct ggt    528
Phe Glu Asn Thr Ala Ala Asp Trp Pro Glu Met Gln Thr Leu Ala Gly
            165             170             175 gct ttt gat tca gac cgg tgg ggc ttc cgg cct cgc acg gtg gtt ctg    576
Ala Phe Asp Ser Asp Arg Trp Gly Phe Arg Pro Arg Thr Val Val Leu
        180             185             190 cac gga aag tca gga att ggg aaa tcg gct cta gcc aga agg atc gtg    624
His Gly Lys Ser Gly Ile Gly Lys Ser Ala Leu Ala Arg Arg Ile Val
    195             200             205 ctg tgc tgg gcg caa ggt gga ctc tac cag gga atg ttc tcc tac gtc    672
Leu Cys Trp Ala Gln Gly Gly Leu Tyr Gln Gly Met Phe Ser Tyr Val
210             215             220 ttc ttc ctc ccc gtt aga gag atg cag cgg aag aag gag agc agt gtc    720
Phe Phe Leu Pro Val Arg Glu Met Gln Arg Lys Lys Glu Ser Ser Val
225             230             235             240 aca gag ttc atc tcc agg gag tgg cca gac tcc cag gct ccg gtg acg    768
Thr Glu Phe Ile Ser Arg Glu Trp Pro Asp Ser Gln Ala Pro Val Thr
            245             250             255 gag atc atg tcc cga cca gaa agg ctg ttg ttc atc att gac ggt ttc    816
Glu Ile Met Ser Arg Pro Glu Arg Leu Leu Phe Ile Ile Asp Gly Phe
        260             265             270 gat gac ctg ggc tct gtc ctc aac aat gac aca aag ctc tgc aaa gac    864
Asp Asp Leu Gly Ser Val Leu Asn Asn Asp Thr Lys Leu Cys Lys Asp
    275             280             285 tgg gct gag aag cag cct ccg ttc acc ctc ata cgc agt ctg ctg agg    912
Trp Ala Glu Lys Gln Pro Pro Phe Thr Leu Ile Arg Ser Leu Leu Arg
290             295             300 aag gtc ctg ctc cct gag tcc ttc ctg atc gtc acc gtc aga gac gtg    960
Lys Val Leu Leu Pro Glu Ser Phe Leu Ile Val Thr Val Arg Asp Val
305             310             315             320 ggc aca gag aag ctc aag tca gag gtc gtg tct ccc cgt tac ctg tta   1008
Gly Thr Glu Lys Leu Lys Ser Glu Val Val Ser Pro Arg Tyr Leu Leu
            325             330             335 gtt aga gga atc tcc ggg gaa caa aga atc cac ttg ctc ctt gag cgc   1056
Val Arg Gly Ile Ser Gly Glu Gln Arg Ile His Leu Leu Leu Glu Arg
        340             345             350 ggg att ggt gag cat cag aag aca caa ggg ttg cgt gcg atc atg aac   1104
Gly Ile Gly Glu His Gln Lys Thr Gln Gly Leu Arg Ala Ile Met Asn
    355             360             365 aac cgt gag ctg ctc gac cag tgc cag gtg ccc gcc gtg ggc tct ctc   1152
Asn Arg Glu Leu Leu Asp Gln Cys Gln Val Pro Ala Val Gly Ser Leu
370             375             380 atc tgc gtg gcc ctg cag ctg cag gac gtg gtg ggg gag agc gtc gcc   1200
Ile Cys Val Ala Leu Gln Leu Gln Asp Val Val Gly Glu Ser Val Ala
385             390             395             400 ccc ttc aac caa acg ctc aca ggc ctg cac gcc gct ttt gtg ttt cat   1248
Pro Phe Asn Gln Thr Leu Thr Gly Leu His Ala Ala Phe Val Phe His
            405             410             415 cag ctc acc cct cga ggc gtg gtc cgg cgc tgt ctc aat ctg gag gaa   1296
Gln Leu Thr Pro Arg Gly Val Val Arg Arg Cys Leu Asn Leu Glu Glu
        420             425             430 aga gtt gtc ctg aag cgc ttc tgc cgt atg gct gtg gag gga gtg tgg   1344
Arg Val Val Leu Lys Arg Phe Cys Arg Met Ala Val Glu Gly Val Trp
    435             440             445
```

-continued

```
aat agg aag tca gtg ttt gat ggt gac gac ctc atg gtt caa gga ctc      1392
Asn Arg Lys Ser Val Phe Asp Gly Asp Asp Leu Met Val Gln Gly Leu
    450                 455                 460 ggg gag tct gag ctc cgt gct ctg ttt cac atg aac atc ctt ctc cca      1440
Gly Glu Ser Glu Leu Arg Ala Leu Phe His Met Asn Ile Leu Leu Pro
465                 470                 475                 480 gac agc cac tgt gag gag tac tac acc ttc ttc cac ctc agt ctc cag      1488
Asp Ser His Cys Glu Glu Tyr Tyr Thr Phe Phe His Leu Ser Leu Gln
                485                 490                 495 gac ttc tgt gcc gcc ttg tac tac gtg tta gag ggc ctg gaa atc gag      1536
Asp Phe Cys Ala Ala Leu Tyr Tyr Val Leu Glu Gly Leu Glu Ile Glu
            500                 505                 510 cca gct ctc tgc cct ctg tac gtt gag aag aca aag agg tcc atg gag      1584
Pro Ala Leu Cys Pro Leu Tyr Val Glu Lys Thr Lys Arg Ser Met Glu
        515                 520                 525 ctt aaa cag gca ggc ttc cat atc cac tcg ctt tgg atg aag cgt ttc      1632
Leu Lys Gln Ala Gly Phe His Ile His Ser Leu Trp Met Lys Arg Phe
    530                 535                 540 ttg ttt ggc ctc gtg agc gaa gac gta agg agg cca ctg gag gtc ctg      1680
Leu Phe Gly Leu Val Ser Glu Asp Val Arg Arg Pro Leu Glu Val Leu
545                 550                 555                 560 ctg ggc tgt ccc gtt ccc ctg ggg gtg aag cag aag ctt ctg cac tgg      1728
Leu Gly Cys Pro Val Pro Leu Gly Val Lys Gln Lys Leu Leu His Trp
                565                 570                 575 gtc tct ctg ttg ggt cag cag cct aat gcc acc acc cca gga gac acc      1776
Val Ser Leu Leu Gly Gln Gln Pro Asn Ala Thr Thr Pro Gly Asp Thr
            580                 585                 590 ctg gac gcc ttc cac tgt ctt ttc gag act caa gac aaa gag ttt gtt      1824
Leu Asp Ala Phe His Cys Leu Phe Glu Thr Gln Asp Lys Glu Phe Val
        595                 600                 605 cgc ttg gca tta aac agc ttc caa gaa gtg tgg ctt ccg att aac cag      1872
Arg Leu Ala Leu Asn Ser Phe Gln Glu Val Trp Leu Pro Ile Asn Gln
    610                 615                 620 aac ctg gac ttg ata gca tct tcc ttc tgc ctc cag cac tgt ccg tat      1920
Asn Leu Asp Leu Ile Ala Ser Ser Phe Cys Leu Gln His Cys Pro Tyr
625                 630                 635                 640 ttg cgg aaa att cgg gtg gat gtc aaa ggg atc ttc cca aga gat gag      1968
Leu Arg Lys Ile Arg Val Asp Val Lys Gly Ile Phe Pro Arg Asp Glu
                645                 650                 655 tcc gct gag gca tgt cct gtg gtc cct cta tgg atg cgg gat aag acc      2016
Ser Ala Glu Ala Cys Pro Val Val Pro Leu Trp Met Arg Asp Lys Thr
            660                 665                 670 ctc att gag gag cag tgg gaa gat ttc tgc tcc atg ctt ggc acc cac      2064
Leu Ile Glu Glu Gln Trp Glu Asp Phe Cys Ser Met Leu Gly Thr His
        675                 680                 685 cca cac ctg cgg cag ctg gac ctg ggc agc agc atc ctg aca gag cgg      2112
Pro His Leu Arg Gln Leu Asp Leu Gly Ser Ser Ile Leu Thr Glu Arg
    690                 695                 700 gcc atg aag acc ctg tgt gcc aag ctg agg cat ccc acc tgc aag ata      2160
Ala Met Lys Thr Leu Cys Ala Lys Leu Arg His Pro Thr Cys Lys Ile
705                 710                 715                 720 cag acc ctg atg ttt aga aat gca cag att acc cct ggt gtg cag cac      2208
Gln Thr Leu Met Phe Arg Asn Ala Gln Ile Thr Pro Gly Val Gln His
                725                 730                 735 ctc tgg aga atc gtc atg gcc aac cgt aac cta aga tcc ctc aac ttg      2256
Leu Trp Arg Ile Val Met Ala Asn Arg Asn Leu Arg Ser Leu Asn Leu
            740                 745                 750 gga ggc acc cac ctg aag gaa gag gat gta agg atg gcg tgt gaa gcc      2304
Gly Gly Thr His Leu Lys Glu Glu Asp Val Arg Met Ala Cys Glu Ala
```

```
                755             760             765
tta aaa cac cca aaa tgt ttg ttg gag tct ttg agg ctg gat tgc tgt    2352
Leu Lys His Pro Lys Cys Leu Leu Glu Ser Leu Arg Leu Asp Cys Cys
        770             775             780 gga ttg acc cat gcc tgt tac ctg aag atc tcc caa atc ctt acg acc    2400
Gly Leu Thr His Ala Cys Tyr Leu Lys Ile Ser Gln Ile Leu Thr Thr
785             790             795             800 tcc ccc agc ctg aaa tct ctg agc ctg gca gga aac aag gtg aca gac    2448
Ser Pro Ser Leu Lys Ser Leu Ser Leu Ala Gly Asn Lys Val Thr Asp
                805             810             815 cag gga gta atg cct ctc agt gat gcc ttg aga gtc tcc cag tgc gcc    2496
Gln Gly Val Met Pro Leu Ser Asp Ala Leu Arg Val Ser Gln Cys Ala
            820             825             830 ctg cag aag ctg ata ctg gag gac tgt ggc atc aca gcc acg ggt tgc    2544
Leu Gln Lys Leu Ile Leu Glu Asp Cys Gly Ile Thr Ala Thr Gly Cys
        835             840             845 cag agt ctg gcc tca gcc ctc gtc agc aac cgg agc ttg aca cac ctg    2592
Gln Ser Leu Ala Ser Ala Leu Val Ser Asn Arg Ser Leu Thr His Leu
    850             855             860 tgc cta tcc aac aac agc ctg ggg aac gaa ggt gta aat cta ctg tgt    2640
Cys Leu Ser Asn Asn Ser Leu Gly Asn Glu Gly Val Asn Leu Leu Cys
865             870             875             880 cga tcc atg agg ctt ccc cac tgt agt ctg cag agg ctg atg ctg aat    2688
Arg Ser Met Arg Leu Pro His Cys Ser Leu Gln Arg Leu Met Leu Asn
                885             890             895 cag tgc cac ctg gac acg gct ggc tgt ggt ttt ctt gca ctt gcg ctt    2736
Gln Cys His Leu Asp Thr Ala Gly Cys Gly Phe Leu Ala Leu Ala Leu
            900             905             910 atg ggt aac tca tgg ctg acg cac ctg agc ctt agc atg aac cct gtg    2784
Met Gly Asn Ser Trp Leu Thr His Leu Ser Leu Ser Met Asn Pro Val
        915             920             925 gaa gac aat ggc gtg aag ctt ctg tgc gag gtc atg aga gaa cca tct    2832
Glu Asp Asn Gly Val Lys Leu Leu Cys Glu Val Met Arg Glu Pro Ser
    930             935             940 tgt cat ctc cag gac ctg gag ttg gta aag tgt cat ctc acc gcc gcg    2880
Cys His Leu Gln Asp Leu Glu Leu Val Lys Cys His Leu Thr Ala Ala
945             950             955             960 tgc tgt gag agt ctg tcc tgt gtg atc tcg agg agc aga cac ctg aag    2928
Cys Cys Glu Ser Leu Ser Cys Val Ile Ser Arg Ser Arg His Leu Lys
                965             970             975 agc ctg gat ctc acg gac aat gcc ctg ggt gac ggt ggg gtt gct gcg    2976
Ser Leu Asp Leu Thr Asp Asn Ala Leu Gly Asp Gly Gly Val Ala Ala
            980             985             990 ctg tgc gag gga ctg aag caa aag aac agt gtt ctg acg aga ctc ggg    3024
Leu Cys Glu Gly Leu Lys Gln Lys Asn Ser Val Leu Thr Arg Leu Gly
        995             1000            1005 ttg aag gca tgt gga ctg act tct gat tgc tgt gag gca ctc tcc ttg    3072
Leu Lys Ala Cys Gly Leu Thr Ser Asp Cys Cys Glu Ala Leu Ser Leu
    1010            1015            1020 gcc ctt tcc tgc aac cgg cat ctg acc agt cta aac ctg gtg cag aat    3120
Ala Leu Ser Cys Asn Arg His Leu Thr Ser Leu Asn Leu Val Gln Asn
1025            1030            1035            1040 aac ttc agt ccc aaa gga atg atg aag ctg tgt tcg gcc ttt gcc tgt    3168
Asn Phe Ser Pro Lys Gly Met Met Lys Leu Cys Ser Ala Phe Ala Cys
                1045            1050            1055 ccc acg tct aac tta cag ata att ggg ctg tgg aaa tgg cag tac cct    3216
Pro Thr Ser Asn Leu Gln Ile Ile Gly Leu Trp Lys Trp Gln Tyr Pro
            1060            1065            1070 gtg caa ata agg aag ctg ctg gag gaa gtg cag cta ctc aag ccc cga    3264
```

-continued

| | | |
|---|---|---|
| gtc gta att gac ggt agt tgg cat tct ttt gat gaa gat gac cga cac<br>Val Val Ile Asp Gly Ser Trp His Ser Phe Asp Glu Asp Asp Arg His<br>1090                   1095                   1100 | | 3312 |
| aaa ata gga ctt act ttc cgg ctc cct gaa agc cgg gca tgg cca tgt<br>Lys Ile Gly Leu Thr Phe Arg Leu Pro Glu Ser Arg Ala Trp Pro Cys<br>1105                     1110                    1115                 1120 | | 3360 |
| gcc ttg ctg tgg ggg atg aac cca gag cag aag aag cgt gtg tcg ctt<br>Ala Leu Leu Trp Gly Met Asn Pro Glu Gln Lys Lys Arg Val Ser Leu<br>                  1125                  1130                 1135 | | 3408 |
| ctg gct gga gac ttc aag agc agt aca cga ttt gcc aag tct ctc tgc<br>Leu Ala Gly Asp Phe Lys Ser Ser Thr Arg Phe Ala Lys Ser Leu Cys<br>                        1140                   1145                1150 | | 3456 |
| ctg gcc acg gca aat ggt gag tcc cag aga gtt gac aac gtg gag cag<br>Leu Ala Thr Ala Asn Gly Glu Ser Gln Arg Val Asp Asn Val Glu Gln<br>1155                   1160                   1165 | | 3504 |
| agc tcc ccg caa ccc atg gca ggc acg gaa cac aaa caa gat aaa atg<br>Ser Ser Pro Gln Pro Met Ala Gly Thr Glu His Lys Gln Asp Lys Met<br>           1170                   1175                   1180 | | 3552 |
| ttg agt gtt gga tat tcc gga gcc tgg tct gaa act gct gag ctc gaa<br>Leu Ser Val Gly Tyr Ser Gly Ala Trp Ser Glu Thr Ala Glu Leu Glu<br>1185                   1190                   1195                 1200 | | 3600 |
| ggg ctt gga tcc aac agt gct gat cat gac cac gga ggt atg gcc tgg<br>Gly Leu Gly Ser Asn Ser Ala Asp His Asp His Gly Gly Met Ala Trp<br>                        1205                   1210                   1215 | | 3648 |
| tca cta ggg aga gag ctg agc tcg agg ggc ttg tgt cca aca gtg ctg<br>Ser Leu Gly Arg Glu Leu Ser Ser Arg Gly Leu Cys Pro Thr Val Leu<br>           1220                   1225                   1230 | | 3696 |
| atg acc aca gcg gtg tgt cct ggt cac tgg gag cgg ctg ggc tct agg<br>Met Thr Thr Ala Val Cys Pro Gly His Trp Glu Arg Leu Gly Ser Arg<br>                  1235                   1240                 1245 | | 3744 |
| ggc tgg tgt ctt aac agt gct gat gac cac agc ggt gtg tcc tgg tca<br>Gly Trp Cys Leu Asn Ser Ala Asp Asp His Ser Gly Val Ser Trp Ser<br>           1250                   1255                   1260 | | 3792 |
| ctg gga gcg gct ggg ctc gag ggg ctt gtg tcc aac agt gct gat gac<br>Leu Gly Ala Ala Gly Leu Glu Gly Leu Val Ser Asn Ser Ala Asp Asp<br>1265                   1270                   1275                 1280 | | 3840 |
| cac agc ggt gtg gcc tgg tca ctg gga gcg gct ggg ctc gag ggg ctt<br>His Ser Gly Val Ala Trp Ser Leu Gly Ala Ala Gly Leu Glu Gly Leu<br>                        1285                   1290                   1295 | | 3888 |
| gtg tcc aac agt gct gat gac cac agc ggt gtg tcc tgg tca ctg gga<br>Val Ser Asn Ser Ala Asp Asp His Ser Gly Val Ser Trp Ser Leu Gly<br>                    1300                   1305                   1310 | | 3936 |
| gcg gct ggg ctc gag ggg ctt gtg tcc aac agt gct gat gac cac agc<br>Ala Ala Gly Leu Glu Gly Leu Val Ser Asn Ser Ala Asp Asp His Ser<br>                1315                   1320                 1325 | | 3984 |
| ggt gtg tcc tgg tca ctg gga gcg gct ggg ctc gag ggg ctg gtg tct<br>Gly Val Ser Trp Ser Leu Gly Ala Ala Gly Leu Glu Gly Leu Val Ser<br>1330                   1335                   1340 | | 4032 |
| taa | | 4035 |

Val Gln Ile Arg Lys Leu Leu Glu Glu Val Gln Leu Leu Lys Pro Arg
        1075                   1080                   1085

<210> SEQ ID NO 6
<211> LENGTH: 1344
<212> TYPE: PRT
<213> ORGANISM: Homo sapiens

<400> SEQUENCE: 6

Met Glu Gly Asp Lys Ser Leu Thr Phe Ser Ser Tyr Gly Leu Gln Trp
1               5                   10                 15

-continued

Cys Leu Tyr Glu Leu Asp Lys Glu Glu Phe Gln Thr Phe Lys Glu Leu
             20                  25                  30

Leu Lys Lys Lys Ser Ser Glu Ser Thr Thr Cys Ser Ile Pro Gln Phe
         35                  40                  45

Glu Ile Glu Asn Ala Asn Val Glu Cys Leu Ala Leu Leu His Glu
     50                  55                  60

Tyr Tyr Gly Ala Ser Leu Ala Trp Ala Thr Ser Ile Ser Ile Phe Glu
65                  70                  75                  80

Asn Met Asn Leu Arg Thr Leu Ser Glu Lys Ala Arg Asp Asp Met Lys
                 85                  90                  95

Lys Ile Ser Gln Ala Met Glu Gln Glu Gly Ala Thr Ala Ala Glu Thr
                100                 105                 110

Glu Glu Gln Glu Ile Ser Gln Ala Met Glu Gln Glu Gly Ala Thr Ala
             115                 120                 125

Ala Glu Thr Glu Glu Gln Gly His Gly Gly Asp Thr Trp Asp Tyr Lys
         130                 135                 140

Ser His Val Met Thr Lys Phe Ala Glu Glu Asp Val Arg Arg Ser
145                 150                 155                 160

Phe Glu Asn Thr Ala Ala Asp Trp Pro Glu Met Gln Thr Leu Ala Gly
                 165                 170                 175

Ala Phe Asp Ser Asp Arg Trp Gly Phe Arg Pro Arg Thr Val Val Leu
             180                 185                 190

His Gly Lys Ser Gly Ile Gly Lys Ser Ala Leu Ala Arg Arg Ile Val
         195                 200                 205

Leu Cys Trp Ala Gln Gly Gly Leu Tyr Gln Gly Met Phe Ser Tyr Val
     210                 215                 220

Phe Phe Leu Pro Val Arg Glu Met Gln Arg Lys Lys Glu Ser Ser Val
225                 230                 235                 240

Thr Glu Phe Ile Ser Arg Glu Trp Pro Asp Ser Gln Ala Pro Val Thr
                 245                 250                 255

Glu Ile Met Ser Arg Pro Glu Arg Leu Leu Phe Ile Ile Asp Gly Phe
             260                 265                 270

Asp Asp Leu Gly Ser Val Leu Asn Asn Asp Thr Lys Leu Cys Lys Asp
         275                 280                 285

Trp Ala Glu Lys Gln Pro Pro Phe Thr Leu Ile Arg Ser Leu Leu Arg
     290                 295                 300

Lys Val Leu Leu Pro Glu Ser Phe Leu Ile Val Thr Val Arg Asp Val
305                 310                 315                 320

Gly Thr Glu Lys Leu Lys Ser Glu Val Val Ser Pro Arg Tyr Leu Leu
                 325                 330                 335

Val Arg Gly Ile Ser Gly Glu Gln Arg Ile His Leu Leu Glu Arg
             340                 345                 350

Gly Ile Gly Glu His Gln Lys Thr Gln Gly Leu Arg Ala Ile Met Asn
         355                 360                 365

Asn Arg Glu Leu Leu Asp Gln Cys Gln Val Pro Ala Val Gly Ser Leu
     370                 375                 380

Ile Cys Val Ala Leu Gln Leu Gln Asp Val Val Gly Glu Ser Val Ala
385                 390                 395                 400

Pro Phe Asn Gln Thr Leu Thr Gly Leu His Ala Ala Phe Val Phe His
                 405                 410                 415

Gln Leu Thr Pro Arg Gly Val Val Arg Arg Cys Leu Asn Leu Glu Glu
             420                 425                 430

-continued

```
Arg Val Val Leu Lys Arg Phe Cys Arg Met Ala Val Glu Gly Val Trp
            435                 440                 445

Asn Arg Lys Ser Val Phe Asp Gly Asp Leu Met Val Gln Gly Leu
    450                 455                 460

Gly Glu Ser Glu Leu Arg Ala Leu Phe His Met Asn Ile Leu Leu Pro
465                 470                 475                 480

Asp Ser His Cys Glu Glu Tyr Tyr Thr Phe Phe His Leu Ser Leu Gln
                485                 490                 495

Asp Phe Cys Ala Ala Leu Tyr Tyr Val Leu Glu Gly Leu Glu Ile Glu
            500                 505                 510

Pro Ala Leu Cys Pro Leu Tyr Val Glu Lys Thr Lys Arg Ser Met Glu
            515                 520                 525

Leu Lys Gln Ala Gly Phe His Ile His Ser Leu Trp Met Lys Arg Phe
    530                 535                 540

Leu Phe Gly Leu Val Ser Glu Asp Val Arg Arg Pro Leu Glu Val Leu
545                 550                 555                 560

Leu Gly Cys Pro Val Pro Leu Gly Val Lys Gln Lys Leu Leu His Trp
                565                 570                 575

Val Ser Leu Leu Gly Gln Gln Pro Asn Ala Thr Thr Pro Gly Asp Thr
            580                 585                 590

Leu Asp Ala Phe His Cys Leu Phe Glu Thr Gln Asp Lys Glu Phe Val
            595                 600                 605

Arg Leu Ala Leu Asn Ser Phe Gln Glu Val Trp Leu Pro Ile Asn Gln
    610                 615                 620

Asn Leu Asp Leu Ile Ala Ser Ser Phe Cys Leu Gln His Cys Pro Tyr
625                 630                 635                 640

Leu Arg Lys Ile Arg Val Asp Val Lys Gly Ile Phe Pro Arg Asp Glu
                645                 650                 655

Ser Ala Glu Ala Cys Pro Val Val Pro Leu Trp Met Arg Asp Lys Thr
            660                 665                 670

Leu Ile Glu Glu Gln Trp Glu Asp Phe Cys Ser Met Leu Gly Thr His
    675                 680                 685

Pro His Leu Arg Gln Leu Asp Leu Gly Ser Ser Ile Leu Thr Glu Arg
    690                 695                 700

Ala Met Lys Thr Leu Cys Ala Lys Leu Arg His Pro Thr Cys Lys Ile
705                 710                 715                 720

Gln Thr Leu Met Phe Arg Asn Ala Gln Ile Thr Pro Gly Val Gln His
                725                 730                 735

Leu Trp Arg Ile Val Met Ala Asn Arg Asn Leu Arg Ser Leu Asn Leu
            740                 745                 750

Gly Gly Thr His Leu Lys Glu Glu Asp Val Arg Met Ala Cys Glu Ala
            755                 760                 765

Leu Lys His Pro Lys Cys Leu Leu Glu Ser Leu Arg Leu Asp Cys Cys
    770                 775                 780

Gly Leu Thr His Ala Cys Tyr Leu Lys Ile Ser Gln Ile Leu Thr Thr
785                 790                 795                 800

Ser Pro Ser Leu Lys Ser Leu Ser Leu Ala Gly Asn Lys Val Thr Asp
                805                 810                 815

Gln Gly Val Met Pro Leu Ser Asp Ala Leu Arg Val Ser Gln Cys Ala
            820                 825                 830

Leu Gln Lys Leu Ile Leu Glu Asp Cys Gly Ile Thr Ala Thr Gly Cys
    835                 840                 845

Gln Ser Leu Ala Ser Ala Leu Val Ser Asn Arg Ser Leu Thr His Leu
```

-continued

```
             850                 855                 860
Cys Leu Ser Asn Asn Ser Leu Gly Asn Glu Gly Val Asn Leu Leu Cys
865                 870                 875                 880

Arg Ser Met Arg Leu Pro His Cys Ser Leu Gln Arg Leu Met Leu Asn
                885                 890                 895

Gln Cys His Leu Asp Thr Ala Gly Cys Gly Phe Leu Ala Leu Ala Leu
                900                 905                 910

Met Gly Asn Ser Trp Leu Thr His Leu Ser Leu Ser Met Asn Pro Val
                915                 920                 925

Glu Asp Asn Gly Val Lys Leu Leu Cys Glu Val Met Arg Glu Pro Ser
930                 935                 940

Cys His Leu Gln Asp Leu Glu Leu Val Lys Cys His Leu Thr Ala Ala
945                 950                 955                 960

Cys Cys Glu Ser Leu Ser Cys Val Ile Ser Arg Ser Arg His Leu Lys
                965                 970                 975

Ser Leu Asp Leu Thr Asp Asn Ala Leu Gly Asp Gly Val Ala Ala
                980                 985                 990

Leu Cys Glu Gly Leu Lys Gln Lys Asn Ser Val Leu Thr Arg Leu Gly
                995                 1000                1005

Leu Lys Ala Cys Gly Leu Thr Ser Asp Cys Cys Glu Ala Leu Ser Leu
                1010                1015                1020

Ala Leu Ser Cys Asn Arg His Leu Thr Ser Leu Asn Leu Val Gln Asn
1025                1030                1035                1040

Asn Phe Ser Pro Lys Gly Met Met Lys Leu Cys Ser Ala Phe Ala Cys
                1045                1050                1055

Pro Thr Ser Asn Leu Gln Ile Ile Gly Leu Trp Lys Trp Gln Tyr Pro
                1060                1065                1070

Val Gln Ile Arg Lys Leu Leu Glu Glu Val Gln Leu Leu Lys Pro Arg
                1075                1080                1085

Val Val Ile Asp Gly Ser Trp His Ser Phe Asp Glu Asp Asp Arg His
                1090                1095                1100

Lys Ile Gly Leu Thr Phe Arg Leu Pro Glu Ser Arg Ala Trp Pro Cys
1105                1110                1115                1120

Ala Leu Leu Trp Gly Met Asn Pro Glu Gln Lys Lys Arg Val Ser Leu
                1125                1130                1135

Leu Ala Gly Asp Phe Lys Ser Ser Thr Arg Phe Ala Lys Ser Leu Cys
                1140                1145                1150

Leu Ala Thr Ala Asn Gly Glu Ser Gln Arg Val Asp Asn Val Glu Gln
                1155                1160                1165

Ser Ser Pro Gln Pro Met Ala Gly Thr Glu His Lys Gln Asp Lys Met
                1170                1175                1180

Leu Ser Val Gly Tyr Ser Gly Ala Trp Ser Glu Thr Ala Glu Leu Glu
1185                1190                1195                1200

Gly Leu Gly Ser Asn Ser Ala Asp His Asp His Gly Met Ala Trp
                1205                1210                1215

Ser Leu Gly Arg Glu Leu Ser Ser Arg Gly Leu Cys Pro Thr Val Leu
                1220                1225                1230

Met Thr Thr Ala Val Cys Pro Gly His Trp Glu Arg Leu Gly Ser Arg
                1235                1240                1245

Gly Trp Cys Leu Asn Ser Ala Asp Asp His Ser Gly Val Ser Trp Ser
                1250                1255                1260

Leu Gly Ala Ala Gly Leu Glu Gly Leu Val Ser Asn Ser Ala Asp Asp
1265                1270                1275                1280
```

-continued

His Ser Gly Val Ala Trp Ser Leu Gly Ala Ala Gly Leu Glu Gly Leu
            1285                1290                1295

Val Ser Asn Ser Ala Asp Asp His Ser Gly Val Ser Trp Ser Leu Gly
        1300                1305                1310

Ala Ala Gly Leu Glu Gly Leu Val Ser Asn Ser Ala Asp Asp His Ser
        1315                1320            1325

Gly Val Ser Trp Ser Leu Gly Ala Ala Gly Leu Glu Gly Leu Val Ser
        1330                1335            1340

<210> SEQ ID NO 7
<211> LENGTH: 294
<212> TYPE: DNA
<213> ORGANISM: Homo sapiens
<220> FEATURE:
<221> NAME/KEY: CDS
<222> LOCATION: (1)...(291)

<400> SEQUENCE: 7

| atg | gca | tct | tct | gca | gag | ctg | gac | ttc | aac | ctg | cag | gct | ctt | ctg | gag | 48 |
| Met | Ala | Ser | Ser | Ala | Glu | Leu | Asp | Phe | Asn | Leu | Gln | Ala | Leu | Leu | Glu | |
| 1 | | | | 5 | | | | | 10 | | | | | 15 | | |

| cag | ctc | agc | cag | gat | gag | ttg | agc | aag | ttc | aag | tct | ctg | atc | aga | aca | 96 |
| Gln | Leu | Ser | Gln | Asp | Glu | Leu | Ser | Lys | Phe | Lys | Ser | Leu | Ile | Arg | Thr | |
| | | | 20 | | | | | 25 | | | | | 30 | | | |

| atc | tcc | ctg | gga | aag | gag | cta | cag | acc | gtc | ccc | cag | aca | gag | gta | gac | 144 |
| Ile | Ser | Leu | Gly | Lys | Glu | Leu | Gln | Thr | Val | Pro | Gln | Thr | Glu | Val | Asp | |
| | | | 35 | | | | | 40 | | | | | 45 | | | |

| aag | gct | aat | ggg | aag | caa | ctg | gta | gaa | atc | ttc | acc | agc | cac | tcc | tgc | 192 |
| Lys | Ala | Asn | Gly | Lys | Gln | Leu | Val | Glu | Ile | Phe | Thr | Ser | His | Ser | Cys | |
| | 50 | | | | | 55 | | | | | 60 | | | | | |

| agc | tac | tgg | gca | ggg | atg | gca | gcc | atc | cag | gtc | ttt | gaa | aag | atg | aat | 240 |
| Ser | Tyr | Trp | Ala | Gly | Met | Ala | Ala | Ile | Gln | Val | Phe | Glu | Lys | Met | Asn | |
| 65 | | | | | 70 | | | | | 75 | | | | | 80 | |

| cga | acg | cat | ctg | tct | ggg | aga | gct | gat | gaa | cac | tgt | gtg | atg | ccc | cca | 288 |
| Arg | Thr | His | Leu | Ser | Gly | Arg | Ala | Asp | Glu | His | Cys | Val | Met | Pro | Pro | |
| | | | | 85 | | | | | 90 | | | | | 95 | | |

| cct | taa | | | | | | | | | | | | | | | 294 |
| Pro | | | | | | | | | | | | | | | | |

<210> SEQ ID NO 8
<211> LENGTH: 97
<212> TYPE: PRT
<213> ORGANISM: Homo sapiens

<400> SEQUENCE: 8

Met Ala Ser Ser Ala Glu Leu Asp Phe Asn Leu Gln Ala Leu Leu Glu
1               5                   10                  15

Gln Leu Ser Gln Asp Glu Leu Ser Lys Phe Lys Ser Leu Ile Arg Thr
            20                  25                  30

Ile Ser Leu Gly Lys Glu Leu Gln Thr Val Pro Gln Thr Glu Val Asp
        35                  40                  45

Lys Ala Asn Gly Lys Gln Leu Val Glu Ile Phe Thr Ser His Ser Cys
    50                  55                  60

Ser Tyr Trp Ala Gly Met Ala Ala Ile Gln Val Phe Glu Lys Met Asn
65                  70                  75                  80

Arg Thr His Leu Ser Gly Arg Ala Asp Glu His Cys Val Met Pro Pro
                85                  90                  95

Pro

<210> SEQ ID NO 9
<211> LENGTH: 425
<212> TYPE: DNA
<213> ORGANISM: Homo sapiens
<220> FEATURE:
<221> NAME/KEY: CDS
<222> LOCATION: (270)...(425)

<400> SEQUENCE: 9

| | | |
|---|---|---|
| tccggttagg tatcaagctg tagctggtag gtaccagcac caccaaacag aagtgaacta | 60 |
| gtgaggtatg ggctaagaga gcccaaactt ggacctgtag agctgtcgga ccaggaaagg | 120 |
| ggatctgttt cgtctcagtc cccaggcttt gcttactggg ctcctggatc aagggagctt | 180 |
| gagttctcgc tgcctcacct ccagctcccc aagtctgaac tgtggtcact ggtcttctgg | 240 |
| tctggacttg atccttcccc cagatcacc atg gcc atg gcc aag gcc aga aag | 293 |
|                                    Met Ala Met Ala Lys Ala Arg Lys |
|                                      1               5              |
| ccc cgg gag gca ttg ctc tgg gcc ttg agt gac ctt gag gag aac gat | 341 |
| Pro Arg Glu Ala Leu Leu Trp Ala Leu Ser Asp Leu Glu Glu Asn Asp |
|      10              15                  20                       |
| ttc aag aag tta aag ttc tac tta cgg gat atg acc ctg tct gag ggg | 389 |
| Phe Lys Lys Leu Lys Phe Tyr Leu Arg Asp Met Thr Leu Ser Glu Gly |
|  25              30                  35                      40  |
| cca gcc ccc act ggc cag agg ggg agt ttg gag ggg                  | 425 |
| Pro Ala Pro Thr Gly Gln Arg Gly Ser Leu Glu Gly                  |
|              45                  50                              |

<210> SEQ ID NO 10
<211> LENGTH: 52
<212> TYPE: PRT
<213> ORGANISM: Homo sapiens

<400> SEQUENCE: 10

Met Ala Met Ala Lys Ala Arg Lys Pro Arg Glu Ala Leu Leu Trp Ala
 1               5                  10                  15

Leu Ser Asp Leu Glu Glu Asn Asp Phe Lys Lys Leu Lys Phe Tyr Leu
             20                  25                  30

Arg Asp Met Thr Leu Ser Glu Gly Pro Ala Pro Thr Gly Gln Arg Gly
             35                  40                  45

Ser Leu Glu Gly
     50

<210> SEQ ID NO 11
<211> LENGTH: 156
<212> TYPE: DNA
<213> ORGANISM: Homo sapiens

<400> SEQUENCE: 11

| | |
|---|---|
| atggccatgg ccaaggccag aaagcccgg gaggcattgc tctgggcctt gagtgacctt | 60 |
| gaggagaacg atttcaagaa gttaaagttc tacttacggg atatgaccct gtctgagggg | 120 |
| ccagccccca ctggccagag ggggagtttg gagggg | 156 |

<210> SEQ ID NO 12
<211> LENGTH: 1968
<212> TYPE: DNA
<213> ORGANISM: Homo sapiens
<220> FEATURE:
<221> NAME/KEY: CDS
<222> LOCATION: (1)...(1965)

<400> SEQUENCE: 12

```
atg gcc atg gcc aag gcc aga aag ccc cgg gag gca ttg ctc tgg gcc      48
Met Ala Met Ala Lys Ala Arg Lys Pro Arg Glu Ala Leu Leu Trp Ala
 1               5                  10                  15 ttg agt gac ctt gag gag aac gat ttc aag aag tta aag ttc tac tta      96
Leu Ser Asp Leu Glu Glu Asn Asp Phe Lys Lys Leu Lys Phe Tyr Leu
             20                  25                  30 cgg gat atg acc ctg tct gag ggc cag ccc cca ctg gcc aga ggg gag     144
Arg Asp Met Thr Leu Ser Glu Gly Gln Pro Pro Leu Ala Arg Gly Glu
         35                  40                  45 ttg gag ggc ctg att ccg gtg gac ctg gca gaa tta ctg att tca aag     192
Leu Glu Gly Leu Ile Pro Val Asp Leu Ala Glu Leu Leu Ile Ser Lys
     50                  55                  60 tat gga gaa aag gag gct gtg aaa gtt gtc ctc aag ggc ttg aag gtc     240
Tyr Gly Glu Lys Glu Ala Val Lys Val Val Leu Lys Gly Leu Lys Val
 65                  70                  75                  80 atg aac ctg ttg gaa ctt gtg gac cag ctc agc cat att tgt ctg cat     288
Met Asn Leu Leu Glu Leu Val Asp Gln Leu Ser His Ile Cys Leu His
             85                  90                  95 gat tac aga gaa gta tac cga gag cat gtg cgc tgc cta gag gaa tgg     336
Asp Tyr Arg Glu Val Tyr Arg Glu His Val Arg Cys Leu Glu Glu Trp
        100                 105                 110 cag gaa gca gga gtc aat ggc aga tac aac cag gtg ctc ctg gtg gcc     384
Gln Glu Ala Gly Val Asn Gly Arg Tyr Asn Gln Val Leu Leu Val Ala
    115                 120                 125 aag ccc agc tca gag agc cca gaa tca ctt gcc tgc ccc ttc ccg gag     432
Lys Pro Ser Ser Glu Ser Pro Glu Ser Leu Ala Cys Pro Phe Pro Glu
130                 135                 140 cag gag ctg gag tct gtc acg gtg gag gct cta ttt gat tca ggg gaa     480
Gln Glu Leu Glu Ser Val Thr Val Glu Ala Leu Phe Asp Ser Gly Glu
145                 150                 155                 160 aag ccc tca ctg gcc cca tcc tta gtt gtg cta cag ggg tcg gct ggc     528
Lys Pro Ser Leu Ala Pro Ser Leu Val Val Leu Gln Gly Ser Ala Gly
                165                 170                 175 act gga aag aca act ctc gcc aga aaa atg gtg ttg gac tgg gcc acc     576
Thr Gly Lys Thr Thr Leu Ala Arg Lys Met Val Leu Asp Trp Ala Thr
            180                 185                 190 ggt act ctg tac cca ggc cgg ttt gat tat gtc ttt tat gta agc tgc     624
Gly Thr Leu Tyr Pro Gly Arg Phe Asp Tyr Val Phe Tyr Val Ser Cys
        195                 200                 205 aaa gaa gtg gtc ctg ctg ctg gag agc aaa ctg gag cag ctc ctt ttc     672
Lys Glu Val Val Leu Leu Leu Glu Ser Lys Leu Glu Gln Leu Leu Phe
    210                 215                 220 tgg tgc tgc ggg gac aat caa gcc cct gtc aca gag att ctg agg cag     720
Trp Cys Cys Gly Asp Asn Gln Ala Pro Val Thr Glu Ile Leu Arg Gln
225                 230                 235                 240 cca gag cgg ctc ctg ttc atc ctg gat ggc ttt gat gag ctg cag agg     768
Pro Glu Arg Leu Leu Phe Ile Leu Asp Gly Phe Asp Glu Leu Gln Arg
                245                 250                 255 ccc ttt gaa gaa aag ttg aag aag agg ggt ttg agt ccc aag gag agc     816
Pro Phe Glu Glu Lys Leu Lys Lys Arg Gly Leu Ser Pro Lys Glu Ser
            260                 265                 270 ctg ctg cac ctt cta att agg aga cat aca ctc ccc acg tgc tcc ctt     864
Leu Leu His Leu Leu Ile Arg Arg His Thr Leu Pro Thr Cys Ser Leu
        275                 280                 285 ctc atc acc acc cgg ccc ctg gct ttg agg aat ctg gag ccc ttg ctg     912
Leu Ile Thr Thr Arg Pro Leu Ala Leu Arg Asn Leu Glu Pro Leu Leu
    290                 295                 300 aaa caa gca cgt cat gtc cat atc cta ggc ttc tct gag gag gag agg     960
Lys Gln Ala Arg His Val His Ile Leu Gly Phe Ser Glu Glu Glu Arg
```

```
                305                 310                 315                 320
gcg agg tac ttc agc tcc tat ttc acg gat gag aag caa gct gac cgt       1008
Ala Arg Tyr Phe Ser Ser Tyr Phe Thr Asp Glu Lys Gln Ala Asp Arg
                325                 330                 335 gcc ttc gac att gta cag aaa aat gac att ctc tac aaa gcg tgt cag       1056
Ala Phe Asp Ile Val Gln Lys Asn Asp Ile Leu Tyr Lys Ala Cys Gln
        340                 345                 350 gtt cca ggc att tgc tgg gtg gtc tgc tcc tgg ctg cag ggg cag atg       1104
Val Pro Gly Ile Cys Trp Val Val Cys Ser Trp Leu Gln Gly Gln Met
            355                 360                 365 gag aga ggc aaa gtt gtc tta gag aca cct aga aac agc act gac atc       1152
Glu Arg Gly Lys Val Val Leu Glu Thr Pro Arg Asn Ser Thr Asp Ile
370                 375                 380 ttc atg gct tac gtc tcc acc ttt ctg ccg ccc gat gat gat ggg ggc       1200
Phe Met Ala Tyr Val Ser Thr Phe Leu Pro Pro Asp Asp Asp Gly Gly
385                 390                 395                 400 tgc tcc gag ctt tcc cgg cac agg gtc ctg agg agt ctg tgc tcc cta       1248
Cys Ser Glu Leu Ser Arg His Arg Val Leu Arg Ser Leu Cys Ser Leu
                405                 410                 415 gca gct gaa ggg att cag cac cag agg ttc cta ttt gaa gaa gct gag       1296
Ala Ala Glu Gly Ile Gln His Gln Arg Phe Leu Phe Glu Glu Ala Glu
            420                 425                 430 ctc agg aaa cat aat tta gat ggc ccc agg ctt gcc gct ttc ctg agt       1344
Leu Arg Lys His Asn Leu Asp Gly Pro Arg Leu Ala Ala Phe Leu Ser
        435                 440                 445 agt aac gac tac caa ttg gga ctt gcc atc aag aag ttc tac agc ttc       1392
Ser Asn Asp Tyr Gln Leu Gly Leu Ala Ile Lys Lys Phe Tyr Ser Phe
450                 455                 460 cgc cac atc agc ttc cag gac ttt ttt cat gcc atg tct tac ctg gtg       1440
Arg His Ile Ser Phe Gln Asp Phe Phe His Ala Met Ser Tyr Leu Val
465                 470                 475                 480 aaa gag gac caa agc cgg ctg ggg aag gag tcc cgc aga gaa gtg caa       1488
Lys Glu Asp Gln Ser Arg Leu Gly Lys Glu Ser Arg Arg Glu Val Gln
                485                 490                 495 agg ctg ctg gag gta aag gag cag gaa ggg aat gat gag atg acc ctc       1536
Arg Leu Leu Glu Val Lys Glu Gln Glu Gly Asn Asp Glu Met Thr Leu
            500                 505                 510 act atg cag ttt tta ctg gac atc tcg aaa aaa gac agc ttc tcg aac       1584
Thr Met Gln Phe Leu Leu Asp Ile Ser Lys Lys Asp Ser Phe Ser Asn
        515                 520                 525 ttg gag ctc aag ttc tgc ttc aga att tct ccc tgt tta gcg cag gat       1632
Leu Glu Leu Lys Phe Cys Phe Arg Ile Ser Pro Cys Leu Ala Gln Asp
530                 535                 540 ctg aag cat ttt aaa gaa cag atg gaa tct atg aag cac aac agg acc       1680
Leu Lys His Phe Lys Glu Gln Met Glu Ser Met Lys His Asn Arg Thr
545                 550                 555                 560 tgg gat ttg gaa ttc tcc ctg tat gaa gct aaa ata aag aat ctg gta       1728
Trp Asp Leu Glu Phe Ser Leu Tyr Glu Ala Lys Ile Lys Asn Leu Val
                565                 570                 575 aaa ggt att cag atg aac aat gta tca ttc aag ata aaa cat tca aat       1776
Lys Gly Ile Gln Met Asn Asn Val Ser Phe Lys Ile Lys His Ser Asn
            580                 585                 590 gaa aag aaa tca cag agc cag aat tta ttt tct gtc aaa agc agc ttg       1824
Glu Lys Lys Ser Gln Ser Gln Asn Leu Phe Ser Val Lys Ser Ser Leu
        595                 600                 605 agt cat gga cct aag gag gag caa aaa tgt cct tct gtc cat gga cag       1872
Ser His Gly Pro Lys Glu Glu Gln Lys Cys Pro Ser Val His Gly Gln
610                 615                 620 aag gag ggc aaa gat aat ata gca gga aca caa aag gaa gct tct act       1920
Lys Glu Gly Lys Asp Asn Ile Ala Gly Thr Gln Lys Glu Ala Ser Thr
```

```
                          -continued

Lys Glu Gly Lys Asp Asn Ile Ala Gly Thr Gln Lys Glu Ala Ser Thr
625                 630                 635                 640 gga aaa ggc aga ggg aca gag gaa aca cca aaa aat act tac ata         1965
Gly Lys Gly Arg Gly Thr Glu Glu Thr Pro Lys Asn Thr Tyr Ile
                    645                 650                 655 taa                                                                 1968

<210> SEQ ID NO 13
<211> LENGTH: 655
<212> TYPE: PRT
<213> ORGANISM: Homo sapiens

<400> SEQUENCE: 13

Met Ala Met Ala Lys Ala Arg Lys Pro Arg Glu Ala Leu Leu Trp Ala
1               5                   10                  15

Leu Ser Asp Leu Glu Glu Asn Asp Phe Lys Lys Leu Lys Phe Tyr Leu
                20                  25                  30

Arg Asp Met Thr Leu Ser Glu Gly Gln Pro Pro Leu Ala Arg Gly Glu
            35                  40                  45

Leu Glu Gly Leu Ile Pro Val Asp Leu Ala Glu Leu Leu Ile Ser Lys
        50                  55                  60

Tyr Gly Glu Lys Glu Ala Val Lys Val Val Leu Lys Gly Leu Lys Val
65                  70                  75                  80

Met Asn Leu Leu Glu Leu Val Asp Gln Leu Ser His Ile Cys Leu His
                85                  90                  95

Asp Tyr Arg Glu Val Tyr Arg Glu His Val Arg Cys Leu Glu Glu Trp
            100                 105                 110

Gln Glu Ala Gly Val Asn Gly Arg Tyr Asn Gln Val Leu Leu Val Ala
        115                 120                 125

Lys Pro Ser Ser Glu Ser Pro Glu Ser Leu Ala Cys Pro Phe Pro Glu
    130                 135                 140

Gln Glu Leu Glu Ser Val Thr Val Glu Ala Leu Phe Asp Ser Gly Glu
145                 150                 155                 160

Lys Pro Ser Leu Ala Pro Ser Leu Val Val Leu Gln Gly Ser Ala Gly
                165                 170                 175

Thr Gly Lys Thr Thr Leu Ala Arg Lys Met Val Leu Asp Trp Ala Thr
            180                 185                 190

Gly Thr Leu Tyr Pro Gly Arg Phe Asp Tyr Val Phe Tyr Val Ser Cys
        195                 200                 205

Lys Glu Val Val Leu Leu Glu Ser Lys Leu Glu Gln Leu Leu Phe
    210                 215                 220

Trp Cys Cys Gly Asp Asn Gln Ala Pro Val Thr Glu Ile Leu Arg Gln
225                 230                 235                 240

Pro Glu Arg Leu Leu Phe Ile Leu Asp Gly Phe Asp Glu Leu Gln Arg
                245                 250                 255

Pro Phe Glu Glu Lys Leu Lys Lys Arg Gly Leu Ser Pro Lys Glu Ser
            260                 265                 270

Leu Leu His Leu Leu Ile Arg Arg His Thr Leu Pro Thr Cys Ser Leu
        275                 280                 285

Leu Ile Thr Thr Arg Pro Leu Ala Leu Arg Asn Leu Glu Pro Leu Leu
    290                 295                 300

Lys Gln Ala Arg His Val His Ile Leu Gly Phe Ser Glu Glu Arg
305                 310                 315                 320

Ala Arg Tyr Phe Ser Ser Tyr Phe Thr Asp Glu Lys Gln Ala Asp Arg
                325                 330                 335
```

```
Ala Phe Asp Ile Val Gln Lys Asn Asp Ile Leu Tyr Lys Ala Cys Gln
                340                 345                 350

Val Pro Gly Ile Cys Trp Val Cys Ser Trp Leu Gln Gly Gln Met
            355                 360                 365

Glu Arg Gly Lys Val Val Leu Glu Thr Pro Arg Asn Ser Thr Asp Ile
        370                 375                 380

Phe Met Ala Tyr Val Ser Thr Phe Leu Pro Pro Asp Asp Gly Gly
385                 390                 395                 400

Cys Ser Glu Leu Ser Arg His Arg Val Leu Arg Ser Leu Cys Ser Leu
                405                 410                 415

Ala Ala Glu Gly Ile Gln His Gln Arg Phe Leu Phe Glu Glu Ala Glu
            420                 425                 430

Leu Arg Lys His Asn Leu Asp Gly Pro Arg Leu Ala Ala Phe Leu Ser
        435                 440                 445

Ser Asn Asp Tyr Gln Leu Gly Leu Ala Ile Lys Lys Phe Tyr Ser Phe
    450                 455                 460

Arg His Ile Ser Phe Gln Asp Phe Phe His Ala Met Ser Tyr Leu Val
465                 470                 475                 480

Lys Glu Asp Gln Ser Arg Leu Gly Lys Glu Ser Arg Glu Val Gln
                485                 490                 495

Arg Leu Leu Glu Val Lys Glu Gln Glu Gly Asn Asp Glu Met Thr Leu
            500                 505                 510

Thr Met Gln Phe Leu Leu Asp Ile Ser Lys Lys Asp Ser Phe Ser Asn
        515                 520                 525

Leu Glu Leu Lys Phe Cys Phe Arg Ile Ser Pro Cys Leu Ala Gln Asp
    530                 535                 540

Leu Lys His Phe Lys Glu Gln Met Glu Ser Met Lys His Asn Arg Thr
545                 550                 555                 560

Trp Asp Leu Glu Phe Ser Leu Tyr Glu Ala Lys Ile Lys Asn Leu Val
                565                 570                 575

Lys Gly Ile Gln Met Asn Asn Val Ser Phe Lys Ile Lys His Ser Asn
            580                 585                 590

Glu Lys Lys Ser Gln Ser Gln Asn Leu Phe Ser Val Lys Ser Ser Leu
        595                 600                 605

Ser His Gly Pro Lys Glu Gln Lys Cys Pro Ser Val His Gly Gln
    610                 615                 620

Lys Glu Gly Lys Asp Asn Ile Ala Gly Thr Gln Lys Glu Ala Ser Thr
625                 630                 635                 640

Gly Lys Gly Arg Gly Thr Glu Glu Thr Pro Lys Asn Thr Tyr Ile
                645                 650                 655

<210> SEQ ID NO 14
<211> LENGTH: 299
<212> TYPE: DNA
<213> ORGANISM: Homo sapiens
<220> FEATURE:
<221> NAME/KEY: CDS
<222> LOCATION: (105)...(299)

<400> SEQUENCE: 14
gcctgtgaat gatgcaatgg aaggtgtgct ggggtcgccc tgtgtcccgt gcataggagc      60
atctcagcct ccaggtcctc tcctttgggg cttacggcac cccc atg cta cga acc     116
                                                 Met Leu Arg Thr
                                                   1 gca ggc agg gac ggc ctc tgt cgc ctg tcc acc tac ttg gaa gaa ctc      164
```

```
Ala Gly Arg Asp Gly Leu Cys Arg Leu Ser Thr Tyr Leu Glu Glu Leu
 5                  10                  15                  20 gag gct gtg gaa ctg aag aag ttc aag tta tac ctg ggg acc gcg aca    212
Glu Ala Val Glu Leu Lys Lys Phe Lys Leu Tyr Leu Gly Thr Ala Thr
         25                  30                  35 gag ctg gga gaa ggc aag atc ccc tgg gga agc atg gag ata gcc ggt    260
Glu Leu Gly Glu Gly Lys Ile Pro Trp Gly Ser Met Glu Ile Ala Gly
         40                  45                  50 ccc ctg gaa atg gcc cag ctg ctc atc acc cac ttc ggg                299
Pro Leu Glu Met Ala Gln Leu Leu Ile Thr His Phe Gly
         55                  60                  65

<210> SEQ ID NO 15
<211> LENGTH: 65
<212> TYPE: PRT
<213> ORGANISM: Homo sapiens

<400> SEQUENCE: 15

Met Leu Arg Thr Ala Gly Arg Asp Gly Leu Cys Arg Leu Ser Thr Tyr
 1               5                  10                  15

Leu Glu Glu Leu Glu Ala Val Glu Leu Lys Lys Phe Lys Leu Tyr Leu
             20                  25                  30

Gly Thr Ala Thr Glu Leu Gly Glu Gly Lys Ile Pro Trp Gly Ser Met
         35                  40                  45

Glu Ile Ala Gly Pro Leu Glu Met Ala Gln Leu Leu Ile Thr His Phe
     50                  55                  60

Gly
 65

<210> SEQ ID NO 16
<211> LENGTH: 195
<212> TYPE: DNA
<213> ORGANISM: Homo sapiens

<400> SEQUENCE: 16
atgctacgaa ccgcaggcag ggacggcctc tgtcgcctgt ccacctactt ggaagaactc     60
gaggctgtgg aactgaagaa gttcaagtta tacctgggga ccgcgacaga gctgggagaa    120
ggcaagatcc cctggggaag catggagata gccggtcccc tggaaatggc ccagctgctc    180
atcacccact cggg                                                      195

<210> SEQ ID NO 17
<211> LENGTH: 3186
<212> TYPE: DNA
<213> ORGANISM: Homo sapiens
<220> FEATURE:
<221> NAME/KEY: CDS
<222> LOCATION: (1)...(3183)

<400> SEQUENCE: 17 atg cta cga acc gca ggc agg gac ggc ctc tgt cgc ctg tcc acc tac     48
Met Leu Arg Thr Ala Gly Arg Asp Gly Leu Cys Arg Leu Ser Thr Tyr
 1               5                  10                  15 ttg gaa gaa ctc gag gct gtg gaa ctg aag aag ttc aag tta tac ctg     96
Leu Glu Glu Leu Glu Ala Val Glu Leu Lys Lys Phe Lys Leu Tyr Leu
             20                  25                  30 ggg acc gcg aca gag ctg gga gaa ggc aag atc ccc tgg gga agc atg    144
Gly Thr Ala Thr Glu Leu Gly Glu Gly Lys Ile Pro Trp Gly Ser Met
         35                  40                  45 gag aag gcc ggt ccc ctg gaa atg gcc cag ctg ctc atc acc cac ttc    192
Glu Lys Ala Gly Pro Leu Glu Met Ala Gln Leu Leu Ile Thr His Phe
     50                  55                  60
```

-continued

| | | | | | | | | |
|---|---|---|---|---|---|---|---|---|
| | | 50 | | 55 | | 60 | | |

```
ggg cca gag gag gcc tgg agg ttg gct ctc agc acc ttt gag cgg ata      240
Gly Pro Glu Glu Ala Trp Arg Leu Ala Leu Ser Thr Phe Glu Arg Ile
 65              70                  75                  80 aac agg aag gac ctg tgg gag aga gga cag aga gag gac ctg gtg agg      288
Asn Arg Lys Asp Leu Trp Glu Arg Gly Gln Arg Glu Asp Leu Val Arg
                 85                  90                  95 gat acc cca cct ggt ggc ccg tcc tca ctt ggg aac cag tca aca tgc      336
Asp Thr Pro Pro Gly Gly Pro Ser Ser Leu Gly Asn Gln Ser Thr Cys
             100                 105                 110 ctt ctg gaa gtc tct ctt gtc act cca aga aaa gat ccc cag gaa acc      384
Leu Leu Glu Val Ser Leu Val Thr Pro Arg Lys Asp Pro Gln Glu Thr
         115                 120                 125 tac agg gac tat gtc cgc agg aaa ttc cgg ctc atg gaa gac cgc aat      432
Tyr Arg Asp Tyr Val Arg Arg Lys Phe Arg Leu Met Glu Asp Arg Asn
     130                 135                 140 gcg cgc cta ggg gaa tgt gtc aac ctc agc cac cgg tac acc cgg ctc      480
Ala Arg Leu Gly Glu Cys Val Asn Leu Ser His Arg Tyr Thr Arg Leu
145                 150                 155                 160 ctg ctg gtg aag gag cac tca aac ccc atg cag gtc cag cag cag ctt      528
Leu Leu Val Lys Glu His Ser Asn Pro Met Gln Val Gln Gln Gln Leu
                165                 170                 175 ctg gac aca ggc cgg gga cac gcg agg acc gtg gga cac cag gct agc      576
Leu Asp Thr Gly Arg Gly His Ala Arg Thr Val Gly His Gln Ala Ser
            180                 185                 190 ccc atc aag ata gag acc ctc ttt gag cca gac gag gag cgc ccc gag      624
Pro Ile Lys Ile Glu Thr Leu Phe Glu Pro Asp Glu Glu Arg Pro Glu
        195                 200                 205 cca ccg cgc acc gtg gtc atg caa ggc gcg gca ggg ata ggc aag tcc      672
Pro Pro Arg Thr Val Val Met Gln Gly Ala Ala Gly Ile Gly Lys Ser
    210                 215                 220 atg ctg gca cac aag gtg atg ctg gac tgg gcg gac ggg aag ctc ttc      720
Met Leu Ala His Lys Val Met Leu Asp Trp Ala Asp Gly Lys Leu Phe
225                 230                 235                 240 caa ggc aga ttt gat tat ctc ttc tac atc aac tgc agg gag atg aac      768
Gln Gly Arg Phe Asp Tyr Leu Phe Tyr Ile Asn Cys Arg Glu Met Asn
                245                 250                 255 cag agt gcc acg gaa tgc agc atg caa gac ctc atc ttc agc tgc tgg      816
Gln Ser Ala Thr Glu Cys Ser Met Gln Asp Leu Ile Phe Ser Cys Trp
            260                 265                 270 cct gag ccc agc gcg cct ctc cag gag ctc atc cga gtt ccc gag cgc      864
Pro Glu Pro Ser Ala Pro Leu Gln Glu Leu Ile Arg Val Pro Glu Arg
        275                 280                 285 ctc ctt ttc atc atc gac ggc ttc gat gag ctc aag cct tct ttc cac      912
Leu Leu Phe Ile Ile Asp Gly Phe Asp Glu Leu Lys Pro Ser Phe His
    290                 295                 300 gat cct cag gga ccc tgg tgc ctc tgc tgg gag gag aaa cgg ccc acg      960
Asp Pro Gln Gly Pro Trp Cys Leu Cys Trp Glu Glu Lys Arg Pro Thr
305                 310                 315                 320 gag ctg ctt ctt aac agc tta att cgg aag aag ctc ctc cct gag cta     1008
Glu Leu Leu Leu Asn Ser Leu Ile Arg Lys Lys Leu Leu Pro Glu Leu
                325                 330                 335 tct ttg ctc atc acc aca cgg ccc acg gct ttg gag aag ctc cac cgt     1056
Ser Leu Leu Ile Thr Thr Arg Pro Thr Ala Leu Glu Lys Leu His Arg
            340                 345                 350 ctg ctg gag cac ccc agg cat gtg gag atc ctg ggc ttc tct gag gca     1104
Leu Leu Glu His Pro Arg His Val Glu Ile Leu Gly Phe Ser Glu Ala
        355                 360                 365 gaa agg aag gaa tac ttc tac aag tat ttc cac aat gca gag cag gcg     1152
```

```
                                      -continued

Glu Arg Lys Glu Tyr Phe Tyr Lys Tyr Phe His Asn Ala Glu Gln Ala
    370             375             380 ggc caa gtc ttc aat tac gtg agg gac aac gag cct ctc ttc acc atg    1200
Gly Gln Val Phe Asn Tyr Val Arg Asp Asn Glu Pro Leu Phe Thr Met
385             390             395             400 tgc ttc gtc ccc ctg gtg tgc tgg gtg gtg tgt acc tgc ctc cag cag    1248
Cys Phe Val Pro Leu Val Cys Trp Val Val Cys Thr Cys Leu Gln Gln
                405             410             415 cag ctg gag ggt ggg ggg ctg ttg aga cag acg tcc agg acc acc act    1296
Gln Leu Glu Gly Gly Gly Leu Leu Arg Gln Thr Ser Arg Thr Thr Thr
            420             425             430 gca gtg tac atg ctc tac ctg ctg agt ctg atg caa ccc aag ccg ggg    1344
Ala Val Tyr Met Leu Tyr Leu Leu Ser Leu Met Gln Pro Lys Pro Gly
        435             440             445 gcc ccg cgc ctc cag ccc cca ccc aac cag aga ggg ttg tgc tcc ttg    1392
Ala Pro Arg Leu Gln Pro Pro Pro Asn Gln Arg Gly Leu Cys Ser Leu
450             455             460 gcg gca gat ggg ctc tgg aat cag aaa atc cta ttt gag gag cag gac    1440
Ala Ala Asp Gly Leu Trp Asn Gln Lys Ile Leu Phe Glu Glu Gln Asp
465             470             475             480 ctc cgg aag cac ggc cta gac ggg gaa gac gtc tct gcc ttc ctc aac    1488
Leu Arg Lys His Gly Leu Asp Gly Glu Asp Val Ser Ala Phe Leu Asn
                485             490             495 atg aac atc ttc cag aag gac atc aac tgt gag agg tac tac agc ttc    1536
Met Asn Ile Phe Gln Lys Asp Ile Asn Cys Glu Arg Tyr Tyr Ser Phe
            500             505             510 atc cac ttg agt ttc cag gaa ttc ttt gca gct atg tac tat atc ctg    1584
Ile His Leu Ser Phe Gln Glu Phe Phe Ala Ala Met Tyr Tyr Ile Leu
        515             520             525 gac gag ggg gag ggc ggg gca ggc cca gac cag gac gtg acc agg ctg    1632
Asp Glu Gly Glu Gly Gly Ala Gly Pro Asp Gln Asp Val Thr Arg Leu
530             535             540 ttg acc gag tac gcg ttt tct gaa agg agc ttc ctg gca ctc acc agc    1680
Leu Thr Glu Tyr Ala Phe Ser Glu Arg Ser Phe Leu Ala Leu Thr Ser
545             550             555             560 cgc ttc ctg ttt gga ctc ctg aac gag gag acc agg agc cac ctg gag    1728
Arg Phe Leu Phe Gly Leu Leu Asn Glu Glu Thr Arg Ser His Leu Glu
                565             570             575 aag agt ctc tgc tgg aag gtc tcg ccg cac atc aag atg gac ctg ttg    1776
Lys Ser Leu Cys Trp Lys Val Ser Pro His Ile Lys Met Asp Leu Leu
            580             585             590 cag tgg atc caa agc aaa gct cag agc gac ggc tcc acc ctg cag cag    1824
Gln Trp Ile Gln Ser Lys Ala Gln Ser Asp Gly Ser Thr Leu Gln Gln
        595             600             605 ggc tcc ttg gag ttc ttc agc tgc ttg tac gag atc cag gag gag gag    1872
Gly Ser Leu Glu Phe Phe Ser Cys Leu Tyr Glu Ile Gln Glu Glu Glu
610             615             620 ttt atc cag cag gcc ctg agc cac ttc cag gtg atc gtg gtc agc aac    1920
Phe Ile Gln Gln Ala Leu Ser His Phe Gln Val Ile Val Val Ser Asn
625             630             635             640 att gcc tcc aag atg gag cac atg gtc tcc tcg ttc tgt ctg aag cgc    1968
Ile Ala Ser Lys Met Glu His Met Val Ser Ser Phe Cys Leu Lys Arg
                645             650             655 tgc agg agc gcc cag gtg ctg cac ttg tat ggc gcc acc tac agc gcg    2016
Cys Arg Ser Ala Gln Val Leu His Leu Tyr Gly Ala Thr Tyr Ser Ala
            660             665             670 gac ggg gaa gac cgc gcg agg tgc tcc gca gga gcg cac acg ctg ttg    2064
Asp Gly Glu Asp Arg Ala Arg Cys Ser Ala Gly Ala His Thr Leu Leu
        675             680             685
```

```
                                                            -continued gtg cag cta cca gag agg acc gtt ctg ctg gac gcc tac agt gaa cat      2112
Val Gln Leu Pro Glu Arg Thr Val Leu Leu Asp Ala Tyr Ser Glu His
        690             695             700 ctg gca gcg gcc ctg tgc acc aat cca aac ctg ata gag ctg tct ctg      2160
Leu Ala Ala Ala Leu Cys Thr Asn Pro Asn Leu Ile Glu Leu Ser Leu
705             710             715             720 tac cga aat gcc ctg ggc agc cgg ggg gtg aag ctg ctc tgt caa gga      2208
Tyr Arg Asn Ala Leu Gly Ser Arg Gly Val Lys Leu Leu Cys Gln Gly
            725             730             735 ctc aga cac ccc aac tgc aaa ctt cag aac ctg agg ctg aag agg tgc      2256
Leu Arg His Pro Asn Cys Lys Leu Gln Asn Leu Arg Leu Lys Arg Cys
        740             745             750 cgc atc tcc agc tca gcc tgc gag gac ctc tct gca gct ctc ata gcc      2304
Arg Ile Ser Ser Ser Ala Cys Glu Asp Leu Ser Ala Ala Leu Ile Ala
        755             760             765 aat aag aat ttg aca agg atg gat ctc agt ggc aac ggc gtt gga ttc      2352
Asn Lys Asn Leu Thr Arg Met Asp Leu Ser Gly Asn Gly Val Gly Phe
770             775             780 cca ggc atg atg ctg ctt tgc gag ggc ctg cgg cat ccc caa tgc agg      2400
Pro Gly Met Met Leu Leu Cys Glu Gly Leu Arg His Pro Gln Cys Arg
785             790             795             800 ctg cag atg att cag ttg agg aag tgt cag ctg gag tcc ggg gct tgt      2448
Leu Gln Met Ile Gln Leu Arg Lys Cys Gln Leu Glu Ser Gly Ala Cys
            805             810             815 cag gag atg gct tct gtg ctt ggc acc aac cca cat ctg gtt gag ttg      2496
Gln Glu Met Ala Ser Val Leu Gly Thr Asn Pro His Leu Val Glu Leu
        820             825             830 gac ctg aca gga aat gca ctg gag gat ttg ggc ctg agg tta cta tgc      2544
Asp Leu Thr Gly Asn Ala Leu Glu Asp Leu Gly Leu Arg Leu Leu Cys
        835             840             845 cag gga ctg agg cac cca gtc tgc aga cta cgg act ttg tgg ctg aag      2592
Gln Gly Leu Arg His Pro Val Cys Arg Leu Arg Thr Leu Trp Leu Lys
850             855             860 atc tgc cgc ctc act gct gct gcc tgt gac gag ctg gcc tca act ctc      2640
Ile Cys Arg Leu Thr Ala Ala Ala Cys Asp Glu Leu Ala Ser Thr Leu
865             870             875             880 agt gtg aac cag agc ctg aga gag ctg gac ctg agc ctg aat gag ctg      2688
Ser Val Asn Gln Ser Leu Arg Glu Leu Asp Leu Ser Leu Asn Glu Leu
            885             890             895 ggg gac ctc ggg gtg ctg ctg ctg tgt gag ggc ctc agg cat ccc acg      2736
Gly Asp Leu Gly Val Leu Leu Leu Cys Glu Gly Leu Arg His Pro Thr
        900             905             910 tgc aag ctc cag acc ctg cgg ttg ggc atc tgc cgg ctg ggc tct gcc      2784
Cys Lys Leu Gln Thr Leu Arg Leu Gly Ile Cys Arg Leu Gly Ser Ala
        915             920             925 gcc tgt gag ggt ctt tct gtg gtg ctc cag gcc aac cac aac ctc cgg      2832
Ala Cys Glu Gly Leu Ser Val Val Leu Gln Ala Asn His Asn Leu Arg
930             935             940 gag ctg gac ttg agt ttc aac gac ctg gga gac tgg ggc ctg tgg ttg      2880
Glu Leu Asp Leu Ser Phe Asn Asp Leu Gly Asp Trp Gly Leu Trp Leu
945             950             955             960 ctg gct gag ggg ctg caa cat ccc gcc tgc aga ctc cag aaa ctg tgg      2928
Leu Ala Glu Gly Leu Gln His Pro Ala Cys Arg Leu Gln Lys Leu Trp
            965             970             975 ctg gat agc tgt ggc ctc aca gcc aag gct tgt gag aat ctt tac ttc      2976
Leu Asp Ser Cys Gly Leu Thr Ala Lys Ala Cys Glu Asn Leu Tyr Phe
        980             985             990 acc ctg ggg atc aac cag acc ttg acc gac ctt tac ctg acc aac aac      3024
Thr Leu Gly Ile Asn Gln Thr Leu Thr Asp Leu Tyr Leu Thr Asn Asn
        995             1000            1005
```

```
gcc cta ggg gac aca ggt gtc cga ctg ctt tgc aag cgg ctg agc cat    3072
Ala Leu Gly Asp Thr Gly Val Arg Leu Leu Cys Lys Arg Leu Ser His
    1010                1015                1020 cct ggc tgc aaa ctc cga gtc ctc tgg tta ttt ggg atg gac ctg aat    3120
Pro Gly Cys Lys Leu Arg Val Leu Trp Leu Phe Gly Met Asp Leu Asn
1025                1030                1035                1040 aaa atg acc cac agt agg ttg gca gcg ctt cga gta aca aaa cct tat    3168
Lys Met Thr His Ser Arg Leu Ala Ala Leu Arg Val Thr Lys Pro Tyr
                1045                1050                1055 ttg gac att ggc tgc tga                                            3186
Leu Asp Ile Gly Cys
            1060
```

<210> SEQ ID NO 18
<211> LENGTH: 1061
<212> TYPE: PRT
<213> ORGANISM: Homo sapiens

<400> SEQUENCE: 18

```
Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
                20                  25                  30

Gly Thr Ala Thr Glu Leu Gly Glu Gly Lys Ile Pro Trp Gly Ser Met
            35                  40                  45

Glu Lys Ala Gly Pro Leu Glu Met Ala Gln Leu Leu Ile Thr His Phe
        50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Thr Pro Pro Gly Gly Pro Ser Ser Leu Gly Asn Gln Ser Thr Cys
            100                 105                 110

Leu Leu Glu Val Ser Leu Val Thr Pro Arg Lys Asp Pro Gln Glu Thr
        115                 120                 125

Tyr Arg Asp Tyr Val Arg Arg Lys Phe Arg Leu Met Glu Asp Arg Asn
    130                 135                 140

Ala Arg Leu Gly Glu Cys Val Asn Leu Ser His Arg Tyr Thr Arg Leu
145                 150                 155                 160

Leu Leu Val Lys Glu His Ser Asn Pro Met Gln Val Gln Gln Leu
                165                 170                 175

Leu Asp Thr Gly Arg Gly His Ala Arg Thr Val Gly His Gln Ala Ser
            180                 185                 190

Pro Ile Lys Ile Glu Thr Leu Phe Glu Pro Asp Glu Arg Pro Glu
        195                 200                 205

Pro Pro Arg Thr Val Val Met Gln Gly Ala Ala Gly Ile Gly Lys Ser
    210                 215                 220

Met Leu Ala His Lys Val Met Leu Asp Trp Ala Asp Gly Lys Leu Phe
225                 230                 235                 240

Gln Gly Arg Phe Asp Tyr Leu Phe Tyr Ile Asn Cys Arg Glu Met Asn
                245                 250                 255

Gln Ser Ala Thr Glu Cys Ser Met Gln Asp Leu Ile Phe Ser Cys Trp
            260                 265                 270

Pro Glu Pro Ser Ala Pro Leu Gln Glu Leu Ile Arg Val Pro Glu Arg
        275                 280                 285
```

-continued

```
Leu Leu Phe Ile Ile Asp Gly Phe Asp Glu Leu Lys Pro Ser Phe His
    290                 295                 300
Asp Pro Gln Gly Pro Trp Cys Leu Cys Trp Glu Glu Lys Arg Pro Thr
305                 310                 315                 320
Glu Leu Leu Leu Asn Ser Leu Ile Arg Lys Lys Leu Leu Pro Glu Leu
                325                 330                 335
Ser Leu Leu Ile Thr Thr Arg Pro Thr Ala Leu Glu Lys Leu His Arg
            340                 345                 350
Leu Leu Glu His Pro Arg His Val Glu Ile Leu Gly Phe Ser Glu Ala
        355                 360                 365
Glu Arg Lys Glu Tyr Phe Tyr Lys Tyr Phe His Asn Ala Glu Gln Ala
    370                 375                 380
Gly Gln Val Phe Asn Tyr Val Arg Asp Asn Glu Pro Leu Phe Thr Met
385                 390                 395                 400
Cys Phe Val Pro Leu Val Cys Trp Val Val Cys Thr Cys Leu Gln Gln
                405                 410                 415
Gln Leu Glu Gly Gly Gly Leu Leu Arg Gln Thr Ser Arg Thr Thr Thr
            420                 425                 430
Ala Val Tyr Met Leu Tyr Leu Leu Ser Leu Met Gln Pro Lys Pro Gly
        435                 440                 445
Ala Pro Arg Leu Gln Pro Pro Asn Gln Arg Gly Leu Cys Ser Leu
    450                 455                 460
Ala Ala Asp Gly Leu Trp Asn Gln Lys Ile Leu Phe Glu Glu Gln Asp
465                 470                 475                 480
Leu Arg Lys His Gly Leu Asp Gly Glu Asp Val Ser Ala Phe Leu Asn
                485                 490                 495
Met Asn Ile Phe Gln Lys Asp Ile Asn Cys Glu Arg Tyr Tyr Ser Phe
            500                 505                 510
Ile His Leu Ser Phe Gln Glu Phe Phe Ala Ala Met Tyr Tyr Ile Leu
        515                 520                 525
Asp Glu Gly Glu Gly Gly Ala Gly Pro Asp Gln Asp Val Thr Arg Leu
    530                 535                 540
Leu Thr Glu Tyr Ala Phe Ser Glu Arg Ser Phe Leu Ala Leu Thr Ser
545                 550                 555                 560
Arg Phe Leu Phe Gly Leu Leu Asn Glu Glu Thr Arg Ser His Leu Glu
                565                 570                 575
Lys Ser Leu Cys Trp Lys Val Ser Pro His Ile Lys Met Asp Leu Leu
            580                 585                 590
Gln Trp Ile Gln Ser Lys Ala Gln Ser Asp Gly Ser Thr Leu Gln Gln
        595                 600                 605
Gly Ser Leu Glu Phe Phe Ser Cys Leu Tyr Glu Ile Gln Glu Glu Glu
    610                 615                 620
Phe Ile Gln Gln Ala Leu Ser His Phe Gln Val Ile Val Ser Asn
625                 630                 635                 640
Ile Ala Ser Lys Met Glu His Met Val Ser Ser Phe Cys Leu Lys Arg
                645                 650                 655
Cys Arg Ser Ala Gln Val Leu His Leu Tyr Gly Ala Thr Tyr Ser Ala
            660                 665                 670
Asp Gly Glu Asp Arg Ala Arg Cys Ser Ala Gly Ala His Thr Leu Leu
        675                 680                 685
Val Gln Leu Pro Glu Arg Thr Val Leu Leu Asp Ala Tyr Ser Glu His
    690                 695                 700
Leu Ala Ala Ala Leu Cys Thr Asn Pro Asn Leu Ile Glu Leu Ser Leu
```

```
                705                 710                 715                 720
Tyr Arg Asn Ala Leu Gly Ser Arg Gly Val Lys Leu Leu Cys Gln Gly
                    725                 730                 735

Leu Arg His Pro Asn Cys Lys Leu Gln Asn Leu Arg Leu Lys Arg Cys
            740                 745                 750

Arg Ile Ser Ser Ala Cys Glu Asp Leu Ser Ala Ala Leu Ile Ala
        755                 760                 765

Asn Lys Asn Leu Thr Arg Met Asp Leu Ser Gly Asn Gly Val Gly Phe
    770                 775                 780

Pro Gly Met Met Leu Leu Cys Glu Gly Leu Arg His Pro Gln Cys Arg
785                 790                 795                 800

Leu Gln Met Ile Gln Leu Arg Lys Cys Gln Leu Glu Ser Gly Ala Cys
                805                 810                 815

Gln Glu Met Ala Ser Val Leu Gly Thr Asn Pro His Leu Val Glu Leu
            820                 825                 830

Asp Leu Thr Gly Asn Ala Leu Glu Asp Leu Gly Leu Arg Leu Leu Cys
        835                 840                 845

Gln Gly Leu Arg His Pro Val Cys Arg Leu Arg Thr Leu Trp Leu Lys
    850                 855                 860

Ile Cys Arg Leu Thr Ala Ala Ala Cys Asp Glu Leu Ala Ser Thr Leu
865                 870                 875                 880

Ser Val Asn Gln Ser Leu Arg Glu Leu Asp Leu Ser Leu Asn Glu Leu
                885                 890                 895

Gly Asp Leu Gly Val Leu Leu Leu Cys Glu Gly Leu Arg His Pro Thr
            900                 905                 910

Cys Lys Leu Gln Thr Leu Arg Leu Gly Ile Cys Arg Leu Gly Ser Ala
        915                 920                 925

Ala Cys Glu Gly Leu Ser Val Val Leu Gln Ala Asn His Asn Leu Arg
    930                 935                 940

Glu Leu Asp Leu Ser Phe Asn Asp Leu Gly Asp Trp Gly Leu Trp Leu
945                 950                 955                 960

Leu Ala Glu Gly Leu Gln His Pro Ala Cys Arg Leu Gln Lys Leu Trp
                965                 970                 975

Leu Asp Ser Cys Gly Leu Thr Ala Lys Ala Cys Glu Asn Leu Tyr Phe
            980                 985                 990

Thr Leu Gly Ile Asn Gln Thr Leu Thr Asp Leu Tyr Leu Thr Asn Asn
        995                 1000                1005

Ala Leu Gly Asp Thr Gly Val Arg Leu Leu Cys Lys Arg Leu Ser His
    1010                1015                1020

Pro Gly Cys Lys Leu Arg Val Leu Trp Leu Phe Gly Met Asp Leu Asn
1025                1030                1035                1040

Lys Met Thr His Ser Arg Leu Ala Ala Leu Arg Val Thr Lys Pro Tyr
                1045                1050                1055

Leu Asp Ile Gly Cys
            1060

<210> SEQ ID NO 19
<211> LENGTH: 1446
<212> TYPE: DNA
<213> ORGANISM: Homo sapiens
<220> FEATURE:
<221> NAME/KEY: CDS
<222> LOCATION: (1)...(1443)

<400> SEQUENCE: 19
```

-continued

```
atg agt gac gtg aat cca ccc tct gac acc ccc att ccc ttt tca tcc    48
Met Ser Asp Val Asn Pro Pro Ser Asp Thr Pro Ile Pro Phe Ser Ser
 1               5                  10                  15 tcc tcc act cac agt tct cat att ctg ccc tgg aca ttc tct tgc tac    96
Ser Ser Thr His Ser Ser His Ile Leu Pro Trp Thr Phe Ser Cys Tyr
                 20                  25                  30 ccc ggc tcc cca tgt gaa aat ggg gtc atg ctg tac atg aga aac gtg   144
Pro Gly Ser Pro Cys Glu Asn Gly Val Met Leu Tyr Met Arg Asn Val
             35                  40                  45 agc cat gag gag cta caa cgg ttc aag cag ctc tta ctg act gag ctc   192
Ser His Glu Glu Leu Gln Arg Phe Lys Gln Leu Leu Leu Thr Glu Leu
 50                  55                  60 agt act ggc acc atg ccc atc acc tgg gac cag gtc gag aca gcc agc   240
Ser Thr Gly Thr Met Pro Ile Thr Trp Asp Gln Val Glu Thr Ala Ser
 65                  70                  75                  80 tgg gca gag gtg gtt cat ctc ttg ata gag cgt ttc cct gga cga cgc   288
Trp Ala Glu Val Val His Leu Leu Ile Glu Arg Phe Pro Gly Arg Arg
                 85                  90                  95 gct tgg gat gtg act tcg aac atc ttt gcc att atg aac tgt gat aaa   336
Ala Trp Asp Val Thr Ser Asn Ile Phe Ala Ile Met Asn Cys Asp Lys
            100                 105                 110 att ggg gtc ccg cag tta ttc tac tgt ctg cat gaa atc cgg gag gaa   384
Ile Gly Val Pro Gln Leu Phe Tyr Cys Leu His Glu Ile Arg Glu Glu
            115                 120                 125 gcc ttt gta agc caa gcc tta aat gat tat cat aaa gtt gtc ttg aga   432
Ala Phe Val Ser Gln Ala Leu Asn Asp Tyr His Lys Val Val Leu Arg
130                 135                 140 att ggc aac aac aaa gaa gtt caa gtg tct gct ttt tgc ctg aag cgg   480
Ile Gly Asn Asn Lys Glu Val Gln Val Ser Ala Phe Cys Leu Lys Arg
145                 150                 155                 160 tgt caa tat ttg cat gag gtg gaa ctg acc gtc acc ctg aac ttc atg   528
Cys Gln Tyr Leu His Glu Val Glu Leu Thr Val Thr Leu Asn Phe Met
                165                 170                 175 aac gtg tgg aag ctc agc tcc agc tcc cat cct ggc tct gac cta agg   576
Asn Val Trp Lys Leu Ser Ser Ser Ser His Pro Gly Ser Asp Leu Arg
            180                 185                 190 cgt gtg aat agc acc atg ttg aac cag gac tta atc ggt gtt ttg acg   624
Arg Val Asn Ser Thr Met Leu Asn Gln Asp Leu Ile Gly Val Leu Thr
            195                 200                 205 ggg aac cag cat ctg aga tac ttg gaa ata caa cat gtg gaa gtg gag   672
Gly Asn Gln His Leu Arg Tyr Leu Glu Ile Gln His Val Glu Val Glu
210                 215                 220 tcc aag gct gtg aag ctt cta tgc agg gcg ctg aga tcc ccc cgg tgc   720
Ser Lys Ala Val Lys Leu Leu Cys Arg Ala Leu Arg Ser Pro Arg Cys
225                 230                 235                 240 cgt ctg cag tgt ctc agg ttg gaa gac tgc ttg gcc acc cct aga att   768
Arg Leu Gln Cys Leu Arg Leu Glu Asp Cys Leu Ala Thr Pro Arg Ile
                245                 250                 255 tgg act gat ctt ggc aat aat ctt caa ggt aac ggg cat cta aag act   816
Trp Thr Asp Leu Gly Asn Asn Leu Gln Gly Asn Gly His Leu Lys Thr
            260                 265                 270 ctc ata cta aga aaa aac tcc ctg gag aac tgt ggg gcg tat tac ctg   864
Leu Ile Leu Arg Lys Asn Ser Leu Glu Asn Cys Gly Ala Tyr Tyr Leu
            275                 280                 285 tct gtg gcc cag ctg gag agg ctg tcg cag agt aag atg ctg acc cac   912
Ser Val Ala Gln Leu Glu Arg Leu Ser Gln Ser Lys Met Leu Thr His
290                 295                 300 ctg agc ttg gca gaa aac gcc ttg aaa gat gaa ggg gcc aag cat att   960
Leu Ser Leu Ala Glu Asn Ala Leu Lys Asp Glu Gly Ala Lys His Ile
305                 310                 315                 320
```

```
tgg aat gcc ctg cca cac ctg aga tgt cct ctg cag agg ctg gta ctg      1008
Trp Asn Ala Leu Pro His Leu Arg Cys Pro Leu Gln Arg Leu Val Leu
            325                 330                 335 aga aag tgt gac ttg acc ttt aat tgc tgt cag gat atg atc tct gcg      1056
Arg Lys Cys Asp Leu Thr Phe Asn Cys Cys Gln Asp Met Ile Ser Ala
    340                 345                 350 ctc tgt aaa aat aaa acc ctg aaa agt ctt gac cta agt ttt aat agc      1104
Leu Cys Lys Asn Lys Thr Leu Lys Ser Leu Asp Leu Ser Phe Asn Ser
355                 360                 365 ctg aag gat gat ggg gtg atc ctg ctg tgt gag gcc ctg aag aac cct      1152
Leu Lys Asp Asp Gly Val Ile Leu Leu Cys Glu Ala Leu Lys Asn Pro
        370                 375                 380 gac tgt aca tta cag atc ctg gag ctg gaa aac tgc ctg ttt acc tcc      1200
Asp Cys Thr Leu Gln Ile Leu Glu Leu Glu Asn Cys Leu Phe Thr Ser
385                 390                 395                 400 atc tgc tgc cag gcc atg gct tcc atg ctc cgc aaa aac caa cat ctg      1248
Ile Cys Cys Gln Ala Met Ala Ser Met Leu Arg Lys Asn Gln His Leu
                405                 410                 415 aga cat ctg gac ttg agc aag aat gcg att gga gtc tat ggt att ctg      1296
Arg His Leu Asp Leu Ser Lys Asn Ala Ile Gly Val Tyr Gly Ile Leu
            420                 425                 430 acc ttg tgc gag gcc ttc tca agc caa aag aag aga gaa gag gtc att      1344
Thr Leu Cys Glu Ala Phe Ser Ser Gln Lys Lys Arg Glu Glu Val Ile
        435                 440                 445 ttc tgt att cct gcc tgg act cga ata act agc ttc tcc cca act cct      1392
Phe Cys Ile Pro Ala Trp Thr Arg Ile Thr Ser Phe Ser Pro Thr Pro
450                 455                 460 cac cca ccc gac ttc acg gga aaa agt gac tgc cta tcc cag att aat      1440
His Pro Pro Asp Phe Thr Gly Lys Ser Asp Cys Leu Ser Gln Ile Asn
465                 470                 475                 480 cct tag                                                              1446
Pro

<210> SEQ ID NO 20
<211> LENGTH: 481
<212> TYPE: PRT
<213> ORGANISM: Homo sapiens

<400> SEQUENCE: 20

Met Ser Asp Val Asn Pro Pro Ser Asp Thr Pro Ile Pro Phe Ser Ser
  1               5                  10                  15

Ser Ser Thr His Ser Ser His Ile Leu Pro Trp Thr Phe Ser Cys Tyr
                20                  25                  30

Pro Gly Ser Pro Cys Glu Asn Gly Val Met Leu Tyr Met Arg Asn Val
            35                  40                  45

Ser His Glu Glu Leu Gln Arg Phe Lys Gln Leu Leu Leu Thr Glu Leu
        50                  55                  60

Ser Thr Gly Thr Met Pro Ile Thr Trp Asp Gln Val Glu Thr Ala Ser
 65                  70                  75                  80

Trp Ala Glu Val Val His Leu Leu Ile Glu Arg Phe Pro Gly Arg Arg
                 85                  90                  95

Ala Trp Asp Val Thr Ser Asn Ile Phe Ala Ile Met Asn Cys Asp Lys
            100                 105                 110

Ile Gly Val Pro Gln Leu Phe Tyr Cys Leu His Glu Ile Arg Glu Glu
        115                 120                 125

Ala Phe Val Ser Gln Ala Leu Asn Asp Tyr His Lys Val Val Leu Arg
    130                 135                 140
```

```
Ile Gly Asn Asn Lys Glu Val Gln Val Ser Ala Phe Cys Leu Lys Arg
145                 150                 155                 160

Cys Gln Tyr Leu His Glu Val Glu Leu Thr Val Thr Leu Asn Phe Met
                165                 170                 175

Asn Val Trp Lys Leu Ser Ser Ser His Pro Gly Ser Asp Leu Arg
            180                 185                 190

Arg Val Asn Ser Thr Met Leu Asn Gln Asp Leu Ile Gly Val Leu Thr
            195                 200                 205

Gly Asn Gln His Leu Arg Tyr Leu Glu Ile Gln His Val Glu Val Glu
        210                 215                 220

Ser Lys Ala Val Lys Leu Leu Cys Arg Ala Leu Arg Ser Pro Arg Cys
225                 230                 235                 240

Arg Leu Gln Cys Leu Arg Leu Glu Asp Cys Leu Ala Thr Pro Arg Ile
                245                 250                 255

Trp Thr Asp Leu Gly Asn Asn Leu Gln Gly Asn Gly His Leu Lys Thr
                260                 265                 270

Leu Ile Leu Arg Lys Asn Ser Leu Glu Asn Cys Gly Ala Tyr Tyr Leu
            275                 280                 285

Ser Val Ala Gln Leu Glu Arg Leu Ser Gln Ser Lys Met Leu Thr His
        290                 295                 300

Leu Ser Leu Ala Glu Asn Ala Leu Lys Asp Glu Gly Ala Lys His Ile
305                 310                 315                 320

Trp Asn Ala Leu Pro His Leu Arg Cys Pro Leu Gln Arg Leu Val Leu
                325                 330                 335

Arg Lys Cys Asp Leu Thr Phe Asn Cys Cys Gln Asp Met Ile Ser Ala
                340                 345                 350

Leu Cys Lys Asn Lys Thr Leu Lys Ser Leu Asp Leu Ser Phe Asn Ser
            355                 360                 365

Leu Lys Asp Asp Gly Val Ile Leu Leu Cys Glu Ala Leu Lys Asn Pro
370                 375                 380

Asp Cys Thr Leu Gln Ile Leu Glu Leu Glu Asn Cys Leu Phe Thr Ser
385                 390                 395                 400

Ile Cys Cys Gln Ala Met Ala Ser Met Leu Arg Lys Asn Gln His Leu
                405                 410                 415

Arg His Leu Asp Leu Ser Lys Asn Ala Ile Gly Val Tyr Gly Ile Leu
                420                 425                 430

Thr Leu Cys Glu Ala Phe Ser Ser Gln Lys Lys Arg Glu Glu Val Ile
            435                 440                 445

Phe Cys Ile Pro Ala Trp Thr Arg Ile Thr Ser Phe Ser Pro Thr Pro
450                 455                 460

His Pro Pro Asp Phe Thr Gly Lys Ser Asp Cys Leu Ser Gln Ile Asn
465                 470                 475                 480

Pro

<210> SEQ ID NO 21
<211> LENGTH: 2691
<212> TYPE: DNA
<213> ORGANISM: Homo sapiens
<220> FEATURE:
<221> NAME/KEY: CDS
<222> LOCATION: (1)...(2688)

<400> SEQUENCE: 21 atg gca gat tca tca tca tct tct ttc ttt cct gat ttt ggg ctg cta    48
Met Ala Asp Ser Ser Ser Ser Ser Phe Phe Pro Asp Phe Gly Leu Leu
1               5                   10                  15
```

-continued

| | |
|---|---|
| ttg tat ttg gag gag cta aac aaa gag gaa tta aat aca ttc aag tta<br>Leu Tyr Leu Glu Glu Leu Asn Lys Glu Glu Leu Asn Thr Phe Lys Leu<br>         20                  25                  30 | 96 |
| ttc cta aag gag acc atg gaa cct gag cat ggc ctg aca ccc tgg act<br>Phe Leu Lys Glu Thr Met Glu Pro Glu His Gly Leu Thr Pro Trp Thr<br>     35                  40                  45 | 144 |
| gaa gtg aag aag gcc agg cgg gag gac ctg gcc aat ttg atg aag aaa<br>Glu Val Lys Lys Ala Arg Arg Glu Asp Leu Ala Asn Leu Met Lys Lys<br> 50                  55                  60 | 192 |
| tat tat cca gga gag aaa gcc tgg agt gtg tct ctc aaa atc ttt ggc<br>Tyr Tyr Pro Gly Glu Lys Ala Trp Ser Val Ser Leu Lys Ile Phe Gly<br>65                  70                  75                  80 | 240 |
| aag atg aac ctg aag gat ctg tgt gag aga gcg aaa gaa gag atc aac<br>Lys Met Asn Leu Lys Asp Leu Cys Glu Arg Ala Lys Glu Glu Ile Asn<br>                 85                  90                  95 | 288 |
| tgg tcg gcc cag act ata gga cca gat gat gcc aag gct gga gag aca<br>Trp Ser Ala Gln Thr Ile Gly Pro Asp Asp Ala Lys Ala Gly Glu Thr<br>            100                 105                 110 | 336 |
| caa gaa gat cag gag gca gtg ctg ggt gat gga aca gaa tac aga aat<br>Gln Glu Asp Gln Glu Ala Val Leu Gly Asp Gly Thr Glu Tyr Arg Asn<br>        115                 120                 125 | 384 |
| aga ata aag gaa aaa ttt tgc atc act tgg gac aag aag tct ttg gct<br>Arg Ile Lys Glu Lys Phe Cys Ile Thr Trp Asp Lys Lys Ser Leu Ala<br>    130                 135                 140 | 432 |
| gga aag cct gaa gat ttc cat cat gga att gca gag aaa gat aga aaa<br>Gly Lys Pro Glu Asp Phe His His Gly Ile Ala Glu Lys Asp Arg Lys<br>145                 150                 155                 160 | 480 |
| ctg ttg gaa cac ttg ttt gat gtg gat gtc aaa acc ggt gca cag cca<br>Leu Leu Glu His Leu Phe Asp Val Asp Val Lys Thr Gly Ala Gln Pro<br>                165                 170                 175 | 528 |
| cag atc gtg gtg ctt cag gga gct gct gga gtt ggg aaa aca acc ttg<br>Gln Ile Val Val Leu Gln Gly Ala Ala Gly Val Gly Lys Thr Thr Leu<br>            180                 185                 190 | 576 |
| gtg aga aag gca atg tta gat tgg gca gag ggc agt ctc tac cag cag<br>Val Arg Lys Ala Met Leu Asp Trp Ala Glu Gly Ser Leu Tyr Gln Gln<br>        195                 200                 205 | 624 |
| agg ttt aag tat gtt ttt tat ctc aat ggg aga gaa att aac cag ctg<br>Arg Phe Lys Tyr Val Phe Tyr Leu Asn Gly Arg Glu Ile Asn Gln Leu<br>    210                 215                 220 | 672 |
| aaa gag aga agc ttt gct caa ttg ata tca aag gac tgg ccc agc aca<br>Lys Glu Arg Ser Phe Ala Gln Leu Ile Ser Lys Asp Trp Pro Ser Thr<br>225                 230                 235                 240 | 720 |
| gaa ggc ccc att gaa gaa atc atg tac cag cca agt agc ctc ttg ttt<br>Glu Gly Pro Ile Glu Glu Ile Met Tyr Gln Pro Ser Ser Leu Leu Phe<br>                245                 250                 255 | 768 |
| att att gac agt ttc gat gaa ctg aac ttt gcc ttt gaa gaa cct gag<br>Ile Ile Asp Ser Phe Asp Glu Leu Asn Phe Ala Phe Glu Glu Pro Glu<br>            260                 265                 270 | 816 |
| ttt gca ctg tgc gaa gac tgg acc caa gaa cac cca gtg tcc ttc ctc<br>Phe Ala Leu Cys Glu Asp Trp Thr Gln Glu His Pro Val Ser Phe Leu<br>        275                 280                 285 | 864 |
| atg agt agt ttg ctg agg aaa gtg atg ctc cct gag gca tcc tta ttg<br>Met Ser Ser Leu Leu Arg Lys Val Met Leu Pro Glu Ala Ser Leu Leu<br>    290                 295                 300 | 912 |
| gtg aca aca aga ctc aca act tct aag aga cta aag cag ttg ttg aag<br>Val Thr Thr Arg Leu Thr Thr Ser Lys Arg Leu Lys Gln Leu Leu Lys<br>305                 310                 315                 320 | 960 |
| aat cac cat tat gta gag cta cta gga atg tct gag gat gca aga gag<br>Asn His His Tyr Val Glu Leu Leu Gly Met Ser Glu Asp Ala Arg Glu | 1008 |

-continued

```
                   325                 330                 335
gag tat att tac cag ttt ttt gaa gat aag agg tgg gcc atg aaa gta      1056
Glu Tyr Ile Tyr Gln Phe Phe Glu Asp Lys Arg Trp Ala Met Lys Val
            340                 345                 350 ttc agt tca cta aaa agc aat gag atg ctg ttt agc atg tgc caa gtc      1104
Phe Ser Ser Leu Lys Ser Asn Glu Met Leu Phe Ser Met Cys Gln Val
            355                 360                 365 ccc cta gtg tgc tgg gcc gct tgt act tgt ctg aag cag caa atg gag      1152
Pro Leu Val Cys Trp Ala Ala Cys Thr Cys Leu Lys Gln Gln Met Glu
370                 375                 380 aag ggt ggt gat gtc aca ttg acc tgc caa aca acc aca gct ctg ttt      1200
Lys Gly Gly Asp Val Thr Leu Thr Cys Gln Thr Thr Thr Ala Leu Phe
385                 390                 395                 400 acc tgc tat att tct agc ttg ttc aca cca gta gat gga ggc tct cct      1248
Thr Cys Tyr Ile Ser Ser Leu Phe Thr Pro Val Asp Gly Gly Ser Pro
                405                 410                 415 agt cta ccc aac caa gcc cag ctg aga aga ctg tgc caa gtc gct gcc      1296
Ser Leu Pro Asn Gln Ala Gln Leu Arg Arg Leu Cys Gln Val Ala Ala
            420                 425                 430 aaa gga ata tgg act atg act tac gtg ttt tac aga gaa aat ctc aga      1344
Lys Gly Ile Trp Thr Met Thr Tyr Val Phe Tyr Arg Glu Asn Leu Arg
            435                 440                 445 agg ctt ggg tta act caa tct gat gtc tct agt ttt atg gac agc aat      1392
Arg Leu Gly Leu Thr Gln Ser Asp Val Ser Ser Phe Met Asp Ser Asn
450                 455                 460 att att cag aag gac gca gag tat gaa aac tgc tat gtg ttc acc cac      1440
Ile Ile Gln Lys Asp Ala Glu Tyr Glu Asn Cys Tyr Val Phe Thr His
465                 470                 475                 480 ctt cat gtt cag gag ttt ttt gca gct atg ttc tat atg ttg aaa ggc      1488
Leu His Val Gln Glu Phe Phe Ala Ala Met Phe Tyr Met Leu Lys Gly
                485                 490                 495 agt tgg gaa gct ggg aac cct tcc tgc cag cct ttt gaa gat ttg aag      1536
Ser Trp Glu Ala Gly Asn Pro Ser Cys Gln Pro Phe Glu Asp Leu Lys
            500                 505                 510 tca tta ctt caa agc aca agt tat aaa gac ccc cat ttg aca cag atg      1584
Ser Leu Leu Gln Ser Thr Ser Tyr Lys Asp Pro His Leu Thr Gln Met
            515                 520                 525 aag tgc ttt ttg ttt ggc ctt ttg aat gaa gat cga gta aaa caa ctg      1632
Lys Cys Phe Leu Phe Gly Leu Leu Asn Glu Asp Arg Val Lys Gln Leu
530                 535                 540 gag agg act ttt aac tgt aaa atg tca ctg aag ata aaa tca aag tta      1680
Glu Arg Thr Phe Asn Cys Lys Met Ser Leu Lys Ile Lys Ser Lys Leu
545                 550                 555                 560 ctt cag tgt atg gaa cac tgc cgg tgt ttg cgg acc atc agg ctg tct      1728
Leu Gln Cys Met Glu His Cys Arg Cys Leu Arg Thr Ile Arg Leu Ser
                565                 570                 575 gta act gtg gta ttt gag aag aag ata tta aaa aca agc ctc cca act      1776
Val Thr Val Val Phe Glu Lys Lys Ile Leu Lys Thr Ser Leu Pro Thr
            580                 585                 590 aac act tgg ttg aaa ttt atc act ttc cct gat ggt tgt cag gat atc      1824
Asn Thr Trp Leu Lys Phe Ile Thr Phe Pro Asp Gly Cys Gln Asp Ile
            595                 600                 605 tct act tct ttg att cat aac aag aat ctg atg cat ctt gac cta aaa      1872
Ser Thr Ser Leu Ile His Asn Lys Asn Leu Met His Leu Asp Leu Lys
610                 615                 620 ggg agt gat ata ggg gat aat gga gta aag tca ttg tgt gaa gcc ttg      1920
Gly Ser Asp Ile Gly Asp Asn Gly Val Lys Ser Leu Cys Glu Ala Leu
625                 630                 635                 640 aaa cac cca gag tgt aaa cta cag act ctc agc tta gaa agc tgt ggt      1968
```

-continued

```
                Lys His Pro Glu Cys Lys Leu Gln Thr Leu Ser Leu Glu Ser Cys Gly
                                    645                 650                 655 ctc aca gag gct ggc tgt gag tat ctt tct ttg gct ctc atc agc aat           2016
Leu Thr Glu Ala Gly Cys Glu Tyr Leu Ser Leu Ala Leu Ile Ser Asn
            660                 665                 670 aaa aga ctg aca cat ttg tgc ttg gca gac aat gtc ttg ggt gat ggt           2064
Lys Arg Leu Thr His Leu Cys Leu Ala Asp Asn Val Leu Gly Asp Gly
        675                 680                 685 gga gta aag ctt atg agt gat gcc ctg caa cat gca caa tgt act ctg           2112
Gly Val Lys Leu Met Ser Asp Ala Leu Gln His Ala Gln Cys Thr Leu
    690                 695                 700 aag agc ctt gta ttg atg ggc tgt gtt ctc act aat gca tgt tgt ctg           2160
Lys Ser Leu Val Leu Met Gly Cys Val Leu Thr Asn Ala Cys Cys Leu
705                 710                 715                 720 gat ctg gct tct gtt att ttg aat aac cca aac ctg agg agc ctg gac           2208
Asp Leu Ala Ser Val Ile Leu Asn Asn Pro Asn Leu Arg Ser Leu Asp
                725                 730                 735 ctt ggg aac aac gat ttg cag gat gat gga gtg aaa att ctg tgt gat           2256
Leu Gly Asn Asn Asp Leu Gln Asp Asp Gly Val Lys Ile Leu Cys Asp
            740                 745                 750 gct ttg aga tat cca aac tgt aac att cag agg ctc ggg ttg gaa tac           2304
Ala Leu Arg Tyr Pro Asn Cys Asn Ile Gln Arg Leu Gly Leu Glu Tyr
        755                 760                 765 tgt ggt ttg aca tct ctc tgc tgt caa gat ctc tcc tct gct ctt atc           2352
Cys Gly Leu Thr Ser Leu Cys Cys Gln Asp Leu Ser Ser Ala Leu Ile
    770                 775                 780 tgc aac aaa aga ctg ata aaa atg aat ctg aca cag aat acc tta gga           2400
Cys Asn Lys Arg Leu Ile Lys Met Asn Leu Thr Gln Asn Thr Leu Gly
785                 790                 795                 800 tat gaa gga att gtg aag tta tat aaa gtc ttg aag tct cct aag tgt           2448
Tyr Glu Gly Ile Val Lys Leu Tyr Lys Val Leu Lys Ser Pro Lys Cys
                805                 810                 815 aaa cta caa gtt cta gga caa cag gat ttc caa gct gcc caa gga aaa           2496
Lys Leu Gln Val Leu Gly Gln Gln Asp Phe Gln Ala Ala Gln Gly Lys
            820                 825                 830 ctc caa caa agg agg cca ttg aag ccg tta aga ccg ggt cag gtg aac           2544
Leu Gln Gln Arg Arg Pro Leu Lys Pro Leu Arg Pro Gly Gln Val Asn
        835                 840                 845 agg aag tta aag act gaa aag gag aca caa aac tgc cga ctt tcc cga           2592
Arg Lys Leu Lys Thr Glu Lys Glu Thr Gln Asn Cys Arg Leu Ser Arg
    850                 855                 860 cgg cga att ggc cct ctg gaa aca gcc gac caa tca cag gca gca ggg           2640
Arg Arg Ile Gly Pro Leu Glu Thr Ala Asp Gln Ser Gln Ala Ala Gly
865                 870                 875                 880 gcg cgc cct gca gcg ggg ctc cgg ctg cgg ttc cgt gga ctc ggc gac           2688
Ala Arg Pro Ala Ala Gly Leu Arg Leu Arg Phe Arg Gly Leu Gly Asp
                885                 890                 895 tag                                                                       2691

<210> SEQ ID NO 22
<211> LENGTH: 896
<212> TYPE: PRT
<213> ORGANISM: Homo sapiens

<400> SEQUENCE: 22

Met Ala Asp Ser Ser Ser Ser Phe Phe Pro Asp Phe Gly Leu Leu
  1               5                  10                  15

Leu Tyr Leu Glu Glu Leu Asn Lys Glu Glu Leu Asn Thr Phe Lys Leu
              20                  25                  30
```

-continued

```
Phe Leu Lys Glu Thr Met Glu Pro Glu His Gly Leu Thr Pro Trp Thr
         35                  40                  45

Glu Val Lys Lys Ala Arg Arg Glu Asp Leu Ala Asn Leu Met Lys Lys
     50                  55                  60

Tyr Tyr Pro Gly Glu Lys Ala Trp Ser Val Ser Leu Lys Ile Phe Gly
 65                  70                  75                  80

Lys Met Asn Leu Lys Asp Leu Cys Glu Arg Ala Lys Glu Glu Ile Asn
                 85                  90                  95

Trp Ser Ala Gln Thr Ile Gly Pro Asp Asp Ala Lys Ala Gly Glu Thr
            100                 105                 110

Gln Glu Asp Gln Glu Ala Val Leu Gly Asp Gly Thr Glu Tyr Arg Asn
            115                 120                 125

Arg Ile Lys Glu Lys Phe Cys Ile Thr Trp Asp Lys Lys Ser Leu Ala
        130                 135                 140

Gly Lys Pro Glu Asp Phe His His Gly Ile Ala Glu Lys Asp Arg Lys
145                 150                 155                 160

Leu Leu Glu His Leu Phe Asp Val Asp Val Lys Thr Gly Ala Gln Pro
                165                 170                 175

Gln Ile Val Val Leu Gln Gly Ala Ala Gly Val Gly Lys Thr Thr Leu
            180                 185                 190

Val Arg Lys Ala Met Leu Asp Trp Ala Glu Gly Ser Leu Tyr Gln Gln
        195                 200                 205

Arg Phe Lys Tyr Val Phe Tyr Leu Asn Gly Arg Glu Ile Asn Gln Leu
    210                 215                 220

Lys Glu Arg Ser Phe Ala Gln Leu Ile Ser Lys Asp Trp Pro Ser Thr
225                 230                 235                 240

Glu Gly Pro Ile Glu Glu Ile Met Tyr Gln Pro Ser Ser Leu Leu Phe
                245                 250                 255

Ile Ile Asp Ser Phe Asp Glu Leu Asn Phe Ala Phe Glu Glu Pro Glu
            260                 265                 270

Phe Ala Leu Cys Glu Asp Trp Thr Gln Glu His Pro Val Ser Phe Leu
        275                 280                 285

Met Ser Ser Leu Leu Arg Lys Val Met Leu Pro Glu Ala Ser Leu Leu
    290                 295                 300

Val Thr Thr Arg Leu Thr Thr Ser Lys Arg Leu Lys Gln Leu Leu Lys
305                 310                 315                 320

Asn His His Tyr Val Glu Leu Leu Gly Met Ser Glu Asp Ala Arg Glu
                325                 330                 335

Glu Tyr Ile Tyr Gln Phe Phe Glu Asp Lys Arg Trp Ala Met Lys Val
            340                 345                 350

Phe Ser Ser Leu Lys Ser Asn Glu Met Leu Phe Ser Met Cys Gln Val
        355                 360                 365

Pro Leu Val Cys Trp Ala Ala Cys Thr Cys Leu Lys Gln Gln Met Glu
    370                 375                 380

Lys Gly Gly Asp Val Thr Leu Thr Cys Gln Thr Thr Ala Leu Phe
385                 390                 395                 400

Thr Cys Tyr Ile Ser Ser Leu Phe Thr Pro Val Asp Gly Gly Ser Pro
                405                 410                 415

Ser Leu Pro Asn Gln Ala Gln Leu Arg Arg Leu Cys Gln Val Ala Ala
            420                 425                 430

Lys Gly Ile Trp Thr Met Thr Tyr Val Phe Tyr Arg Glu Asn Leu Arg
        435                 440                 445

Arg Leu Gly Leu Thr Gln Ser Asp Val Ser Ser Phe Met Asp Ser Asn
```

```
                450                 455                 460
Ile Ile Gln Lys Asp Ala Glu Tyr Glu Asn Cys Tyr Val Phe Thr His
465                 470                 475                 480

Leu His Val Gln Glu Phe Phe Ala Ala Met Phe Tyr Met Leu Lys Gly
                485                 490                 495

Ser Trp Glu Ala Gly Asn Pro Ser Cys Gln Pro Phe Glu Asp Leu Lys
                500                 505                 510

Ser Leu Leu Gln Ser Thr Ser Tyr Lys Asp Pro His Leu Thr Gln Met
                515                 520                 525

Lys Cys Phe Leu Phe Gly Leu Leu Asn Glu Asp Arg Val Lys Gln Leu
                530                 535                 540

Glu Arg Thr Phe Asn Cys Lys Met Ser Leu Lys Ile Lys Ser Lys Leu
545                 550                 555                 560

Leu Gln Cys Met Glu His Cys Arg Cys Leu Arg Thr Ile Arg Leu Ser
                565                 570                 575

Val Thr Val Phe Glu Lys Lys Ile Leu Lys Thr Ser Leu Pro Thr
                580                 585                 590

Asn Thr Trp Leu Lys Phe Ile Thr Phe Pro Asp Gly Cys Gln Asp Ile
                595                 600                 605

Ser Thr Ser Leu Ile His Asn Lys Asn Leu Met His Leu Asp Leu Lys
                610                 615                 620

Gly Ser Asp Ile Gly Asp Asn Gly Val Lys Ser Leu Cys Glu Ala Leu
625                 630                 635                 640

Lys His Pro Glu Cys Lys Leu Gln Thr Leu Ser Leu Glu Ser Cys Gly
                645                 650                 655

Leu Thr Glu Ala Gly Cys Glu Tyr Leu Ser Leu Ala Leu Ile Ser Asn
                660                 665                 670

Lys Arg Leu Thr His Leu Cys Leu Ala Asp Asn Val Leu Gly Asp Gly
                675                 680                 685

Gly Val Lys Leu Met Ser Asp Ala Leu Gln His Ala Gln Cys Thr Leu
                690                 695                 700

Lys Ser Leu Val Leu Met Gly Cys Val Leu Thr Asn Ala Cys Cys Leu
705                 710                 715                 720

Asp Leu Ala Ser Val Ile Leu Asn Asn Pro Asn Leu Arg Ser Leu Asp
                725                 730                 735

Leu Gly Asn Asn Asp Leu Gln Asp Asp Gly Val Lys Ile Leu Cys Asp
                740                 745                 750

Ala Leu Arg Tyr Pro Asn Cys Asn Ile Gln Arg Leu Gly Leu Glu Tyr
                755                 760                 765

Cys Gly Leu Thr Ser Leu Cys Cys Gln Asp Leu Ser Ser Ala Leu Ile
                770                 775                 780

Cys Asn Lys Arg Leu Ile Lys Met Asn Leu Thr Gln Asn Thr Leu Gly
785                 790                 795                 800

Tyr Glu Gly Ile Val Lys Leu Tyr Lys Val Leu Lys Ser Pro Lys Cys
                805                 810                 815

Lys Leu Gln Val Leu Gly Gln Gln Asp Phe Gln Ala Ala Gln Gly Lys
                820                 825                 830

Leu Gln Gln Arg Arg Pro Leu Lys Pro Leu Arg Pro Gly Gln Val Asn
                835                 840                 845

Arg Lys Leu Lys Thr Glu Lys Glu Thr Gln Asn Cys Arg Leu Ser Arg
                850                 855                 860

Arg Arg Ile Gly Pro Leu Glu Thr Ala Asp Gln Ser Gln Ala Ala Gly
865                 870                 875                 880
```

```
                Ala Arg Pro Ala Ala Gly Leu Arg Leu Arg Phe Arg Gly Leu Gly Asp
                            885                 890                 895

<210> SEQ ID NO 23
<211> LENGTH: 3368
<212> TYPE: DNA
<213> ORGANISM: Homo sapiens
<220> FEATURE:
<221> NAME/KEY: CDS
<222> LOCATION: (70)...(3051)

<400> SEQUENCE: 23
ggcacgagga tttatttatt gttcctggtc actgtctctt tgaggattgg tatctctgct         60 ccagaaaag atg gca gcc tct ttc ttc tct gat ttt ggt ctt atg tgg tat       111
          Met Ala Ala Ser Phe Phe Ser Asp Phe Gly Leu Met Trp Tyr
            1               5                  10 ctg gag gag ctc aaa aag gag gag ttc agg aaa ttt aaa gaa cat ctc         159
Leu Glu Glu Leu Lys Lys Glu Glu Phe Arg Lys Phe Lys Glu His Leu
 15                  20                  25                  30 aag caa atg act ttg cag ctt gaa ctc aag cag att ccc tgg act gag         207
Lys Gln Met Thr Leu Gln Leu Glu Leu Lys Gln Ile Pro Trp Thr Glu
                 35                  40                  45 gtc aaa aaa gca tcc cgg gaa gaa ctt gca aac ctc ttg atc aag cac         255
Val Lys Lys Ala Ser Arg Glu Glu Leu Ala Asn Leu Leu Ile Lys His
             50                  55                  60 tat gaa gaa caa caa gct tgg aac ata acc tta aga atc ttt caa aag         303
Tyr Glu Glu Gln Gln Ala Trp Asn Ile Thr Leu Arg Ile Phe Gln Lys
 65                  70                  75 atg gat aga aag gat ctc tgc atg aag gtc atg agg gag aga aca gga         351
Met Asp Arg Lys Asp Leu Cys Met Lys Val Met Arg Glu Arg Thr Gly
             80                  85                  90 tac aca aag acc tat caa gct cac gca aag cag aaa ttc agc cgc tta         399
Tyr Thr Lys Thr Tyr Gln Ala His Ala Lys Gln Lys Phe Ser Arg Leu
 95                 100                 105                 110 tgg tcc agc aag tct gtc act gag att cac cta tac ttt gag gag gaa         447
Trp Ser Ser Lys Ser Val Thr Glu Ile His Leu Tyr Phe Glu Glu Glu
                115                 120                 125 gtc aag caa gaa gaa tgt gac cat ttg gac cgc ctt ttt gct ccc aag         495
Val Lys Gln Glu Glu Cys Asp His Leu Asp Arg Leu Phe Ala Pro Lys
            130                 135                 140 gaa act ggg aaa cag cca cgt aca gtg att att caa gga cca caa gga         543
Glu Thr Gly Lys Gln Pro Arg Thr Val Ile Ile Gln Gly Pro Gln Gly
            145                 150                 155 att gga aaa acg aca ctc ctg atg aag ctg atg atg gcc tgg tcg gac         591
Ile Gly Lys Thr Thr Leu Leu Met Lys Leu Met Met Ala Trp Ser Asp
160                 165                 170 aac aag atc ttt cgg gat agg ttc ctg tac acg ttc tat ttc tgc tgc         639
Asn Lys Ile Phe Arg Asp Arg Phe Leu Tyr Thr Phe Tyr Phe Cys Cys
175                 180                 185                 190 aga gaa ctg agg gag ttg ccg cca acg agt ttg gct gac ttg att tcc         687
Arg Glu Leu Arg Glu Leu Pro Pro Thr Ser Leu Ala Asp Leu Ile Ser
                195                 200                 205 aga gag tgg cct gac ccc gct gct cct ata aca gag atc gtg tct caa         735
Arg Glu Trp Pro Asp Pro Ala Ala Pro Ile Thr Glu Ile Val Ser Gln
            210                 215                 220 ccg gag aga ctc ttg ttc gtc atc gac agc ttc gaa gag ctg cag ggc         783
Pro Glu Arg Leu Leu Phe Val Ile Asp Ser Phe Glu Glu Leu Gln Gly
            225                 230                 235 ggc ttg aac gaa ccc gat tcg gat ctg tgt ggt gac ttg atg gag aaa         831
Gly Leu Asn Glu Pro Asp Ser Asp Leu Cys Gly Asp Leu Met Glu Lys
```

-continued

```
            240                 245                 250
cgg ccg gtg cag gtg ctt ctg agc agt ttg ctg agg aag aag atg ctc    879
Arg Pro Val Gln Val Leu Leu Ser Ser Leu Leu Arg Lys Lys Met Leu
255                 260                 265                 270 ccg gag gcc tcc ctg ctc atc gcc atc aaa ccc gtg tgc ccg aag gag    927
Pro Glu Ala Ser Leu Leu Ile Ala Ile Lys Pro Val Cys Pro Lys Glu
                275                 280                 285 ctc cgg gat cag gtg acg atc tca gaa atc tac cag ccc cgg gga ttc    975
Leu Arg Asp Gln Val Thr Ile Ser Glu Ile Tyr Gln Pro Arg Gly Phe
            290                 295                 300 aac gag agt gat agg tta gtg tat ttc tgc tgt ttc ttc aaa gac ccg   1023
Asn Glu Ser Asp Arg Leu Val Tyr Phe Cys Cys Phe Phe Lys Asp Pro
        305                 310                 315 aaa aga gcc atg gaa gcc ttc aat ctt gta aga gaa agt gaa cag ctg   1071
Lys Arg Ala Met Glu Ala Phe Asn Leu Val Arg Glu Ser Glu Gln Leu
    320                 325                 330 ttt tcc ata tgc caa atc ccg ctc ctc tgc tgg atc ctg tgt acc agt   1119
Phe Ser Ile Cys Gln Ile Pro Leu Leu Cys Trp Ile Leu Cys Thr Ser
335                 340                 345                 350 ctg aag caa gag atg cag aaa gga aaa gac ctg gcc ctg acc tgc cag   1167
Leu Lys Gln Glu Met Gln Lys Gly Lys Asp Leu Ala Leu Thr Cys Gln
                355                 360                 365 agc act acc tct gtg tac tcc tct ttc gtc ttt aac ctg ttc aca cct   1215
Ser Thr Thr Ser Val Tyr Ser Ser Phe Val Phe Asn Leu Phe Thr Pro
            370                 375                 380 gag ggt gcc gag ggc ccg act ccg caa acc cag cac cag ctg aag gcc   1263
Glu Gly Ala Glu Gly Pro Thr Pro Gln Thr Gln His Gln Leu Lys Ala
        385                 390                 395 ctg tgc tcc ctg gct gca gag ggt atg tgg aca gac aca ttt gag ttt   1311
Leu Cys Ser Leu Ala Ala Glu Gly Met Trp Thr Asp Thr Phe Glu Phe
    400                 405                 410 tgt gaa gac gac ctc cgg aga aat ggg gtt gtt gac gct gac atc cct   1359
Cys Glu Asp Asp Leu Arg Arg Asn Gly Val Val Asp Ala Asp Ile Pro
415                 420                 425                 430 gcg ctg ctg ggc acc aag ata ctt ctg aag tac ggg gag cgt gag agc   1407
Ala Leu Leu Gly Thr Lys Ile Leu Leu Lys Tyr Gly Glu Arg Glu Ser
                435                 440                 445 tcc tac gtg ttc ctc cac gtg tgt atc cag gag ttc tgt gcc gcc ttg   1455
Ser Tyr Val Phe Leu His Val Cys Ile Gln Glu Phe Cys Ala Ala Leu
            450                 455                 460 ttc tat ttg ctc aag agc cac ctt gat cat cct cac cca gct gtg aga   1503
Phe Tyr Leu Leu Lys Ser His Leu Asp His Pro His Pro Ala Val Arg
        465                 470                 475 tgt gta cag gaa ttg cta gtt gcc aat ttt gaa aaa gca agg aga gca   1551
Cys Val Gln Glu Leu Leu Val Ala Asn Phe Glu Lys Ala Arg Arg Ala
    480                 485                 490 cat tgg att ttt ttg ggg tgt ttt cta act ggc ctt tta aat aaa aag   1599
His Trp Ile Phe Leu Gly Cys Phe Leu Thr Gly Leu Leu Asn Lys Lys
495                 500                 505                 510 gaa caa gaa aaa ctg gat gcg ttt ttt ggc ttc caa ctg tcc caa gag   1647
Glu Gln Glu Lys Leu Asp Ala Phe Phe Gly Phe Gln Leu Ser Gln Glu
                515                 520                 525 ata aag cag caa att cac cag tgc ctg aag agc tta ggg gag cgt ggc   1695
Ile Lys Gln Gln Ile His Gln Cys Leu Lys Ser Leu Gly Glu Arg Gly
            530                 535                 540 aat cct cag gga cag gtg gat tcc ttg gcg ata ttt tac tgt ctc ttt   1743
Asn Pro Gln Gly Gln Val Asp Ser Leu Ala Ile Phe Tyr Cys Leu Phe
        545                 550                 555 gaa atg cag gat cct gcc ttt gtg aag cag gca gtg aac ctc ctc caa   1791
```

-continued

```
            Glu Met Gln Asp Pro Ala Phe Val Lys Gln Ala Val Asn Leu Leu Gln
                560                 565                 570 gaa gct aac ttt cat att att gac aac gtg gac ttg gtg gtt tct gcc       1839
Glu Ala Asn Phe His Ile Ile Asp Asn Val Asp Leu Val Val Ser Ala
575                 580                 585                 590 tac tgc tta aaa tac tgc tcc agc ttg agg aaa ctc tgt ttt tcc gtt       1887
Tyr Cys Leu Lys Tyr Cys Ser Ser Leu Arg Lys Leu Cys Phe Ser Val
                595                 600                 605 caa aat gtc ttt aag aaa gag gat gaa cac agc tct acg tcg gat tac       1935
Gln Asn Val Phe Lys Lys Glu Asp Glu His Ser Ser Thr Ser Asp Tyr
            610                 615                 620 agc ctc atc tgt tgg cat cac atc tgc tct gtg ctc acc acc agc ggg       1983
Ser Leu Ile Cys Trp His His Ile Cys Ser Val Leu Thr Thr Ser Gly
        625                 630                 635 cac ctc aga gag ctc cag gtg cag gac agc acc ctc agc gag tcg acc       2031
His Leu Arg Glu Leu Gln Val Gln Asp Ser Thr Leu Ser Glu Ser Thr
    640                 645                 650 ttt gtg acc tgg tgt aac cag ctg agg cat ccc agc tgt cgc ctt cag       2079
Phe Val Thr Trp Cys Asn Gln Leu Arg His Pro Ser Cys Arg Leu Gln
655                 660                 665                 670 aag ctt gga ata aat aac gtt tcc ttt tct ggc cag agt gtt ctg ctc       2127
Lys Leu Gly Ile Asn Asn Val Ser Phe Ser Gly Gln Ser Val Leu Leu
                675                 680                 685 ttt gag gtg ctc ttt tat cag cca gac ttg aaa tac ctg agc ttc acc       2175
Phe Glu Val Leu Phe Tyr Gln Pro Asp Leu Lys Tyr Leu Ser Phe Thr
            690                 695                 700 ctc acg aaa ctc tct cgt gat gac atc agg tcc ctc tgt gat gcc ttg       2223
Leu Thr Lys Leu Ser Arg Asp Asp Ile Arg Ser Leu Cys Asp Ala Leu
        705                 710                 715 aac tac cca gca ggc aac gtc aaa gag cta gcg ctg gta aat tgt cac       2271
Asn Tyr Pro Ala Gly Asn Val Lys Glu Leu Ala Leu Val Asn Cys His
    720                 725                 730 ctc tca ccc att gat tgt gaa gtc ctt gct ggc ctt cta acc aac aac       2319
Leu Ser Pro Ile Asp Cys Glu Val Leu Ala Gly Leu Leu Thr Asn Asn
735                 740                 745                 750 aag aag ctg acg tat ctg aat gta tcc tgc aac cag tta gac aca ggc       2367
Lys Lys Leu Thr Tyr Leu Asn Val Ser Cys Asn Gln Leu Asp Thr Gly
                755                 760                 765 gtg ccc ctt ttg tgt gaa gcc ctg tgc agc cca gac acg gtc ctg gta       2415
Val Pro Leu Leu Cys Glu Ala Leu Cys Ser Pro Asp Thr Val Leu Val
            770                 775                 780 tac ctg atg ttg gct ttc tgc cac ctc agc gag cag tgc tgc gaa tac       2463
Tyr Leu Met Leu Ala Phe Cys His Leu Ser Glu Gln Cys Cys Glu Tyr
        785                 790                 795 atc tct gaa atg ctt ctg cgt aac aag agc gtg cgc tat cta gac ctc       2511
Ile Ser Glu Met Leu Leu Arg Asn Lys Ser Val Arg Tyr Leu Asp Leu
    800                 805                 810 agt gcc aat gtc ctg aag gac gaa gga ctg aaa act ctc tgc gag gcc       2559
Ser Ala Asn Val Leu Lys Asp Glu Gly Leu Lys Thr Leu Cys Glu Ala
815                 820                 825                 830 ttg aaa cat ccg gac tgc tgc ctg gat tca ctg tgt ttg gta aaa tgt       2607
Leu Lys His Pro Asp Cys Cys Leu Asp Ser Leu Cys Leu Val Lys Cys
                835                 840                 845 ttt atc act gct gct ggc tgt gaa gac ctc gcc tct gct ctc atc agc       2655
Phe Ile Thr Ala Ala Gly Cys Glu Asp Leu Ala Ser Ala Leu Ile Ser
            850                 855                 860 aat caa aac ctg aag att ctg caa att ggg tgc aat gaa atc gga gat       2703
Asn Gln Asn Leu Lys Ile Leu Gln Ile Gly Cys Asn Glu Ile Gly Asp
        865                 870                 875
```

-continued

| | | |
|---|---|---|
| gtg ggt gtg cag ctg ttg tgt cgg gct ctg acg cat acg gat tgc cgc<br>Val Gly Val Gln Leu Leu Cys Arg Ala Leu Thr His Thr Asp Cys Arg<br>880      885      890 | | 2751 |
| tta gag att ctt ggg ttg gaa gaa tgt ggg tta acg agc acc tgc tgt<br>Leu Glu Ile Leu Gly Leu Glu Glu Cys Gly Leu Thr Ser Thr Cys Cys<br>895      900      905      910 | | 2799 |
| aag gat ctc gcg tct gtt ctc acc tgc agt aag acc ctg cag cag ctc<br>Lys Asp Leu Ala Ser Val Leu Thr Cys Ser Lys Thr Leu Gln Gln Leu<br>      915      920      925 | | 2847 |
| aac ctg acc ttg aac acc ttg gac cac aca ggg gtg gtt gta ctc tgt<br>Asn Leu Thr Leu Asn Thr Leu Asp His Thr Gly Val Val Val Leu Cys<br>930      935      940 | | 2895 |
| gag gcc ctg aga cac cca gag tgt gcc ctg cag gtg ctc ggg ctg aga<br>Glu Ala Leu Arg His Pro Glu Cys Ala Leu Gln Val Leu Gly Leu Arg<br>945      950      955 | | 2943 |
| aaa act gat ttt gat gag gaa acc cag gca ctt ctg acg gct gag gaa<br>Lys Thr Asp Phe Asp Glu Glu Thr Gln Ala Leu Leu Thr Ala Glu Glu<br>960      965      970 | | 2991 |
| gag aga aat cct aac ctg acc atc aca gat gac tgt gac aca atc aca<br>Glu Arg Asn Pro Asn Leu Thr Ile Thr Asp Asp Cys Asp Thr Ile Thr<br>975      980      985      990 | | 3039 |
| agg gta gag atc tgattgcgag gaacctgggc tctgactcga acacctgcaa<br>Arg Val Glu Ile | | 3091 |
| aggacaggga ctgggaccgt tacttacatg acactgcacc caggagatac aaatcattga | | 3151 |
| cactctgagt tgtgagattt ctggcacccc attcatagat ttgatatgat acacgtggtt | | 3211 |
| tttatgtgct ctgtggcctt ggatgagtca ctgaaaggcc ttcatggtct ctcggtctca | | 3271 |
| caaggacctc ttaacccctc aataaagtgt tacatttcta acattggaa aaaaaaaaa | | 3331 |
| aaaaaaaaaa aaaaaaaaaa aaaaaaaaa aaaaaaa | | 3368 |

<210> SEQ ID NO 24
<211> LENGTH: 994
<212> TYPE: PRT
<213> ORGANISM: Homo sapiens

<400> SEQUENCE: 24

Met Ala Ala Ser Phe Phe Ser Asp Phe Gly Leu Met Trp Tyr Leu Glu
1      5      10      15

Glu Leu Lys Lys Glu Glu Phe Arg Lys Phe Lys Glu His Leu Lys Gln
      20      25      30

Met Thr Leu Gln Leu Glu Leu Lys Gln Ile Pro Trp Thr Glu Val Lys
    35      40      45

Lys Ala Ser Arg Glu Glu Leu Ala Asn Leu Leu Ile Lys His Tyr Glu
  50      55      60

Glu Gln Gln Ala Trp Asn Ile Thr Leu Arg Ile Phe Gln Lys Met Asp
65      70      75      80

Arg Lys Asp Leu Cys Met Lys Val Met Arg Glu Arg Thr Gly Tyr Thr
      85      90      95

Lys Thr Tyr Gln Ala His Ala Lys Gln Lys Phe Ser Arg Leu Trp Ser
      100      105      110

Ser Lys Ser Val Thr Glu Ile His Leu Tyr Phe Glu Glu Val Lys
    115      120      125

Gln Glu Glu Cys Asp His Leu Asp Arg Leu Phe Ala Pro Lys Glu Thr
  130      135      140

Gly Lys Gln Pro Arg Thr Val Ile Ile Gln Gly Pro Gln Gly Ile Gly
145      150      155      160

-continued

```
Lys Thr Thr Leu Leu Met Lys Leu Met Met Ala Trp Ser Asp Asn Lys
            165                 170                 175

Ile Phe Arg Asp Arg Phe Leu Tyr Thr Phe Tyr Phe Cys Cys Arg Glu
            180                 185                 190

Leu Arg Glu Leu Pro Pro Thr Ser Leu Ala Asp Leu Ile Ser Arg Glu
            195                 200                 205

Trp Pro Asp Pro Ala Ala Pro Ile Thr Glu Ile Val Ser Gln Pro Glu
210                 215                 220

Arg Leu Leu Phe Val Ile Asp Ser Phe Glu Glu Leu Gln Gly Gly Leu
225                 230                 235                 240

Asn Glu Pro Asp Ser Asp Leu Cys Gly Asp Leu Met Glu Lys Arg Pro
            245                 250                 255

Val Gln Val Leu Leu Ser Ser Leu Leu Arg Lys Lys Met Leu Pro Glu
            260                 265                 270

Ala Ser Leu Leu Ile Ala Ile Lys Pro Val Cys Pro Lys Glu Leu Arg
            275                 280                 285

Asp Gln Val Thr Ile Ser Glu Ile Tyr Gln Pro Arg Gly Phe Asn Glu
            290                 295                 300

Ser Asp Arg Leu Val Tyr Phe Cys Cys Phe Phe Lys Asp Pro Lys Arg
305                 310                 315                 320

Ala Met Glu Ala Phe Asn Leu Val Arg Glu Ser Glu Gln Leu Phe Ser
            325                 330                 335

Ile Cys Gln Ile Pro Leu Leu Cys Trp Ile Leu Cys Thr Ser Leu Lys
            340                 345                 350

Gln Glu Met Gln Lys Gly Lys Asp Leu Ala Leu Thr Cys Gln Ser Thr
            355                 360                 365

Thr Ser Val Tyr Ser Ser Phe Val Phe Asn Leu Phe Thr Pro Glu Gly
370                 375                 380

Ala Glu Gly Pro Thr Pro Gln Thr Gln His Gln Leu Lys Ala Leu Cys
385                 390                 395                 400

Ser Leu Ala Ala Glu Gly Met Trp Thr Asp Thr Phe Glu Phe Cys Glu
            405                 410                 415

Asp Asp Leu Arg Arg Asn Gly Val Val Asp Ala Asp Ile Pro Ala Leu
            420                 425                 430

Leu Gly Thr Lys Ile Leu Leu Lys Tyr Gly Glu Arg Glu Ser Ser Tyr
            435                 440                 445

Val Phe Leu His Val Cys Ile Gln Glu Phe Cys Ala Ala Leu Phe Tyr
            450                 455                 460

Leu Leu Lys Ser His Leu Asp His Pro His Pro Ala Val Arg Cys Val
465                 470                 475                 480

Gln Glu Leu Leu Val Ala Asn Phe Glu Lys Ala Arg Arg Ala His Trp
            485                 490                 495

Ile Phe Leu Gly Cys Phe Leu Thr Gly Leu Leu Asn Lys Lys Glu Gln
            500                 505                 510

Glu Lys Leu Asp Ala Phe Phe Gly Phe Gln Leu Ser Gln Glu Ile Lys
            515                 520                 525

Gln Gln Ile His Gln Cys Leu Lys Ser Leu Gly Glu Arg Gly Asn Pro
            530                 535                 540

Gln Gly Gln Val Asp Ser Leu Ala Ile Phe Tyr Cys Leu Phe Glu Met
545                 550                 555                 560

Gln Asp Pro Ala Phe Val Lys Gln Ala Val Asn Leu Leu Gln Glu Ala
            565                 570                 575

Asn Phe His Ile Ile Asp Asn Val Asp Leu Val Val Ser Ala Tyr Cys
```

-continued

```
                580                 585                 590
Leu Lys Tyr Cys Ser Ser Leu Arg Lys Leu Cys Phe Ser Val Gln Asn
                595                 600                 605
Val Phe Lys Lys Glu Asp Glu His Ser Ser Thr Ser Asp Tyr Ser Leu
            610                 615                 620
Ile Cys Trp His His Ile Cys Ser Val Leu Thr Thr Ser Gly His Leu
625                 630                 635                 640
Arg Glu Leu Gln Val Gln Asp Ser Thr Leu Ser Glu Ser Thr Phe Val
                    645                 650                 655
Thr Trp Cys Asn Gln Leu Arg His Pro Ser Cys Arg Leu Gln Lys Leu
                660                 665                 670
Gly Ile Asn Asn Val Ser Phe Ser Gly Gln Ser Val Leu Leu Phe Glu
                    675                 680                 685
Val Leu Phe Tyr Gln Pro Asp Leu Lys Tyr Leu Ser Phe Thr Leu Thr
                690                 695                 700
Lys Leu Ser Arg Asp Asp Ile Arg Ser Leu Cys Asp Ala Leu Asn Tyr
705                 710                 715                 720
Pro Ala Gly Asn Val Lys Glu Leu Ala Leu Val Asn Cys His Leu Ser
                    725                 730                 735
Pro Ile Asp Cys Glu Val Leu Ala Gly Leu Leu Thr Asn Asn Lys Lys
                740                 745                 750
Leu Thr Tyr Leu Asn Val Ser Cys Asn Gln Leu Asp Thr Gly Val Pro
                755                 760                 765
Leu Leu Cys Glu Ala Leu Cys Ser Pro Asp Thr Val Leu Val Tyr Leu
        770                 775                 780
Met Leu Ala Phe Cys His Leu Ser Glu Gln Cys Cys Glu Tyr Ile Ser
785                 790                 795                 800
Glu Met Leu Leu Arg Asn Lys Ser Val Arg Tyr Leu Asp Leu Ser Ala
                    805                 810                 815
Asn Val Leu Lys Asp Glu Gly Leu Lys Thr Leu Cys Glu Ala Leu Lys
                820                 825                 830
His Pro Asp Cys Cys Leu Asp Ser Leu Cys Leu Val Lys Cys Phe Ile
                835                 840                 845
Thr Ala Ala Gly Cys Glu Asp Leu Ala Ser Ala Leu Ile Ser Asn Gln
        850                 855                 860
Asn Leu Lys Ile Leu Gln Ile Gly Cys Asn Glu Ile Gly Asp Val Gly
865                 870                 875                 880
Val Gln Leu Leu Cys Arg Ala Leu Thr His Thr Asp Cys Arg Leu Glu
                    885                 890                 895
Ile Leu Gly Leu Glu Glu Cys Gly Leu Thr Ser Thr Cys Cys Lys Asp
                    900                 905                 910
Leu Ala Ser Val Leu Thr Cys Ser Lys Thr Leu Gln Gln Leu Asn Leu
            915                 920                 925
Thr Leu Asn Thr Leu Asp His Thr Gly Val Val Leu Cys Glu Ala
        930                 935                 940
Leu Arg His Pro Glu Cys Ala Leu Gln Val Leu Gly Leu Arg Lys Thr
945                 950                 955                 960
Asp Phe Asp Glu Glu Thr Gln Ala Leu Leu Thr Ala Glu Glu Arg
                965                 970                 975
Asn Pro Asn Leu Thr Ile Thr Asp Cys Asp Thr Ile Thr Arg Val
                980                 985                 990
Glu Ile
```

<210> SEQ ID NO 25
<211> LENGTH: 2982
<212> TYPE: DNA
<213> ORGANISM: Homo sapiens

<400> SEQUENCE: 25

| | | | | | |
|---|---|---|---|---|---|
| atggcagcct | ctttcttctc | tgattttggt | cttatgtggt | atctggagga | gctcaaaaag | 60 |
| gaggagttca | ggaaatttaa | agaacatctc | aagcaaatga | ctttgcagct | tgaactcaag | 120 |
| cagattccct | ggactgaggt | caaaaaagca | tcccgggaag | aacttgcaaa | cctcttgatc | 180 |
| aagcactatg | aagaacaaca | agcttggaac | ataaccttaa | gaatctttca | aaagatggat | 240 |
| agaaaggatc | tctgcatgaa | ggtcatgagg | gagagaacag | gatacacaaa | gacctatcaa | 300 |
| gctcacgcaa | agcagaaatt | cagccgctta | tggtccagca | agtctgtcac | tgagattcac | 360 |
| ctatactttg | aggaggaagt | caagcaagaa | gaatgtgacc | atttggaccg | ccttttttgct | 420 |
| cccaaggaaa | ctgggaaaca | gccacgtaca | gtgattattc | aaggaccaca | aggaattgga | 480 |
| aaaacgacac | tcctgatgaa | gctgatgatg | gcctggtcgg | acaacaagat | ctttcgggat | 540 |
| aggttcctgt | acacgttcta | tttctgctgc | agagaactga | gggagttgcc | gccaacgagt | 600 |
| ttggctgact | tgatttccag | agagtggcct | gaccccgctg | ctcctataac | agagatcgtg | 660 |
| tctcaaccgg | agagactctt | gttcgtcatc | gacagcttcg | aagagctgca | gggcggcttg | 720 |
| aacgaacccg | attcggatct | gtgtggtgac | ttgatggaga | acggccggt | gcaggtgctt | 780 |
| ctgagcagtt | tgctgaggaa | gagatgctcc | cggaggcct | ccctgctcat | cgccatcaaa | 840 |
| cccgtgtgcc | cgaaggagct | ccgggatcag | gtgacgatct | cagaaatcta | ccagccccgg | 900 |
| ggattcaacg | agagtgatag | gttagtgtat | ttctgctgtt | tcttcaaaga | cccgaaaaga | 960 |
| gccatggaag | ccttcaatct | tgtaagagaa | agtgaacagc | tgttttccat | atgccaaatc | 1020 |
| ccgctcctct | gctggatcct | gtgtaccagt | ctgaagcaag | agatgcagaa | aggaaaagac | 1080 |
| ctggccctga | cctgccagag | cactacctct | gtgtactcct | ctttcgtctt | taacctgttc | 1140 |
| acacctgagg | gtgccgaggg | cccgactccg | caaacccagc | accagctgaa | ggccctgtgc | 1200 |
| tccctggctg | cagagggtat | gtggacagac | acatttgagt | tttgtgaaga | cgacctccgg | 1260 |
| agaaatgggg | ttgttgacgc | tgacatccct | gcgctgctgg | gcaccaagat | acttctgaag | 1320 |
| tacggggagc | gtgagagctc | ctacgtgttc | ctccacgtgt | gtatccagga | gttctgtgcc | 1380 |
| gccttgttct | atttgctcaa | gagccacctt | gatcatcctc | acccagctgt | gagatgtgta | 1440 |
| caggaattgc | tagttgccaa | ttttgaaaaa | gcaaggagag | cacattggat | tttttttgggg | 1500 |
| tgttttctaa | ctggcctttt | aaataaaaag | gaacaagaaa | aactggatgc | gttttttggc | 1560 |
| ttccaactgt | cccaagagat | aaagcagcaa | attcaccagt | gcctgaagag | cttaggggag | 1620 |
| cgtggcaatc | tcagggaca | ggtggattcc | ttggcgatat | tttactgtct | ctttgaaatg | 1680 |
| caggatcctg | cctttgtgaa | gcaggcagtg | aacctcctcc | aagaagctaa | cttcatatt | 1740 |
| attgacaacg | tggacttggt | ggtttctgcc | tactgcttaa | atactgctc | cagcttgagg | 1800 |
| aaactctgtt | tttccgttca | aaatgtcttt | aagaaagagg | atgaacacag | ctctacgtcg | 1860 |
| gattacagcc | tcatctgttg | gcatcacatc | tgctctgtgc | tcaccaccag | cgggcacctc | 1920 |
| agagagctcc | aggtgcagga | cagcaccctc | agcgagtcga | cctttgtgac | ctggtgtaac | 1980 |
| cagctgaggc | atcccagctg | tcgccttcag | aagcttggaa | taataacgt | ttccttttct | 2040 |
| ggccagagtg | ttctgctctt | tgaggtgctc | ttttatcagc | cagacttgaa | atacctgagc | 2100 |
| ttcacccctca | cgaaactctc | tcgtgatgac | atcaggtccc | tctgtgatgc | cttgaactac | 2160 |

```
ccagcaggca acgtcaaaga gctagcgctg gtaaattgtc acctctcacc cattgattgt    2220
gaagtccttg ctggccttct aaccaacaac aagaagctga cgtatctgaa tgtatcctgc    2280
aaccagttag acacaggcgt gcccctttttg tgtgaagccc tgtgcagccc agacacggtc   2340
ctggtatacc tgatgttggc tttctgccac ctcagcgagc agtgctgcga atacatctct    2400
gaaatgcttc tgcgtaacaa gagcgtgcgc tatctagacc tcagtgccaa tgtcctgaag    2460
gacgaaggac tgaaaactct ctgcgaggcc ttgaaacatc cggactgctg cctggattca    2520
ctgtgtttgg taaatgtttt tatcactgct gctggctgtg aagacctcgc ctctgctctc    2580
atcagcaatc aaaacctgaa gattctgcaa attgggtgca atgaaatcgg agatgtgggt    2640
gtgcagctgt tgtgtcgggc tctgacgcat acggattgcc gcttagagat tcttgggttg    2700
gaagaatgtg ggttaacgag cacctgctgt aaggatctcg cgtctgttct cacctgcagt    2760
aagaccctgc agcagctcaa cctgaccttg aacaccttgg accacacagg ggtggttgta    2820
ctctgtgagg ccctgagaca cccagagtgt gccctgcagg tgctcgggct gagaaaaact    2880
gattttgatg aggaaaccca ggcacttctg acggctgagg aagagagaaa tcctaacctg    2940
accatcacag atgactgtga cacaatcaca agggtagaga tc                       2982
```

MOLECULES OF THE PYRIN/NBS/LRR PROTEIN FAMILY AND USES THEREOF

RELATED APPLICATIONS

This application is a continuation-in-part and claims priority to U.S. application Ser. No. 10/066,521, filed on Jan. 31, 2002, which claims priority to U.S. provisional application No. 60/265,231, filed on Jan. 31, 2001, and U.S. provisional application No. 60/318,645, filed on Sep. 10, 2001, the contents of which are incorporated herein by reference.

BACKGROUND OF THE INVENTION

Many cytoplasmic plant proteins involved in plant resistance to pathogens, generally referred to as "R" proteins, possess both a nucleotide binding site (NBS) and a leucine rich repeat (LRR). R proteins are involved in both a rapid defense response (hypersensitive response) and more long-term nonspecific resistance (systemic acquired resistance). The hypersensitive response involves a form of programmed death localized to the site of infection and changes in gene expression that are thought to prevent further infection. The LRR of the R proteins is believed to recognize and bind to pathogen-derived proteins, triggering the defensive responses and resulting in a rapid and localized host cell death. Many R proteins have an amino terminal effector domain (e.g., a TIR domain or a leucine zipper domain) that is thought to play a role in downstream signaling of events triggered by infection and, possibly, other stresses.

The R proteins are structurally similar to APAF-1, which mediates the activation of caspases, the proteases directly responsible for the degradation of cellular proteins that leads to the morphological changes seen in cells undergoing apoptosis. A domain, designated the NB-ARC domain ("nucleotide-binding adaptor shared by APAF-1, certain R gene products and CED-4"), contains a series of motifs and residues that are conserved among plant resistance proteins (e.g., R proteins) and regulators of cell death (e.g., APAF-1 and CED-4) (van der Bizen and Jones (1999) Current Biology 8:226–228). In addition to the NBS, APAF-1 has a CARD domain, functionally analogous to the effector domain of R proteins, and a WD-40 domain, functionally analogous to the LRR domain of R proteins.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA.

The various signals that trigger apoptosis are thought to bring about these events by converging on a common cell death pathway, the core components of which are highly conserved from worms, such as *C. elegans*, to humans. In fact, invertebrate model systems have been invaluable tools in identifying and characterizing the genes that control apoptosis. Despite this conservation of certain core components, apoptotic signaling in mammals is much more complex than in invertebrates. For example, in mammals there are multiple homologues of the core components in the cell death signaling pathway.

Caspases, a class of proteins central to the apoptotic program, are responsible for the degradation of cellular proteins that leads to the morphological changes seen in cells undergoing apoptosis. Caspases (cysteinyl aspartate-specific proteinases) are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an autoproteolytic mechanism that is often dependent upon oligomerization directed by association of the caspase with an adapter molecule.

Nuclear factor-κB (NF-κB) is a transcription factor expressed in many cell types and which activates homologous or heterologous genes that have κB sites in their promoters. Molecules that regulate NF-κB activation play a critical role in both apoptosis and inflammation. Quiescent NF-κB resides in the cytoplasm as a heterodimer of proteins referred to as p50 and p65 and is complexed with the regulatory protein IκB. NF-κB binding to IκB causes NF-κB to remain in the cytoplasm. At least two dozen stimuli that activate NF-κB are known (New England Journal of Medicine 336:1066, 1997) and they include cytokines, protein kinase C activators, oxidants, viruses, and immune system stimuli. NF-κB activating stimuli activate specific IκB kinases that phosphorylate IκB leading to its degradation. Once liberated from IκB, NF-κB translocates to the nucleus and activates genes with κB sites in their promoters. The proinflammatory cytokines TNF-α and IL-1 induce NF-κB activation by binding their cell-surface receptors and activating the NF-κB-inducing kinase, NIK, and NF-κB. NIK phosphorylates the IκB kinases α and β which phosphorylate IκB, leading to its degradation.

NF-κB and the NF-κB pathway has been implicated in mediating chronic inflammation in inflammatory diseases such as asthma, ulcerative colitis, rheumatoid arthritis (Epstein, New England Journal of Medicine 336:1066, 1997) and inhibiting NF-κB or NF-κB pathways may be an effective way of treating these diseases. NF-κB and the NF-κB pathway has also been implicated in atherosclerosis (Navab et al., American Journal of Cardiology 76:18C, 1995), especially in mediating fatty streak formation, and inhibiting NF-κB or NF-κB pathways may be an effective therapy for atherosclerosis. Among the genes activated by NF-κB are cIAP-1, cIAP-2, TRAF1, and TRAF2, all of which have been shown to protect cells from TNF-α induced cell death (Wang et al., Science 281:1680–83, 1998). CLAP, a protein which includes a CARD, activates the Apaf-1-caspase-9 pathway and activates NF-κB by acting upstream of NIK and IκB kinase (Srinivasula et al., supra).

CARD-4 is a member of the CED-4/Apaf-1 family that interacts with RICK, a serine threonine kinase, and induces NF-κB via the signaling protein TRAF-6 and NIK (Bertin et al. (1999) J. Biol. Chem. 274:12955). CARD-4 includes domains that are similar to the nucleotide binding site domain (NBS) and leucine rich repeat (LRR) domains found in plant R proteins that mediate resistance to pathogens.

SUMMARY OF THE INVENTION

The invention features nucleic acid molecules encoding human PYRIN-2, human PYRIN-3, human PYRIN-5, human PYRIN-6, human PYRIN-7, human PYRIN-8, human PYRIN-10, and human PYRIN-11.

Each of PYRIN-2, PYRIN-3, PYRIN-5, PYRIN-6, PYRIN-7, PYRIN-8, PYRIN-10, and PYRIN-11 has a pyrin domain, so-named for its homology to a portion of pyrin (marenostrin). Mutations in the pyrin gene are associated with familial Mediterranean fever (FMF), an inherited inflammatory disease.

Each of PYRIN-2, PYRIN-3, PYRIN-5, PYRIN-7, PYRIN-8, and PYRIN-11 has a nucleotide binding site (NBS) domain, which is present in a number of proteins that transmit signals which activate apoptotic and inflammatory pathways in response to stress and other stimuli.

Each of PYRIN-2, PYRIN-3, PYRIN-5, PYRIN-8, PYRIN-10, and PYRIN-11 has a leucine rich repeat domain (LRR) domain, another domain present in a number of proteins involved in apoptotic and inflammatory pathways.

The predicted cDNA described herein encoding PYRIN-6 is truncated in the homologous regions of PYRIN-2, PYRIN-3, PYRIN-5, PYRIN-7, PYRIN-8, PYRIN-10, and PYRIN-11 that encode a NBS domain and an LRR domain. The full length PYRIN-6 cDNA may encode NBS domains and LRR domains. The predicted cDNA described herein encoding PYRIN-10 is truncated in the homologous regions of PYRIN-2, PYRIN-3, PYRIN-5, PYRIN-7, PYRIN-8, and PYRIN-11 that encode a NBS domain. The full length PYRIN-10 cDNA is predicted to encode a NBS domain. The predicted cDNA described herein encoding PYRIN-7 is truncated in the homologous regions of PYRIN-2, PYRIN-3, PYRIN-5, PYRIN-8, PYRIN-10, and PYRIN-11 that encode a LRR domain. The full length PYRIN-7 cDNA is predicted to encode a LRR domain.

PYRIN-2, PYRIN-3, PYRIN-5, PYRIN-6, PYRIN-7, PYRIN-8, PYRIN-10, and PYRIN-11 nucleic acids and polypeptides, as well as modulators of PYRIN-2, PYRIN-3, PYRIN-5, PYRIN-6, PYRIN-7, PYRIN-8, PYRIN-10, or PYRIN-11 activity or expression, are expected to be useful in the modulation of stress-related, apoptotic and inflammatory responses, e.g., for the treatment of apoptotic and inflammatory disorders. In addition, PYRIN-2, PYRIN-3, PYRIN-5, PYRIN-6, PYRIN-7, PYRIN-8, PYRIN-10, and PYRIN-11 nucleic acids and polypeptides are expected to be useful in the diagnosis of apoptotic and inflammatory disorders as well as in screening assays which can be used to identify compounds which can be used to modulate stress-related, apoptotic and inflammatory responses.

NBS-1, NBS-2, NBS-3, PYRIN-12/NBS-4, NBS-5, and Pyrin-1 have a pyrin domain, a NBS domain, and a LRR domain. As described herein, the pyrin domain is an effector domain thought to be involved in homophilic protein-protein interactions. Detailed information concerning NBS-1, NBS-2, NBS-3, PYRIN-12/NBS-4, NBS-5, and Pyrin-1 can be found in U.S. application Ser. No. 09/506,067, filed Feb. 17, 2000, U.S. application Ser. No. 09/506,067, filed Sep. 1, 2000, and U.S. application Ser. No. 09/848,035, filed May 3, 2001, all of which are incorporated herein by reference.

CARD-4, CARD-7, and CARD-12 have both an NBS domain and an LRR domain as well as a CARD domain (detailed information concerning CARD-4, CARD-7, and CARD-12 can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, U.S. application Ser. No. 09/428,252, filed Oct. 27, 1999, U.S. application Ser. No. 60/161,822, filed Oct. 27, 1999, and U.S. application Ser. No. 09/841,739, filed Apr. 24, 2001, all of which are incorporated herein by reference). The CARD domain, which is present in a number of apoptotic signaling molecules, is an effector domain that is thought to be involved in homophilic protein-protein interactions, e.g., with downstream CARD-containing signaling molecules. For example, the CARD domain of CARD-4 interacts with the CARD domain of RICK (RIP2, CARDIAK), a serine-threonine kinase that activates NF-κB signaling pathways.

In general, an NBS domain includes a kinase 1a domain (P-loop), a kinase 2 domain (Walker B box) and a kinase 3a domain. PYRIN-2, PYRIN-3, PYRIN-5, PYRIN-6, PYRIN-7, PYRIN-8, PYRIN-10, and PYRIN-11 are believed to belong to the NACHT (NAIP, CIIA, HET-E and TP1) subfamily of NBS-domain containing proteins. Members of the NACHT subfamily contain additional motifs common among subfamily members (see, e.g., Koonin et al. (2000) Trends Biochem. Sci. 25:223). NACHT NTPase subfamily members have been implicated in apoptosis and MHC transcription activation. Other members of the NACHT NTPase subfamily include CARD-4, CARD-7, NAIP, NBS-1, NBS-2, NBS-3, PYRIN-12/NBS-4, NBS-5, and Pyrin-1.

An LRR domain usually is composed of several leucine rich repeats.

Without being bound by a particular theory, it is possible that the LRR domain of PYRIN-2, PYRIN-3, PYRIN-5, PYRIN-6, PYRIN-7, PYRIN-8, PYRIN-10, or PYRIN-11 interacts with an upstream signaling molecule that is associated with stress, infection, and/or inflammation. This interaction triggers a conformational change in PYRIN-2, PYRIN-3, PYRIN-5, PYRIN-6, PYRIN-7, PYRIN-8, PYRIN-10, or PYRIN-11 that exposes an effector domain, e.g., the pyrin domain of PYRIN-2, PYRIN-3, PYRIN-5, PYRIN-6, PYRIN-7, PYRIN-8, PYRIN-10, or PYRIN-11. The exposed effector domain then mediates interaction with a downstream signaling molecule or molecules to transmit a stress-related, apoptotic or inflammatory signal. In this model, the conformational change is dependent upon hydrolysis of a nucleotide triphosphate (ATP or GTP) bound to the NBS domain. Based on this model, full-length PYRIN-6, PYRIN-7, and PYRIN-10 are expected to include NBS domains and LRR domains.

PYRIN-2, PYRIN-3, PYRIN-5, PYRIN-6, PYRIN-7, PYRIN-8, PYRIN-10, and PYRIN-11 molecules are useful as modulating agents in regulating a variety of cellular processes including cell growth and cell death. In one aspect, this invention provides isolated nucleic acid molecules encoding PYRIN-2, PYRIN-3, PYRIN-5, PYRIN-6, PYRIN-7, PYRIN-8, PYRIN-10, or PYRIN-11 proteins or biologically active portions thereof, as well as nucleic acid fragments suitable as primers or hybridization probes for the detection of PYRIN-2, PYRIN-3, PYRIN-5, PYRIN-6, PYRIN-7, PYRIN-8, PYRIN-10, or PYRIN-11 encoding nucleic acids.

PYRIN-2, PYRIN-3, PYRIN-5, PYRIN-6, PYRIN-7, PYRIN-8, PYRIN-10, or PYRIN-11 polypeptides, nucleic acids and modulators of PYRIN-2, PYRIN-3, PYRIN-5, PYRIN-6, PYRIN-7, PYRIN-8, PYRIN-10, or PYRIN-11 expression or activity can be useful for modulating an inflammatory response, modulating NF-κB activation, modulating an apoptotic response, treating inflammatory disorders, e.g., auto-inflammatory disorders and disorders associated with an inappropriate level of apoptosis, and treating immune system disorders. The inflammatory and immune disorders include, but are not limited to, chronic inflammatory diseases and disorders and/or inflammatory bowel disorders, such as Crohn's disease, ulcerative colitis, reactive arthritis, rheumatoid arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, respiratory inflammatory diseases and disorders, such as asthma and chronic obstructive pulmonary disease, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Ischemia is often accompanied by inflammation that causes cell death. Because PYRIN-2, PYRIN-3, PYRIN-5, PYRIN-6, PYRIN-7, PYRIN-8, PYRIN-10, and PYRIN-11 are expected to play a role in stress-related response, inflammation and apoptosis, PYRIN-2, PYRIN-3, PYRIN-5, PYRIN-6, PYRIN-7, PYRIN-8, PYRIN-10, or PYRIN-11 polypeptides, nucleic acids, and modulators of PYRIN-2, PYRIN-3, PYRIN-5, PYRIN-6, PYRIN-7, PYRIN-8, PYRIN-10, or PYRIN-11 expression or activity can be used to treat cells death accompanying inflammatory responses triggered by ischemia.

Invasive infection with Gram-negative bacteria and Gram-positive bacteria often results in septic shock. PYRIN-2, PYRIN-3, PYRIN-5, PYRIN-6, PYRIN-7, PYRIN-8, PYRIN-10, and PYRIN-11 may recognize and bind components of Gram-negative bacteria and Gram-positive bacteria or other infectious agents (e.g., intracellular parasites), triggering an inflammatory response. Thus, PYRIN-2, PYRIN-3, PYRIN-5, PYRIN-6, PYRIN-7, PYRIN-8, PYRIN-10, and PYRIN-11 may play a role in innate immune system responses that is similar to that of Toll-like receptor 2 (TLR2), a receptor which has some structural similarity to plant R proteins and IL-1R. TLR2 is a signaling receptor that, in association with CD14, is activated by LPS in a response that requires LPS-binding protein. The interaction of TLR2 with LPS leads to TLR2 oligomerization and recruitment of IRAK (Yang et al. (1998) Nature 395:284–88; Yang et al (1999) J. Immunol. 163:639–43; and Yoshimura et al. (1999) J. Immunol. 163: 105). Thus, TLR2 is thought to be a direct mediator of signaling by LPS. TLR2 is also thought to mediate cell activation induced by peptidoglycan and lipoteichoic acid, the main stimulatory components of Gram-positive bacteria (Schwandner et al. (1999) J. Biol. Chem. 274:17406–09).

In addition to the aforementioned disorders, PYRIN-2, PYRIN-3, PYRIN-5, PYRIN-6, PYRIN-7, PYRIN-8, PYRIN-10, or PYRIN-11 polypeptides, nucleic acids, and modulators of PYRIN-2, PYRIN-3, PYRIN-5, PYRIN-6, PYRIN-7, PYRIN-8, PYRIN-10, or PYRIN-11 expression or activity can be used to treat septic shock and other disorders associated with an innate immune response. For example, PYRIN-2, PYRIN-3, PYRIN-5, PYRIN-6, PYRIN-7, PYRIN-8, PYRIN-10, or PYRIN-11 may bind to a component of an intracellular infectious agent or a component of an infectious agent that is brought into a cell expressing PYRIN-2, PYRIN-3, PYRIN-5, PYRIN-6, PYRIN-7, PYRIN-8, PYRIN-10, or PYRIN-11, e.g., a component that enters a cell through a receptor or is expressed by a viral gene.

The invention encompasses methods of diagnosing and treating patients who are suffering from a disorder associated with an abnormal level or rate (undesirably high or undesirably low) of apoptotic cell death, abnormal activity of stress-related pathways of the endoplasmic reticulum (ER), abnormal activity of the Fas/APO-1 receptor complex, abnormal activity of the TNF receptor complex, or abnormal activity of a caspase by administering a compound that modulates the expression of PYRIN-2, PYRIN-3, PYRIN-5, PYRIN-6, PYRIN-7, PYRIN-8, PYRIN-10, or PYRIN-11 (at the DNA, mRNA or protein level, e.g., by altering mRNA splicing) or by altering the activity of PYRIN-2, PYRIN-3, PYRIN-5, PYRIN-6, PYRIN-7, PYRIN-8, PYRIN-10, or PYRIN-11. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. PYRIN-2, PYRIN-3, PYRIN-5, PYRIN-6, PYRIN-7, PYRIN-8, PYRIN-10, or PYRIN-11 and compounds that modulate the expression or activity of PYRIN-2, PYRIN-3, PYRIN-5, PYRIN-6, PYRIN-7, PYRIN-8, PYRIN-10, or PYRIN-11 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat infections such as infections by bacteria, fungus, parasites, or viruses (such as those caused by herpesviruses, poxyiruses, and adenoviruses). Failure to remove autoimmune cells that arise during development or that develop as a result of somatic mutation during an immune response can result in autoimmune disease. Thus, an autoimmune disorder can be caused by an undesirably low level of apoptosis. Accordingly, PYRIN-2, PYRIN-3, PYRIN-5, PYRIN-6, PYRIN-7, PYRIN-8, PYRIN-10, or PYRIN-11 and modulators of PYRIN-2, PYRIN-3, PYRIN-5, PYRIN-6, PYRIN-7, PYRIN-8, PYRIN-10, or PYRIN-11 activity or expression can be used to treat autoimmune disorders (e.g., systemic lupus erythematosis, immune-mediated glomerulonephritis, and arthritis).

Many diseases are associated with an undesirably high rate of apoptosis. PYRIN-2, PYRIN-3, PYRIN-5, PYRIN-6, PYRIN-7, PYRIN-8, PYRIN-10, or PYRIN-11 and modulators of PYRIN-2, PYRIN-3, PYRIN-5, PYRIN-6, PYRIN-7, PYRIN-8, PYRIN-10, or PYRIN-11 expression or activity can be used to treat or diagnose such disorders. A wide variety of neurological diseases are characterized by the gradual loss of specific sets of neurons. Such disorders include Alzheimer's disease, Parkinson's disease, amyotrophic lateral sclerosis (ALS), retinitis pigmentosa, spinal muscular atrophy, Huntington's disease, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarction and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. Additional diseases associated with an undesirably high rate of apoptosis include: ischemic and hypoxic brain injury, traumatic and excitotoxic brain damage, neuronal transplantation, acute bacterial meningitis, kidney ischemia/reperfusion injury, and liver disease.

PYRIN-2, PYRIN-3, PYRIN-5, PYRIN-6, PYRIN-7, PYRIN-8, PYRIN-10, or PYRIN-11 and modulators of PYRIN-2, PYRIN-3, PYRIN-5, PYRIN-6, PYRIN-7, PYRIN-8, PYRIN-10, or PYRIN-11 may therefore be useful in treating and diagnosing these conditions.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

In addition to the aforementioned disorders, PYRIN-2, PYRIN-3, PYRIN-5, PYRIN-6, PYRIN-7, PYRIN-8, PYRIN-10, or PYRIN-11 polypeptides, nucleic acids, and modulators of PYRIN-2, PYRIN-3, PYRIN-5, PYRIN-6, PYRIN-7, PYRIN-8, PYRIN-10, or PYRIN-11 expression or activity can be used to treat disorders of cell signaling and disorders of tissues in which PYRIN-2, PYRIN-3, PYRIN-5, PYRIN-6, PYRIN-7, PYRIN-8, PYRIN-10, or PYRIN-11 is expressed.

The invention features a nucleic acid molecule which is at least 45% (or 55%, 65%, 75%, 85%, 95%, or 98%) identical to the nucleotide sequence shown in SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement thereof.

The invention features a nucleic acid molecule which includes a fragment of at least 150 (300, 325, 350, 375, 400, 425, 450, 500, 550, 600, 650, 700, 800, 900, 1000, 1100, 1200, 1300, 1400, 1500, 1600, 1800, 2000, 2250, 2500, 2750, 3000, 3250, 3500, 3750, or 4000) nucleotides of the nucleotide sequence shown in SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement thereof.

The invention also features a nucleic acid molecule that hybridizes to a nucleic acid molecule consisting of the nucleotide sequence of SEQ ID NO:1, SEQ ID NO:3, SEQ ID NO:5, SEQ ID NO:7, SEQ ID NO:11, SEQ ID NO:12, SEQ ID NO:16, SEQ ID NO:17, SEQ ID NO:19, SEQ ID NO:21, SEQ ID NO:25, or a complement thereof, under conditions of incubation at 45° C. in 6.0×SSC followed by washing in 0.2×SSC/0.1% SDS at 65° C.

In an embodiment, a PYRIN-2 nucleic acid molecule has the nucleotide sequence shown in SEQ ID NO:1.

Also within the invention is a nucleic acid molecule which encodes a fragment of a polypeptide having the amino acid sequence of SEQ ID NO:2.

The invention includes a nucleic acid molecule which encodes a naturally occurring allelic variant of a polypeptide comprising the amino acid sequence of SEQ ID NO:2, wherein the nucleic acid molecule hybridizes to a nucleic acid molecule consisting of SEQ ID NO:1 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:1 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-2 protein having an amino acid sequence that is at least about 65%, preferably 75%, 85%, 95%, or 98% identical to the amino acid sequence of SEQ ID NO:2; an isolated PYRIN-2 protein having an amino acid sequence that is at least about 65%, preferably 75%, 85%, 95%, or 98% identical to the pyrin domain of SEQ ID NO:2 (e.g., about amino acid residues 1–93 of SEQ ID NO:2); an isolated PYRIN-2 protein having an amino acid sequence that is at least about 65%, preferably 75%, 85%, 95%, or 98% identical to the NBS domain of SEQ ID NO:2 (e.g., about amino acids 146–169 of SEQ ID NO:2); an isolated PYRIN-2 protein having an amino acid sequence that is at least about 65%, preferably 75%, 85%, 95%, or 98% identical to the kinase 1a domain of SEQ ID NO:2 (e.g., about amino acids 146–169 of SEQ ID NO:2); an isolated PYRIN-2 protein having an amino acid sequence that is at least about 65%, preferably 75%, 85%, 95%, or 98% identical to the LRR domain of SEQ ID NO:2 (e.g., about amino acids 196–449 of SEQ ID NO:2); and an isolated PYRIN-2 protein having an amino acid sequence that is at least about 65%, preferably 75%, 85%, 95%, or 98% identical to one or more of the leucine rich repeats of SEQ ID NO:2 (e.g., about amino acids residues 196–223, 250–278, 280–307, 308–335, 337–364, 365–392, 394–421, and 422–449 of SEQ ID NO:2).

In an embodiment, a PYRIN-3 nucleic acid molecule has the nucleotide sequence shown in SEQ ID NO:3, SEQ ID NO:23, or SEQ ID NO:25.

Also within the invention is a nucleic acid molecule which encodes a fragment of a polypeptide having the amino acid sequence of SEQ ID NO:4 or SEQ ID NO:24.

The invention includes a nucleic acid molecule which encodes a naturally occurring allelic variant of a polypeptide comprising the amino acid sequence of SEQ ID NO:4 or SEQ ID NO:24, wherein the nucleic acid molecule hybridizes to a nucleic acid molecule consisting of SEQ ID NO:3 or SEQ ID NO:25 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:3 or SEQ ID NO:25 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-3 protein having an amino acid sequence that is at least about 65%, preferably 75%, 85%, 95%, or 98% identical to the amino acid sequence of SEQ ID NO:4 or SEQ ID NO:24; and an isolated PYRIN-3 protein having an amino acid sequence that is at least about 65%, preferably 75%, 85%, 95%, or 98% identical to the pyrin domain of SEQ ID NO:4 or SEQ ID NO:24 (e.g., about amino acid residues 1–83 of SEQ ID NO:4 or SEQ ID NO:24); an isolated PYRIN-3 protein having an amino acid sequence that is at least about 65%, preferably 75%, 85%, 95%, or 98% identical to the NBS domain of SEQ ID NO:24 (e.g., about amino acids 150–466 of SEQ ID NO:24); an isolated PYRIN-3 protein having an amino acid sequence that is at least about 65%, preferably 75%, 85%, 95%, or 98% identical to the kinase 1a domain of SEQ ID NO:24 (e.g., about amino acids 150–172 of SEQ ID NO:24); an isolated PYRIN-3 protein having an amino acid sequence that is at least about 65%, preferably 75%, 85%, 95%, or 98% identical to the Motif II domain of SEQ ID NO:24 (e.g., about amino acids 179–209 of SEQ ID NO:24); an isolated PYRIN-3 protein having an amino acid sequence that is at least about 65%, preferably 75%, 85%, 95%, or 98% identical to the kinase 2 domain of SEQ ID NO:24 (e.g., about amino acids 213–236 of SEQ ID NO:24); an isolated PYRIN-3 protein having an amino acid sequence that is at least about 65%, preferably 75%, 85%, 95%, or 98% identical to the kinase 3a domain of SEQ ID NO:24 (e.g., about amino acids 257–282 of SEQ ID NO:24); an isolated PYRIN-3 protein having an amino acid sequence that is at least about 65%, preferably 75%, 85%, 95%, or 98% identical to the Motif V domain of SEQ ID NO:24 (e.g., about amino acids 333–353 of SEQ ID NO:24); an isolated PYRIN-3 protein having an amino acid sequence that is at least about 65%, preferably 75%, 85%, 95%, or 98% identical to the Motif VI domain of SEQ ID NO:24 (e.g., about amino acids 421–436 of SEQ ID NO:24); an isolated PYRIN-3 protein having an amino acid sequence that is at least about 65%, preferably 75%, 85%, 95%, or 98% identical to the Motif VII domain of SEQ ID NO:24 (e.g., about amino acids 447–466 of SEQ ID NO:24); an isolated PYRIN-3 protein having an amino acid sequence that is at least about 65%, preferably 75%, 85%, 95%, or 98% identical to the LRR domain of SEQ ID NO:24 (e.g., about amino acids 637–947 of SEQ ID NO:24); and an isolated PYRIIN-3 protein having an amino acid sequence that is at least about 65%, preferably 75%, 85%, 95%, or 98% identical to one or more of the leucine rich repeats of SEQ ID NO:24 (e.g., about amino acids residues 637–664, 722–749, 750–776, 806–833, 835–862, 863–890, 892–919, and 920–947 SEQ ID NO:24).

In an embodiment, a PYRIN-5 nucleic acid molecule has the nucleotide sequence shown in SEQ ID NO:5.

Also within the invention is a nucleic acid molecule which encodes a fragment of a polypeptide having the amino acid sequence of SEQ ID NO:6.

The invention includes a nucleic acid molecule which encodes a naturally occurring allelic variant of a polypeptide comprising the amino acid sequence of SEQ ID NO:6, wherein the nucleic acid molecule hybridizes to a nucleic acid molecule consisting of SEQ ID NO:5 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:5 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-5 protein having an amino acid sequence that is at least about 65%, preferably 75%, 85%, 95%, or 98% identical to the amino acid sequence of SEQ ID NO:6; an isolated PYRIN-5 protein having an amino acid sequence that is at least about 65%, preferably 75%, 85%, 95%, or 98% identical to the pyrin domain of SEQ ID NO:6 (e.g., about amino acid residues 1–91 of SEQ ID NO:6); an isolated PYRIN-5 protein having an amino acid sequence that is at least about 65%, preferably 75%, 85%, 95%, or 98% identical to the NBS domain of SEQ ID NO:6 (e.g., about amino acids 188–506 of SEQ ID NO:6); an isolated PYRIN-5 protein having an amino acid sequence that is at least about 65%, preferably 75%, 85%, 95%, or 98% identical to the kinase 1a domain of SEQ ID NO:6 (e.g., about amino acids 188–211 of SEQ ID NO:6); an isolated PYRIN-5 protein having an amino acid sequence that is at least about 65%, preferably 75%, 85%, 95%, or 98% identical to the Motif II domain of SEQ ID NO:6 (e.g., about amino acids 218–248 of SEQ ID NO:6); an isolated PYRIN-5 protein having an amino acid sequence that is at least about 65%, preferably 75%, 85%, 95%, or 98% identical to the kinase 2 domain of SEQ ID NO:6 (e.g., about amino acids 252–275 of SEQ ID NO:6); an isolated PYRIN-5 protein having an amino acid sequence that is at least about 65%, preferably 75%, 85%, 95%, or 98% identical to the kinase 3a domain of SEQ ID NO:6 (e.g., about amino acids 295–320 of SEQ ID NO:6); an isolated PYRIN-5 protein having an amino acid sequence that is at least about 65%, preferably 75%, 85%, 95%, or 98% identical to the Motif V domain of SEQ ID NO:6 (e.g., about amino acids 371–391 of SEQ ID NO:6); an isolated PYRIN-5 protein having an amino acid sequence that is at least about 65%, preferably 75%, 85%, 95%, or 98% identical to the Motif VI domain of SEQ ID NO:6 (e.g., about amino acids 461–476 of SEQ ID NO:6); an isolated PYRIN-5 protein having an amino acid sequence that is at least about 65%, preferably 75%, 85%, 95%, or 98% identical to the Motif VII domain of SEQ ID NO:6 (e.g., about amino acids 487–506 of SEQ ID NO:6); an isolated PYRIN-5 protein having an amino acid sequence that is at least about 65%, preferably 75%, 85%, 95%, or 98% identical to the LRR domain of SEQ ID NO:6 (e.g., about amino acids 688–1056 of SEQ ID NO:6); and an isolated PYRIN-5 protein having an amino acid sequence that is at least about 65%, preferably 75%, 85%, 95%, or 98% identical to one or more of the leucine rich repeats of SEQ ID NO:6 (e.g., about amino acids residues 688–715, 744–771, 773–800, 801–828, 830–857, 858–885, 887–914, 915–942, 944–971, 972–1000, 1001–1028, and 1029–1056 of SEQ ID NO:6).

In an embodiment, a PYRIN-6 nucleic acid molecule has the nucleotide sequence shown in SEQ ID NO:7.

Also within the invention is a nucleic acid molecule which encodes a fragment of a polypeptide having the amino acid sequence of SEQ ID NO:8.

The invention includes a nucleic acid molecule which encodes a naturally occurring allelic variant of a polypeptide comprising the amino acid sequence of SEQ ID NO:8, wherein the nucleic acid molecule hybridizes to a nucleic acid molecule consisting of SEQ ID NO:7 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:7 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-6 protein having an amino acid sequence that is at least about 65%, preferably 75%, 85%, 95%, or 98% identical to the amino acid sequence of SEQ ID NO:8; and an isolated PYRIN-6 protein having an amino acid sequence that is at least about 65%, preferably 75%, 85%, 95%, or 98% identical to the pyrin domain of SEQ ID NO:8 (e.g., about amino acid residues 1–91 of SEQ ID NO:8).

In an embodiment, a PYRIN-7 nucleic acid molecule has the nucleotide sequence shown in SEQ ID NO:9, SEQ ID NO:11 or SEQ ID NO:12.

Also within the invention is a nucleic acid molecule which encodes a fragment of a polypeptide having the amino acid sequence of SEQ ID NO:10 or SEQ ID NO:13.

The invention includes a nucleic acid molecule which encodes a naturally occurring allelic variant of a polypeptide comprising the amino acid sequence of SEQ ID NO:10 or SEQ ID NO:13, wherein the nucleic acid molecule hybridizes to a nucleic acid molecule consisting of SEQ ID NO:9, SEQ ID NO:11, or SEQ ID NO:12 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:9, SEQ ID NO:11, or SEQ ID NO:12 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-7 protein having an amino acid sequence that is at least about 65%, preferably 75%, 85%, 95%, or 98% identical to the amino acid sequence of SEQ ID NO:10 or SEQ ID NO:13; an isolated PYRIN-7 protein having an amino acid sequence that is at least about 65%, preferably 75%, 85%, 95%, or 98% identical to the pyrin domain of SEQ ID NO:10 or SEQ ID NO:13 (e.g., about amino acid residues 1–52 of SEQ ID NO:10 or 1–98 of SEQ ID NO:13); an isolated PYRIN-7 protein having an amino acid sequence that is at least about 65%, preferably 75%, 85%, 95%, or 98% identical to the NBS domain of SEQ ID NO:10 or SEQ ID NO:13 (e.g., about amino acids 167–480 of SEQ ID NO:13); an isolated PYRIN-7 protein having an amino acid sequence that is at least about 65%, preferably 75%, 85%, 95%, or 98% identical to the kinase 1a domain of SEQ ID NO:10 or SEQ ID NO:13 (e.g., about amino acids 167–190 of SEQ ID NO:13); an isolated PYRIN-7 protein having an amino acid sequence that is at least about 65%, preferably 75%, 85%, 95%, or 98% identical to the Motif II domain of SEQ ID NO:10 or SEQ ID NO:13 (e.g., about amino acids 197–227 of SEQ ID NO:13); an isolated PYRIN-7 protein having an amino acid sequence that is at least about 65%, preferably 75%, 85%, 95%, or 98% identical to the kinase 2 domain of SEQ ID NO:10 or SEQ ID NO:13 (e.g., about amino acids 231–254 of SEQ ID NO:13); an isolated PYRIN-7 protein having an amino acid sequence that is at least about 65%, preferably 75%, 85%, 95%, or 98% identical to the kinase 3a domain of SEQ ID NO:10 or SEQ ID NO:13 (e.g., about amino acids 270–295 of SEQ ID NO:13); an isolated PYRIN-7 protein having an amino acid sequence that is at least about 65%, preferably 75%, 85%, 95%, or 98% identical to the Motif V domain of SEQ ID NO:10 or SEQ ID NO:13 (e.g., about amino acids 346–366 of SEQ ID NO:13); an isolated PYRIN-7 protein having an amino acid sequence that is at least about 65%, preferably 75%, 85%, 95%, or 98% identical to the Motif VI domain of SEQ ID NO:10 or SEQ ID NO:13 (e.g., about amino acids 435–450 of SEQ ID NO:13); and an isolated PYRIN-7 protein having an amino acid sequence that is at least about 65%, preferably 75%, 85%, 95%, or 98% identical to the Motif VII domain of SEQ ID NO:10 or SEQ ID NO:13 (e.g., about amino acids 461–480 of SEQ ID NO:13).

In an embodiment, a PYRIN-8 nucleic acid molecule has the nucleotide sequence shown in SEQ ID NO:14, SEQ ID NO:16, or SEQ ID NO:17.

Also within the invention is a nucleic acid molecule which encodes a fragment of a polypeptide having the amino acid sequence of SEQ ID NO:15 or SEQ ID NO:18.

The invention includes a nucleic acid molecule which encodes a naturally occurring allelic variant of a polypeptide comprising the amino acid sequence of SEQ ID NO:15 or SEQ ID NO:18, wherein the nucleic acid molecule hybridizes to a nucleic acid molecule consisting of SEQ ID NO:14, SEQ ID NO:16 or SEQ ID NO:17 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:14, SEQ ID NO:16, or SEQ ID NO:17 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-8 protein having an amino acid sequence that is at least about 65%, preferably 75%, 85%, 95%, or 98% identical to the amino acid sequence of SEQ ID NO:15; or SEQ ID NO:18; an isolated PYRIN-8 protein having an amino acid sequence that is at least about 65%, preferably 75%, 85%, 95%, or 98% identical to the pyrin domain of SEQ ID NO:15 or SEQ ID NO:18 (e.g., about amino acid residues 1–65 of SEQ ID NO:15 or 1–107 of SEQ ID NO:18); an isolated PYRIN-8 protein having an amino acid sequence that is at least about 65%, preferably 75%, 85%, 95%, or 98% identical to the NBS domain of SEQ ID NO:15 or SEQ ID NO:18 (e.g., about amino acids 212–528 of SEQ ID NO:18); an isolated PYRIN-8 protein having an amino acid sequence that is at least about 65%, preferably 75%, 85%, 95%, or 98% identical to the kinase 1a domain of SEQ ID NO:15 or SEQ ID NO:18 (e.g., about amino acids 212–234 of SEQ ID NO:18); an isolated PYRIN-8 protein having an amino acid sequence that is at least about 65%, preferably 75%, 85%, 95%, or 98% identical to the Motif II domain of SEQ ID NO:15 or SEQ ID NO:18 (e.g., about amino acids 241–272 of SEQ ID NO:18); an isolated PYRIN-8 protein having an amino acid sequence that is at least about 65%, preferably 75%, 85%, 95%, or 98% identical to the kinase 2 domain of SEQ ID NO:15 or SEQ ID NO:18 (e.g., about amino acids 276–299 of SEQ ID NO:18); an isolated PYRIN-8 protein having an amino acid sequence that is at least about 65%, preferably 75%, 85%, 95%, or 98% identical to the kinase 3a domain of SEQ ID NO:15 or SEQ ID NO:18 (e.g., about amino acids 320–345 of SEQ ID NO:18); an isolated PYRIN-8 protein having an amino acid sequence that is at least about 65%, preferably 75%, 85%, 95%, or 98% identical to the Motif V domain of SEQ ID NO:15 or SEQ ID NO:18 (e.g., about amino acids 396–416 of SEQ ID NO:18); an isolated PYRIN-8 protein having an amino acid sequence that is at least about 65%, preferably 75%, 85%, 95%, or 98% identical to the Motif VI domain of SEQ ID NO:15 or SEQ ID NO:18 (e.g., about amino acids 483–498 of SEQ ID NO:18); an isolated PYRIN-8 protein having an amino acid sequence that is at least about 65%, preferably 75%, 85%, 95%, or 98% identical to the Motif VII domain of SEQ ID NO:15 or SEQ ID NO:18 (e.g., about amino acids 509–528 of SEQ ID NO:18); an isolated PYRIN-8 protein having an amino acid sequence that is at least about 65%, preferably 75%, 85%, 95%, or 98% identical to the LRR domain of SEQ ID NO:15 or SEQ ID NO:18 (e.g., about amino acids 712–1052 of SEQ ID NO:18); and an isolated PYRIN-8 protein having an amino acid sequence that is at least about 65%, preferably 75%, 85%, 95%, or 98% identical to one or more of the leucine rich repeats of SEQ ID NO:15 or SEQ ID NO:18 (e.g., about amino acids residues 712–739, 741–768, 769–796, 798–825, 826–853, 855–882, 883–910, 912–939, 940–967, 969–996, 997–1024, and 1026–1052 of SEQ ID NO:18).

In an embodiment, a PYRIN-10 nucleic acid molecule has the nucleotide sequence shown in SEQ ID NO:19.

Also within the invention is a nucleic acid molecule which encodes a fragment of a polypeptide having the amino acid sequence of SEQ ID NO:20.

The invention includes a nucleic acid molecule which encodes a naturally occurring allelic variant of a polypeptide comprising the amino acid sequence of SEQ ID NO:20, wherein the nucleic acid molecule hybridizes to a nucleic acid molecule consisting of SEQ ID NO:19 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:19 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-10 protein having an amino acid sequence that is at least about 65%, preferably 75%, 85%, 95%, or 98% identical to the amino acid sequence of SEQ ID NO:20; an isolated PYRIN-10 protein having an amino acid sequence that is at least about 65%, preferably 75%, 85%, 95%, or 98% identical to the pyrin domain of SEQ ID NO:20 (e.g., about amino acid residues 41–112 of SEQ ID NO:20); an isolated PYRIIN-10 protein having an amino acid sequence that is at least about 65%, preferably 75%, 85%, 95%, or 98% identical to the LRR domain of SEQ ID NO:20 (e.g., about amino acids 210–440 of SEQ ID NO:20); and an isolated PYRIN-10 protein having an amino acid sequence that is at least about 65%, preferably 75%, 85%, 95%, or 98% identical to one or more of the leucine rich repeats of SEQ ID NO:20 (e.g., about amino acids residues 210–237, 267–294, 299–326, 356–383, 385–412, and 413–440 of SEQ ID NO:20).

In an embodiment, a PYRIN-11 nucleic acid molecule has the nucleotide sequence shown in SEQ ID NO:21.

Also within the invention is a nucleic acid molecule which encodes a fragment of a polypeptide having the amino acid sequence of SEQ ID NO:22.

The invention includes a nucleic acid molecule which encodes a naturally occurring allelic variant of a polypeptide comprising the amino acid sequence of SEQ ID NO:22, wherein the nucleic acid molecule hybridizes to a nucleic acid molecule consisting of SEQ ID NO:21 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:21 under stringent conditions (e.g., hybridization in 6× sodium chloride/sodium citrate (SSC) at about 60° C., followed by one or more washes in 0.2×SSC, 0.1% SDS at 65° C.). Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-11 protein having an amino acid sequence that is at least about 65%, preferably 75%, 85%, 95%, or 98% identical to the amino acid sequence of SEQ ID NO:22; an isolated PYRIN-11 protein having an amino acid sequence that is at least about 65%, preferably 75%, 85%, 95%, or 98% identical to the pyrin domain of SEQ ID NO:22 (e.g., about amino acid residues 1–102 of SEQ ID NO:22); an isolated PYRIN-11 protein having an amino acid sequence that is at least about 65%, preferably 75%, 85%, 95%, or 98% identical to the NBS domain of SEQ ID NO:22 (e.g., about amino acids 177–494 of SEQ ID NO:22); an isolated PYRIN-11 protein having an amino acid sequence that is at least about 65%, preferably 75%, 85%, 95%, or 98% identical to the kinase 1a domain of SEQ ID NO:22 (e.g., about amino acids 177–200 of SEQ ID NO:22); an isolated PYRIN-11 protein having an amino acid sequence that is at least about 65%, preferably 75%, 85%, 95%, or 98% identical to the Motif II domain of SEQ ID NO:22 (e.g., about amino acids 207–237 of SEQ ID NO:22); an isolated PYRIN-11 protein having an amino acid sequence that is at least about 65%, preferably 75%, 85%, 95%, or 98% identical to the kinase 2 domain of SEQ ID NO:22 (e.g., about amino acids 241–264 of SEQ ID NO:22); an isolated PYRIN-11 protein having an amino acid sequence that is at least about 65%, preferably 75%, 85%, 95%, or 98% identical to the kinase 3a domain of SEQ ID NO:22 (e.g., about amino acids 285–310 of SEQ ID NO:22); an isolated PYRIN-11 protein having an amino acid sequence that is at least about 65%, preferably 75%, 85%, 95%, or 98% identical to the Motif V domain of SEQ ID NO:22 (e.g., about amino acids 361–381 of SEQ ID NO:22); an isolated PYRIN-11 protein having an amino acid sequence that is at least about 65%, preferably 75%, 85%, 95%, or 98% identical to the Motif VI domain of SEQ ID NO:22 (e.g., about amino acids 449–464 of SEQ ID NO:22);

an isolated PYRIN-1 1 protein having an amino acid sequence that is at least about 65%, preferably 75%, 85%, 95%, or 98% identical to the Motif VII domain of SEQ ID NO:22 (e.g., about amino acids 475–494 of SEQ ID NO:22); an isolated PYRIN-11 protein having an amino acid sequence that is at least about 65%, preferably 75%, 85%, 95%, or 98% identical to the LRR domain of SEQ ID NO:22 (e.g., about amino acids 615–813 of SEQ ID NO:22); and an isolated PYRIN-11 protein having an amino acid sequence that is at least about 65%, preferably 75%, 85%, 95%, or 98% identical to one or more of the leucine rich repeats of SEQ ID NO:22 (e.g., about amino acids residues 615–642, 644–671, 672–699, 701–728, 729–756, 758–785, and 786–813 of SEQ ID NO:22).

Also within the invention are: an isolated PYRIN-2 protein which is encoded by a nucleic acid molecule having a nucleotide sequence that is at least about 65%, preferably 75%, 85%, or 95% identical to SEQ ID NO:1; an isolated PYRIN-2 protein which is encoded by a nucleic acid molecule having a nucleotide sequence at least about 65% preferably 75%, 85%, or 95% identical to the pyrin domain encoding portion of SEQ ID NO:1; an isolated PYRIN-2 protein which is encoded by a nucleic acid molecule having a nucleotide sequence at least about 65% preferably 75%, 85%, or 95% identical to the NBS domain encoding portion of SEQ ID NO:1; an isolated PYRIN-2 protein which is encoded by a nucleic acid molecule having a nucleotide sequence at least about 65% preferably 75%, 85%, or 95% identical to the kinase 1a encoding portion of SEQ ID NO:1; an isolated PYRIN-2 protein which is encoded by a nucleic acid molecule having a nucleotide sequence at least about 65% preferably 75%, 85%, or 95% identical to the LRR domain encoding portion of SEQ ID NO:1 or one or more leucine rich repeat encoding portions of SEQ ID NO:1; and an isolated PYRIN-2 protein which is encoded by a nucleic acid molecule having a nucleotide sequence which hybridizes under stringent hybridization conditions to a nucleic acid molecule having the nucleotide sequence of SEQ ID NO:1.

Also within the invention are: an isolated PYRIN-3 protein which is encoded by a nucleic acid molecule having a nucleotide sequence that is at least about 65%, preferably 75%, 85%, or 95% identical to SEQ ID NO:3, SEQ ID NO:23, or SEQ ID NO:25; an isolated PYRIN-3 protein which is encoded by a nucleic acid molecule having a nucleotide sequence at least about 65% preferably 75%, 85%, or 95% identical to the pyrin domain encoding portion of SEQ ID NO:3, SEQ ID NO:23, or SEQ ID NO:25; an isolated PYRIN-3 protein which is encoded by a nucleic acid molecule having a nucleotide sequence at least about 65% preferably 75%, 85%, or 95% identical to the NBS domain encoding portion of SEQ ID NO:23 or SEQ ID NO:25; an isolated PYRIN-3 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII encoding portion of SEQ ID NO:23 or SEQ ID NO:25; an isolated PYRIN-3 protein which is encoded by a nucleic acid molecule having a nucleotide sequence at least about 65% preferably 75%, 85%, or 95% identical to the LRR domain encoding portion of SEQ ID NO:23 or SEQ ID NO:25 or one or more leucine rich repeat encoding portions of SEQ ID NO:23 or SEQ ID NO:25; and an isolated PYRIN-3 protein which is encoded by a nucleic acid molecule having a nucleotide sequence which hybridizes under stringent hybridization conditions to a nucleic acid molecule having the nucleotide sequence of SEQ ID NO:3, SEQ ID NO:23, or SEQ ID NO:25.

Also within the invention are: an isolated PYRIN-5 protein which is encoded by a nucleic acid molecule having a nucleotide sequence that is at least about 65%, preferably 75%, 85%, or 95% identical to SEQ ID NO:5; an isolated PYRIN-5 protein which is encoded by a nucleic acid molecule having a nucleotide sequence at least about 65% preferably 75%, 85%, or 95% identical to the pyrin domain encoding portion of SEQ ID NO:5; an isolated PYRIN-5 protein which is encoded by a nucleic acid molecule having a nucleotide sequence at least about 65% preferably 75%, 85%, or 95% identical to the NBS domain encoding portion of SEQ ID NO:5; an isolated PYRIN-5 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII encoding portion of SEQ ID NO:5; an isolated PYRIN-5 protein which is encoded by a nucleic acid molecule having a nucleotide sequence at least about 65% preferably 75%, 85%, or 95% identical to the LRR domain encoding portion of SEQ ID NO:5 or one or more leucine rich repeat encoding portions of SEQ ID NO:5; and an isolated PYRIN-5 protein which is encoded by a nucleic acid molecule having a nucleotide sequence which hybridizes under stringent hybridization conditions to a nucleic acid molecule having the nucleotide sequence of SEQ ID NO:5.

Also within the invention are: an isolated PYRIN-6 protein which is encoded by a nucleic acid molecule having a nucleotide sequence that is at least about 65%, preferably 75%, 85%, or 95% identical to SEQ ID NO:7; an isolated PYRIN-6 protein which is encoded by a nucleic acid molecule having a nucleotide sequence at least about 65% preferably 75%, 85%, or 95% identical to the pyrin domain encoding portion of SEQ ID NO:7; and an isolated PYRIN-6 protein which is encoded by a nucleic acid molecule having a nucleotide sequence which hybridizes under stringent hybridization conditions to a nucleic acid molecule having the nucleotide sequence of SEQ ID NO:7.

Also within the invention are: an isolated PYRIN-7 protein which is encoded by a nucleic acid molecule having a nucleotide sequence that is at least about 65%, preferably 75%, 85%, or 95% identical to SEQ ID NO:9, SEQ ID NO:11, or SEQ ID NO:12; an isolated PYRIN-7 protein which is encoded by a nucleic acid molecule having a nucleotide sequence at least about 65% preferably 75%, 85%, or 95% identical to the pyrin domain encoding portion of SEQ ID NO:9, SEQ ID NO:11, or SEQ ID NO:12; an isolated PYRIN-7 protein which is encoded by a nucleic acid molecule having a nucleotide sequence at least about 65% preferably 75%, 85%, or 95% identical to the NBS domain encoding portion of SEQ ID NO:9, SEQ ID NO:11, or SEQ ID NO:12; an isolated PYRIN-7 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII encoding portion of SEQ ID NO:9, SEQ ID NO:11, or SEQ ID NO:12; and an isolated PYRIN-7 protein which is encoded by a nucleic acid molecule having a nucleotide sequence which hybridizes under stringent hybridization conditions to a nucleic acid molecule having the nucleotide sequence of SEQ ID NO:9, SEQ ID NO:11, or SEQ ID NO:12.

Also within the invention are: an isolated PYRIN-8 protein which is encoded by a nucleic acid molecule having a nucleotide sequence that is at least about 65%, preferably 75%, 85%, or 95% identical to SEQ ID NO:14, SEQ ID NO:16, or SEQ ID NO:17; an isolated PYRIN-8 protein which is encoded by a nucleic acid molecule having a nucleotide sequence at least about 65% preferably 75%, 85%, or 95% identical to the pyrin domain encoding portion of SEQ ID NO:14, SEQ ID NO:16, or SEQ ID NO:17; an isolated PYRIN-8 protein which is encoded by a nucleic acid molecule having a nucleotide sequence at least about 65% preferably 75%, 85%, or 95% identical to the NBS domain encoding portion of SEQ ID NO:14, SEQ ID NO:16, or SEQ ID NO:17; an isolated PYRIN-8 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII encoding portion of SEQ ID NO:14, SEQ ID NO:16, or SEQ ID NO:17; an isolated PYRIN-8 protein which is encoded by a nucleic acid molecule having a nucleotide sequence at least about 65% preferably 75%, 85%, or 95% identical to the LRR domain encoding portion of SEQ ID NO:14, SEQ ID NO:16, or SEQ ID NO:17 or one or more leucine rich repeat encoding portions of SEQ ID NO:14, SEQ ID NO:16, or SEQ ID NO:17; and an isolated PYRIN-8 protein which is encoded by a nucleic acid molecule having a nucleotide sequence which hybridizes under stringent hybridization conditions to a nucleic acid molecule having the nucleotide sequence of SEQ ID NO:14, SEQ ID NO:16, or SEQ ID NO:17.

Also within the invention are: an isolated PYRIN-10 protein which is encoded by a nucleic acid molecule having a nucleotide sequence that is at least about 65%, preferably 75%, 85%, or 95% identical to SEQ ID NO:19; an isolated PYRIN-10 protein which is encoded by a nucleic acid molecule having a nucleotide sequence at least about 65% preferably 75%, 85%, or 95% identical to the pyrin domain encoding portion of SEQ ID NO:19; an isolated PYRIN-10 protein which is encoded by a nucleic acid molecule having a nucleotide sequence at least about 65% preferably 75%, 85%, or 95% identical to the LRR domain encoding portion of SEQ ID NO:19 or one or more leucine rich repeat encoding portions of SEQ ID NO:19; and an isolated PYRIN-10 protein which is encoded by a nucleic acid molecule having a nucleotide sequence which hybridizes under stringent hybridization conditions to a nucleic acid molecule having the nucleotide sequence of SEQ ID NO:19.

Also within the invention are: an isolated PYRIN-11 protein which is encoded by a nucleic acid molecule having a nucleotide sequence that is at least about 65%, preferably 75%, 85%, or 95% identical to SEQ ID NO:21; an isolated PYRIN-11 protein which is encoded by a nucleic acid molecule having a nucleotide sequence at least about 65% preferably 75%, 85%, or 95% identical to the pyrin domain encoding portion of SEQ ID NO:21; an isolated PYRIN-11 protein which is encoded by a nucleic acid molecule having a nucleotide sequence at least about 65% preferably 75%, 85%, or 95% identical to the NBS domain encoding portion of SEQ ID NO:21; an isolated PYRIN-11 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII encoding portion of SEQ ID NO:21; an isolated PYRIN-11 protein which is encoded by a nucleic acid molecule having a nucleotide sequence at least about 65% preferably 75%, 85%, or 95% identical to the LRR domain encoding portion of SEQ ID NO:21 or one or more leucine rich repeat encoding portions of SEQ ID NO:21; and an isolated PYRIN-11 protein which is encoded by a nucleic acid molecule having a nucleotide sequence which hybridizes under stringent hybridization conditions to a nucleic acid molecule having the nucleotide sequence of SEQ ID NO:21.

The PYRIN-2, PYRIN-3, PYRIN-5, PYRIN-6, PYRIN-7, PYRIN-8, PYRIN-10, or PYRIN-11 nucleic acids, polypeptides, and antibodies of the invention may be useful for mapping the location of either the PYRIN-2, PYRIN-3, PYRIN-5, PYRIN-6, PYRIN-7, PYRIN-8, PYRIN-10, or PYRIN-11 genes.

Another embodiment of the invention features PYRIN-2, PYRIN-3, PYRIN-5, PYRIN-6, PYRIN-7, PYRIN-8, PYRIN-10, or PYRIN-11 nucleic acid molecules which specifically detect PYRIN-2, PYRIN-3, PYRIN-5, PYRIN-6, PYRIN-7, PYRIN-8, PYRIN-10, or PYRIN-11 nucleic acid molecules, relative to nucleic acid molecules encoding other members of the PYRIN/NBS/LRR superfamily. For example, in one embodiment, a PYRIN-2, PYRIN-3, PYRIN-5, PYRIN-6, PYRIN-7, PYRIN-8, PYRIN-10, or PYRIN-11 nucleic acid molecule hybridizes under stringent conditions to a nucleic acid molecule comprising the nucleotide sequence of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement thereof. In another embodiment, the PYRIN-2, PYRIN-3, PYRIN-5, PYRIN-6, PYRIN-7, PYRIN-8, PYRIN-10, or PYRIN-11 nucleic acid molecule is at least 300 (350, 400, 450, 500, 550, 600, 650, 700, 800, 900, 1000, 1100, 1200, 1300, 1400, 1500, 1600, 1800, 2000, 2250, 2500, 2750, 3000, 3250, 3500, 3750, or 4000) nucleotides in length and hybridizes under stringent conditions to a nucleic acid molecule comprising the nucleotide sequence shown in SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement thereof. In another embodiment, an isolated PYRIN-2, PYRIN-3, PYRIN-5, PYRIN-6, PYRIN-7, PYRIN-8, PYRIN-10, or PYRIN-11 nucleic acid molecule comprises the pyrin domain encoding portion of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement thereof. In another embodiment, an isolated PYRIN-2, PYRIN-3, PYRIN-5, PYRIN-6, PYRIN-7, PYRIN-8, PYRIN-10, or PYRIN-11 nucleic acid molecule comprises the NBS domain encoding portion of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement thereof. In another embodiment, an isolated PYRIN-2, PYRIN-3, PYRIN-5, PYRIN-6, PYRIN-7, PYRIN-8, PYRIN-10, or PYRIN-11 nucleic acid molecule comprises the LRR domain encoding portion of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement thereof. In yet another embodiment, the invention provides an isolated nucleic acid molecule which is antisense to the coding strand of a PYRIN-2, PYRIN-3, PYRIN-5, PYRIN-6, PYRIN-7, PYRIN-8, PYRIN-10, or PYRIN-11 nucleic acid.

Another aspect of the invention provides a vector, e.g., a recombinant expression vector, comprising a PYRIN-2, PYRIN-3, PYRIN-5, PYRIN-6, PYRIN-7, PYRIN-8, PYRIN-10, or PYRIN-11 nucleic acid molecule of the invention. In another embodiment the invention provides a host cell containing such a vector. The invention also provides a method for producing PYRIN-2, PYRIN-3, PYRIN-5, PYRIN-6, PYRIN-7, PYRIN-8, PYRIN-10, or PYRIN-11 protein by culturing, in a suitable medium, a host cell of the invention containing a recombinant expression vector such that a PYRIN-2, PYRIN-3, PYRIN-5, PYRIN-6, PYRIN-7, PYRIN-8, PYRIN-10, or PYRIN-11 protein is produced.

Another aspect of this invention features isolated or recombinant PYRIN-2, PYRIN-3, PYRIN-5, PYRIN-6, PYRIN-7, PYRIN-8, PYRIN-10, or PYRIN-11 proteins and polypeptides. Preferred PYRIN-2, PYRIN-3, PYRIN-5, PYRIN-6, PYRIN-7, PYRIN-8, PYRIN-10, or PYRIN-11 proteins and polypeptides possess at least one biological activity possessed by naturally occurring human PYRIN-2, PYRIN-3, PYRIN-5, PYRIN-6, PYRIN-7, PYRIN-8, PYRIN-10, or PYRIN-11, e.g., (1) the ability to form protein:protein interactions with proteins in an apoptotic and/or inflammatory signaling pathway; (2) the ability to form pyrin domain-pyrin domain interactions with proteins in an apoptotic and/or inflammatory signaling pathway; (3) the ability to bind to and/or hydrolyze a nucleotide, e.g., ATP or GTP; (4) the ability to bind a PYRIN-2, PYRIN-3, PYRIN-5, PYRIN-6, PYRIN-7, PYRIN-8, PYRIN-10, or PYRIN-11 ligand; and (5) the ability to bind to an intracellular target. Other activities include: (1) modulation of cellular proliferation; (2) modulation of cellular differentiation; (3) modulation of cellular death; (4) modulation of ER-specific apoptosis pathways; (5) modulation of amyloid-γ-mediated neurotoxicity; (6) modulation of the NF-kB pathway; and (7) modulation of stress-responsive signaling pathways.

The PYRIN-2, PYRIN-3, PYRIN-5, PYRIN-6, PYRIN-7, PYRIN-8, PYRIN-10, or PYRIN-11 proteins of the present invention, or biologically active portions thereof, can be operatively linked to a non-PYRIN-2, PYRIN-3, PYRIN-5, PYRIN-6, PYRIN-7, PYRIN-8, PYRIN-10, or PYRIN-11 polypeptide (e.g., heterologous amino acid sequences) to form PYRIN-2, PYRIN-3, PYRIN-5, PYRIN-6, PYRIN-7, PYRIN-8, PYRIN-10, or PYRIN-11 fusion proteins, respectively. The invention further features antibodies that specifically bind PYRIN-2, PYRIN-3, PYRIN-5, PYRIN-6, PYRIN-7, PYRIN-8, PYRIN-10, or PYRIN-11 proteins, such as monoclonal or polyclonal antibodies. In addition, the PYRIN-2, PYRIN-3, PYRIN-5, PYRIN-6, PYRIN-7, PYRIN-8, PYRIN-10, or PYRIN-11 proteins or biologically active portions thereof can be incorporated into pharmaceutical compositions, which optionally include pharmaceutically acceptable carriers.

In another aspect, the present invention provides a method for detecting the presence of PYRIN-2, PYRIN-3, PYRIN-5, PYRIN-6, PYRIN-7, PYRIN-8, PYRIN-10, or PYRIN-11 activity or expression in a biological sample by contacting the biological sample with an agent capable of detecting an indicator of PYRIN-2, PYRIN-3, PYRIN-5, PYRIN-6, PYRIN-7, PYRIN-8, PYRIN-10, or PYRIN-11 activity such that the presence of PYRIN-2, PYRIN- 3, PYRIN-5, PYRIN-6, PYRIN-7, PYRIN-8, PYRIN-10, or PYRIN-11 activity is detected in the biological sample.

In another aspect, the invention provides a method for modulating PYRIN-2, PYRIN-3, PYRIN-5, PYRIN-6, PYRIN-7, PYRIN-8, PYRIN-10, or PYRIN-11 activity comprising contacting a cell with an agent that modulates (inhibits or stimulates) PYRIN-2, PYRIN-3, PYRIN-5, PYRIN-6, PYRIN-7, PYRIN-8, PYRIN-10, or PYRIN-11 activity or expression such that PYRIN-2, PYRIN-3, PYRIN-5, PYRIN-6, PYRIN-7, PYRIN-8, PYRIN-10, or PYRIN-11 activity or expression in the cell is modulated. In one embodiment, the agent is an antibody that specifically binds to PYRIN-2, PYRIN-3, PYRIN-5, PYRIN-6, PYRIN-7, PYRIN-8, PYRIN-10, or PYRIN-11 protein. In another embodiment, the agent modulates expression of PYRIN-2, PYRIN-3, PYRIN-5, PYRIN-6, PYRIN-7, PYRIN-8, PYRIN-10, or PYRIN-11 by modulating transcription of a PYRIN-2, PYRIN-3, PYRIN-5, PYRIN-6, PYRIN-7, PYRIN-8, PYRIN-10, or PYRIN-11 gene, splicing of a PYRIN-2, PYRIN-3, PYRIN-5, PYRIN-6, PYRIN-7, PYRIN-8, PYRIN-10, or PYRIN-11 mRNA, or translation of a PYRIN-2, PYRIN-3, PYRIN-5, PYRIN-6, PYRIN-7, PYRIN-8, PYRIN-10, or PYRIN-11 mRNA. In yet another embodiment, the agent is a nucleic acid molecule having a nucleotide sequence that is antisense to the coding strand of the PYRIN-2, PYRIN-3, PYRIN-5, PYRIN-6, PYRIN-7, PYRIN-8, PYRIN-10, or PYRIN-11 mRNA or the PYRIN-2, PYRIN-3, PYRIN-5, PYRIN-6, PYRIN-7, PYRIN-8, PYRIN-10, or PYRIN-11 gene.

In one embodiment, the methods of the present invention are used to treat a subject having a disorder characterized by aberrant PYRIN-2, PYRIN-3, PYRIN-5, PYRIN-6, PYRIN-7, PYRIN-8, PYRIN-10, or PYRIN-11 protein or nucleic acid expression or activity or related to PYRIN-2, PYRIN-3, PYRIN-5, PYRIN-6, PYRIN-7, PYRIN-8, PYRIN-10, or PYRIN-11 expression or activity by administering an agent which is a PYRIN-2, PYRIN-3, PYRIN-5, PYRIN-6, PYRIN-7, PYRIN-8, PYRIN-10, or PYRIN-11 modulator to the subject. In one embodiment, the PYRIN-2, PYRIN-3, PYRIN-5, PYRIN-6, PYRIN-7, PYRIN-8, PYRIN-10, or PYRIN-11 modulator is a PYRIN-2, PYRIN-3, PYRIN-5, PYRIN-6, PYRIN-7, PYRIN-8, PYRIN-10, or PYRIN-11 protein. In another embodiment the PYRIN-2, PYRIN-3, PYRIN-5, PYRIN-6, PYRIN-7, PYRIN-8, PYRIN-10, or PYRIN-11 modulator is a PYRIN-2, PYRIN-3, PYRIN-5, PYRIN-6, PYRIN-7, PYRIN-8, PYRIN-10, or PYRIN-11 nucleic acid molecule. In other embodiments, the PYRIN-2, PYRIN-3, PYRIN-5, PYRIN-6, PYRIN-7, PYRIN-8, PYRIN-10, or PYRIN-11 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a PYRIN-2, PYRIN-3, PYRIN-5, PYRIN-6, PYRIN-7, PYRIN-8, PYRIN-10, or PYRIN-11 protein; (ii) mis-regulation of a gene encoding a PYRIN-2, PYRIN-3, PYRIN-5, PYRIN-6, PYRIN-7, PYRIN-8, PYRIN-10, or PYRIN-11 protein; (iii) aberrant RNA splicing; and (iv) aberrant post-translational modification of a PYRIN-2, PYRIN-3, PYRIN-5, PYRIN-6, PYRIN-7, PYRIN-8, PYRIN-10, or PYRIN-11 protein, wherein a wild-type form of the gene encodes a protein with a PYRIN-2, PYRIN-3, PYRIN-5, PYRIN-6, PYRIN-7, PYRIN-8, PYRIN-10, or PYRIN-11 activity.

In another aspect, the invention provides a method for identifying a compound that binds to or modulates the activity of a PYRIN-2, PYRIN-3, PYRIN-5, PYRIN-6, PYRIN-7, PYRIN-8, PYRIN-10, or PYRIN-11 protein. In general, such methods entail measuring a biological activity of a PYRIN-2, PYRIN-3, PYRIN-5, PYRIN-6, PYRIN-7, PYRIN-8, PYRIN-10, or PYRIN-11 protein in the presence and absence of a test compound and identifying those compounds that alter the activity of the PYRIN-2, PYRIN-3, PYRIN-5, PYRIN-6, PYRIN-7, PYRIN-8, PYRIN-10, or PYRIN-11 protein.

The invention also features methods for identifying a compound that modulates the expression of PYRIN-2, PYRIN-3, PYRIN-5, PYRIN-6, PYRIN-7, PYRIN-8, PYRIN-10, or PYRIN-11 by measuring the expression of PYRIN-2, PYRIN-3, PYRIN-5, PYRIN-6, PYRIN-7, PYRIN-8, PYRIN-10, or PYRIN-11 in the presence and absence of a compound.

The invention also features methods for identifying a compound that alters (increases or decreases) the binding of PYRIN-2, PYRIN-3, PYRIN-5, PYRIN-6, PYRIN-7, PYRIN-8, PYRIN-10, or PYRIN-11 (or a pyrin, NBS, or LRR domain containing portion thereof) to another protein (e.g., a PYRIN-2, PYRIN-3, PYRIN-5, PYRIN-6, PYRIN-7, PYRIN-8, PYRIN-10, or PYRIN-11 protein) or molecule. For example, the method includes measuring the binding of the protein (or polypeptides) to each other in the presence and absence of a test compound and identifying the test compound as a compound that alters binding if the binding in the presence of test compound differs from the binding in the absence of the test compound.

The invention also features a method for identifying a compound that binds to the NBS domain of PYRIN-2, PYRIN-3, PYRIN-5, PYRIN-6, PYRIN-7, PYRIN-8, PYRIN-10, or PYRIN-11 by measuring the binding of a test compound to a polypeptide comprising the NBS domain of PYRIN-2, PYRIN-3, PYRIN-5, PYRIN-6, PYRIN-7, PYRIN-8, PYRIN-10, or PYRIN-11. The binding can be measured in the presence of a nucleotide (e.g., an NTP such as ATP) for a competitive binding assay. Alternatively, the binding can be measured in the absence of a nucleotide that binds to the NBS site.

The invention also features a method for identifying a candidate compound for modulating (increasing or decreasing) the binding of PYRIN-8 to CARD-5, the method including: (a) measuring the binding of a first polypeptide comprising the pyrin domain of CARD-5 to a second polypeptide comprising the pyrin domain of PYRIN-8 in the presence of a test compound; and (b) comparing the binding of the first polypeptide to the second polypeptide measured in step (a) to the binding of the first polypeptide to the second polypeptide in the absence of the test compound, wherein altered binding of the first polypeptide to the second polypeptide in the presence of the test compound compared the binding in the absence of the test compound indicates that the test compound modulates the binding of PYRIN-8 to CARD-5. The binding of PYRIN-8 to CARD-5 can be detected directly or indirectly (e.g., by detecting a biological response that results from the interaction of PYRIN-8 and CARD-5, such as NF-kB activation and/or caspase-1 activation).

In another embodiment the method includes a method for identifying a candidate compound for modulating the CARD-5-mediated activation of NF-kB, the method comprising: a) measuring the binding of a first polypeptide comprising the pyrin domain of CARD-5 to a second polypeptide comprising the pyrin domain of PYRIN-8 in the presence of a test compound; and b) comparing the binding of the first polypeptide to the second polypeptide measured in step (a) to the binding of the first polypeptide to the second polypeptide in the absence of the test compound, wherein altered binding of the first polypeptide to the second polypeptide in the presence of the test compound compared the binding in the absence of the test compound indicates that the test compound is candidate compound for modulating the CARD-5-mediated activation of NF-kB.

In another embodiment the invention features a method for identifying a modulator of NF-kB activity, the method comprising: a) providing a cell expressing recombinant CARD-5 and recombinant PYRIN-8; b) exposing the cell to a test compound; and c) measuring the NK-kB activity of the cell in the presence of the test compound, wherein altered activation in the presence of the test compound compared to the absence of the test compound indicates that the compound is a modulator of NF-kB activity.

In another embodiment the invention features a method for identifying a candidate compound for modulating the CARD-5-mediated activation of NF-kB, the method comprising: a) measuring the binding of a test compound to the LRR domain of PYRIN-8; and b) determining that the test compound is a candidate compound for modulating the CARD-5-mediated activation of NF-kB when the test compound binds to the LRR domain of PYRIN-8.

In another embodiment the invention features a method for identifying a candidate modulator of PYRIN-8, the method comprising: a) contacting a purified polypeptide comprising the NBS domain of PYRIN-8 with a test compound in the presence of a nucleotide that binds to the NBS domain in the absence of the test compound; b) measuring the binding of the nucleotide to the NBS domain in the presence of the test compound; and c) identifying the test compound as a candidate modulator of PYRIN-8 if the test compound reduces the binding of the nucleotide to the NBS domain. In various embodiments: the nucleotide is bound to the NBS domain before the polypeptide is exposed to the test compound, the test compound is exposed to the polypeptide before the polypeptide is exposed to the nucleotide, the nucleotide is selected from the group consisting of an adenine nucleotide, a guanidine nucleotide, a thymidine nucleotide, a cytosine nucleotide, and a uridine nucleotide, the nucleotide is selected from the group consisting of a ribonucleotide and a dideoxribonucleotide, and the nucleotide is selected from the group consisting of: ATP, ADP, TTP, TDP, UTP, UDP, CTP, CDP, GTP, and GTP.

In another embodiment the invention features a method for identifying a candidate modulator of PYRIN-8, the method comprising: a) contacting a purified polypeptide comprising the NBS domain of PYRIN-8 with a test compound in the presence of a nucleotide triphosphate that binds to the NBS domain in the absence of the test compound; b) measuring the hydrolysis of the nucleotide triphosphate in the presence of the test compound; and c) identifying the test compound is a candidate modulator of PYRIN-8 if the test compound reduces the hydrolysis of the nucleotide triphosphate.

The invention also features a method for identifying an inhibitor of caspase activity, the method including: (a) providing a cell expressing recombinant CARD-5 and recombinant PYRIN-8; (b) exposing the cell to a test compound; and (c) measuring the caspase activity, e.g., caspase-1 activity, of the cell in the presence of the test compound.

The invention also features a method for identifying a compound that modulates the ability of PYRIN-8 to activate caspase-1, the method including: (a) contacting a polypeptide comprising SEQ ID NO:18 or a fragment thereof (e.g., a fragment including a domain described herein) with a test compound; and (b) determining the effect of the test compound on the ability of the polypeptide to activate caspase-1.

The invention also features methods for treating disorders associated with inappropriate apoptosis (e.g., Alzheimer's diseases or other neurological disorders associated with neuronal apoptosis) or inflammation by modulating the expression or activity of PYRIN-2, PYRIN-3, PYRIN-5, PYRIN-6, PYRIN-7, PYRIN-8, PYRIN-10, or PYRIN-11.

In one example, the invention features a method of treating a disorder associated with inappropriate apoptosis, including the steps of: selecting an individual that has a disorder associated with inappropriate apoptosis; and modulating the expression or activity of a polypeptide containing the amino acid sequence of SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24.

In another example, the invention features a method of treating an inflammatory disorder, including the steps of: selecting an individual that has an inflammatory disorder; and modulating the expression or activity of a polypeptide containing the amino acid sequence of SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24.

Other features and advantages of the invention will be apparent from the following detailed description and claims.

BRIEF DESCRIPTION OF THE DRAWINGS

FIGS. 1A–1C depict a predicted cDNA sequence (SEQ ID NO:1) and a predicted amino acid sequence (SEQ ID NO:2) of human PYRIN-2.

FIG. 2 depicts a predicted cDNA sequence (SEQ ID NO:3) and a predicted amino acid sequence (SEQ ID NO:4) of human PYRIN-3.

FIGS. 3A–3G depict a predicted cDNA sequence (SEQ ID NO:5) and a predicted amino acid sequence (SEQ ID NO:6) of human PYRIN-5.

FIG. 4 depicts a predicted cDNA sequence (SEQ ID NO:7) and a predicted amino acid sequence (SEQ ID NO:8) of human PYRIN-6.

FIG. 5 depicts a predicted cDNA sequence (SEQ ID NO:9) and a predicted amino acid sequence (SEQ ID NO:10) of human PYRIN-7. The open reading frame of PYRIN-7 extends from nucleotide 270 to nucleotide 425 of SEQ ID NO:9 (SEQ ID NO:11).

FIGS. 6A–6D depict a predicted cDNA sequence (SEQ ID NO:12) and a predicted amino acid sequence (SEQ ID NO:13) of human PYRIN-7.

FIG. 7 depicts a predicted cDNA sequence (SEQ ID NO:14) and a predicted amino acid sequence (SEQ ID NO:15) of human PYRIN-8. The open reading frame of PYRIN-8 extends from nucleotide 105 to nucleotide 299 of SEQ ID NO:14 (SEQ ID NO:16).

FIGS. 8A–8F depict a predicted cDNA sequence (SEQ ID NO:17) and a predicted amino acid sequence (SEQ ID NO:18) of human PYRIN-8.

FIGS. 9A–9C depict a predicted cDNA sequence (SEQ ID NO:19) and a predicted amino acid sequence (SEQ ID NO:20) of human PYRIN-10.

FIGS. 10A–10E depict a predicted cDNA sequence (SEQ ID NO:21) and a predicted amino acid sequence (SEQ ID NO:22) of human PYRIN-11.

FIGS. 11A–11E depict a predicted cDNA sequence (SEQ ID NO:23) and a predicted amino acid sequence (SEQ ID NO:24) of human PYRIN-3. The open reading frame of PYRIN-3 extends from nucleotide 70 to nucleotide 3051 of SEQ ID NO:23 (SEQ ID NO:25).

DETAILED DESCRIPTION OF THE INVENTION

Human PYRIN-2

Figure 12A:
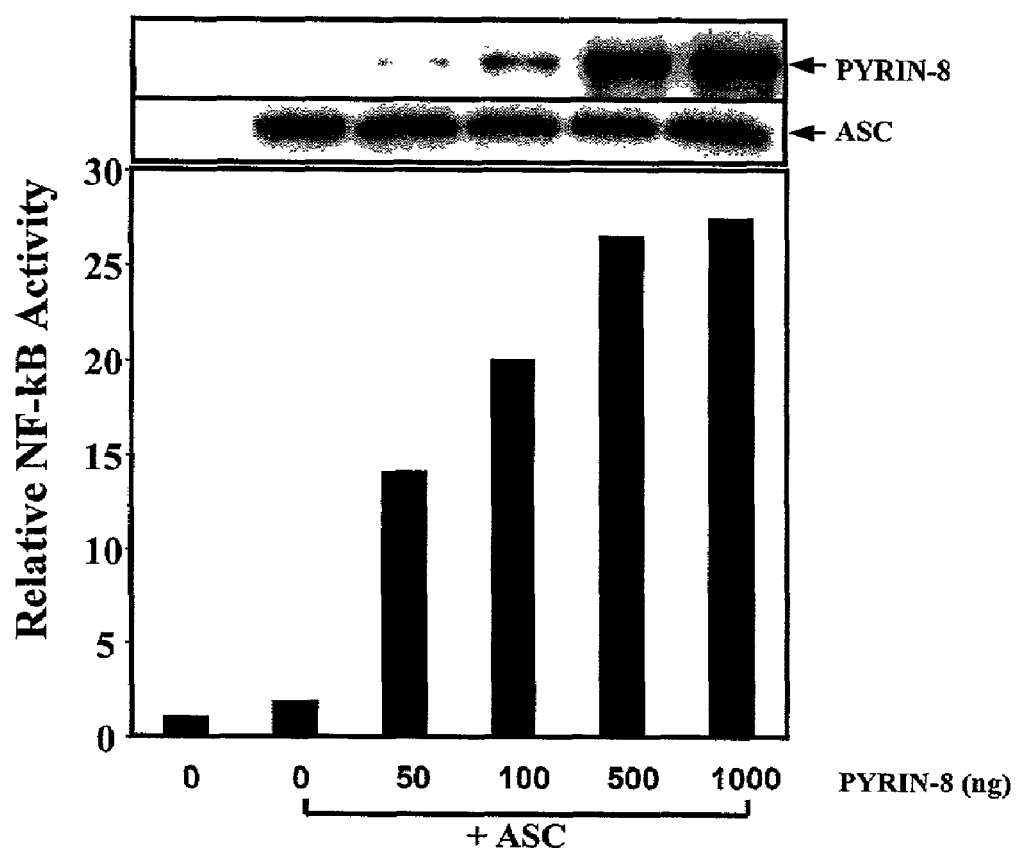
FIGS. 12A–12C are graphs depicting: (A) PYRIN-8 synergizing with CARD-5 (ASC) to induce NF-kB activation; (B) the importance of the N-terminal PYRIN domain of PYRIN-8 in synergizing with CARD-5 (ASC) to induce NF-kB activation; and (C) the activation of NF-kB activity by PYRIN-8 and CARD-5 through the IKK complex.

The present invention is based, in part, on the identification of a sequence encoding a human PYRIN-2 protein in a search of the Celera Genomics (Rockville, Md.) genomic database. GENSCAN analysis was performed to identify potential exons. This analysis identified a predicted PYRIN-2 cDNA sequence represented in SEQ ID NO:1 and a predicted 501 amino acid PYRIN-2 protein represented in SEQ ID NO:2 (see FIGS. 1A–1C).

An analysis of the predicted PYRIN-2 protein showed it to contain a pyrin domain (e.g., about amino acid residues 1–93 of SEQ ID NO:2), a nucleotide binding site (NBS; e.g., about amino acid residues 146–169 of SEQ ID NO:2), and several leucine rich repeats (e.g., about amino acid residues 196–223, 250–278, 280–307, 308–335, 337–364, 365–392, 394–421, and 422–449 of SEQ ID NO:2) which form a LRR domain (e.g., about amino acid residues 196–449 of SEQ ID NO:2). Within the predicted NBS there is a kinase 1a domain (Motif I; P-loop) (e.g., about amino acid residues 146–169 of SEQ ID NO:2).

Human PYRIN-3

The present invention is based, in part, on the identification of a sequence encoding a human PYRIN-3 protein in a search of the HTG genomic database. A predicted PYRIN-3 cDNA sequence is represented in SEQ ID NO:3 and a predicted 110 amino acid PYRIN-3 protein is represented in SEQ ID NO:4 (see FIG. 2).

A full length PYRIN-3 cDNA sequence was identified by a search of publicly available databases using the sequence of SEQ ID NO:3. This search identified GenBank™ Accession No. BE278926 as containing a 5' portion of a predicted PYRIN-3 cDNA. GenBank™ Accession No. BE278926 was obtained and sequenced in its entirety. This sequencing and subsequent analysis identified a predicted PYRIN-3 cDNA sequence represented in SEQ ID NO:23 and a predicted 994 amino acid PYRIN-3 protein represented in SEQ ID NO:24 (see FIGS. 11A–11E). The open reading frame of PYRIN-3 extends from nucleotide 70 to nucleotide 3051 of SEQ ID NO:23 (SEQ ID NO:25).

An analysis of the predicted PYRIN-3 amino acid sequence showed it to contain a pyrin domain (e.g., about amino acid residues 1–83 of SEQ ID NO:4 and SEQ ID NO:24), a nucleotide binding site (NBS; e.g., about amino acid residues 150–466 of SEQ ID NO:24), and several leucine rich repeats (e.g., about amino acid residues 637–664, 722–749, 750–776, 806–833, 835–862, 863–890, 892–919, and 920–947 of SEQ ID NO:24) which form a LRR domain (e.g., about amino acid residues 637–947 of SEQ ID NO:24). Within the predicted NBS there is a kinase 1a domain (Motif I; P-loop) (e.g., about amino acid residues 150–172 of SEQ ID NO:24), a Motif II domain (e.g., about amino acid residues 179–209 of SEQ ID NO:24), a kinase 2 domain (Motif III; Walker B box) (e.g., about amino acid residues 213–236 of SEQ ID NO:24), a kinase 3a domain (Motif IV) (e.g., about amino acid residues 257–282 of SEQ ID NO:24), a Motif V domain (e.g., about amino acid residues 333–353 of SEQ ID NO:24), a Motif VI domain (e.g., about amino acid residues 421–436 of SEQ ID NO:24), and a Motif VII domain (e.g., about amino acid residues 447–466 of SEQ ID NO:24).

Human PYRIN-5

The present invention is based, in part, on the identification of a sequence encoding a human PYRIN-5 protein in a search of the Celera Genomics (Rockville, Md.) genomic database. GENSCAN analysis was performed to identify potential exons. This analysis identified a predicted PYRIN-5 cDNA sequence represented in SEQ ID NO:5 and a predicted 1344 amino acid PYRIN-5 protein represented in SEQ ID NO:6 (see FIGS. 3A–3G).

An analysis of the predicted PYRIN-5 amino acid sequence showed it to contain a pyrin domain (e.g., about amino acid residues 1–91 of SEQ ID NO:6), a nucleotide binding site (NBS; e.g., about amino acid residues 188–506 of SEQ ID NO:6), and several leucine rich repeats (e.g., about amino acid residues 688–715, 744–771, 773–800, 801–828, 830–857, 858–885, 887–914, 915–942, 944–971, 972–1000, 1001–1028, and 1029–1056 of SEQ ID NO:6) which form a LRR domain (e.g., about amino acid residues 688–1056 of SEQ ID NO:6). Within the predicted NBS there is a kinase 1a domain (Motif I; P-loop) (e.g., about amino acid residues 188–211 of SEQ ID NO:6), a Motif II domain (e.g., about amino acid residues 218–248 of SEQ ID NO:6), a kinase 2 domain (Motif III; Walker B box) (e.g., about amino acid residues 252–275 of SEQ ID NO:6), a kinase 3a domain (Motif IV) (e.g., about amino acid residues 295–320 of SEQ ID NO:6), a Motif V domain (e.g., about amino acid residues 371–391 of SEQ ID NO:6), a Motif VI domain (e.g., about amino acid residues 461–476 of SEQ ID NO:6), and a Motif VII domain (e.g., about amino acid residues 487–506 of SEQ ID NO:6).

Human PYRIN-6

The present invention is based, in part, on the identification of a sequence encoding a human PYRIN-6 protein in a search of the HTG genomic database. A predicted PYRIN-6 cDNA sequence is represented in SEQ ID NO:7 and a predicted 97 amino acid PYRIN-6 protein is represented in SEQ ID NO:8 (see FIG. 4).

An analysis of the predicted PYRIN-6 amino acid sequence showed it to contain a pyrin domain (e.g., about amino acid residues 1–91 of SEQ ID NO:8).

Human PYRIN-7

The present invention is based, in part, on the identification of a sequence encoding a human PYRIN-7 protein. FIG. 5 depicts the sequence of a 425 nucleotide partial cDNA (SEQ ID NO:9) which includes a predicted open reading frame (SEQ ID NO:11; nucleotides 270–425 of SEQ ID NO:9) encoding 52 amino acids of a human PYRIN-7 protein (SEQ ID NO:10).

A search of the Celera Genomics (Rockville, Md.) genomic database was performed to identify additional PYRIN-7 sequences. GENSCAN analysis was performed to identify potential exons. This analysis identified a predicted PYRIN-7 cDNA sequence represented in SEQ ID NO:12 and a predicted 655 amino acid PYRIN-7 protein represented in SEQ ID NO:13 (see FIGS. 6A–6D).

An analysis of the predicted PYRIN-7 amino acid sequence showed it to contain a pyrin domain (e.g., about amino acid residues 1–52 of SEQ ID NO:10 or 1–98 of SEQ ID NO:13) and a nucleotide binding site (NBS; e.g., about amino acid residues 167–480 of SEQ ID NO:13). Within the predicted NBS there is a kinase 1a domain (Motif I; P-loop) (e.g., about amino acid residues 167–190 of SEQ ID NO:13), a Motif II domain (e.g., about amino acid residues 197–227 of SEQ ID NO:13), a kinase 2 domain (Motif III; Walker B box) (e.g., about amino acid residues 231–254 of SEQ ID NO:13), a kinase 3a domain (Motif IV) (e.g., about amino acid residues 270–295 of SEQ ID NO:13), a Motif V domain (e.g., about amino acid residues 346–366 of SEQ ID NO:13), a Motif VI domain (e.g., about amino acid residues 435–450 of SEQ ID NO:13), and a Motif VII domain (e.g., about amino acid residues 461–480 of SEQ ID NO:13).

Human PYRIN-8

The present invention is based, in part, on the identification of a sequence encoding a human PYRIN-8 protein. FIG. 7 depicts the sequence of a 299 nucleotide partial cDNA (SEQ ID NO:14) which includes a predicted open reading frame (SEQ ID NO:16; nucleotides 105–299 of SEQ ID NO:14) encoding 65 amino acids of a human PYRIN-8 protein (SEQ ID NO:15).

A search of the Incyte (Palo Alto, Calif.) Life Gold Templates cDNA database was performed using a pyrin domain. This search identified a PYRIN-8 cDNA (clone number 2490690). Clone number 2490690 was obtained and sequenced in its entirety. This analysis identified a predicted PYRIN-8 cDNA sequence represented in SEQ ID NO:17 and a predicted 1061 amino acid PYRIN-8 protein represented in SEQ ID NO:18 (see FIGS. 8A–8F). The predicted molecular mass of the PYRIN-8 polypeptide of SEQ ID NO:18 is about 120 kDa.

The gene encoding PYRIN-8 maps to chromosome 19q13.4, a locus that contains a cluster of genes encoding related PYRIN-containing Apaf1-like (PYPAF) proteins.

An analysis of the predicted PYRIN-8 amino acid sequence showed it to contain a pyrin domain (e.g., about amino acid residues 1–65 of SEQ ID NO:15 or 1–107 of SEQ ID 30 NO:18), a nucleotide binding site (NBS; e.g., about amino acid residues 212–528 of SEQ ID NO:18), and several leucine rich repeats (e.g., about amino acid residues 712–739, 741–768, 769–796, 798–825, 826–853, 855–882, 883–910, 912–939, 940–967, 969–996, 997–1024, and 1026–1052 of SEQ ID NO:18) which form a LRR domain (e.g., about amino acid residues 712–1052 of SEQ ID NO:18). Within the predicted NBS there is a kinase 1a domain (Motif I; P-loop) (e.g., about amino acid residues 212–234 of SEQ ID NO:18), a Motif II domain (e.g., about amino acid residues 241–272 of SEQ ID NO:18), a kinase 2 domain (Motif III; Walker B box) (e.g., about amino acid residues 276–299 of SEQ ID NO:18), a kinase 3a domain (Motif IV) (e.g., about amino acid residues 320–345 of SEQ ID NO:18), a Motif V domain (e.g., about amino acid residues 396–416 of SEQ ID NO:18), a Motif VI domain (e.g., about amino acid residues 483–498 of SEQ ID NO:18), and a Motif VII domain (e.g., about amino acid residues 509–528 of SEQ ID NO:18).

As detailed herein, PYRIN-8 expression was found to be largely restricted to immune cells. Co-expression of PYRIN-8 with CARD-5 resulted in the recruitment of PYRIN-8 to distinct cytoplasmic loci and induced a potent synergistic activation of NF-kB activity. In addition, co-expression of PYRIN-8 and CARD-5 resulted in the synergistic activation of caspase-1 and the secretion of interleukin-1β (IL-1β).

The experimental findings presented herein indicate that PYRIN-8 participates in inflammatory signal transduction pathways by regulating caspase-1-dependent cytokine processing and the activation of NF-kB in response to pro-inflammatory stimuli. These findings are consistent with roles that have been identified for other related pyrin-domain containing proteins in inflammatory signaling. For example, mutations in PYRIN-1 (PYPAF1) have been associated with Muckle-Wells syndrome and familial cold urticaria, two genetically determined auto-inflammatory disorders that are similar to Mediterranean fever (Hoffman et al. (2002) Nat. Genet. 29, 301–305).

Human PYRIN-10

The present invention is based, in part, on the identification of a sequence encoding a human PYRIN-10 protein in a search of the Celera Genomics (Rockville, Md.) genomic database. GENSCAN analysis was performed to identify potential exons. This analysis identified a predicted PYRIN-10 cDNA sequence represented in SEQ ID NO:19 and a predicted 481 amino acid PYRIN-10 protein represented in SEQ ID NO:20 (see FIGS. 9A–9C).

An analysis of the predicted PYRIN-10 amino acid sequence showed it to contain a pyrin domain (e.g., about amino acid residues 41–112 of SEQ ID NO:20) and several leucine rich repeats (e.g., about amino acid residues 210–237, 267–294, 299–326, 356–383, 385–412, and 413–440 of SEQ ID NO:20) which form a LRR domain (e.g., about amino acid residues 210–440 of SEQ ID NO:20).

Human PYRIN-11

The present invention is based, in part, on the identification of a sequence encoding a human PYRIN-11 protein in a search of the Celera Genomics (Rockville, Md.) genomic database. GENSCAN analysis was performed to identify potential exons. This analysis identified a predicted PYRIN-11 cDNA sequence represented in SEQ ID NO:21 and a predicted 896 amino acid PYRIN-11 protein represented in SEQ ID NO:22 (see FIGS. 10A–10E).

An analysis of the predicted PYRIN-11 amino acid sequence showed it to contain a pyrin domain (e.g., about amino acid residues 1–102 of SEQ ID NO:22), a nucleotide binding site (NBS; e.g., about amino acid residues 177–494 of SEQ ID NO:22), and several leucine rich repeats (e.g., about amino acid residues 615–642, 644–671, 672–699, 701–728, 729–756, 758–785, and 786–813 of SEQ ID NO:22) which form a LRR domain (e.g., about amino acid residues 615–813 of SEQ ID NO:22). Within the predicted NBS there is a kinase 1a domain (Motif I; P-loop) (e.g., about amino acid residues 177–200 of SEQ ID NO:22), a Motif II domain (e.g., about amino acid residues 207–237 of SEQ ID NO:22), a kinase 2 domain (Motif III; Walker B box) (e.g., about amino acid residues 241–264 of SEQ ID NO:22), a kinase 3a domain (Motif IV) (e.g., about amino acid residues 285–310 of SEQ ID NO:22), a Motif V domain (e.g., about amino acid residues 361–381 of SEQ ID NO:22), a Motif VI domain (e.g., about amino acid residues 449–464 of SEQ ID NO:22), and a Motif VII domain (e.g., about amino acid residues 475–494 of SEQ ID NO:22).

TABLE 1

Summary of PYRIN-2, PYRIN-3, PYRIN-5, PYRIN-6, PYRIN-7, PYRIN-8, PYRIN-10, and PYRIN-11 Sequence Information

| Gene | cDNA | Protein | ORF | Figure |
|---|---|---|---|---|
| Human PYRIN-2 | SEQ ID NO: 1 | SEQ ID NO: 2 | | FIGS. 1A–C |
| Human PYRIN-3 | SEQ ID NO: 3; | SEQ ID NO: 4; | | FIG. 2; |
|  | SEQ ID NO: 23 | SEQ ID NO: 24 | SEQ ID NO: 25 | FIGS. 11A–E |
| Human PYRIN-5 | SEQ ID NO: 5 | SEQ ID NO: 6 | | FIGS. 3A–G |
| Human PYRIN-6 | SEQ ID NO: 7 | SEQ ID NO: 8 | | FIG. 4 |
| Human PYRIN-7 | SEQ ID NO: 9; | SEQ ID NO: 10; | SEQ ID NO: 11 | FIG. 5; |
|  | SEQ ID NO: 12 | SEQ ID NO: 13 | | FIGS. 6A–D |
| Human PYRIN-8 | SEQ ID NO: 14; | SEQ ID NO: 15; | SEQ ID NO: 16 | FIG. 7; |
|  | SEQ ID NO: 17 | SEQ ID NO: 18 | | FIGS. 8A–F |
| Human PYRIN-10 | SEQ ID NO: 19 | SEQ ID NO: 20 | | FIGS. 9A–C |
| Human PYRIN-11 | SEQ ID NO: 21 | SEQ ID NO: 22 | | FIGS. 10A–E |

TABLE 2

Summary of Domains of PYRIN-2

| Domain | Location |
|---|---|
| Pyrin domain | about amino acid residues 1–93 of SEQ ID NO: 2 |
| NBS domain | about amino acid residues 146–169 of SEQ ID NO: 2 |
| Kinase 1a domain (Motif I; P-loop) | about amino acid residues 146–169 of SEQ ID NO: 2 |
| Leucine rich repeats | about amino acids residues 196–223, 250–278, 280–307, 308–335, 337–364, 365–392, 394–421, and 422–449 of SEQ ID NO: 2 |
| LRR domain | about amino acid residues 196-449 of SEQ ID NO: 2 |

TABLE 3

Summary of Domains of PYRIN-3

| Domain | Location |
|---|---|
| Pyrin domain | about amino acid residues 1–83 of SEQ ID NO: 4; about amino acid residues 1–83 of SEQ ID NO: 24 |
| NBS domain | about amino acid residues 150–466 of SEQ ID NO: 24 |
| Kinase 1a domain (Motif I; P-loop) | about amino acid residues 150–172 of SEQ ID NO: 24 |
| Motif II | about amino acid residues 179–209 of SEQ ID NO: 24 |
| Kinase 2 domain (Motif III; Walker B box) | about amino acid residues 213–236 of SEQ ID NO: 24 |
| Kinase 3a domain (Motif IV) | about amino acid residues 257–282 of SEQ ID NO: 24 |
| Motif V | about amino acid residues 333–353 of SEQ ID NO: 24 |
| Motif VI | about amino acid residues 421–436 of SEQ ID NO: 24 |
| Motif VII | about amino acid residues 447–466 of SEQ ID NO: 24 |
| Leucine rich repeats | about amino acids residues 637–664, 722–749, 750–776, 806–833, 835–862, 863–890, 892–919, and 920–947 of SEQ ID NO: 24 |
| LRR domain | about amino acid residues 637–947 of SEQ ID NO: 24 |

TABLE 4

Summary of Domains of PYRIN-5

| Domain | Location |
|---|---|
| Pyrin domain | about amino acid residues 1–91 of SEQ ID NO: 6 |
| NBS domain | about amino acid residues 188–506 of SEQ ID NO: 6 |
| Kinase 1a domain (Motif I; P-loop) | about amino acid residues 188–211 of SEQ ID NO: 6 |
| Motif II | about amino acid residues 218–248 of SEQ ID NO: 6 |
| Kinase 2 domain (Motif III; Walker B box) | about amino acid residues 252–275 of SEQ ID NO: 6 |
| Kinase 3a domain (Motif IV) | about amino acid residues 295–320 of SEQ ID NO: 6 |
| Motif V | about amino acid residues 371–391 of SEQ ID NO: 6 |
| Motif VI | about amino acid residues 461–476 of SEQ ID NO: 6 |
| Motif VII | about amino acid residues 487–506 of SEQ ID NO: 6 |
| Leucine rich repeats | about amino acids residues 688–715, 744–771, 773–800, 801–828, 830–857, 858–885, 887–914, 915–942, 944–971, 972–1000, 1001–1028, and 1029–1056 of SEQ ID NO: 6 |
| LRR domain | about amino acid residues 688–1056 of SEQ ID NO: 6 |

TABLE 5

Summary of Domains of PYRIN-6

| Domain | Location |
|---|---|
| Pyrin domain | about amino acid residues 1–91 of SEQ ID NO: 8 |

TABLE 6

Summary of Domains of PYRIN-7

| Domain | Location |
|---|---|
| Pyrin domain | about amino acid residues 1–52 of SEQ ID NO: 10; about amino acid residues 1–98 of SEQ ID NO: 13 |
| NBS domain | about amino acid residues 167–480 of SEQ ID NO: 13 |
| Kinase 1a domain (Motif I; P-loop) | about amino acid residues 167–190 of SEQ ID NO: 13 |
| Motif II | about amino acid residues 197–227 of SEQ ID NO: 13 |
| Kinase 2 domain (Motif III; Walker B box) | about amino acid residues 231–254 of SEQ ID NO: 13 |
| Kinase 3a domain (Motif IV) | about amino acid residues 270–295 of SEQ ID NO: 13 |
| Motif V | about amino acid residues 346–366 of SEQ ID NO: 13 |
| Motif VI | about amino acid residues 435–450 of SEQ ID NO: 13 |
| Motif VII | about amino acid residues 461–480 of SEQ ID NO: 13 |

TABLE 7

Summary of Domains of PYRIN-8

| Domain | Location |
|---|---|
| Pyrin domain | about amino acid residues 1–65 of SEQ ID NO: 15; about amino acid residues 1–107 of SEQ ID NO: 18 |
| NBS domain | about amino acid residues 212–528 of SEQ ID NO: 18 |
| Kinase 1a domain (Motif I; P-loop) | about amino acid residues 212–234 of SEQ ID NO: 18 |
| Motif II | about amino acid residues 241–272 of SEQ ID NO: 18 |
| Kinase 2 domain (Motif III; Walker B box) | about amino acid residues 276–299 of SEQ ID NO: 18 |
| Kinase 3a domain (Motif IV) | about amino acid residues 320–345 of SEQ ID NO: 18 |
| Motif V | about amino acid residues 396–416 of SEQ ID NO: 18 |
| Motif VI | about amino acid residues 483–498 of SEQ ID NO: 18 |
| Motif VII | about amino acid residues 509–528 of SEQ ID NO: 18 |
| Leucine rich repeats | about amino acids residues 712–739, 741–768, 769–796, 798–825, 826–853, 855–882, 883–910, 912–939, 940–967, 969–996, 997–1024, and 1026–1052 of SEQ ID NO: 18 |
| LRR domain | about amino acid residues 712–1052 of SEQ ID NO: 18 |

TABLE 8

Summary of Domains of PYRIN-10

| Domain | Location |
|---|---|
| Pyrin domain | about amino acid residues 41–112 of SEQ ID NO: 20 |
| Leucine rich repeats | about amino acids residues 210–237, 267–294, 299–326, 356–383, 385–412, and 413–440 of SEQ ID NO: 20 |
| LRR domain | about amino acid residues 210–440 of SEQ ID NO: 20 |

TABLE 9

Summary of Domains of PYRIN-11

| Domain | Location |
|---|---|
| Pyrin domain | about amino acid residues 1–102 of SEQ ID NO: 22 |
| NBS domain | about amino acid residues 177–494 of SEQ ID NO: 22 |
| Kinase 1a domain (Motif I; P-loop) | about amino acid residues 177–200 of SEQ ID NO: 22 |
| Motif II | about amino acid residues 207–237 of SEQ ID NO: 22 |
| Kinase 2 domain (Motif III; Walker B box) | about amino acid residues 241–264 of SEQ ID NO: 22 |
| Kinase 3a domain (Motif IV) | about amino acid residues 285–310 of SEQ ID NO: 22 |
| Motif V | about amino acid residues 361–381 of SEQ ID NO: 22 |
| Motif VI | about amino acid residues 449–464 of SEQ ID NO: 22 |
| Motif VII | about amino acid residues 475–494 of SEQ ID NO: 22 |
| Leucine rich repeats | about amino acids residues 615–642, 644–671, 672–699, 701–728, 729–756, 758–785, and 786–813 of SEQ ID NO: 22 |
| LRR domain | about amino acid residues 615–813 of SEQ ID NO: 22 |

Stimulation of NF-kB Activity by PYRIN-8

The ability of PYRIN-8 to modulate NF-kB activation was investigated. PYRIN-8 regulation of the NF-kB pathway is of interest because the NF-kB pathway is involved in many diseases (see, e.g., New England Journal of Medicine 336:1066 (1997) and American Journal of Cardiology 76:18C (1995)). Participation of PYRIN-8 in the NF-kB pathway makes PYRIN-8 an attractive target for drugs that modulate the NF-kB pathway for treatment of NF-kB pathway-dependent diseases, conditions, and biological processes.

293T cell were co-transfected the pNF-kB-Luc firefly luciferase reporter (Stratagene, Inc; La Jolla, Calif.), pRL-TK renilla reporter (Promega), and with plasmids expressing PYRIN-8-FL (1000 ng) and/or CARD-5 (ASC) (32 ng). The amount of DNA in each transfection was kept constant by the addition of empty vector. Twenty hours after transfection, cells were harvested and relative luciferase activity was determined as a measure of NF-kB activity.

PYRIN-8 (1000 ng) or CARD-5 (32 ng) when expressed alone induced little or no NF-kB activity. However, co-expression of PYRIN-8 and CARD-5 resulted in a 150 fold increase in NF-kB activity. Thus, PYRIN-8 and CARD-5 were found to cooperate to stimulate NF-kB activity.

CARD-5 has previously been shown to interact with caspase-1 and induce apoptosis (see, e.g., U.S. application Ser. No. 09/841,879, filed Apr. 24, 2001, and U.S. application Ser. No. 09/728,721, filed Dec. 1, 2000, the contents of which are incorporated by reference). Thus, based upon the findings presented herein, PYRIN-8 is also expected to participate in apoptotic and/or inflammatory signaling pathways.

Expression of PYRIN-8 and PYRIN-9

PYRIN-8 and PYRIN-9 gene expression was determined using the Perkin-Elmer/ABI 7700 Sequence Detection System which employs TaqMan technology. TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of PYRIN-8 and PYRIN-9 in various human tissues a primer/probe set was designed. Total RNA was prepared from a series of human tissues using. First strand cDNA was prepared from 1 µg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Tables 10–13.

As depicted in Tables 10–13, PYRIN-8 and PYRIN-9 mRNA was detected in cell types involved in inflammation and/or immunity. For example, Table 10 shows PYRIN-8 to be expressed in monocytes and macrophages, as well as in spleen, lung, and chronic obstructive pulmonary disease (COPD) samples. In addition, Tables 11–13 show PYRIN-9 to be expressed in T cells, granulocytes, and eosinophils. These expression patterns of PYRIN-8 and PYRIN-9 further suggest their role in inflammation.

TABLE 10

Expression of PYRIN-8

| Cell Type | Relative Expression |
| --- | --- |
| CD4-resting | 0.04 |
| CD4-aCD3/CD28 4/24 h | 0.01 |
| CD8-resting | 0.01 |
| CD8-aCD3/CD28 4/24 h | 0.01 |
| CD14-resting | 4.04 |
| CD14-LPS 4/24 h | 2.06 |
| CD19-resting | 0.00 |
| CD19-LPS 4/24 h | 0.00 |
| CD19-CD40L 4/24 h | 0.17 |
| Macrophage-resting | 0.58 |
| Macrophage-LPS 4/24 h | 0.18 |
| Macrophage-IFNg 4/24 h | 0.32 |
| Macrophage-CD40L 4/24 h | 0.33 |

TABLE 10-continued

Expression of PYRIN-8

| Cell Type | Relative Expression |
| --- | --- |
| Th1-1/6/24 h (46) | 0.00 |
| Th2-1/6/24 h (46) | 0.00 |
| FLS-resting | 0.00 |
| FLS-TNF 4/24 h | 0.00 |
| FLS-IL1 4/24 h | 0.00 |
| NHBE-resting | 0.00 |
| NHBE-IL-4 4/24 h | 0.00 |
| NHBE-IL-13 4/24 h | 0.05 |
| BSMC-resting | 0.01 |
| BSMC-TNF 4/24 h | 0.00 |
| BSMC-IFNg 4/24 h | 0.00 |
| HMVEC-resting | 0.64 |
| HMVEC-IFNg 4/24 h | 0.07 |
| HMVEC-TNF 4/24 h | 0.03 |
| NSYN7/26/01 | 1.93 |
| RASYN7/16/01 | 0.42 |
| OA 7/16/01 | 0.74 |
| Normal Colon pool | 0.44 |
| Colitis Colon pool | 0.34 |
| Crohns Colon pool | 1.23 |
| Normal Brain (NDR 169) | 0.25 |
| Normal Heart | 1.82 |
| Normal Liver | 0.36 |
| Normal Kidney | 0.09 |
| Normal Spleen | 3.50 |
| Normal Tonsil | 0.07 |
| Normal Lymph Node | 0.08 |
| Normal Lung pool | 1.45 |
| COPD-1 | 1.64 |
| COPD-2 | 1.02 |

TABLE 11

Expression of PYRIN-9

| Cell Type | Relative Expression |
| --- | --- |
| CD4-resting | 2.36 |
| CD4-aCD3/CD28 4/24 h | 2.53 |
| CD8-resting | 1.66 |
| CD8-aCD3/CD28 4/24 h | 3.67 |
| CD14-resting | 0.15 |
| CD14-LPS 4/24 h | 0.14 |
| CD19-resting | 0.22 |
| CD19-LPS 4/24 h | 0.71 |
| CD19-CD40L 4/24 h | 0.35 |
| Macrophage-resting | 0.02 |
| Macrophage-LPS 4/24 h | 0.12 |
| Macrophage-IFNg 4/24 h | 0.09 |
| Macrophage-CD40L 4/24 h | 0.00 |
| Th1-1/6/24 h (46) | 10.25 |
| Th2-1/6/24 h (46) | 5.89 |
| FLS-resting | 0.01 |
| FLS-TNF 4/24 h | 0.00 |
| FLS-IL1 4/24 h | 0.01 |
| NHBE-resting | 0.04 |
| NHBE-IL-4 4/24 h | 0.04 |
| NHBE-IL-13 4/24 h | 0.35 |
| BSMC-resting | 0.43 |
| BSMC-TNF 4/24 h | 0.01 |
| BSMC-IFNg 4/24 h | 0.10 |
| HMVEC-resting | 0.01 |
| HMVEC-IFNg 4/24 h | 0.00 |
| HMVEC-TNF 4/24 h | 0.07 |
| NSYN7/26/01 | 0.33 |
| RASYN7/16/01 | 3.22 |
| OA 7/16/01 | 0.05 |
| Normal Colon pool | 3.55 |
| Colitis Colon pool | 1.77 |
| Crohns Colon pool | 1.36 |
| Normal Brain (pool) | 0.18 |
| Normal Heart | 0.10 |

TABLE 11-continued

Expression of PYRIN-9

| Cell Type | Relative Expression |
| --- | --- |
| Normal Liver | 3.05 |
| Normal Kidney | 24.72 |
| Normal Spleen | 3.99 |
| Normal Tonsil | 3.03 |
| Normal Lymph Node | 7.30 |
| Normal Lung pool | 1.12 |
| COPD-1 | 6.62 |
| COPD-2 | 2.39 |

TABLE 12

Expression of PYRIN-9

| Cell Type | Relative Expression |
| --- | --- |
| CD4 resting | 0.42 |
| CD4 aCD3 4 hr | 1.38 |
| CD4 aCD3 24 hr | 0.29 |
| CD4 aCD3/CD28 4 hr | 1.86 |
| CD4 aCD3/CD28 24 hr | 0.27 |
| CD8 resting | 0.85 |
| CD8 aCD3 4 hr | 0.79 |
| CD8 aCD3 24 hr | 1.01 |
| CD8 aCD3/CD28 4 hr | 1.41 |
| CD8 aCD3/CD28 24 hr | 0.58 |
| Eos resting | 0.33 |
| Eos IL-4 4 hr | 0.09 |
| Eos IL-4 24 hr | 0.87 |
| Macrophage-resting | 0.00 |
| Macrophage-LPS 4 hr | 0.00 |
| Macrophage-LPS 24 hr | 0.00 |
| Macrophage-IFNg 4 hr | 0.00 |
| Macrophage-IFNg 24 hr | 0.02 |
| Granulocytes resting | 1.39 |
| Granulocytes INFg 4 hr | 0.89 |
| Granulocytes INFg 24 hr | 0.26 |
| Granulocytes TNFa 4 hr | 1.49 |
| Granulocytes TNFa 24 hr | 0.67 |
| TH0(RL)-0 | 0.24 |
| TH0(RL)-1 | 1.16 |
| TH0(RL)-6 | 0.23 |
| TH0(RL)-24 | 0.11 |
| TH1(RL)-0 | 0.71 |
| TH1(RL)-1 | 1.89 |
| TH1(RL)-6 | 0.63 |
| TH1(RL)-24 | 0.17 |
| TH2(RL)-0 | 0.05 |
| TH2(RL)-1 | 1.74 |
| TH2(RL)-6 | 0.10 |
| TH2(RL)-24 | 0.06 |
| NHBE resting | 0.00 |
| NHBE IL-4 4 hr | 0.02 |
| NHBE IL-4 24 hr | 0.01 |
| NHBE IL-13 4 hr | 0.04 |
| NHBE IL-13 24 hr | 0.00 |
| NHBE IL-4/IL-13 4 hr | 0.00 |
| NHBE IL-4/IL-13 24 hr | 0.00 |

TABLE 13

Expression of PYRIN-9

| Cell Type | Relative Expression |
| --- | --- |
| BSMC resting | 0.03 |
| BSMC IL-1 4 hr | 0.00 |
| BSMC IL-1 24 hr | 0.01 |
| BSMC IFNg 4 hr | 0.00 |
| BSMC IFNg 24 hr | 0.00 |
| BSMC TNFa 4 hr | 0.00 |

TABLE 13-continued

Expression of PYRIN-9

| Cell Type | Relative Expression |
| --- | --- |
| BSMC TNFa 24 hr | 0.00 |
| NHLF resting | 0.00 |
| NHLF TGFb 4 hr | 0.01 |
| NHLF TGFb 24 hr | 0.00 |
| NHLF TNFa 4 hr | 0.00 |
| NHLF TNFa 24 hr | 0.00 |
| NHDF resting | 0.07 |
| NHDF TGFb 4 hr | 0.00 |
| NHDF TNFa 4 hr | 0.01 |
| NHDF TNFa 24 hr | 0.00 |
| Jag 3, 4, 9 Bronchitis | 0.09 |
| JAG 1, 2, 5, 7 Asthma | 0.04 |
| EUR 64 | 0.24 |
| AMC 362 | 0.03 |
| AMC 364 | 0.17 |
| AMC 365 | 0.07 |
| AMC 366 | 0.06 |
| N Lung PIT 242 | 0.29 |
| N Lung CHT 427 | 0.05 |
| N Lung CHT 810 | 0.00 |
| N Lung CHT 894 | 0.06 |
| N Lung CHT 1242 | 0.12 |
| N Lung CHT 700 | 0.01 |
| N Lung CHT 702 | 0.07 |
| N Lung CHT 834 | 0.00 |
| N Lung MDA 180 | 0.06 |
| N Lung MDA 184 | 0.02 |
| N Lung MDA 185 | 0.01 |
| COPD MDA 177 | 0.15 |
| COPD NDR 187 | 1.08 |
| COPD NDR 188 | 0.06 |
| COPD MDA 189 | 0.04 |
| COPD CHT 743 | 1.01 |
| IPF B | 0.23 |
| IPF C | 1.11 |
| IPF D3 | 0.15 |
| IPF E4 | 4.78 |
| Norm. Liver NDR200 | 0.14 |
| NDR 141 | 0.29 |
| NDR 191 | 0.64 |

Northern blot analysis using a multiple tissue expression array (CLONTECH, Palo Alto, Calif.) showed PYRIN-8 expression in peripheral blood leukocytes. Little or no expression was detected in approximately 75 other tissues and cancer cell lines tested, indicating a role for PYRIN-8 in inflammatory signaling.

To determine the particular cell types that express PYRIN-8, peripheral blood leukocytes were fractionated into distinct cell populations. RT-QPCR analysis showed PYRIN-8 was predominantly expressed in eosinophils and granulocytes, with some expression in monocytes.

The restricted expression of PYRIN-8 to immune cells further indicates a role for the protein and its binding-partners in inflammatory signaling.

Co-Localization of PYRIN-8 and CARD-5

Cellular co-localization studies were carried out to determine whether PYRIN-8 interacts with CARD-5 (also known as ASC) when the two proteins were overexpressed in 293T embryonic kidney cells. Plasmids expressing either full-length PYRIN-8 (PYRIN-8-FL, residues 1–1061 of SEQ ID NO:18) or a PYRIN-8 truncation mutant lacking the PYRIN domain (PYRIN-8ΔPYRIN, residues 89–1061 of SEQ ID NO:18) with a C-terminal FLAG epitope were constructed using pCI (Promega). FLAG-tagged PYRIN-8 and HA-tagged CARD-5 were expressed in cells and detected using a mixture of anti-HA and anti-FLAG antibodies.

When expressed alone, PYRIN-8 (PYRIN-8-FL) showed a broad cytoplasmic distribution that excluded the nucleus. CARD-5, when expressed alone, localized to cytoplasmic punctate structures. However, when PYRIN-8 and CARD-5 were co-expressed, PYRIN-8-FL was found to co-localize with CARD-5.

A PYRIN-8 mutant lacking the N-terminal PYRIN domain (PYRIN-8ΔPYRIN) was also examined for its ability to be recruited to the CARD-5 punctate structures. When expressed alone, PYRIN-8ΔPYRIN showed a broad cytoplasmic distribution similar to that of PYRIN-8-FL. However, PYRIN-8ΔPYRIN failed to associate with the CARD-5 punctate structures, suggesting that the PYRIN domain of PYRIN-8 participates in the recruitment and assembly in a CARD-5 complex. Taken together, these findings suggest that the N-terminal PYRIN domain of PYRIN-8 mediates recruitment and assembly of a cytoplasmic PYRIN-8/CARD-5 complex.

In immunostaining assays to detect cellular localization, 293T cells were transfected in poly-D-lysine-coated glass chamber slides (BioCoat, Becton-Dickinson Labware) with plasmids expressing HA-tagged CARD-5 and either FLAG-tagged PYRIN-8 or PYRIN-8ΔPYRIN using SuperFect transfection reagent (Qiagen). Cells were fixed 24 hours after transfection in 4% paraformaldehyde, permeabilized and blocked in a buffer containing 0.3% Triton X-100, and incubated with the following primary and secondary antibodies: rabbit anti-HA polyclonal Y-11 (Santa Cruz Biotechnology), mouse anti-FLAG monoclonal antibody M2 (Sigma), Alexa-350 goat anti-rabbit IgG (Molecular Probes), and Alexa-598 goat anti-mouse IgG (Molecular Probes). Images were acquired as described previously (Bertin et al. (2001) J. Biol. Chem. 276:11877–11882).

Immunoprecipitation of FLAG-tagged PYRIN-8 failed to co-precipitate HA-tagged CARD-5. This inability to detect an interaction by immunoprecipitation may be due to the relative insolubility of PYRIN-8/CARD-5 complexes that form in a cell when both proteins are overexpressed. A similar difficulty in co-immunoprecipitating CARD-5 with other PYRIN-containing proteins has been reported in other studies (see, e.g., Manji et al. (2002) J. Biol. Chem. 277 (13):11570–75).

CARD-5 is described in U.S. patent application Ser. No. 09/841,879, filed Apr. 24, 2001, U.S. patent application Ser. No. 09/728,721, filed Dec. 1, 2000, U.S. patent application Ser. No. 09/340,620, filed Jun. 28, 1999, the entire contents of which are incorporated by reference.

PYRIN-8 Synergizes with CARD-5 to Induce NF-kB Activity

Figure 12B:
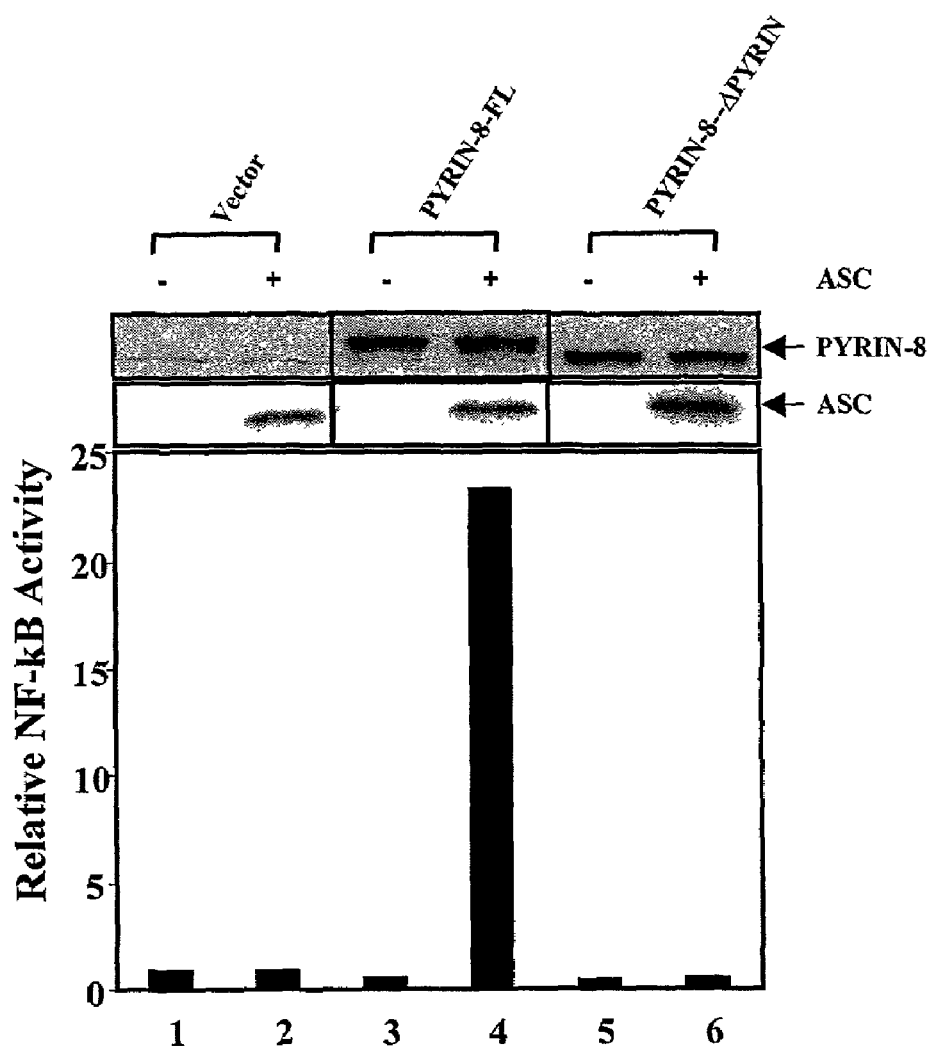

NF-kB is activated when high levels of CARD-5 are expressed in a cell. Experiments were carried out to determine whether PYRIN-8 synergizes with CARD-5 to activate NF-kB. When CARD-5 was expressed at low protein levels that did not activate NF-kB, co-expression with increasing amounts of PYRIN-8 resulted in a dose-dependent increase in NF-κB activity (FIG. 12A). The N-terminal PYRIN domain of PYRIN-8 participated in NF-kB signaling, since deletion of this domain (PYRIN-8ΔPYRIN) eliminated the synergistic induction of NF-kB activity (FIG. 12B, compare lanes 4 to 6). Immunoblot analysis revealed that CARD-5 protein levels were not increased when co-expressed with PYRIN-8, demonstrating that the activation of NF-kB was not due to increased levels of CARD-5 (FIG. 12B, upper panels in lanes 2 and 4).

Figure 12C:
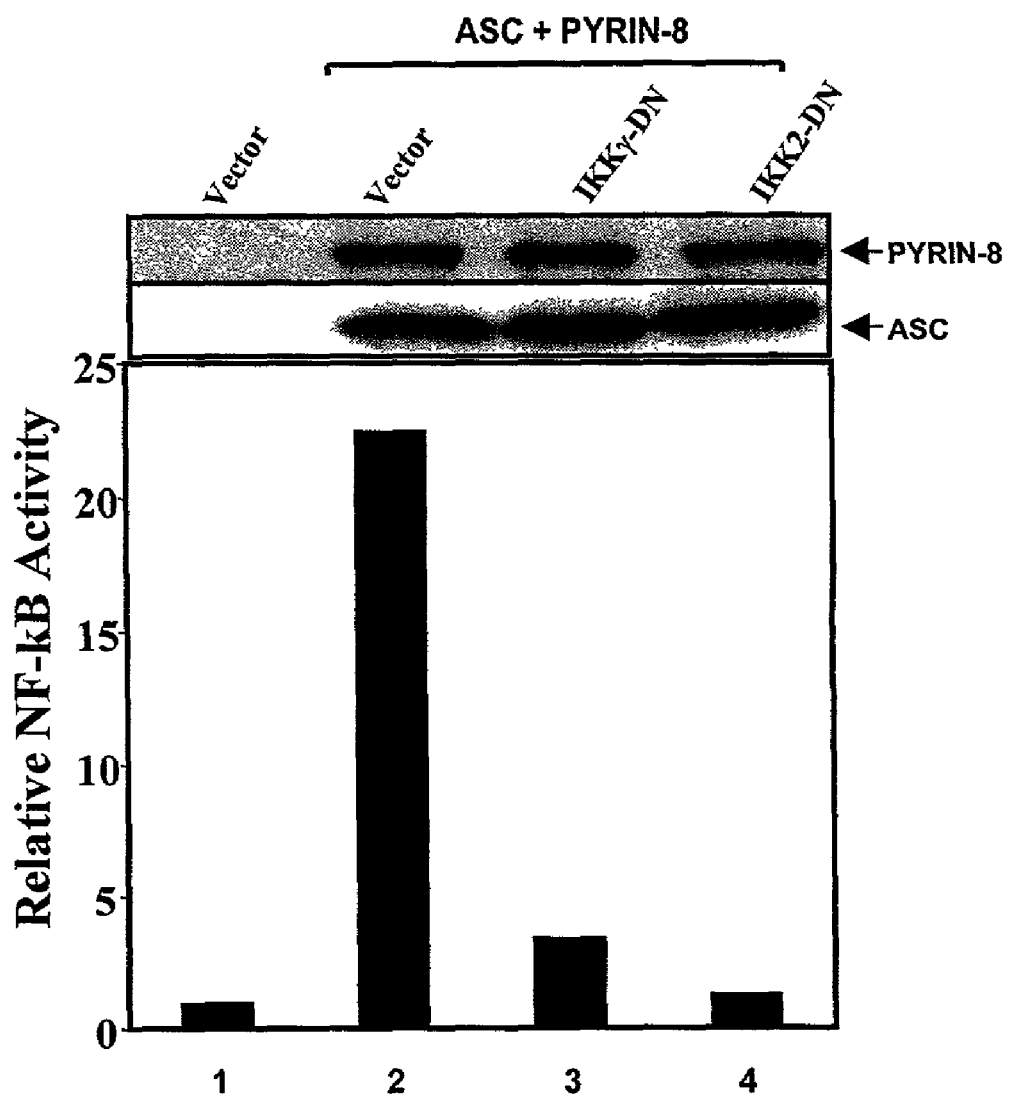

NF-kB signaling occurred through the IKK complex, as demonstrated by dominant-negative versions of IKK-γ and IKK-2 blocking the ability of PYRIN-8 and CARD-5 to synergistically activate NF-kB (FIG. 12C, lanes 3 and 4). These data demonstrate that PYRIN-8 functions as an activator of CARD-5 activity and is an upstream regulator of NF-kB signaling.

NF-κB assays were carried out as described by Wang et al. (2001) J. Biol. Chem. 276:21405–21409. 293T cells were transfected with pNF-κB luciferase reporter (Stratagene), pRL-TK Renilla reporter (Promega), and indicated expression plasmids. Cells were harvested and firefly and Renilla luciferase activities were determined using the Dual-Luciferase reporter assay system (Promega).

PYRIN-8 Synergizes with CARD-5 to Activate Caspase-1

Figure 13A:
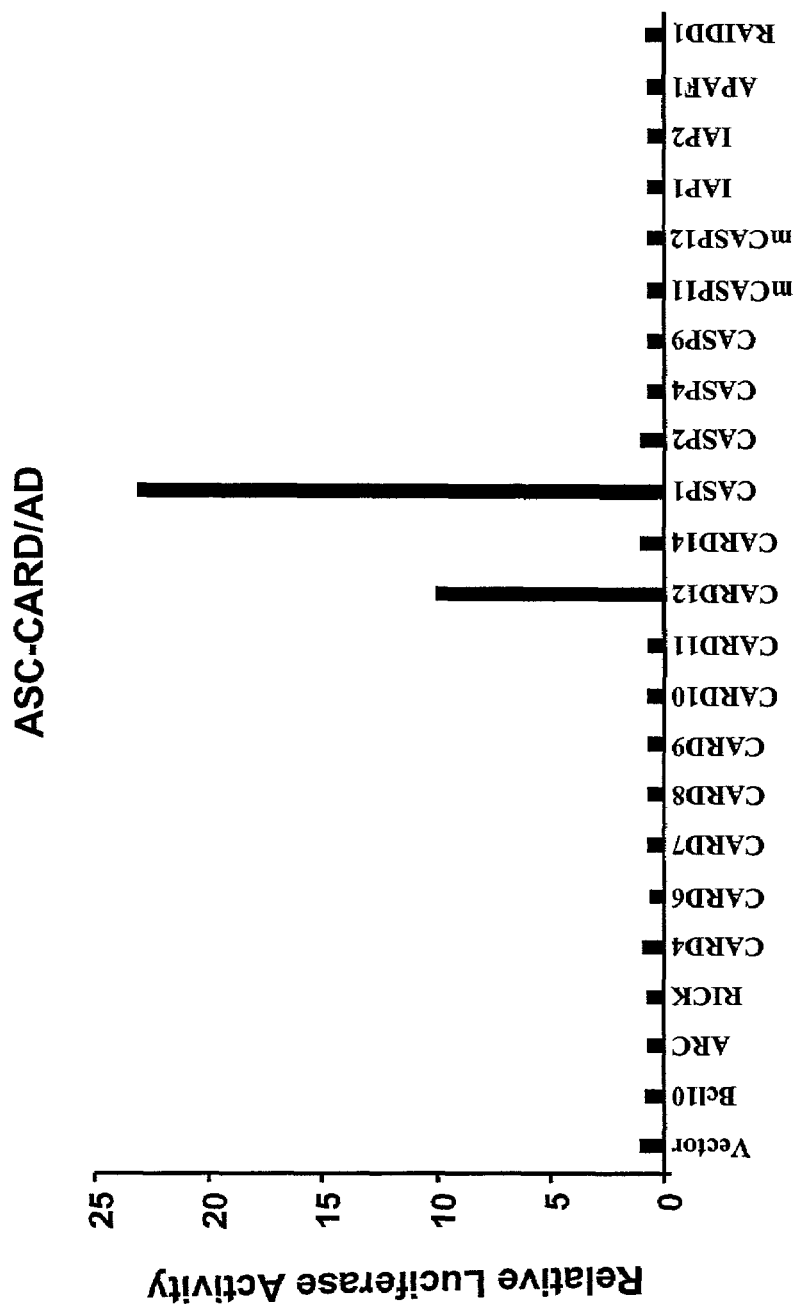
FIGS. 13A–13B are graphs depicting: (A) the CARD of CARD-5 (ASC) interacting with the CARD of caspase-1; and (B) CARD-5 (ASC) interacting with caspase-1. Cell extracts were immunoprecipitated (IP) with anti-HA antibodies and immunoblotted (WB) with an anti-caspase-1 antibody (upper panel). CARD-5 (ASC) and caspase-1 protein levels in cell lysates were confirmed by immunoblot analysis (WB, bottom panels).

CARD-5 is a relatively small protein containing an N-terminal PYRIN domain and a C-terminal CARD domain (see, e.g., Masumoto et al. (1999) J. Biol. Chem. 274:33835–38). To identify whether the CARD domain of a CARD-containing protein interacted with the CARD of CARD-5, mammalian two-hybrid analysis was carried out using the CARD domains of 22 CARD-containing proteins (FIG. 13A). Mammalian two-hybrid assays were performed as described by Wang et al. (2001) J. Biol. Chem. 276:21405–21409. 293T cells were transfected with pCMV/AD and pCMV/BD plasmids, pFR-Luc firefly reporter (Stratagene), and pRL-TK Renilla reporter (Promega).

Figure 13B:
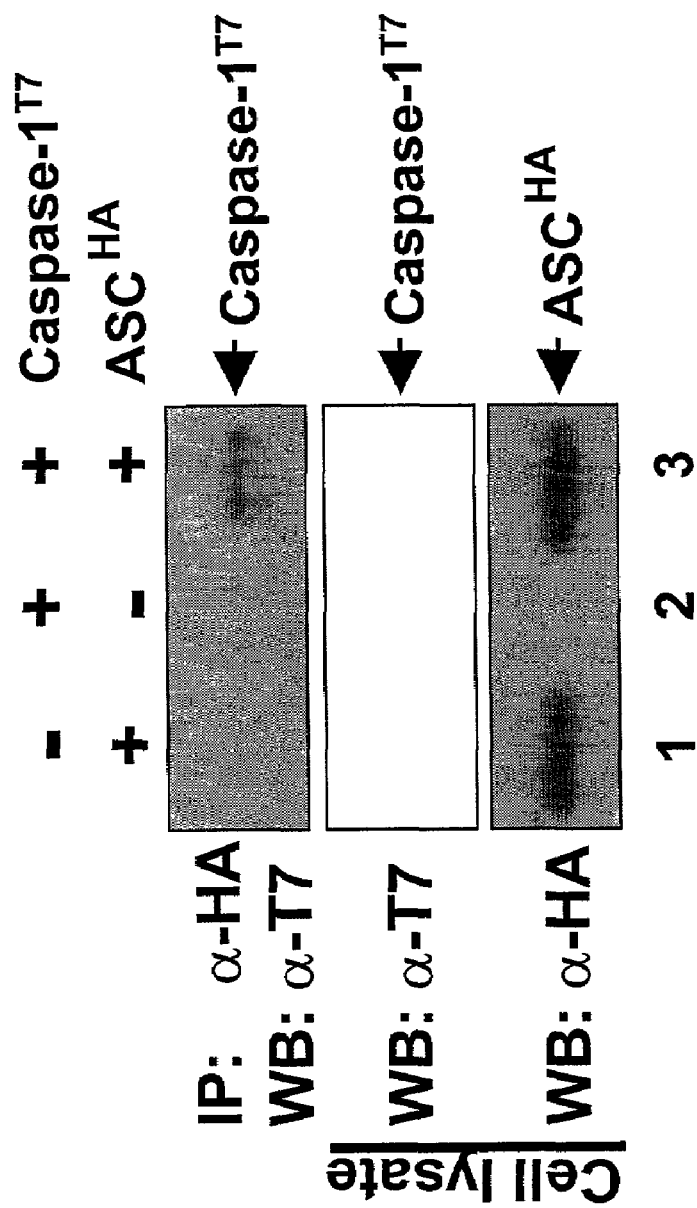

The CARD of CARD-5 was found to interact selectively with the CARD of caspase-1, resulting in a 24-fold activation of luciferase activity (FIG. 13A). The CARD of CARD-12 also interacted with the CARD domain of CARD-5. In addition to two hybrid analyses, immunoprecipitation of HA-tagged CARD-5 quantitatively co-precipitated T7-tagged caspase-1 (FIG. 13B). Taken together, these findings suggest that CARD-5 binds to caspase-1 through its C-terminal CARD.

Experiments were next carried out using an IL-1β secretion assay to determine whether CARD-5 and PYRIN-8 induce activation of caspase-1. Active caspase-1 cleaves pro-IL-1β, resulting in the secretion of bioactive IL-1β from cells. In the IL-1β secretion assays, COS-7L cells (GIBCO) were co-transfected in 12-well (22-mm) plates using LipofectAMINE 200 reagent (Invitrogen) with plasmids encoding mouse pro-IL-1β and indicated expression plasmids (total DNA=1.04 μg). Supernatants were collected 24 hours after transfection and subjected to ELISA for mouse IL-1β according to the manufacturer's protocol (R&D Systems).

Figure 14A:
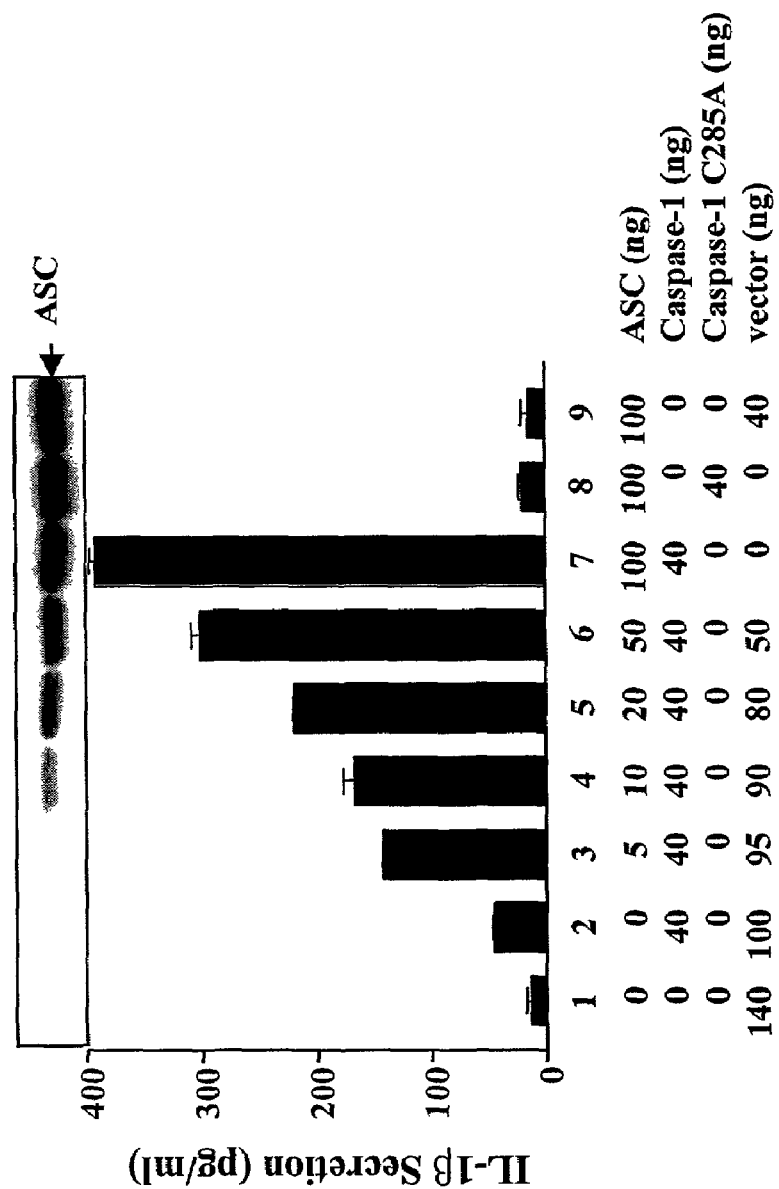
FIGS. 14A–14C are graphs depicting: (A) the activation of caspase-1 by CARD-5 (ASC); (B) the activation of caspase-1 by PYRIN-8; and (c) the dependence of PYRIN-8/CARD-5 (ASC) induction of IL-1β secretion on active caspase-1.

When caspase-1 was expressed at low protein levels that result in minimal levels of IL-1β secretion, co-expression with CARD-5 resulted in a dose-dependent increase in the levels of secreted IL-1β ranging from 150 to 400 pg/ml (FIG. 14A). The increase in IL-1β production was dependent on functional caspase-1, because substitution with a caspase-1 active site C285A mutant failed to show activity when co-expressed with CARD-5 (FIG. 14A, lane 8).

Figure 14B:
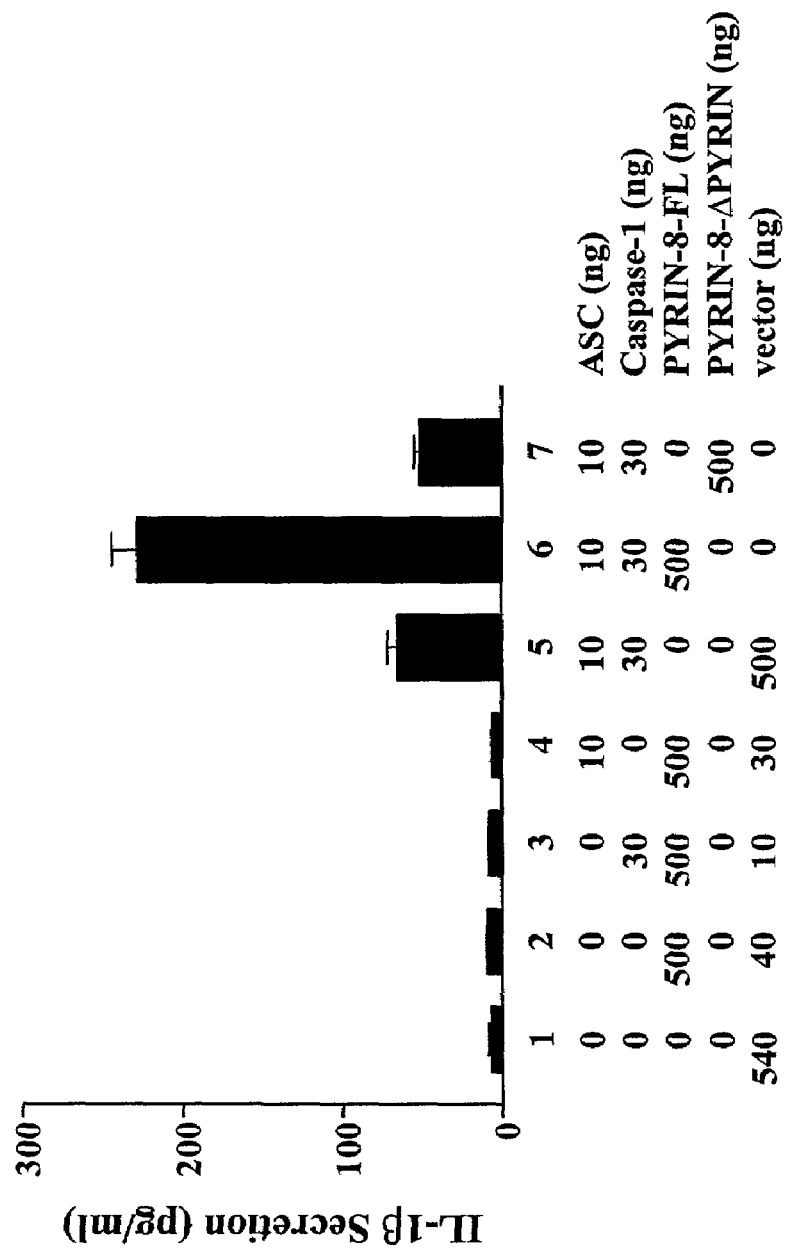
Figure 14C:
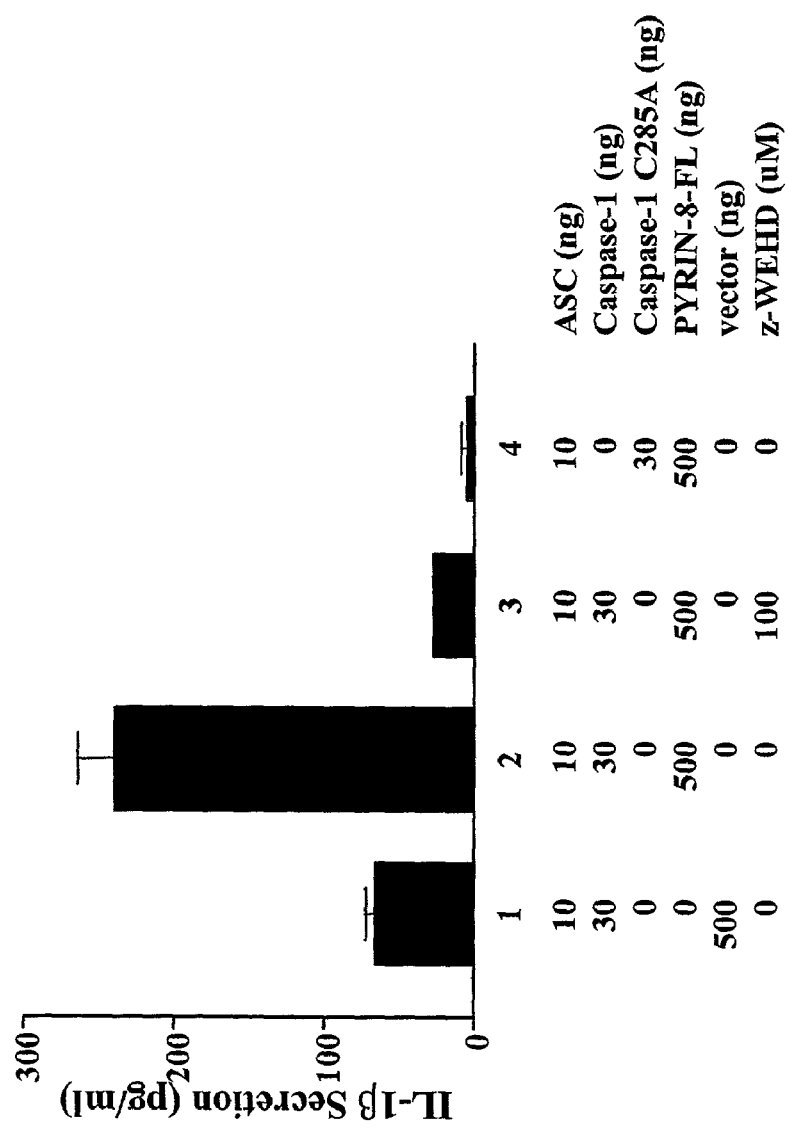

When caspase-1 and CARD-5 were expressed at low protein levels that result in minimal levels of IL-1β secretion, co-expression with PYRIN-8 resulted in the activation of caspase-1 and a corresponding increase in IL-1β production (FIG. 14B, compare lanes 5 and 6). The N-terminal PYRIN domain of PYRIN-8 was required for caspase-1 activation, since deletion of this domain (PYRIN-8ΔPYRIN) eliminated the synergistic production of IL-1β (FIG. 14B, compare lanes 6 and 7). Immunoblot analysis revealed that PYRIN-8ΔPYRIN was expressed at levels similar to that of PYRIN-8, indicating that loss of function was not due to reduced protein levels. The increase in IL-1β production was dependent on functional caspase-1, because a caspase-1 active site C285A mutant failed to show activity when co-expressed with CARD-5 and PYRIN-8 (FIG. 14C, compare lanes 2 and 4). Moreover, addition of a specific inhibitor of caspase-1 (Z-WEHD; R&D Systems) blocked the ability of PYRIN-8 and CARD-5 to induce the secretion of IL-1β (FIG. 14C, lane 4). The caspase-1 inhibitor Z-WEHD-FMK was added to cells following transfection at a final concentration of 100 μM. Taken together, these data demonstrate that PYRIN-8, when co-expressed with CARD-5, synergistically activates caspase-1-dependent cytokine processing.

Each of PYRIN-2, PYRIN-3, PYRIN-5, PYRIN-6, PYRIN-7, PYRIN-8, PYRIN-10, and PYRIN-11 are members of a family of molecules (PYRIN-2, PYRIN-3, PYRIN-5, PYRIN-6, PYRIN-7, PYRIN-8, PYRIN-10, and PYRIN-11 families, respectively) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

Preferred PYRIN-2, PYRIN-3, PYRIN-5, PYRIN-6, PYRIN-7, PYRIN-8, PYRIN-10, or PYRIN-11 polypeptides of the present invention include an amino acid sequence sufficiently identical to one or more of the following domains: a pyrin domain, and NBS domain, and/or a LRR domain.

As used interchangeably herein a "PYRIN-2, PYRIN-3, PYRIN-5, PYRIN-6, PYRIN-7, PYRIN-8, PYRIN-10, or PYRIN-11 activity", "biological activity of PYRIN-2, PYRIN-3, PYRIN-5, PYRIN-6, PYRIN-7, PYRIN-8, PYRIN-10, or PYRIN-11" or "functional activity of PYRIN-2, PYRIN-3, PYRIN-5, PYRIN-6, PYRIN-7, PYRIN-8, PYRIN-10, or PYRIN-11", refers to an activity exerted by a PYRIN-2, PYRIN-3, PYRIN-5, PYRIN-6, PYRIN-7, PYRIN-8, PYRIN-10, or PYRIN-11 protein, polypeptide or nucleic acid molecule on a PYRIN-2, PYRIN-3, PYRIN-5, PYRIN-6, PYRIN-7, PYRIN-8, PYRIN-10, or PYRIN-11 responsive cell as determined in vivo, or in vitro, according to standard techniques. PYRIN-2, PYRIN-3, PYRIN-5, PYRIN-6, PYRIN-7, PYRIN-8, PYRIN-10, or PYRIN-11 may act as a pro-apoptotic protein or an anti-apoptotic protein (i.e., it might act to decrease or increase apoptosis). A PYRIN-2, PYRIN-3, PYRIN-5, PYRIN-6, PYRIN-7, PYRIN-8, PYRIN-10, or PYRIN-11 activity can be a direct activity, such as an association with or an enzymatic activity on a second protein or an indirect activity, such as a cellular signaling activity mediated by interaction of the PYRIN-2, PYRIN-3, PYRIN-5, PYRIN-6, PYRIN-7, PYRIN-8, PYRIN-10, or PYRIN-11 protein with a second protein.

In one embodiment, a PYRIN-2, PYRIN-3, PYRIN-5, PYRIN-6, PYRIN-7, PYRIN-8, PYRIN-10, or PYRIN-11 activity can include at least one or more of the following activities: (i) the ability to interact with proteins in an apoptotic or inflammatory signaling pathway, e.g., CARD-5 and/or caspase-1; (ii) the ability to interact with a PYRIN-2, PYRIN-3, PYRIN-5, PYRIN-6, PYRIN-7, PYRIN-8, PYRIN-10, or PYRIN-11; (iii) the ability to bind to and/or hydrolyze a nucleotide, e.g., ATP or GTP; (iv) the ability to interact with an intracellular target protein; (v) the ability to interact, directly or indirectly, with one or more proteins having a pyrin domain, a CARD domain, or other domain associated with apoptotic and/or inflammatory signaling; (vi) the ability to modulate, directly or indirectly, the activity of a caspase, e.g., caspase-1 or caspase-9; (vii) the ability to induce the activity of caspase-1; (viii) the ability to modulate of ER-specific apoptosis pathways; (ix) the ability to modulate (increase or decrease), directly or indirectly, the activity of NF-kB; (x) the ability to increase the activity of NF-kB; (xi) the ability to modulate, directly or indirectly, Apaf-1; (xii) the ability to modulate apoptosis and/or inflammation; (xiii) the ability to interact, directly or indirectly, with a Bcl-2 family member; (xiv) the ability to modulate, directly or indirectly, the activity of a stress activated kinase (e.g., JNK/p38); and (xv) the ability to modulate, directly or indirectly, phosphorylation of CHOP (GADD 153). PYRIN-2, PYRIN-3, PYRIN-5, PYRIN-6, PYRIN-7, PYRIN-8, PYRIN-10, or PYRIN-11 nucleic acids and polypeptides as well as modulators of activity or expression of PYRIN-2, PYRIN-3, PYRIN-5, PYRIN-6, PYRIN-7, PYRIN-8, PYRIN-10, or PYRIN-11 might be used to modulate an Apaf-1 signaling pathway.

Accordingly, another embodiment of the invention features isolated PYRIN-2, PYRIN-3, PYRIN-5, PYRIN-6, PYRIN-7, PYRIN-8, PYRIN-10, or PYRIN-11 proteins and polypeptides having a PYRIN-2, PYRIN-3, PYRIN-5, PYRIN-6, PYRIN-7, PYRIN-8, PYRIN-10, or PYRIN-11 activity.

Various aspects of the invention are described in further detail in the following subsections.

I. Isolated Nucleic Acid Molecules

One aspect of the invention pertains to isolated nucleic acid molecules that encode PYRIN-2, PYRIN-3, PYRIN-5, PYRIN-6, PYRIN-7, PYRIN-8, PYRIN-10, or PYRIN-11 proteins or biologically active portions thereof, as well as nucleic acid molecules sufficient for use as hybridization probes to identify PYRIN-2, PYRIN-3, PYRIN-5, PYRIN-6, PYRIN-7, PYRIN-8, PYRIN-10, or PYRIN-11-encoding nucleic acids (e.g., PYRIN-2, PYRIN-3, PYRIN-5, PYRIN-6, PYRIN-7, PYRIN-8, PYRIN-10, or PYRIN-11 mRNA) and fragments for use as PCR primers for the amplification or mutation of PYRIN-2, PYRIN-3, PYRIN-5, PYRIN-6, PYRIN-7, PYRIN-8, PYRIN-10, or PYRIN-11 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated PYRIN-2, PYRIN-3, PYRIN-5, PYRIN-6, PYRIN-7, PYRIN-8, PYRIN-10, or PYRIN-11 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a complement of any of these nucleotide sequences, can be isolated using standard molecular biology techniques and the sequence information provided herein. Using all or portion of the nucleic acid sequences of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25, as a hybridization probe, PYRIN-2, PYRIN-3, PYRIN-5, PYRIN-6, PYRIN-7, PYRIN-8, PYRIN-10, or PYRIN-11 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to PYRIN-2, PYRIN-3, PYRIN-5, PYRIN-6, PYRIN-7, PYRIN-8, PYRIN-10, or PYRIN-11 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding PYRIN-2, PYRIN-3, PYRIN-5, PYRIN-6, PYRIN-7, PYRIN-8, PYRIN-10, or PYRIN-11, for example, a fragment which can be used as a probe or primer or a fragment encoding a biologically active portion of PYRIN-2, PYRIN-3, PYRIN-5, PYRIN-6, PYRIN-7, PYRIN-8, PYRIN-10, or PYRIN-11. The nucleotide sequence determined from the cloning of the PYRIN-2, PYRIN-3, PYRIN-5, PYRIN-6, PYRIN-7, PYRIN-8, PYRIN-10, or PYRIN-11 gene allows for the generation of probes and primers designed for use in identifying and/or cloning PYRIN-2, PYRIN-3, PYRIN-5, PYRIN-6, PYRIN-7, PYRIN-8, PYRIN-10, or PYRIN-11 homologues in other cell types, e.g., from other tissues, as well as PYRIN-2, PYRIN-3, PYRIN-5, PYRIN-6, PYRIN-7, PYRIN-8, PYRIN-10, or PYRIN-11 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or of a naturally occurring mutant of one of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23 or SEQ ID NO:25.

Probes based on the PYRIN-2, PYRIN-3, PYRIN-5, PYRIN-6, PYRIN-7, PYRIN-8, PYRIN-10, or PYRIN-11 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the PYRIN-2, PYRIN-3, PYRIN-5, PYRIN-6, PYRIN-7, PYRIN-8, PYRIN-10, or PYRIN-11 proteins of the present invention, identifying cells or tissue which mis-express a PYRIN-2, PYRIN-3, PYRIN-5, PYRIN-6, PYRIN-7, PYRIN-8, PYRIN-10, or PYRIN-11 protein, such as by measuring a level of a PYRIN-2, PYRIN-3, PYRIN-5, PYRIN-6, PYRIN-7, PYRIN-8, PYRIN-10, or PYRIN-11-encoding nucleic acid in a sample of cells from a subject, e.g., detecting PYRIN-2, PYRIN-3, PYRIN-5, PYRIN-6, PYRIN-7, PYRIN-8, PYRIN-10, or PYRIN-11 mRNA levels or determining whether a genomic PYRIN-2, PYRIN-3, PYRIN-5, PYRIN-6, PYRIN-7, PYRIN-8, PYRIN-10, or PYRIN-11 gene has been mutated or deleted.

A nucleic acid fragment encoding a "biologically active portion" of PYRIN-2, PYRIN-3, PYRIN-5, PYRIN-6, PYRIN-7, PYRIN-8, PYRIN-10, or PYRIN-11 can be prepared by isolating a portion of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25, or which encodes a polypeptide having a PYRIN-2, PYRIN-3, PYRIN-5, PYRIN-6, PYRIN-7, PYRIN-8, PYRIN-10, or PYRIN-11 biological activity, expressing the encoded portion of PYRIN-2, PYRIN-3, PYRIN-5, PYRIN-6, PYRIN-7, PYRIN-8, PYRIN-10, or PYRIN-11 protein (e.g., by recombinant expression in vitro) and assessing the activity of the encoded portion of PYRIN-2, PYRIN-3, PYRIN-5, PYRIN-6, PYRIN-7, PYRIN-8, PYRIN-10, or PYRIN-11.

The invention further encompasses nucleic acid molecules that differ from the nucleotide sequence of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23 or SEQ ID NO:25, due to degeneracy of the genetic code and thus encode the same PYRIN-2, PYRIN-3, PYRIN-5, PYRIN-6, PYRIN-7, PYRIN-8, PYRIN-10, or PYRIN-11 protein as that encoded by the nucleotide sequence shown in SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25.

In addition to the PYRIN-2, PYRIN-3, PYRIN-5, PYRIN-6, PYRIN-7, PYRIN-8, PYRIN-10, or PYRIN-11 nucleotide sequences shown in SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25, it will be appreciated by those skilled in the art that DNA sequence polymorphisms that lead to changes in the amino acid sequences of PYRIN-2, PYRIN-3, PYRIN-5, PYRIN-6, PYRIN-7, PYRIN-8, PYRIN-10, or PYRIN-11 may exist within a population (e.g., the human population). Such genetic polymorphism in the PYRIN-2, PYRIN-3, PYRIN-5, PYRIN-6, PYRIN-7, PYRIN-8, PYRIN-10, or PYRIN-11 gene may exist among individuals within a population due to natural allelic variation. As used herein, the terms "gene" and "recombinant gene" refer to nucleic acid molecules comprising an open reading frame encoding a PYRIN-2, PYRIN-3, PYRIN-5, PYRIN-6, PYRIN-7, PYRIN-8, PYRIN-10, or PYRIN-11 protein, preferably a mammalian PYRIN-2, PYRIN-3, PYRIN-5, PYRIN-6, PYRIN-7, PYRIN-8, PYRIN-10, or PYRIN-11 protein. Such natural allelic variations can typically result in 1–5% variance in the nucleotide sequence of the PYRIN-2, PYRIN-3, PYRIN-5, PYRIN-6, PYRIN-7, PYRIN-8, PYRIN-10, or PYRIN-11 gene. Any and all such nucleotide variations and resulting amino acid polymorphisms in PYRIN-2, PYRIN-3, PYRIN-5, PYRIN-6, PYRIN-7, PYRIN-8, PYRIN-10, or PYRIN-11 that are the result of natural allelic variation and that do not alter the functional activity of PYRIN-2, PYRIN-3, PYRIN-5, PYRIN-6, PYRIN-7, PYRIN-8, PYRIN-10, or PYRIN-11 are intended to be within the scope of the invention. Thus, e.g., 1%, 2%, 3%, 4%, or 5% of the amino acids in PYRIN-2, PYRIN-3, PYRIN-5, PYRIN-6, PYRIN-7, PYRIN-8, PYRIN-10, or PYRIN-11 (e.g., 1, 2, 3, 4, 5, 6, 8, 10, 15, or 17 amino acids) are replaced by another amino acid, preferably by conservative substitution.

Moreover, nucleic acid molecules encoding PYRIN-2, PYRIN-3, PYRIN-5, PYRIN-6, PYRIN-7, PYRIN-8, PYRIN-10, or PYRIN-11 proteins from other species (PYRIN-2, PYRIN-3, PYRIN-5, PYRIN-6, PYRIN-7, PYRIN-8, PYRIN-10, or PYRIN-11 orthologs/homologues), which have a nucleotide sequence which differs from that of a PYRIN-2, PYRIN-3, PYRIN-5, PYRIN-6, PYRIN-7, PYRIN-8, PYRIN-10, or PYRIN-11 disclosed herein, are intended to be within the scope of the invention.

Accordingly, in another embodiment, an isolated nucleic acid molecule of the invention is at least 150 (300, 325, 350, 375, 400, 425, 450, 500, 550, 600, 650, 700, 800, 900, 1000, 1100, 1200, 1300, 1400, 1500, 1600, 1800, 2000, 2250, or 2500) nucleotides in length and hybridizes under stringent conditions to the nucleic acid molecule comprising the nucleotide sequence, preferably the coding sequence, of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23 or SEQ ID NO:25.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6× sodium chloride/sodium citrate (SSC) at about 45° C., followed by one or more washes in 0.2×SSC, 0.1% SDS at 50–65° C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

In addition to naturally-occurring allelic variants of the PYRIN-2, PYRIN-3, PYRIN-5, PYRIN-6, PYRIN-7, PYRIN-8, PYRIN-10, or PYRIN-11 sequence that may exist in the population, the skilled artisan will further appreciate that changes can be introduced by mutation into the nucleotide sequence of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23 or SEQ ID NO:25, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of PYRIN-2, PYRIN-3, PYRIN-5, PYRIN-6, PYRIN-7, PYRIN-8, PYRIN-10, or PYRIN-11 protein without altering the biological activity, whereas an "essential" amino acid residue is required for biological activity. For example, amino acid residues that are conserved among the PYRIN-2, PYRIN-3, PYRIN-5, PYRIN-6, PYRIN-7, PYRIN-8, PYRIN-10, or PYRIN-11, proteins of various species are predicted to be particularly unamenable to alteration.

For example, preferred PYRIN-2, PYRIN-3, PYRIN-5, PYRIN-6, PYRIN-7, PYRIN-8, PYRIN-10, or PYRIN-11 proteins of the present invention contain at least one domain identified herein. Such conserved domains are less likely to be amenable to mutation. Other amino acid residues, however, (e.g., those that are not conserved or only semi-conserved among PYRIN-2, PYRIN-3, PYRIN-5, PYRIN-6, PYRIN-7, PYRIN-8, PYRIN-10, or PYRIN-11 of various species) may not be essential for activity and thus are likely to be amenable to alteration.

Accordingly, another aspect of the invention pertains to nucleic acid molecules encoding PYRIN-2, PYRIN-3, PYRIN-5, PYRIN-6, PYRIN-7, PYRIN-8, PYRIN-10, or PYRIN-11 proteins that contain changes in amino acid residues that are not essential for activity. Such PYRIN-2, PYRIN-3, PYRIN-5, PYRIN-6, PYRIN-7, PYRIN-8, PYRIN-10, or PYRIN-11 proteins differ in amino acid sequence from SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24 and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24. An isolated nucleic acid molecule encoding a PYRIN-2, PYRIN-3, PYRIN-5, PYRIN-6, PYRIN-7, PYRIN-8, PYRIN-10, or PYRIN-11 protein having a sequence which differs from that of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25 can be created by introducing one or more nucleotide substitutions, additions or deletions into the nucleotide sequence of PYRIN-2, PYRIN-3, PYRIN-5, PYRIN-6, PYRIN-7, PYRIN-8, PYRIN-10, or PYRIN-11 (SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in PYRIN-2, PYRIN-3, PYRIN-5, PYRIN-6, PYRIN-7, PYRIN-8, PYRIN-10, or PYRIN-11 is preferably replaced with another amino acid residue from the same side chain family. Alternatively, mutations can be introduced randomly along all or part of a PYRIN-2, PYRIN-3, PYRIN-5, PYRIN-6, PYRIN-7, PYRIN-8, PYRIN-10, or PYRIN-11 coding sequence, such as by saturation mutagenesis, and the resultant mutants can be screened for PYRIN-2, PYRIN-3, PYRIN-5, PYRIN-6, PYRIN-7, PYRIN-8, PYRIN-10, or PYRIN-11 biological activity to identify mutants that retain activity. Following mutagenesis, the encoded protein can be expressed recombinantly and the activity of the protein can be determined.

In an embodiment, a mutant PYRIN-2, PYRIN-3, PYRIN-5, PYRIN-6, PYRIN-7, PYRIN-8, PYRIN-10, or PYRIN-11 protein can be assayed for: (1) the ability to form protein:protein interactions with proteins in the apoptotic signaling pathway; (2) the ability to bind a PYRIN-2, PYRIN-3, PYRIN-5, PYRIN-6, PYRIN-7, PYRIN-8, PYRIN-10, or PYRIN-11 ligand; or (3) the ability to bind to an intracellular target protein.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PYRIN-2, PYRIN-3, PYRIN-5, PYRIN-6, PYRIN-7, PYRIN-8, PYRIN-10, or PYRIN-11 coding strand, or to only a portion thereof, e.g., all or part of the protein coding region (or open reading frame). An antisense nucleic acid molecule can be antisense to a noncoding region of the coding strand of a nucleotide sequence encoding PYRIN-2, PYRIN-3, PYRIN-5, PYRIN-6, PYRIN-7, PYRIN-8, PYRIN-10, or PYRIN-11. The noncoding regions ("5' and 3' untranslated regions") are the 5' and 3' sequences that flank the coding region and are not translated into amino acids. Given the coding strand sequences encoding PYRIN-2, PYRIN-3, PYRIN-5, PYRIN-6, PYRIN-7, PYRIN-8, PYRIN-10, or PYRIN-11 disclosed herein, antisense nucleic acids of the invention can be designed according to the rules of Watson and Crick base pairing. The antisense nucleic acid molecule can be complementary to the entire coding region of PYRIN-2, PYRIN-3, PYRIN-5, PYRIN-6, PYRIN-7, PYRIN-8, PYRIN-10, or PYRIN-11 mRNA, but more preferably is an oligonucleotide which is antisense to only a portion of the coding or noncoding region of PYRIN-2, PYRIN-3, PYRIN-5, PYRIN-6, PYRIN-7, PYRIN-8, PYRIN-10, or PYRIN-11 mRNA. For example, the antisense oligonucleotide can be complementary to the region surrounding the translation start site of PYRIN-2, PYRIN-3, PYRIN-5, PYRIN-6, PYRIN-7, PYRIN-8, PYRIN-10, or PYRIN-11 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PYRIN-2, PYRIN-3, PYRIN-5, PYRIN-6, PYRIN-7, PYRIN-8, PYRIN-10, or PYRIN-11 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention can be administered by direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave PYRIN-2, PYRIN-3, PYRIN-5, PYRIN-6, PYRIN-7, PYRIN-8, PYRIN-10, or PYRIN-11 mRNA transcripts to thereby inhibit translation of PYRIN-2, PYRIN-3, PYRIN-5, PYRIN-6, PYRIN-7, PYRIN-8, PYRIN-10, or PYRIN-11 mRNA. A ribozyme having specificity for a PYRIN-2, PYRIN-3, PYRIN-5, PYRIN-6, PYRIN-7, PYRIN-8, PYRIN-10, or PYRIN-11-encoding nucleic acid can be designed based upon the nucleotide sequence of a PYRIN-2, PYRIN-3, PYRIN-5, PYRIN-6, PYRIN-7, PYRIN-8, PYRIN-10, or PYRIN-11 cDNA disclosed herein. For example, a derivative of a Tetrahymena L-19 IVS RNA can be constructed in which the nucleotide sequence of the active site is complementary to the nucleotide sequence to be cleaved in a PYRIN-2, PYRIN-3, PYRIN-5, PYRIN-6, PYRIN-7, PYRIN-8, PYRIN-10, or PYRIN-11-encoding mRNA. See, e.g., Cech et al. U.S. Pat. No. 4,987,071; and Cech et al. U.S. Pat. No. 5,116,742. Alternatively, PYRIN-2, PYRIN-3, PYRIN-5, PYRIN-6, PYRIN-7, PYRIN-8, PYRIN-10, or PYRIN-11 mRNA can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, PYRIN-2, PYRIN-3, PYRIN-5, PYRIN-6, PYRIN-7, PYRIN-8, PYRIN-10, or PYRIN-11 gene expression can be inhibited by targeting nucleotide sequences complementary to the regulatory region of the PYRIN-2, PYRIN-3, PYRIN-5, PYRIN-6, PYRIN-7, PYRIN-8, PYRIN-10, or PYRIN-11 (e.g., the PYRIN-2, PYRIN-3, PYRIN-5, PYRIN-6, PYRIN-7, PYRIN-8, PYRIN-10, or PYRIN-11 promoter and/or enhancers) to form triple helical structures that prevent transcription of the PYRIN-2, PYRIN-3, PYRIN-5, PYRIN-6, PYRIN-7, PYRIN-8, PYRIN-10, or PYRIN-11 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670–675.

PNAs of PYRIN-2, PYRIN-3, PYRIN-5, PYRIN-6, PYRIN-7, PYRIN-8, PYRIN-10, or PYRIN-11 can be used for therapeutic and diagnostic applications. For example, PNAs can be used as antisense or antigene agents for sequence-specific modulation of gene expression by, e.g., inducing transcription or translation arrest or inhibiting replication. PNAs of PYRIN-2, PYRIN-3, PYRIN-5, PYRIN-6, PYRIN-7, PYRIN-8, PYRIN-10, or PYRIN-11 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

In another embodiment, PNAs of PYRIN-2, PYRIN-3, PYRIN-5, PYRIN-6, PYRIN-7, PYRIN-8, PYRIN-10, or PYRIN-11 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of PYRIN-2, PYRIN-3, PYRIN-5, PYRIN-6, PYRIN-7, PYRIN-8, PYRIN-10, or PYRIN-11 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated PYRIN-2, PYRIN-3, PYRIN-5, PYRIN-6, PYRIN-7, PYRIN-8, PYRIN-10, or PYRIN-11 Proteins and Anti-PYRIN-2, PYRIN-3, PYRIN-5, PYRIN-6, PYRIN-7, PYRIN-8, PYRIN-10, or PYRIN-11 Antibodies One aspect of the invention pertains to isolated PYRIN-2, PYRIN-3, PYRIN-5, PYRIN-6, PYRIN-7, PYRIN-8, PYRIN-10, or PYRIN-11 proteins, and biologically active portions thereof, as well as polypeptide fragments suitable for use as immunogens to raise anti-PYRIN-2, PYRIN-3, PYRIN-5, PYRIN-6, PYRIN-7, PYRIN-8, PYRIN-10, or PYRIN-11 antibodies. In one embodiment, native PYRIN-2, PYRIN-3, PYRIN-5, PYRIN-6, PYRIN-7, PYRIN-8, PYRIN-10, or PYRIN-11 proteins can be isolated from cells or tissue sources by an appropriate purification scheme using standard protein purification techniques. In another embodiment, PYRIN-2, PYRIN-3, PYRIN-5, PYRIN-6, PYRIN-7, PYRIN-8, PYRIN-10, or PYRIN-11 proteins are produced by recombinant DNA techniques. Alternative to recombinant expression, a PYRIN-2, PYRIN-3, PYRIN-5, PYRIN-6, PYRIN-7, PYRIN-8, PYRIN-10, or PYRIN-11 protein or polypeptide can be synthesized chemically using standard peptide synthesis techniques.

An "isolated" or "purified" protein or biologically active portion thereof is substantially free of cellular material or other contaminating proteins from the cell or tissue source from which the PYRIN-2, PYRIN-3, PYRIN-5, PYRIN-6, PYRIN-7, PYRIN-8, PYRIN-10, or PYRIN-11 protein is derived, or substantially free from chemical precursors or other chemicals when chemically synthesized. The language "substantially free of cellular material" includes preparations of PYRIN-2, PYRIN-3, PYRIN-5, PYRIN-6, PYRIN-7, PYRIN-8, PYRIN-10, or PYRIN-11 protein in which the protein is separated from cellular components of the cells from which it is isolated or recombinantly produced. Thus, PYRIN-2, PYRIN-3, PYRIN-5, PYRIN-6, PYRIN-7, PYRIN-8, PYRIN-10, or PYRIN-11 protein that is substantially free of cellular material includes preparations of PYRIN-2, PYRIN-3, PYRIN-5, PYRIN-6, PYRIN-7, PYRIN-8, PYRIN-10, or PYRIN-11 protein having less than about 30%, 20%, 10%, or 5% (by dry weight) of non-PYRIN-2, PYRIN-3, PYRIN-5, PYRIN-6, PYRIN-7, PYRIN-8, PYRIN-10, or PYRIN-11 protein (also referred to herein as a "contaminating protein"). When the PYRIN-2, PYRIN-3, PYRIN-5, PYRIN-6, PYRIN-7, PYRIN-8, PYRIN-10, or PYRIN-11 protein or biologically active portion thereof is recombinantly produced, it is also preferably substantially free of culture medium, i.e., culture medium represents less than about 20%, 10%, or 5% of the volume of the protein preparation. When PYRIN-2, PYRIN-3, PYRIN-5, PYRIN-6, PYRIN-7, PYRIN-8, PYRIN-10, or PYRIN-11 protein is produced by chemical synthesis, it is preferably substantially free of chemical precursors or other chemicals, i.e., it is separated from chemical precursors or other chemicals which are involved in the synthesis of the protein. Accordingly such preparations of PYRIN-2, PYRIN-3, PYRIN-5, PYRIN-6, PYRIN-7, PYRIN-8, PYRIN-10, or PYRIN-11 protein have less than about 30%, 20%, 10%, 5% (by dry weight) of chemical precursors or non-PYRIN-2, PYRIN-3, PYRIN-5, PYRIN-6, PYRIN-7, PYRIN-8, PYRIN-10, or PYRIN-11 chemicals.

Biologically active portions of a PYRIN-2, PYRIN-3, PYRIN-5, PYRIN-6, PYRIN-7, PYRIN-8, PYRIN-10, or PYRIN-11 protein include peptides comprising amino acid sequences sufficiently identical to or derived from the amino acid sequence of the PYRIN-2, PYRIN-3, PYRIN-5, PYRIN-6, PYRIN-7, PYRIN-8, PYRIN-10, or PYRIN-11 protein (e.g., the amino acid sequence shown in SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24), which include less amino acids than the full length PYRIN-2, PYRIN-3, PYRIN-5, PYRIN-6, PYRIN-7, PYRIN-8, PYRIN-10, or PYRIN-11 protein, and exhibit at least one activity of a PYRIN-2, PYRIN-3, PYRIN-5, PYRIN-6, PYRIN-7, PYRIN-8, PYRIN-10, or PYRIN-11 protein. Typically, biologically active portions comprise a domain or motif with at least one activity of the PYRIN-2, PYRIN-3, PYRIN-5, PYRIN-6, PYRIN-7, PYRIN-8, PYRIN-10, or PYRIN-11 protein. A biologically active portion of a PYRIN-2, PYRIN-3, PYRIN-5, PYRIN-6, PYRIN-7, PYRIN-8, PYRIN-10, or PYRIN-11 protein can be a polypeptide which is, for example, 10, 25, 50, 72, 100, 125, 150, 175, 200, 225, 250, 272, 300, 325, 350, 375, 400, 425, 450 or more amino acids in length. Preferred biologically active polypeptides include one or more identified PYRIN-2, PYRIN-3, PYRIN-5, PYRIN-6, PYRIN-7, PYRIN-8, PYRIN-10, or PYRIN-11 structural domains, e.g., the NBS domain.

Moreover, other biologically active portions, in which other regions of the protein are deleted, can be prepared by recombinant techniques and evaluated for one or more of the functional activities of a native PYRIN-2, PYRIN-3, PYRIN-5, PYRIN-6, PYRIN-7, PYRIN-8, PYRIN-10, or PYRIN-11 protein.

Human PYRIN-2, PYRIN-3, PYRIN-5, PYRIN-6, PYRIN-7, PYRIN-8, PYRIN-10, and PYRIN-11 proteins have the amino acid sequences of SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24. Other useful PYRIN-2, PYRIN-3, PYRIN-5, PYRIN-6, PYRIN-7, PYRIN-8, PYRIN-10, or PYRIN-11 proteins are substantially identical to SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24 and retain the functional activity of the protein of SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24 yet differ in amino acid sequence due to natural allelic variation or mutagenesis. A useful PYRIN-2, PYRIN-3, PYRIN-5, PYRIN-6, PYRIN-7, PYRIN-8, PYRIN-10, or PYRIN-11 protein is a protein which includes an amino acid sequence at least about 45%, preferably 55%, 65%, 75%, 85%, 95%, or 99% identical to the amino acid sequence of SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24 and retains the functional activity of the PYRIN-2, PYRIN-3, PYRIN-5, PYRIN-6, PYRIN-7, PYRIN-8, PYRIN-10, or PYRIN-11 protein of SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to PYRIN-2, PYRIN-3, PYRIN-5, PYRIN-6, PYRIN-7, PYRIN-8, PYRIN-10, or PYRIN-11 nucleic acid molecules of the invention. To obtain gapped alignments for comparison purposes, Gapped BLAST can be utilized as described in Altschul et al. (1997) Nucleic Acids Res. 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12, and a gap penalty of 4 can be used. Another preferred example of a mathematical algorithm utilized for the comparison of sequences is the Needleman and Wunsch (J. Mol. Biol. (48):444–453 (1970)) algorithm which has been incorporated into the GAP program in the GCG software package (available at gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6.

The percent identity between two sequences can be determined using techniques similar to those described above, with or without allowing gaps. In calculating percent identity, typically exact matches are counted.

The invention also provides PYRIN-2, PYRIN-3, PYRIN-5, PYRIN-6, PYRIN-7, PYRIN-8, PYRIN-10, or PYRIN-11 chimeric or fusion proteins. As used herein, a PYRIN-2, PYRIN-3, PYRIN-5, PYRIN-6, PYRIN-7, PYRIN-8, PYRIN-10, or PYRIN-11 "chimeric protein" or "fusion protein" comprises a PYRIN-2, PYRIN-3, PYRIN-5, PYRIN-6, PYRIN-7, PYRIN-8, PYRIN-10, or PYRIN-11 polypeptide operatively linked to a non-PYRIN-2, PYRIN-3, PYRIN-5, PYRIN-6, PYRIN-7, PYRIN-8, PYRIN-10, or PYRIN-11 polypeptide. A "PYRIN-2, PYRIN-3, PYRIN-5, PYRIN-6, PYRIN-7, PYRIN-8, PYRIN-10, or PYRIN-11 polypeptide" refers to a polypeptide having an amino acid sequence corresponding to all or a portion (preferably a biologically active portion) of a PYRIN-2, PYRIN-3, PYRIN-5, PYRIN-6, PYRIN-7, PYRIN-8, PYRIN-10, or PYRIN-11, whereas a "non-PYRIN-2, PYRIN-3, PYRIN-5, PYRIN-6, PYRIN-7, PYRIN-8, PYRIN-10, or PYRIN-11 polypeptide" refers to a polypeptide having an amino acid sequence corresponding to a protein which is not substantially identical to the PYRIN-2, PYRIN-3, PYRIN-5, PYRIN-6, PYRIN-7, PYRIN-8, PYRIN-10, or PYRIN-11 protein, e.g., a protein which is different from the PYRIN-2, PYRIN-3, PYRIN-5, PYRIN-6, PYRIN-7, PYRIN-8, PYRIN-10, or PYRIN-11 proteins and which is derived from the same or a different organism. Within the fusion protein, the term "operatively linked" is intended to indicate that the PYRIN-2, PYRIN-3, PYRIN-5, PYRIN-6, PYRIN-7, PYRIN-8, PYRIN-10, or PYRIN-11 polypeptide and the non-PYRIN-2, PYRIN-3, PYRIN-5, PYRIN-6, PYRIN-7, PYRIN-8, PYRIN-10, or PYRIN-11 polypeptide are fused in-frame to each other. The heterologous polypeptide can be fused to the N-terminus or C-terminus of the PYRIN-2, PYRIN-3, PYRIN-5, PYRIN-6, PYRIN-7, PYRIN-8, PYRIN-10, or PYRIN-11 polypeptide.

One useful fusion protein is a GST fusion protein in which the PYRIN-2, PYRIN-3, PYRIN-5, PYRIN-6, PYRIN-7, PYRIN-8, PYRIN-10, or PYRIN-11 sequences are fused to the C-terminus of the GST sequences. Such fusion proteins can facilitate the purification of recombinant PYRIN-2, PYRIN-3, PYRIN-5, PYRIN-6, PYRIN-7, PYRIN-8, PYRIN-10, or PYRIN-11. In another embodiment, the fusion protein contains a signal sequence from another protein. In certain host cells (e.g., mammalian host cells), expression and/or secretion of PYRIN-2, PYRIN-3, PYRIN-5, PYRIN-6, PYRIN-7, PYRIN-8, PYRIN-10, or PYRIN-11 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a PYRIN-2, PYRIN-3, PYRIN-5, PYRIN-6, PYRIN-7, PYRIN-8, PYRIN-10, or PYRIN-11-immunoglobulin fusion protein in which all or part of PYRIN-2, PYRIN-3, PYRIN-5, PYRIN-6, PYRIN-7, PYRIN-8, PYRIN-10, or PYRIN-11 is fused to sequences derived from a member of the immunoglobulin protein family. The PYRIN-2, PYRIN-3, PYRIN-5, PYRIN-6, PYRIN-7, PYRIN-8, PYRIN-10, or PYRIN-11-immunoglobulin fusion proteins of the invention can be incorporated into pharmaceutical compositions and administered to a subject to inhibit an interaction between a PYRIN-2, PYRIN-3, PYRIN-5, PYRIN-6, PYRIN-7, PYRIN-8, PYRIN-10, or PYRIN-11 ligand and a PYRIN-2, PYRIN-3, PYRIN-5, PYRIN-6, PYRIN-7, PYRIN-8, PYRIN-10, or PYRIN-11 protein on the surface of a cell, to thereby suppress PYRIN-2, PYRIN-3, PYRIN-5, PYRIN-6, PYRIN-7, PYRIN-8, PYRIN-10, or PYRIN-1-mediated signal transduction in vivo. The PYRIN-2, PYRIN-3, PYRIN-5, PYRIN-6, PYRIN-7, PYRIN-8, PYRIN-10, or PYRIN-11-immunoglobulin fusion proteins can be used to affect the bioavailability of a PYRIN-2, PYRIN-3, PYRIN-5, PYRIN-6, PYRIN-7, PYRIN-8, PYRIN-10, or PYRIN-11 cognate ligand. Inhibition of the PYRIN-2, PYRIN-3, PYRIN-5, PYRIN-6, PYRIN-7, PYRIN-8, PYRIN-10, or PYRIN-11 ligand/PYRIN-2, PYRIN-3, PYRIN-5, PYRIN-6, PYRIN-7, PYRIN-8, PYRIN-10, or PYRIN-11 interaction may be useful therapeutically for both the treatment of proliferative and differentiative disorders, as well as modulating (e.g., promoting or inhibiting) cell survival. Moreover, the PYRIN-2, PYRIN-3, PYRIN-5, PYRIN-6, PYRIN-7, PYRIN-8, PYRIN-10, or PYRIN-11-immunoglobulin fusion proteins of the invention can be used as immunogens to produce anti-PYRIN-2, PYRIN-3, PYRIN-5, PYRIN-6, PYRIN-7, PYRIN-8, PYRIN-10, or PYRIN-11 antibodies in a subject, to purify PYRIN-2, PYRIN-3, PYRIN-5, PYRIN-6, PYRIN-7, PYRIN-8, PYRIN-10, or PYRIN-11 ligands and in screening assays to identify molecules which inhibit the interaction of PYRIN-2, PYRIN-3, PYRIN-5, PYRIN-6, PYRIN-7, PYRIN-8, PYRIN-10, or PYRIN-11 with a PYRIN-2, PYRIN-3, PYRIN-5, PYRIN-6, PYRIN-7, PYRIN-8, PYRIN-10, or PYRIN-11 ligand.

Preferably, a PYRIN-2, PYRIN-3, PYRIN-5, PYRIN-6, PYRIN-7, PYRIN-8, PYRIN-10, or PYRIN-11 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A PYRIN-2, PYRIN-3, PYRIN-5, PYRIN-6, PYRIN-7, PYRIN-8, PYRIN-10, or PYRIN-11-encoding nucleic acid can be cloned into such an expression vector such that the fusion moiety is linked in-frame to the PYRIN-2, PYRIN-3, PYRIN-5, PYRIN-6, PYRIN-7, PYRIN-8, PYRIN-10, or PYRIN-11 protein.

The present invention also pertains to variants of the PYRIN-2, PYRIN-3, PYRIN-5, PYRIN-6, PYRIN-7,PYRIN-8, PYRIN-10, or PYRIN-11 proteins which function as either PYRIN-2, PYRIN-3, PYRIN-5, PYRIN-6, PYRIN-7, PYRIN-8, PYRIN-10, or PYRIN-11 agonists (mimetics) or as PYRIN-2, PYRIN-3, PYRIN-5, PYRIN-6, PYRIN-7, PYRIN-8, PYRIN-10, or PYRIN-11 antagonists. Variants of the PYRIN-2, PYRIN-3, PYRIN-5, PYRIN-6, PYRIN-7, PYRIN-8, PYRIN-10, or PYRIN-11 proteins can be generated by mutagenesis, e.g., discrete point mutation or truncation of the PYRIN-2, PYRIN-3, PYRIN-5, PYRIN-6, PYRIN-7, PYRIN-8, PYRIN-10, or PYRIN-11 proteins. An agonist of the PYRIN-2, PYRIN-3, PYRIN-5, PYRIN-6, PYRIN-7, PYRIN-8, PYRIN-10, or PYRIN-11 protein can retain substantially the same, or a subset, of the biological activities of the naturally occurring form of the PYRIN-2, PYRIN-3, PYRIN-5, PYRIN-6, PYRIN-7, PYRIN-8, PYRIN-10, or PYRIN-11 protein. An antagonist of the PYRIN-2, PYRIN-3, PYRIN-5, PYRIN-6, PYRIN-7, PYRIN-8, PYRIN-10, or PYRIN-11 protein can inhibit one or more of the activities of the naturally occurring form of the PYRIN-2, PYRIN-3, PYRIN-5, PYRIN-6, PYRIN-7, PYRIN-8, PYRIN-10, or PYRIN-11 protein by, for example, competitively binding to a downstream or upstream member of a cellular signaling cascade which includes the PYRIN-2, PYRIN-3, PYRIN-5, PYRIN-6, PYRIN-7, PYRIN-8, PYRIN- 10, or PYRIN-11 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the PYRIN-2, PYRIN-3, PYRIN-5, PYRIN-6, PYRIN-7, PYRIN-8, PYRIN-10, or PYRIN-11 proteins.

Variants of the PYRIN-2, PYRIN-3, PYRIN-5, PYRIN-6, PYRIN-7, PYRIN-8, PYRIN-10, or PYRIN-11 protein which function as either PYRIN-2, PYRIN-3, PYRIN-5, PYRIN-6, PYRIN-7, PYRIN-8, PYRIN-10, or PYRIN-11 agonists (mimetics) or as PYRIN-2, PYRIN-3, PYRIN-5, PYRIN-6, PYRIN-7, PYRIN-8, PYRIN-10, or PYRIN-11 antagonists can be identified by screening combinatorial libraries of mutants, e.g., truncation mutants of the PYRIN-2, PYRIN-3, PYRIN-5, PYRIN-6, PYRIN-7, PYRIN-8, PYRIN-10, or PYRIN-11 protein for PYRIN-2, PYRIN-3, PYRIN-5, PYRIN-6, PYRIN-7, PYRIN-8, PYRIN-10, or PYRIN-11 protein agonist or antagonist activity. In one embodiment, a variegated library of PYRIN-2, PYRIN-3, PYRIN-5, PYRIN-6, PYRIN-7, PYRIN-8, PYRIN-10, or PYRIN-11 variants is generated by combinatorial mutagenesis at the nucleic acid level and is encoded by a variegated gene library. A variegated library of PYRIN-2, PYRIN-3, PYRIN-5, PYRIN-6, PYRIN-7, PYRIN-8, PYRIN-10, or PYRIN-11 variants can be produced by, for example, enzymatically ligating a mixture of synthetic oligonucleotides into gene sequences such that a degenerate set of potential PYRIN-2, PYRIN-3, PYRIN-5, PYRIN-6, PYRIN-7, PYRIN-8, PYRIN-10, or PYRIN-11 sequences is expressible as individual polypeptides, or alternatively, as a set of larger fusion proteins (e.g., for phage display) containing the set of PYRIN-2, PYRIN-3, PYRIN-5, PYRIN-6, PYRIN-7, PYRIN-8, PYRIN-10, or PYRIN-11 sequences therein. There are a variety of methods which can be used to produce libraries of potential PYRIN-2, PYRIN-3, PYRIN-5, PYRIN-6, PYRIN-7, PYRIN-8, PYRIN-10, or PYRIN-11 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PYRIN-2, PYRIN-3, PYRIN-5, PYRIN-6, PYRIN-7, PYRIN-8, PYRIN-10, or PYRIN-11 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of PYRIN-2, PYRIN-3, PYRIN-5, PYRIN-6, PYRIN-7, PYRIN-8, PYRIN-10, or PYRIN-11, include fragments comprising or consisting of a domain or subdomain described herein, e.g., LRR or NBS or pyrin domain.

In addition, libraries of fragments of the PYRIN-2, PYRIN-3, PYRIN-5, PYRIN-6, PYRIN-7, PYRIN-8, PYRIN-10, or PYRIN-11 protein coding sequence can be used to generate a variegated population of PYRIN-2, PYRIN-3, PYRIN-5, PYRIN-6, PYRIN-7, PYRIN-8, PYRIN-10, or PYRIN-11 fragments for screening and subsequent selection of variants of a PYRIN-2, PYRIN-3, PYRIN-5, PYRIN-6, PYRIN-7, PYRIN-8, PYRIN-10, or PYRIN-11 protein. In one embodiment, a library of coding sequence fragments can be generated by treating a double stranded PCR fragment of a PYRIN-2, PYRIN-3, PYRIN-5, PYRIN-6, PYRIN-7, PYRIN-8, PYRIN-10, or PYRIN-11 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the PYRIN-2, PYRIN-3, PYRIN-5, PYRIN-6, PYRIN-7, PYRIN-8, PYRIN-10, or PYRIN-11 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PYRIN-2, PYRIN-3, PYRIN-5, PYRIN-6, PYRIN-7, PYRIN-8, PYRIN-10, or PYRIN-11 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify PYRIN-2, PYRIN-3, PYRIN-5, PYRIN-6, PYRIN-7, PYRIN-8, PYRIN-10, or PYRIN-11 variants (Arkin and Yourvan (1992) Proc. Natl. Acad. Sci. USA 89:7811–7815; Delgrave et al. (1993) Protein Engineering 6(3):327–331).

An isolated PYRIN-2, PYRIN-3, PYRIN-5, PYRIN-6, PYRIN-7, PYRIN-8, PYRIN-10, or PYRIN-11 protein, or a portion or fragment thereof, can be used as an immunogen to generate antibodies that bind PYRIN-2, PYRIN-3, PYRIN-5, PYRIN-6, PYRIN-7, PYRIN-8, PYRIN-10, or PYRIN-11 using standard techniques for polyclonal and monoclonal antibody preparation. The full-length PYRIN-2, PYRIN-3, PYRIN-5, PYRIN-6, PYRIN-7, PYRIN-8, PYRIN-10, or PYRIN-11 protein can be used or, alternatively, the invention provides antigenic peptide fragments of PYRIN-2, PYRIN-3, PYRIN-5, PYRIN-6, PYRIN-7, PYRIN-8, PYRIN-10, or PYRIN-11 for use as immunogens. The antigenic peptide of PYRIN-2, PYRIN-3, PYRIN-5, PYRIN-6, PYRIN-7, PYRIN-8, PYRIN-10, or PYRIN-1 comprises at least 8 (preferably 10, 15, 20, or 30) amino acid residues of the amino acid sequence shown in SEQ ID NO:2, SEQ ID NO:4, SEQ ID NO:6, SEQ ID NO:8, SEQ ID NO:10, SEQ ID NO:13, SEQ ID NO:15, SEQ ID NO:18, SEQ ID NO:20, SEQ ID NO:22, or SEQ ID NO:24 and encompasses an epitope of PYRIN-2, PYRIN-3, PYRIN-5, PYRIN-6, PYRIN-7, PYRIN-8, PYRIN-10, or PYRIN-11 such that an antibody raised against the peptide forms a specific immune complex with PYRIN-2, PYRIN-3, PYRIN-5, PYRIN-6, PYRIN-7, PYRIN-8, PYRIN-10, or PYRIN-11.

Useful antibodies include antibodies which bind to a domain or subdomain of PYRIN-2, PYRIN-3, PYRIN-5, PYRIN-6, PYRIN-7, PYRIN-8, PYRIN-10, or PYRIN-11 described herein (e.g., a LRR or NBS or pyrin domain).

Preferred epitopes encompassed by the antigenic peptide are regions of PYRIN-2, PYRIN-3, PYRIN-5, PYRIN-6, PYRIN-7, PYRIN-8, PYRIN-10, or PYRIN-11 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm).

A PYRIN-2, PYRIN-3, PYRIN-5, PYRIN-6, PYRIN-7, PYRIN-8, PYRIN-10, or PYRIN-11 immunogen typically is used to prepare antibodies by immunizing a suitable subject, (e.g., rabbit, goat, mouse or other mammal) with the immunogen. An appropriate immunogenic preparation can contain, for example, recombinantly expressed PYRIN-2, PYRIN-3, PYRIN-5, PYRIN-6, PYRIN-7, PYRIN-8, PYRIN-10, or PYRIN-11 protein or a chemically synthesized PYRIN-2, PYRIN-3, PYRIN-5, PYRIN-6, PYRIN-7, PYRIN-8, PYRIN-10, or PYRIN-11 polypeptide. The preparation can further include an adjuvant, such as Freund's complete or incomplete adjuvant, or similar immunostimulatory agent. Immunization of a suitable subject with an immunogenic PYRIN-2, PYRIN-3, PYRIN-5, PYRIN-6, PYRIN-7, PYRIN-8, PYRIN-10, or PYRIN-11 preparation induces a polyclonal anti-PYRIN-2, PYRIN-3, PYRIN-5, PYRIN-6, PYRIN-7, PYRIN-8, PYRIN-10, or PYRIN-11 antibody response.

Accordingly, another aspect of the invention pertains to anti-PYRIN-2, PYRIN-3, PYRIN-5, PYRIN-6, PYRIN-7, PYRIN-8, PYRIN-10, or PYRIN-11 antibodies. The term "antibody" as used herein refers to immunoglobulin molecules and immunologically active portions of immunoglobulin molecules, i.e., molecules that contain an antigen binding site which specifically binds an antigen, such as PYRIN-2, PYRIN-3, PYRIN-5, PYRIN-6, PYRIN-7, PYRIN-8, PYRIN-10, or PYRIN-11. A molecule which specifically binds to PYRIN-2, PYRIN-3, PYRIN-5, PYRIN-6, PYRIN-7, PYRIN-8, PYRIN-10, or PYRIN-11 is a molecule which binds PYRIN-2, PYRIN-3, PYRIN-5, PYRIN-6, PYRIN-7, PYRIN-8, PYRIN-10, or PYRIN-11, but does not substantially bind other molecules in a sample, e.g., a biological sample, which naturally contains PYRIN-2, PYRIN-3, PYRIN-5, PYRIN-6, PYRIN-7, PYRIN-8, PYRIN-10, or PYRIN-11. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PYRIN-2, PYRIN-3, PYRIN-5, PYRIN-6, PYRIN-7, PYRIN-8, PYRIN-10, or PYRIN-11. The term "monoclonal antibody" or "monoclonal antibody composition", as used herein, refers to a population of antibody molecules that contain only one species of an antigen binding site capable of immunoreacting with a particular epitope of PYRIN-2, PYRIN-3, PYRIN-5, PYRIN-6, PYRIN-7, PYRIN-8, PYRIN-10, or PYRIN-11. A monoclonal antibody composition thus typically displays a single binding affinity for a particular PYRIN-2, PYRIN-3, PYRIN-5, PYRIN-6, PYRIN-7, PYRIN-8, PYRIN-10, or PYRIN-11 protein with which it immunoreacts.

Polyclonal anti-PYRIN-2, PYRIN-3, PYRIN-5, PYRIN-6, PYRIN-7, PYRIN-8, PYRIN-10, or PYRIN-11 antibodies can be prepared as described above by immunizing a suitable subject with a PYRIN-2, PYRIN-3, PYRIN-5, PYRIN-6, PYRIN-7, PYRIN-8, PYRIN-10, or PYRIN-11 immunogen. The anti-PYRIN-2, PYRIN-3, PYRIN-5, PYRIN-6, PYRIN-7, PYRIN-8, PYRIN-10, or PYRIN-11 antibody titer in the immunized subject can be monitored over time by standard techniques, such as with an enzyme linked immunosorbent assay (ELISA) using immobilized PYRIN-2, PYRIN-3, PYRIN-5, PYRIN-6, PYRIN-7, PYRIN-8, PYRIN-10, or PYRIN-11. If desired, the antibody molecules directed against PYRIN-2, PYRIN-3, PYRIN-5, PYRIN-6, PYRIN-7, PYRIN-8, PYRIN-10, or PYRIN-11 can be isolated from the mammal (e.g., from the blood) and further purified by well-known techniques, such as protein A chromatography to obtain the IgG fraction. At an appropriate time after immunization, e.g., when the anti-PYRIN-2, PYRIN-3, PYRIN-5, PYRIN-6, PYRIN-7, PYRIN-8, PYRIN-10, or PYRIN-11 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a PYRIN-2, PYRIN-3, PYRIN-5, PYRIN-6, PYRIN-7, PYRIN-8, PYRIN-10, or PYRIN-11 immunogen as described above, and the culture supernatants of the resulting hybridoma cells are screened to identify a hybridoma producing a monoclonal antibody that binds PYRIN-2, PYRIN-3, PYRIN-5, PYRIN-6, PYRIN-7, PYRIN-8, PYRIN-10, or PYRIN-11.

Any of the many well known protocols used for fusing lymphocytes and immortalized cell lines can be applied for the purpose of generating an anti-PYRIN-2, PYRIN-3, PYRIN-5, PYRIN-6, PYRIN-7, PYRIN-8, PYRIN-10, or PYRIN-11 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PYRIN-2, PYRIN-3, PYRIN-5, PYRIN-6, PYRIN-7, PYRIN-8, PYRIN-10, or PYRIN-11, e.g., using a standard ELISA assay.

Alternative to preparing monoclonal antibody-secreting hybridomas, a monoclonal anti-PYRIN-2, PYRIN-3, PYRIN-5, PYRIN-6, PYRIN-7, PYRIN-8, PYRIN-10, or PYRIN-11 antibody can be identified and isolated by screening a recombinant combinatorial immunoglobulin library (e.g., an antibody phage display library) with PYRIN-2, PYRIN-3, PYRIN-5, PYRIN-6, PYRIN-7, PYRIN-8, PYRIN-10, or PYRIN-11 to thereby isolate immunoglobulin library members that bind PYRIN-2, PYRIN-3, PYRIN-5, PYRIN-6, PYRIN-7, PYRIN-8, PYRIN-10, or PYRIN-11. Kits for generating and screening phage display libraries are commercially available (e.g., the Pharmacia Recombinant Phage Antibody System, Catalog No. 27–9400–01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-PYRIN-2, PYRIN-3, PYRIN-5, PYRIN-6, PYRIN-7, PYRIN-8, PYRIN-10, or PYRIN-11 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-PYRIN-2, PYRIN-3, PYRIN-5, PYRIN-6, PYRIN-7, PYRIN-8, PYRIN-10, or PYRIN-11 antibody (e.g., monoclonal antibody) can be used to isolate PYRIN-2, PYRIN-3, PYRIN-5, PYRIN-6, PYRIN-7, PYRIN-8, PYRIN-10, or PYRIN-11 by standard techniques, such as affinity chromatography or immunoprecipitation. An anti-PYRIN-2, PYRIN-3, PYRIN-5, PYRIN-6, PYRIN-7, PYRIN-8, PYRIN-10, or PYRIN-11 antibody can facilitate the purification of natural PYRIN-2, PYRIN-3, PYRIN-5, PYRIN-6, PYRIN-7, PYRIN-8, PYRIN-10, or PYRIN-11 from cells and of recombinantly produced PYRIN-2, PYRIN-3, PYRIN-5, PYRIN-6, PYRIN-7, PYRIN-8, PYRIN-10, or PYRIN-11 expressed in host cells. Moreover, an anti-PYRIN-2, PYRIN-3, PYRIN-5, PYRIN-6, PYRIN-7, PYRIN-8, PYRIN-10, or PYRIN-11 antibody can be used to detect PYRIN-2, PYRIN-3, PYRIN-5, PYRIN-6, PYRIN-7, PYRIN-8, PYRIN-10, or PYRIN-11 protein (e.g., in a cellular lysate or cell supernatant) in order to evaluate the abundance and pattern of expression of the PYRIN-2, PYRIN-3, PYRIN-5, PYRIN-6, PYRIN-7, PYRIN-8, PYRIN-10, or PYRIN-11 protein. Anti-PYRIN-2, PYRIN-3, PYRIN-5, PYRIN-6, PYRIN-7, PYRIN-8, PYRIN-10, or PYRIN-11 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Techniques for conjugating such therapeutic moiety to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243–56 (Alan R. Liss, Inc. 1985); Hellstrom et al., "Antibodies for Drug Delivery", in Controlled Drug Delivery (2nd Ed.), Robinson et al. (eds.), pp. 623–53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475–506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp. 303–16 (Academic Press 1985), and Thorpe et al., "The Preparation and Cytotoxic Properties of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

Another aspect of the invention relates to a method for inducing an immunological response in a mammal which comprises inoculating the mammal with a PYRIN-2, PYRIN-3, PYRIN-5, PYRIN-6, PYRIN-7, PYRIN-8, PYRIN-10, or PYRIN-11 polypeptide, adequate to produce antibody and/or T cell immune response to protect the animal from the diseases hereinbefore mentioned, amongst others. Yet another aspect of the invention relates to a method of inducing immunological response in a mammal which comprises, delivering a PYRIN-2, PYRIN-3, PYRIN-5, PYRIN-6, PYRIN-7, PYRIN-8, PYRIN-10, or PYRIN-11 polypeptide via a vector directing expression of the polynucleotide and coding for the polypeptide in vivo in order to induce such an immunological response to produce antibody to protect the animal from diseases.

A further aspect of the invention relates to an immunological/vaccine formulation (composition) which, when introduced into a mammalian host, induces an immunological response in that mammal to a PYRIN-2, PYRIN-3, PYRIN-5, PYRIN-6, PYRIN-7, PYRIN-8, PYRIN-10, or PYRIN-11 polypeptide of the present invention wherein the composition comprises a polypeptide or polynucleotide of PYRIN-2, PYRIN-3, PYRIN-5, PYRIN-6, PYRIN-7,PYRIN-8,PYRIN-10, or PYRIN-11. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

III. Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. This skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a work processing test file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or a target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration formed upon the folding of the target motif. There are a variety of target motifs know in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of know algorithms are disclosed publicly and a variety of commercially available software for conducting search means are and can be used in the computer-based systems of the present invention. Examples of such software include, but is not limited to, MacPattern (EMBL), BLASTIN and BLASTX (NCBIA).

For example, software that implements the BLAST (Altschul et al. (1990) J. of Mol. Biol. 215:403–410) and BLAZE (Brutlag et al. (1993) Comp. Chem. 17:203–207) search algorithms on a Sybase system can be used to identify open reading frames (ORFs) of the sequences of the invention which contain homology to ORFs or proteins from other libraries. Such ORFs are protein-encoding fragments and are useful in producing commercially important proteins such as enzymes used in various reactions and in the production of commercially useful metabolites.

IV. Recombinant Expression Vectors and Host Cells

Another aspect of the invention pertains to vectors, preferably expression vectors, containing a nucleic acid encoding PYRIN-2, PYRIN-3, PYRIN-5, PYRIN-6, PYRIN-7, PYRIN-8, PYRIN-10, or PYRIN-11 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PYRIN-2, PYRIN-3, PYRIN-5, PYRIN-6, PYRIN-7, PYRIN-8, PYRIN-10, or PYRIN-11 proteins, mutant forms of PYRIN-2, PYRIN-3, PYRIN-5, PYRIN-6, PYRIN-7, PYRIN-8, PYRIN-10, or PYRIN-11, fusion proteins, etc.).

The recombinant expression vectors of the invention can be designed for expression of PYRIN-2, PYRIN-3, PYRIN-5, PYRIN-6, PYRIN-7, PYRIN-8, PYRIN-10, or PYRIN-11 in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gp10-lac fusion promoter mediated by a coexpressed viral RNA polymerase (T7 gn1). This viral polymerase is supplied by host strains BL21(DE3) or HMS174 (DE3) from a resident e prophage harboring a T7 gn1 gene under the transcriptional control of the lacUV5 promoter.

One strategy to maximize recombinant protein expression in E. coli is to express the protein in a bacterial having an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences of the invention can be carried out by standard DNA synthesis techniques.

In another embodiment, the PYRIN-2, PYRIN-3, PYRIN-5, PYRIN-6, PYRIN-7, PYRIN-8, PYRIN-10, or PYRIN-11 expression vector is a yeast expression vector. Examples of vectors for expression in yeast S. cerivisae include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299–1308), pYPGE15 (Brunelli and Pall, (1993) Yeast 9:1309–1318), pACTII (Dr. S. E. Elledge, Baylor College of Medicine), and picZ (InVitrogen Corp, San Diego, Calif.). Alternatively, PYRIN-2, PYRIN-3, PYRIN-5, PYRIN-6, PYRIN-7, PYRIN-8, PYRIN-10, or PYRIN-11 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra). In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PYRIN-2, PYRIN-3, PYRIN-5, PYRIN-6, PYRIN-7, PYRIN-8, PYRIN-10, or PYRIN-11 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, PYRIN-2, PYRIN-3, PYRIN-5, PYRIN-6, PYRIN-7, PYRIN-8, PYRIN-10, or PYRIN-11 protein can be expressed in bacterial cells such as E. coli, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding PYRIN-2, PYRIN-3, PYRIN-5, PYRIN-6, PYRIN-7, PYRIN-8, PYRIN-10, or PYRIN-11 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a PYRIN-2, PYRIN-3, PYRIN-5, PYRIN-6, PYRIN-7, PYRIN-8, PYRIN-10, or PYRIN-11 protein. Accordingly, the invention further provides methods for producing PYRIN-2, PYRIN-3, PYRIN-5, PYRIN-6, PYRIN-7, PYRIN-8, PYRIN-10, or PYRIN-11 protein using the host cells of the invention. In one embodiment, the method comprises culturing the host cell of the invention (into which a recombinant expression vector or isolated nucleic acid molecule encoding PYRIN-2, PYRIN-3, PYRIN-5, PYRIN-6, PYRIN-7, PYRIN-8, PYRIN-10, or PYRIN-11 has been introduced) in a suitable medium such that PYRIN-2, PYRIN-3, PYRIN-5, PYRIN-6, PYRIN-7, PYRIN-8, PYRIN-10, or PYRIN-11 protein is produced. In another embodiment, the method further comprises isolating PYRIN-2, PYRIN-3, PYRIN-5, PYRIN-6, PYRIN-7, PYRIN-8, PYRIN-10, or PYRIN-11 from the medium or the host cell.

PYRIN-2, PYRIN-3, PYRIN-5, PYRIN-6, PYRIN-7, PYRIN-8, PYRIN-10, and PYRIN-11 nucleic acid molecules can be used in viral gene delivery systems for gene therapy, e.g., adenoviral or retroviral gene delivery systems.

PYRIN-2, PYRIN-3, PYRIN-5, PYRIN-6, PYRIN-7, PYRIN-8, PYRIN-10, and PYRIN-11 nucleic acid molecules can also be used in non-viral gene delivery systems for gene therapy. Thus, another aspect of the invention pertains to non-viral gene delivery systems, such as plasmid-based gene delivery systems. Non-viral gene delivery systems are described in detail by Huang et al. ((1999) Nonviral Vectors for Gene Therapy, Academic Press, San Diego, Calif.). Nonviral vectors have several potential advantages over their viral counterparts, including: reduced immunogenicity; low acute toxicity; simplicity; and ease of large scale production. Nonviral vectors can be delivered as naked DNA, by bioballistic bombardment, and in various complexes, including liposome/DNA complexes (lipoplexes), polymer/DNA complexes (polyplexes), and liposome/polymer/DNA complexes (lipopolyplexes). Nonviral vectors may be administered by various routes, e.g., intravenous injection, peritoneal injection, intramuscular injection, subcutaneous injection, intratracheal injection, and aerosolization.

Naked DNA (i.e. free from association with, e.g., transfection-facilitating proteins, viral particles, liposomal formulations, charged lipids and calcium phosphate precipitating), can be expressed at its injection site or at a remote site. For example, naked DNA can be injected directly into skeletal muscle, liver, heart muscle, and tumor tissue. For systemic administration, plasmid DNA may need to be protected from degradation by endonucleases during delivery from the site of administration to the site of gene expression.

Bioballistic bombardment, also known as gene gun, allows for the penetration of target cells in vitro, ex vivo, or in vivo. In this technique, DNA-coated gold particles are accelerated to a high velocity by an electric arc generated by a high voltage discharge. The method is effective for a variety of organ types, including skin, liver, muscle, spleen, and pancreas. The gene gun transfer method is not dependent upon specific cell surface receptors, cell cycle status, or the size of the DNA vector. Useful gene gun devices include the Accell® (PowderJect Vaccines, Inc.) and the Helios™ (Bio-Rad). These devices create a compressed shock wave of helium gas, accelerating DNA-coated gold (or tungsten) particles to high speed, whereby the particles have sufficient momentum to penetrate a target tissue.

Lipoplexes are typically made up of three components: a cationic lipid, a neutral colipid, and plasmid DNA that encodes one or more genes of interest. Commonly used cationic lipids include DOTMA, DMRIE, DC-chol, DOTAP, DMRIE, DDAB, DODAB/C, DOGS, DOSPA, SAINT-n, DOSPER, DPPES, DORIE, GAP-DLRIE, and DOTIM. Dioleoyl (DO) and dimyristoyl (DM) chains are thought to be especially effective for gene delivery. Cationic lipids are typically composed of a positively charged headgroup, a hydrophobic lipid anchor, and a linker that connects the headgroup and anchor. Catioinc lipids used in lipoplexes can be divided into two broad classes: those that use cholesterol as the lipid anchor and those that use diacyl chains of varying lengths and extent of saturation. The number of protonatable amines on the headgroup may affect transfection activity, with multivalent headgroups being generally more active than monovalent headgroups. The linker can be made of a variety of chemical structures, e.g., ether, amide, carbamate, amine, urea, ester, and peptide bonds. Neutral colipids of lipoplexes commonly include DOPE, DOPC, and cholesterol. Generally, DOPE is used as the neutral colipid with catioinc lipids that are based on cholesterol (e.g., DC-chol, GL-67) and cholesterol is used as the neutral colipid with cationic lipids that harbor diacyl chains as the hydrophobic anchor (e.g., DOTAP, DOTIM).

Polyplexes are formed when cationic polymers are mixed with DNA. Cationic polymers used to from polyplexes are of two general types: linear polymers such as polylysine and spermine; and the branched chain, spherical, or globular polycations such as polyethyleneimine and dendrimers. Lipopolyplexes are formed by the incorporation of polylysine into a lipoplex to form ternary complexes. DNA can be complexed with a natural biopolymer, e.g., gelatin or chitosan, functioning as a gene carrier to form nanospheres. Such biodegradable nanospheres have several advantages, including the coencapsulation of bioactive agents, e.g. nucleic acids and drugs, and the sustained release of the DNA. Gelatin-DNA or chitosan-DNA nanospheres are synthesized by mixing the DNA solution with an aqueous solution of gelatin or chitosan.

The effectiveness nonviral vectors may be enhanced by conjugation to ligands that direct the vector either to a particular cell type or to a particular location within a cell. Antibodies and other site-specific proteins can be attached to a vector, e.g., on the surface of the vector or incorporated in the membrane. Following injection, these vectors bind efficiently and specifically to a target site. With respect to liposomes, ligands to a cell surface receptor can be incorporated into the surface of a liposome by covalently modifying the ligand with a lipid group and adding it during the formation of liposomes. The following classes of ligands can be incorporated into the nonviral DNA delivery complexes of the invention in order to make them more effective for gene delivery: (1) peptides, e.g., peptides having a specific cell surface receptor so that complexes will be targeted to specific cells bearing the receptor; (2) nuclear localization signals, e.g., to promote efficient entry of DNA into the nucleus; (3) pH-sensitive ligands, to encourage endosomal escape; (4) steric stabilizing agents, to prevent destabilization of the complexes after introduction into the biological milieu. Gene chemistry approaches, e.g. peptide nucleic acids, can be used to couple ligands to DNA to improve the in vivo bioavailability and expression of the DNA.

In plasmid-based, non-viral gene delivery systems it is often useful to link a polypeptide (e.g., an antibody), nucleic acid molecule, or other compound to the gene delivery plasmid such that the polypeptide, nucleic acid molecule or other compound remains associated with the plasmid following intracellular delivery in a manner that does not interfere with the transcriptional activity of the plasmid. This can be accomplished using an appropriate biotin-conjugated peptide nucleic acid (PNA) clamp. A sequence complementary to the biotin-conjugated PNA clamp is inserted into the gene delivery plasmid. The biotin-conjugated PNA will bind essentially irreversibly to the complementary sequence inserted into the plasmid. A polypeptide, nucleic acid molecule or other compound of interest can be conjugated to streptavidin. The streptavidin conjugate can bind to the biotin-PNA clamp bound to the plasmid. In this manner, a polypeptide, nucleic acid molecule or other compound can be bound to a gene delivery plasmid such that the polypeptide, nucleic acid molecule or other compound remains bound to the plasmid even within a cell. Importantly, the PNA clamp-binding site in the plasmid must be chosen so as not to interfere with a needed promoter/enhancer or coding region or otherwise disrupt the expression of the gene in the plasmid. An alternative approach employs a maleimide-conjugated PNA clamp. Polypeptides, nucleic acid molecules and other compounds containing a free thiol residue may be conjugated directly to the maleimide-PNA-DNA hybrid. As with the biotin-conjugated method, this conjugation does not disturb the transcriptional activity of the plasmid if the PNA-binding site is chosen to be in a region of the plasmid not essential for gene activity. Both of these approaches are described in detail by Zelphati et al. ((2000) BioTechniques 28:304–315).

The host cells of the invention can also be used to produce nonhuman transgenic animals. For example, in one embodiment, a host cell of the invention is a fertilized oocyte or an embryonic stem cell into which PYRIN-2, PYRIN-3, PYRIN-5, PYRIN-6, PYRIN-7, PYRIN-8, PYRIN-10, or PYRIN-11-coding sequences have been introduced. Such host cells can then be used to create non-human transgenic animals in which exogenous PYRIN-2, PYRIN-3, PYRIN-5, PYRIN-6, PYRIN-7, PYRIN-8, PYRIN-10, or PYRIN-11 sequences have been introduced into their genome or homologous recombinant animals in which endogenous PYRIN-2, PYRIN-3, PYRIN-5, PYRIN-6, PYRIN-7, PYRIN-8, PYRIN-10, or PYRIN-11 sequences have been altered. Such animals are useful for studying the function and/or activity of PYRIN-2, PYRIN-3, PYRIN-5, PYRIN-6, PYRIN-7, PYRIN-8, PYRIN-10, or PYRIN-11 and for identifying and/or evaluating modulators of PYRIN-2, PYRIN-3, PYRIN-5, PYRIN-6, PYRIN-7, PYRIN-8, PYRIN-10, or PYRIN-11 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous PYRIN-2, PYRIN-3, PYRIN-5, PYRIN-6, PYRIN-7, PYRIN-8, PYRIN-10, or PYRIN-11 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing PYRIN-2, PYRIN-3, PYRIN-5, PYRIN-6, PYRIN-7, PYRIN-8, PYRIN-10, or PYRIN-11-encoding nucleic acid into the male pronuclei of a fertilized oocyte, e.g., by microinjection, retroviral infection, and allowing the oocyte to develop in a pseudopregnant female foster animal. The PYRIN-2, PYRIN-3, PYRIN-5, PYRIN-6, PYRIN-7, PYRIN-8, PYRIN-10, or PYRIN-11 cDNA sequence, e.g., that of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25, can be introduced as a transgene into the genome of a non-human animal. Alternatively, a nonhuman homolog or ortholog of the human PYRIN-2, PYRIN-3, PYRIN-5, PYRIN-6, PYRIN-7, PYRIN-8, PYRIN-10, or PYRIN-11 gene, such as a mouse PYRIN-2, PYRIN-3, PYRIN-5, PYRIN-6, PYRIN-7, PYRIN-8, PYRIN-10, or PYRIN-11 gene, can be isolated based on hybridization to the human PYRIN-2, PYRIN-3, PYRIN-5, PYRIN-6, PYRIN-7, PYRIN-8, PYRIN-10, or PYRIN-11 cDNA and used as a transgene. Intronic sequences and polyadenylation signals can also be included in the transgene to increase the efficiency of expression of the transgene. A tissue-specific regulatory sequence(s) can be operably linked to the PYRIN-2, PYRIN-3, PYRIN-5, PYRIN-6, PYRIN-7, PYRIN-8, PYRIN-10, or PYRIN-11 transgene to direct expression of PYRIN-2, PYRIN-3, PYRIN-5, PYRIN-6, PYRIN-7, PYRIN-8, PYRIN-10, or PYRIN-11 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the PYRIN-2, PYRIN-3, PYRIN-5, PYRIN-6, PYRIN-7, PYRIN-8, PYRIN-10, or PYRIN-11 transgene in its genome and/or expression of PYRIN-2, PYRIN-3, PYRIN-5, PYRIN-6, PYRIN-7, PYRIN-8, PYRIN-10, or PYRIN-11 mRNA in tissues or cells of the animals. A transgenic founder animal can then be used to breed additional animals carrying the transgene. Moreover, transgenic animals carrying a transgene encoding PYRIN-2, PYRIN-3, PYRIN-5, PYRIN-6, PYRIN-7, PYRIN-8, PYRIN-10, or PYRIN-11 can further be bred to other transgenic animals carrying other transgenes.

To create an homologous recombinant animal, a vector is prepared which contains at least a portion of a PYRIN-2, PYRIN-3, PYRIN-5, PYRIN-6, PYRIN-7, PYRIN-8, PYRIN-10, or PYRIN-11 gene (e.g., a human or a non-human homolog of the PYRIN-2, PYRIN-3, PYRIN-5, PYRIN-6, PYRIN-7, PYRIN-8, PYRIN-10, or PYRIN-11 gene, e.g., a murine PYRIN-2, PYRIN-3, PYRIN-5, PYRIN-6, PYRIN-7, PYRIN-8, PYRIN-10, or PYRIN-11 gene) into which a deletion, addition or substitution has been introduced to thereby alter, e.g., functionally disrupt, the PYRIN-2, PYRIN-3, PYRIN-5, PYRIN-6, PYRIN-7, PYRIN-8, PYRIN-10, or PYRIN-11 gene. In an embodiment, the vector is designed such that, upon homologous recombination, the endogenous PYRIN-2, PYRIN-3, PYRIN-5, PYRIN-6, PYRIN-7, PYRIN-8, PYRIN-10, or PYRIN-11 gene is functionally disrupted (i.e., no longer encodes a functional protein; also referred to as a "knock out" vector). Alternatively, the vector can be designed such that, upon homologous recombination, the endogenous PYRIN-2, PYRIN-3, PYRIN-5, PYRIN-6, PYRIN-7, PYRIN-8, PYRIN-10, or PYRIN-11 gene is mutated or otherwise altered but still encodes functional protein (e.g., the upstream regulatory region can be altered to thereby alter the expression of the endogenous PYRIN-2, PYRIN-3, PYRIN-5, PYRIN-6, PYRIN-7, PYRIN-8, PYRIN-10, or PYRIN-11 protein). In the homologous recombination vector, the altered portion of the PYRIN-2, PYRIN-3, PYRIN-5, PYRIN-6, PYRIN-7, PYRIN-8, PYRIN-10, or PYRIN-11 gene is flanked at its 5' and 3' ends by additional nucleic acid of the PYRIN-2, PYRIN-3, PYRIN-5, PYRIN-6, PYRIN-7, PYRIN-8, PYRIN-10, or PYRIN-11 gene to allow for homologous recombination to occur between the exogenous PYRIN-2, PYRIN-3, PYRIN-5, PYRIN-6, PYRIN-7, PYRIN-8, PYRIN-10, or PYRIN-11 gene carried by the vector and an endogenous PYRIN-2, PYRIN-3, PYRIN-5, PYRIN-6, PYRIN-7, PYRIN-8, PYRIN-10, or PYRIN-11 gene in an embryonic stem cell. The additional flanking PYRIN-2, PYRIN-3, PYRIN-5, PYRIN-6, PYRIN-7, PYRIN-8, PYRIN-10, or PYRIN-11 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced PYRIN-2, PYRIN-3, PYRIN-5, PYRIN-6, PYRIN-7, PYRIN-8, PYRIN-10, or PYRIN-11 gene has homologously recombined with the endogenous PYRIN-2, PYRIN-3, PYRIN-5, PYRIN-6, PYRIN-7, PYRIN-8, PYRIN-10, or PYRIN-11 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

In another embodiment, the expression characteristics of an endogenous PYRIN-2, PYRIN-3, PYRIN-5, PYRIN-6, PYRIN-7, PYRIN-8, PYRIN-10, or PYRIN-11 gene within a cell line or microorganism may be modified by inserting a heterologous DNA regulatory element into the genome of a stable cell line or cloned microorganism such that the inserted regulatory element is operatively linked with the endogenous PYRIN-2, PYRIN-3, PYRIN-5, PYRIN-6, PYRIN-7, PYRIN-8, PYRIN-10, or PYRIN-11 gene. For example, an endogenous PYRIN-2, PYRIN-3, PYRIN-5, PYRIN-6, PYRIN-7, PYRIN-8, PYRIN-10, or PYRIN-11 which is normally "transcriptionally silent," i.e. a PYRIN-2, PYRIN-3, PYRIN-5, PYRIN-6, PYRIN-7, PYRIN-8, PYRIN-10, or PYRIN-11 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous PYRIN-2, PYRIN-3, PYRIN-5, PYRIN-6, PYRIN-7, PYRIN-8, PYRIN-10, or PYRIN-11 gene may be activated by insertion of a promiscuous regulatory element that works across cell types.

A heterologous regulatory element may be inserted into a stable cell line or cloned microorganism, such that it is operatively linked with an endogenous PYRIN-2, PYRIN-3, PYRIN-5, PYRIN-6, PYRIN-7, PYRIN-8, PYRIN-10, or PYRIN-11 gene, using techniques, such as targeted homologous recombination, which are well known to those of skill in the art, and described e.g., in Chappel, U.S. Pat. No. 5,272,071; PCT publication No. WO 91/06667, published May 16, 1991.

V. Pharmaceutical Compositions

The PYRIN-2, PYRIN-3, PYRIN-5, PYRIN-6, PYRIN-7, PYRIN-8, PYRIN-10, or PYRIN-11 nucleic acid molecules, PYRIN-2, PYRIN-3, PYRIN-5, PYRIN-6, PYRIN-7, PYRIN-8, PYRIN-10, or PYRIN-11 proteins, and anti-PYRIN-2, PYRIN-3, PYRIN-5, PYRIN-6, PYRIN-7, PYRIN-8, PYRIN-10, or PYRIN-11 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PYRIN-2, PYRIN-3, PYRIN-5, PYRIN-6, PYRIN-7, PYRIN-8, PYRIN-10, or PYRIN-11 protein or anti-PYRIN-2, PYRIN-3, PYRIN-5, PYRIN-6, PYRIN-7, PYRIN-8, PYRIN-10, or PYRIN-11 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of protein, polypeptide, or antibody can include a single treatment or, preferably, can include a series of treatments.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The gene therapy vectors of the invention can be either viral or non-viral. Examples of plasmid-based, non-viral vectors are discussed in Huang et al. (1999) Nonviral Vectors for Gene Therapy (supra). A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) Bio Techniques 28:304–315). The attachment of proteins and/or oligonucleotides may influence the delivery and trafficking of the plasmid and thus render it a more effective pharmaceutical composition.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A PYRIN-2, PYRIN-3, PYRIN-5, PYRIN-6, PYRIN-7, PYRIN-8, PYRIN-10, or PYRIN-11 protein interacts with other cellular proteins and can thus be used for (i) regulation of cellular proliferation; (ii) regulation of cellular differentiation; and (iii) regulation of cell survival. The isolated nucleic acid molecules of the invention can be used to express PYRIN-2, PYRIN-3, PYRIN-5, PYRIN-6, PYRIN-7, PYRIN-8, PYRIN-10, or PYRIN-11 protein (e.g., via a recombinant expression vector in a host cell in gene therapy applications), to detect PYRIN-2, PYRIN-3, PYRIN-5, PYRIN-6, PYRIN-7, PYRIN-8, PYRIN-10, or PYRIN-11 mRNA (e.g., in a biological sample) or a genetic lesion in a PYRIN-2, PYRIN-3, PYRIN-5, PYRIN-6, PYRIN-7, PYRIN-8, PYRIN-10, or PYRIN-11 gene, and to modulate PYRIN-2, PYRIN-3, PYRIN-5, PYRIN-6, PYRIN-7, PYRIN-8, PYRIN-10, or PYRIN-11 activity. In addition, the PYRIN-2, PYRIN-3, PYRIN-5, PYRIN-6, PYRIN-7, PYRIN-8, PYRIN-10, or PYRIN-11 proteins can be used to screen drugs or compounds which modulate the PYRIN-2, PYRIN-3, PYRIN-5, PYRIN-6, PYRIN-7, PYRIN-8, PYRIN-10, or PYRIN-11 activity or expression as well as to treat disorders characterized by insufficient or excessive production of PYRIN-2, PYRIN-3, PYRIN-5, PYRIN-6, PYRIN-7, PYRIN-8, PYRIN-10, or PYRIN-11 protein or production of PYRIN-2, PYRIN-3, PYRIN-5, PYRIN-6, PYRIN-7, PYRIN-8, PYRIN-10, or PYRIN-11 protein forms which have decreased or aberrant activity compared to PYRIN-2, PYRIN-3, PYRIN-5, PYRIN-6, PYRIN-7, PYRIN-8, PYRIN-10, or PYRIN-11 wild type protein. In addition, the anti-PYRIN-2, PYRIN-3, PYRIN-5, PYRIN-6, PYRIN-7, PYRIN-8, PYRIN-10, or PYRIN-11 antibodies of the invention can be used to detect and isolate PYRIN-2, PYRIN-3, PYRIN-5, PYRIN-6, PYRIN-7, PYRIN-8, PYRIN-10, or PYRIN-11 proteins and modulate PYRIN-2, PYRIN-3, PYRIN-5, PYRIN-6, PYRIN-7, PYRIN-8, PYRIN-10, or PYRIN-11 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to PYRIN-2, PYRIN-3, PYRIN-5, PYRIN-6, PYRIN-7, PYRIN-8, PYRIN-10, or PYRIN-11 proteins or biologically active portions thereof or have a stimulatory or inhibitory effect on, for example, PYRIN-2, PYRIN-3, PYRIN-5, PYRIN-6, PYRIN-7, PYRIN-8, PYRIN-10, or PYRIN-11 expression or PYRIN-2, PYRIN-3, PYRIN-5, PYRIN-6, PYRIN-7, PYRIN-8, PYRIN-10, or PYRIN-11 activity. Examples of biologically active portions of human PYRIN-2, PYRIN-3, PYRIN-5, PYRIN-6, PYRIN-7, PYRIN-8, PYRIN-10, or PYRIN-11 are domains described herein, such as a pyrin domain, an NBS domain (or a motif of an NBS domain), and a LRR domain (or a leucine rich repeat of a LRR domain).

Among the screening assays provided by the invention are screening to identify molecules that prevent the interaction of PYRIN-2, PYRIN-3, PYRIN-5, PYRIN-6, PYRIN-7, PYRIN-8, PYRIN-10, or PYRIN-11 with another protein or biological molecule and screening to identify a competitive inhibitor of the binding of a nucleotide to the nucleotide binding site of PYRIN-2, PYRIN-3, PYRIN-5, PYRIN-6, PYRIN-7, PYRIN-8, PYRIN-10, or PYRIN-11. Such assays can employ full-length PYRIN-2, PYRIN-3, PYRIN-5, PYRIN-6, PYRIN-7, PYRIN-8, PYRIN-10, or PYRIN-11 or a portion of PYRIN-2, PYRIN-3, PYRIN-5, PYRIN-6, PYRIN-7, PYRIN-8, PYRIN-10, or PYRIN-11, e.g., a domain defined herein.

Molecules that bind to and/or alter the activity of an NBS domain of PYRIN-2, PYRIN-3, PYRIN-5, PYRIN-6, PYRIN-7, PYRIN-8, PYRIN-10, or PYRIN-11 may be useful for modulating the activity of PYRIN-2, PYRIN-3, PYRIN-5, PYRIN-6, PYRIN-7, PYRIN-8, PYRIN-10, or PYRIN-11. For example, molecules can be tested for their ability to modulate, e.g., antagonize, the hydrolysis of an NTP, e.g., ATP, by the NBS domain (or a fragment of an NBS domain such as an NBS motif described herein) of PYRIN-2, PYRIN-3, PYRIN-5, PYRIN-6, PYRIN-7, PYRIN-8, PYRIN-10, or PYRIN-11. Methods of detecting the hydrolysis of a NTP by a protein containing a nucleotide-binding site are described in, for example, Li et al. (1996) J. Biol. Chem. 271:28463–28468 and Gadsby et al. (1999) Physiol. Rev. 79:S77–S107.

A purified protein containing an NBS domain of PYRIN-2, PYRIN-3, PYRIN-5, PYRIN-6, PYRIN-7, PYRIN-8, PYRIN-10, or PYRIN-11 can be evaluated for its ability to mediate NTPase activity in vitro. The assay can be performed in the presence of a test compound to determine the ability of the test compound to modulate the NTPase activity of the purified protein. In addition, or alternatively, the purified protein used in an NTPase activity assay can be a variant or a fragment of PYRIN-2, PYRIN-3, PYRIN-5, PYRIN-6, PYRIN-7, PYRIN-8, PYRIN-10, or PYRIN-11, and the assay can be performed to determine the NTPase activity of the fragment or variant.

In one example, an NBS domain can be assayed for its ability to hydrolyze ATP. ATPase activity can be measured as the production of $[\alpha^{32}\text{-P}]$ADP from $[\alpha^{32}\text{-P}]$ATP, using polyethyleneimine-cellulose chromatography for separation of the nucleotides. The assay can be carried out in a 15 µl reaction mixture containing 50 mM Tris, 50 mM NaCl, pH 7.5, 2 mM $MgCl_2$, 10% glycerol, 0.5 mM CHAPS, and 8 µCi of $[\alpha^{32}\text{-P}]$ATP. Reaction mixtures are incubated at 30° C. and are stopped by the addition of 5 µl of 10% SDS. One µl samples are spotted on a polyethyleneimine-cellulose plate and developed in 1 M formic acid, 0.5 M LiCl. The location and quantitation of the radiolabeled ATP and ADP can determined with a Molecular Dynamics PhosphorImager. Data can be analyzed using the ImageQuant software package (Molecular Dynamics). See, e.g., Li et al. (1996) J. Biol. Chem. 271:28463–28468 for additional details on methods detecting ATPase activity by nucleotide binding site-containing proteins and variants thereof. Thin layer chromatography techniques similar to those described above can also be used for the measurement of NTPase activity such as GTPase activity (see, e.g., Gout et al. (1993) Cell 75:25–36).

Screening assays can be used to identify molecules that bind to and/or modulate the activity of a pyrin domain or a LRR domain of a PYRIN-2, PYRIN-3, PYRIN-5, PYRIN-6, PYRIN-7, PYRIN-8, PYRIN-10, or PYRIN-11 protein, fragment, or variant thereof.

Screening assays can also be used to identify molecules which modulate a PYRIN-2, PYRIN-3, PYRIN-5, PYRIN-6, PYRIN-7, PYRIN-8, PYRIN-10, or PYRIN-11 mediated increase in transcription of genes having an AP-1 or NF-κB binding site. For example, expression of a reporter gene under the control of NF-κB (or AP-1) is measured in the presence and absence of a candidate molecule and in the presence and absence of PYRIN-2, PYRIN-3, PYRIN-5, PYRIN-6, PYRIN-7, PYRIN-8, PYRIN-10, or PYRIN-11 to identify those molecules which alter expression of the reporter in a PYRIN-2, PYRIN-3, PYRIN-5, PYRIN-6, PYRIN-7, PYRIN-8, PYRIN-10, or PYRIN-11 dependent manner. In addition, screening assays can be used to identify molecules that modulate a PYRIN-2, PYRIN-3, PYRIN-5, PYRIN-6, PYRIN-7, PYRIN-8, PYRIN-10, or PYRIN-11 mediated increase in CHOP phosphorylation. For example, the expression of a reporter gene under the control of CHOP is measured in the presence and absence of a candidate small molecule and in the presence and absence of PYRIN-2, PYRIN-3, PYRIN-5, PYRIN-6, PYRIN-7, PYRIN-8, PYRIN-10, or PYRIN-11 to identify those molecules that alter expression of the reporter in a PYRIN-2, PYRIN-3, PYRIN-5, PYRIN-6, PYRIN-7, PYRIN-8, PYRIN-10, or PYRIN-11 dependent manner. A screening assay can be carried out to identify molecules which modulate the PYRIN-2, PYRIN-3, PYRIN-5, PYRIN-6, PYRIN-7, PYRIN-8, PYRIN-10, or PYRIN-11 mediated increase in CHOP phosphorylation. For example, CHOP phosphorylation is measured in the presence and absence of a candidate molecule and in the presence and absence of PYRIN-2, PYRIN-3, PYRIN-5, PYRIN-6, PYRIN-7, PYRIN-8, PYRIN-10, or PYRIN-11. Phosphorylation of CHOP can be measured using an antibody which binds to phosphorylated CHOP, but not to non-phosphorylated CHOP.

In one embodiment, the invention provides assays for screening candidate or test compounds which bind to or modulate the activity of a PYRIN-2, PYRIN-3, PYRIN-5, PYRIN-6, PYRIN-7, PYRIN-8, PYRIN-10, or PYRIN-11 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

In one embodiment, an assay is one in which a polypeptide of the invention, or a biologically active portion thereof, is contacted with a test compound and the ability of the test compound to bind to the polypeptide determined. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

Determining the ability of the test compound to modulate the activity of PYRIN-2, PYRIN-3, PYRIN-5, PYRIN-6, PYRIN-7, PYRIN-8, PYRIN-10, or PYRIN-11 or a biologically active portion thereof can be accomplished, for example, by determining the ability of the PYRIN-2, PYRIN-3, PYRIN-5, PYRIN-6, PYRIN-7, PYRIN-8, PYRIN-10, or PYRIN-11 protein to bind to or interact with a PYRIN-2, PYRIN-3, PYRIN-5, PYRIN-6, PYRIN-7, PYRIN-8, PYRIN-10, or PYRIN-11 target molecule. As used herein, a "target molecule" is a molecule with which a PYRIN-2, PYRIN-3, PYRIN-5, PYRIN-6, PYRIN-7, PYRIN-8, PYRIN-10, or PYRIN-11 protein binds or interacts in nature, for example, a molecule associated with the internal surface of a cell membrane or a cytoplasmic molecule. A PYRIN-2, PYRIN-3, PYRIN-5, PYRIN-6, PYRIN-7, PYRIN-8, PYRIN-10, or PYRIN-11 target molecule can be a non-PYRIN-2, PYRIN-3, PYRIN-5, PYRIN-6, PYRIN-7, PYRIN-8, PYRIN-10, or PYRIN-11 molecule or a PYRIN-2, PYRIN-3, PYRIN-5, PYRIN-6, PYRIN-7, PYRIN-8, PYRIN-10, or PYRIN-11 protein or polypeptide of the present invention. In one embodiment, a PYRIN-2, PYRIN-3, PYRIN-5, PYRIN-6, PYRIN-7, PYRIN-8, PYRIN-10, or PYRIN-11 target molecule is a component of an apoptotic signal transduction pathway. The target, for example, can be a second intracellular protein which has catalytic activity or a protein which facilitates the association of downstream signaling molecules with PYRIN-2, PYRIN-3, PYRIN-5, PYRIN-6, PYRIN-7, PYRIN-8, PYRIN-10, or PYRIN-11. In particular the target can be another protein having a pyrin domain (or a pyrin domain containing fragment thereof).

Determining the ability of the test compound to modulate the activity of PYRIN-2, PYRIN-3, PYRIN-5, PYRIN-6, PYRIN-7, PYRIN-8, PYRIN-10, or PYRIN-11 or a biologically active portion thereof can be accomplished, for example, by determining the ability of the PYRIN-2, PYRIN-3, PYRIN-5, PYRIN-6, PYRIN-7, PYRIN-8, PYRIN-10, or PYRIN-11 protein to bind to or interact with any of the specific proteins listed in the previous paragraph as PYRIN-2, PYRIN-3, PYRIN-5, PYRIN-6, PYRIN-7, PYRIN-8, PYRIN-10, or PYRIN-11 target molecules. In another embodiment, PYRIN-2, PYRIN-3, PYRIN-5, PYRIN-6, PYRIN-7, PYRIN-8, PYRIN-10, or PYRIN-11 target molecules include all proteins that bind to a PYRIN-2, PYRIN-3, PYRIN-5, PYRIN-6, PYRIN-7, PYRIN-8, PYRIN-10, or PYRIN-11 protein or a fragment thereof in a two-hybrid system binding assay which can be used without undue experimentation to isolate such proteins from cDNA or genomic two-hybrid system libraries. The binding assays described in this section can be cell-based or cell free (described subsequently).

Determining the ability of the PYRIN-2, PYRIN-3, PYRIN-5, PYRIN-6, PYRIN-7, PYRIN-8, PYRIN-10, or PYRIN-11 protein to bind to or interact with a PYRIN-2, PYRIN-3, PYRIN-5, PYRIN-6, PYRIN-7, PYRIN-8, PYRIN-10, or PYRIN-11 target molecule can be accomplished by one of the methods described above for determining direct binding. In an embodiment, determining the ability of the PYRIN-2, PYRIN-3, PYRIN-5, PYRIN-6, PYRIN-7, PYRIN-8, PYRIN-10, or PYRIN-11 protein to bind to or interact with a PYRIN-2, PYRIN-3, PYRIN-5, PYRIN-6, PYRIN-7, PYRIN-8, PYRIN-10, or PYRIN-11 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a PYRIN-2, PYRIN-3, PYRIN-5, PYRIN-6, PYRIN-7, PYRIN-8, PYRIN-10, or PYRIN-11-responsive regulatory element operatively linked to a nucleic acid encoding a detectable marker, e.g. luciferase), or detecting a cellular response, for example, cell survival, cellular differentiation, or cell proliferation. The activity of a target molecule can be monitored by assaying the caspase 9-mediated apoptosis cellular response or caspase 9 enzymatic activity. In addition, and in another embodiment, genes induced by PYRIN-2, PYRIN-3, PYRIN-5, PYRIN-6, PYRIN-7, PYRIN-8, PYRIN-10, or PYRIN-11 expression can be identified by expressing PYRIN-2, PYRIN-3, PYRIN-5, PYRIN-6, PYRIN-7, PYRIN-8, PYRIN-10, or PYRIN-11 in a cell line and conducting a transcriptional profiling experiment wherein the mRNA expression patterns of the cell line transformed with an empty expression vector and the cell line transformed with a PYRIN-2, PYRIN-3, PYRIN-5, PYRIN-6, PYRIN-7, PYRIN-8, PYRIN-10, or PYRIN-11 expression vector are compared. The promoters of genes induced by PYRIN-2, PYRIN-3, PYRIN-5, PYRIN-6, PYRIN-7, PYRIN-8, PYRIN-10, or PYRIN-11 expression can be operatively linked to reporter genes suitable for screening such as luciferase, secreted alkaline phosphatase, or beta-galactosidase and the resulting constructs could be introduced into appropriate expression vectors. A recombinant cell line containing PYRIN-2, PYRIN-3, PYRIN-5, PYRIN-6, PYRIN-7, PYRIN-8, PYRIN-10, or PYRIN-11 and transfected with an expression vector containing a PYRIN-2, PYRIN-3, PYRIN-5, PYRIN-6, PYRIN-7, PYRIN-8, PYRIN-10, or PYRIN-11 responsive promoter operatively linked to a reporter gene can be used to identify test compounds that modulate PYRIN-2, PYRIN-3, PYRIN-5, PYRIN-6, PYRIN-7, PYRIN-8, PYRIN-10, or PYRIN-11 activity by assaying the expression of the reporter gene in response to contacting the recombinant cell line with test compounds. PYRIN-2, PYRIN-3, PYRIN-5, PYRIN-6, PYRIN-7, PYRIN-8, PYRIN-10, or PYRIN-11 agonists can be identified as increasing the expression of the reporter gene and PYRIN-2, PYRIN-3, PYRIN-5, PYRIN-6, PYRIN-7, PYRIN-8, PYRIN-10, or PYRIN-11 antagonists can be identified as decreasing the expression of the reporter gene.

In another embodiment of the invention, the ability of a test compound to modulate the activity of PYRIN-2, PYRIN-3, PYRIN-5, PYRIN-6, PYRIN-7, PYRIN-8, PYRIN-10, or PYRIN-11, or biologically active portions thereof can be determined by assaying the ability of the test compound to modulate PYRIN-2, PYRIN-3, PYRIN-5, PYRIN-6, PYRIN-7, PYRIN-8, PYRIN-10, or PYRIN-11-dependent pathways or processes where the PYRIN-2, PYRIN-3, PYRIN-5, PYRIN-6, PYRIN-7, PYRIN-8, PYRIN-10, or PYRIN-11 target proteins that mediate the PYRIN-2, PYRIN-3, PYRIN-5, PYRIN-6, PYRIN-7, PYRIN-8, PYRIN-10, or PYRIN-11 effect are known or unknown. Potential PYRIN-2, PYRIN-3, PYRIN-5, PYRIN-6, PYRIN-7, PYRIN-8, PYRIN-10, or PYRIN-11-dependent pathways or processes include, but are not limited to, the modulation of cellular signal transduction pathways and their related second messenger molecules (e.g., intracellular Ca2+, diacylglycerol, IP3, cAMP etc.), cellular enzymatic activities, cellular responses (e.g., cell survival, cellular differentiation, or cell proliferation), or the induction or repression of cellular or heterologous mRNAs or proteins. PYRIN-2, PYRIN-3, PYRIN-5, PYRIN-6, PYRIN-7, PYRIN-8, PYRIN-10, or PYRIN-11-dependent pathways or processes could be assayed by standard cell-based or cell free assays appropriate for the specific pathway or process under study. In another embodiment, cells cotransfected with PYRIN-2, PYRIN-3, PYRIN-5, PYRIN-6, PYRIN-7, PYRIN-8, PYRIN-10, or PYRIN-11 and a NF-κB luciferase reporter gene could be contacted with a test compound and test compounds that block PYRIN-2, PYRIN-3, PYRIN-5, PYRIN-6, PYRIN-7, PYRIN-8, PYRIN-10, or PYRIN-11 activity could be identified by their reduction of PYRIN-2, PYRIN-3, PYRIN-5, PYRIN-6, PYRIN-7, PYRIN-8, PYRIN-10, or PYRIN-11-dependent NF-κB pathway luciferase reporter gene expression. Test compounds that agonize PYRIN-2, PYRIN-3, PYRIN-5, PYRIN-6, PYRIN-7, PYRIN-8, PYRIN-10, or PYRIN-11 would be expected to increase reporter gene expression. In another embodiment, PYRIN-2, PYRIN-3, PYRIN-5, PYRIN-6, PYRIN-7, PYRIN-8, PYRIN-10, or PYRIN-11 could be expressed in a cell line and the recombinant PYRIN-2, PYRIN-3, PYRIN-5, PYRIN-6, PYRIN-7, PYRIN-8, PYRIN-10, or PYRIN-11-expressing cell line could be contacted with a test compound. Test compounds that inhibit PYRIN-2, PYRIN-3, PYRIN-5, PYRIN-6, PYRIN-7, PYRIN-8, PYRIN-10, or PYRIN-11 activity could be identified by their reduction of PYRIN-2, PYRIN-3, PYRIN-5, PYRIN-6, PYRIN-7, PYRIN-8, PYRIN-10, or PYRIN-11-depended NF-κB pathway stimulation as measured by the assay of a NF-κB pathway reporter gene, NF-κB nuclear localization, IκB phosphorylation or proteolysis, or other standard assays for NF-κB pathway activation known to those skilled in the art.

In yet another embodiment, an assay of the present invention is a cell-free assay comprising contacting a PYRIN-2, PYRIN-3, PYRIN-5, PYRIN-6, PYRIN-7, PYRIN-8, PYRIN-10, or PYRIN-11 protein or biologically active portion thereof with a test compound and determining the ability of the test compound to bind to the PYRIN-2, PYRIN-3, PYRIN-5, PYRIN-6, PYRIN-7, PYRIN-8, PYRIN-10, or PYRIN-11 protein or biologically active portion thereof. Binding of the test compound to the PYRIN-2, PYRIN-3, PYRIN-5, PYRIN-6, PYRIN-7, PYRIN-8, PYRIN-10, or PYRIN-11 protein can be determined either directly or indirectly as described above. In one embodiment, a competitive binding assay includes contacting the PYRIN-2, PYRIN-3, PYRIN-5, PYRIN-6, PYRIN-7, PYRIN-8, PYRIN-10, or PYRIN-11 protein or biologically active portion thereof with a compound known to bind PYRIN-2, PYRIN-3, PYRIN-5, PYRIN-6, PYRIN-7, PYRIN-8, PYRIN-10, or PYRIN-11 to form an assay mixture, contacting the assay mixture with a test compound, and determining the ability of the test compound to interact with a PYRIN-2, PYRIN-3, PYRIN-5, PYRIN-6, PYRIN-7, PYRIN-8, PYRIN-10, or PYRIN-11 protein, wherein determining the ability of the test compound to interact with a PYRIN-2, PYRIN-3, PYRIN-5, PYRIN-6, PYRIN-7, PYRIN-8, PYRIN-10, or PYRIN-11 protein comprises determining the ability of the test compound to preferentially bind to PYRIN-2, PYRIN-3, PYRIN-5, PYRIN-6, PYRIN-7, PYRIN-8, PYRIN-10, or PYRIN-11 or biologically active portion thereof as compared to the known binding compound.

In another embodiment, an assay is a cell-free assay comprising contacting PYRIN-2, PYRIN-3, PYRIN-5, PYRIN-6, PYRIN-7, PYRIN-8, PYRIN-10, or PYRIN-11 protein or biologically active portion thereof with a test compound and determining the ability of the test compound to modulate (e.g., stimulate or inhibit) the activity of the PYRIN-2, PYRIN-3, PYRIN-5, PYRIN-6, PYRIN-7, PYRIN-8, PYRIN-10, or PYRIN-11 protein or biologically active portion thereof. Determining the ability of the test compound to modulate the activity of PYRIN-2, PYRIN-3, PYRIN-5, PYRIN-6, PYRIN-7, PYRIN-8, PYRIN-10, or PYRIN-11 can be accomplished, for example, by determining the ability of the PYRIN-2, PYRIN-3, PYRIN-5, PYRIN-6, PYRIN-7, PYRIN-8, PYRIN-10, or PYRIN-11 protein to bind to or interact with a PYRIN-2, PYRIN-3, PYRIN-5, PYRIN-6, PYRIN-7, PYRIN-8, PYRIN-10, or PYRIN-11 target molecule by one of the methods described above for determining direct binding. In an alternative embodiment, determining the ability of the test compound to modulate the activity of PYRIN-2, PYRIN-3, PYRIN-5, PYRIN-6, PYRIN-7, PYRIN-8, PYRIN-10, or PYRIN-11 can be accomplished by determining the ability of the PYRIN-2, PYRIN-3, PYRIN-5, PYRIN-6, PYRIN-7, PYRIN-8, PYRIN-10, or PYRIN-11 protein to further modulate a PYRIN-2, PYRIN-3, PYRIN-5, PYRIN-6, PYRIN-7, PYRIN-8, PYRIN- 10, or PYRIN-11 target molecule. For example, the catalytic/enzymatic activity of the target molecule on an appropriate substrate can be determined as previously described.

In yet another embodiment, the cell-free assay comprises contacting the PYRIN-2, PYRIN-3, PYRIN-5, PYRIN-6, PYRIN-7, PYRIN-8, PYRIN-10, or PYRIN-11 protein or biologically active portion thereof with a known compound which binds PYRIN-2, PYRIN-3, PYRIN-5, PYRIN-6, PYRIN-7, PYRIN-8, PYRIN-10, or PYRIN-11 to form an assay mixture, contacting the assay mixture with a test compound, and determining the ability of the test compound to interact with a PYRIN-2, PYRIN-3, PYRIN-5, PYRIN-6, PYRIN-7, PYRIN-8, PYRIN-10, or PYRIN-11 protein, wherein determining the ability of the test compound to interact with a PYRIN-2, PYRIN-3, PYRIN-5, PYRIN-6, PYRIN-7, PYRIN-8, PYRIN-10, or PYRIN-11 protein comprises determining the ability of the PYRIN-2, PYRIN-3, PYRIN-5, PYRIN-6, PYRIN-7, PYRIN-8, PYRIN-10, or PYRIN-11 protein to preferentially bind to or modulate the activity of a PYRIN-2, PYRIN-3, PYRIN-5, PYRIN-6, PYRIN-7, PYRIN-8, PYRIN-10, or PYRIN-11 target molecule. The cell-free assays of the present invention are amenable to use of either the soluble form or a membrane-associated form of PYRIN-2, PYRIN-3, PYRIN-5, PYRIN-6, PYRIN-7, PYRIN-8, PYRIN-10, or PYRIN-11. A membrane-associated form of PYRIN-2, PYRIN-3, PYRIN-5, PYRIN-6, PYRIN-7, PYRIN-8, PYRIN-10, or PYRIN-11 refers to PYRIN-2, PYRIN-3, PYRIN-5, PYRIN-6, PYRIN-7, PYRIN-8, PYRIN-10, or PYRIN-11 that interacts with a membrane-bound target molecule. In the case of cell-free assays comprising the membrane-associated form of PYRIN-2, PYRIN-3, PYRIN-5, PYRIN-6, PYRIN-7, PYRIN-8, PYRIN-10, or PYRIN-11, it may be desirable to utilize a solubilizing agent such that the membrane-associated form of PYRIN-2, PYRIN-3, PYRIN-5, PYRIN-6, PYRIN-7, PYRIN-8, PYRIN-10, or PYRIN-11 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either PYRIN-2, PYRIN-3, PYRIN-5, PYRIN-6, PYRIN-7, PYRIN-8, PYRIN-10, or PYRIN-11 or its target molecule to facilitate separation of complexed from uncomplexed forms of one or both of the proteins, as well as to accommodate automation of the assay. Binding of a test compound to PYRIN-2, PYRIN-3, PYRIN-5, PYRIN-6, PYRIN-7, PYRIN-8, PYRIN-10, or PYRIN-11, or interaction of PYRIN-2, PYRIN-3, PYRIN-5, PYRIN-6, PYRIN-7, PYRIN-8, PYRIN-10, or PYRIN-11 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/PYRIN-2, PYRIN-3, PYRIN-5, PYRIN-6, PYRIN-7, PYRIN-8, PYRIN-10, or PYRIN-11 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or PYRIN-2, PYRIN-3, PYRIN-5, PYRIN-6, PYRIN-7, PYRIN-8, PYRIN-10, or PYRIN-11 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PYRIN-2, PYRIN-3, PYRIN-5, PYRIN-6, PYRIN-7, PYRIN-8, PYRIN-10, or PYRIN-11 binding or activity determined using standard techniques. In an alternative embodiment, MYC or HA epitope tag PYRIN-2, PYRIN-3, PYRIN-5, PYRIN-6, PYRIN-7, PYRIN-8, PYRIN-10, or PYRIN-11 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or PYRIN-2, PYRIN-3, PYRIN-5, PYRIN-6, PYRIN-7, PYRIN-8, PYRIN-10, or PYRIN-11 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PYRIN-2, PYRIN-3, PYRIN-5, PYRIN-6, PYRIN-7, PYRIN-8, PYRIN-10, or PYRIN-11 binding or activity determined using standard techniques.

Other techniques for immobilizing proteins on matrices can also be used in the screening assays of the invention. For example, PYRIN-2, PYRIN-3, PYRIN-5, PYRIN-6, PYRIN-7, PYRIN-8, PYRIN-10, or PYRIN-11 or its target molecule can be immobilized utilizing conjugation of biotin and streptavidin. Biotinylated PYRIN-2, PYRIN-3, PYRIN-5, PYRIN-6, PYRIN-7, PYRIN-8, PYRIN-10, or PYRIN-11 target molecules can be prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with PYRIN-2, PYRIN-3, PYRIN-5, PYRIN-6, PYRIN-7, PYRIN-8, PYRIN-10, or PYRIN-11 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the PYRIN-2, PYRIN-3, PYRIN-5, PYRIN-6, PYRIN-7, PYRIN-8, PYRIN-10, or PYRIN-11 or target molecule, as well as enzyme-linked assays which rely on detecting an enzymatic activity associated with the PYRIN-2, PYRIN-3, PYRIN-5, PYRIN-6, PYRIN-7, PYRIN-8, PYRIN-10, or PYRIN-11 or a target molecule.

In another embodiment, modulators of PYRIN-2, PYRIN-3, PYRIN-5, PYRIN-6, PYRIN-7, PYRIN-8, PYRIN-10, or PYRIN-11 expression are identified in a method in which a cell is contacted with a candidate compound and the expression of the PYRIN-2, PYRIN-3, PYRIN-5, PYRIN-6, PYRIN-7, PYRIN-8, PYRIN-10, or PYRIN-11 promoter, mRNA or protein in the cell is determined. The level of expression of PYRIN-2, PYRIN-3, PYRIN-5, PYRIN-6, PYRIN-7, PYRIN-8, PYRIN-10, or PYRIN-11 mRNA or protein in the presence of the candidate compound is compared to the level of expression of PYRIN-2, PYRIN-3, PYRIN-5, PYRIN-6, PYRIN-7, PYRIN-8, PYRIN-10, or PYRIN-11 mRNA or protein in the absence of the candidate compound. The candidate compound can then be identified as a modulator of PYRIN-2, PYRIN-3, PYRIN-5, PYRIN-6, PYRIN-7, PYRIN-8, PYRIN-10, or PYRIN-11 expression based on this comparison. For example, when expression of PYRIN-2, PYRIN-3, PYRIN-5, PYRIN-6, PYRIN-7, PYRIN-8, PYRIN-10, or PYRIN-11 mRNA or protein is greater (statistically significantly greater) in the presence of the candidate compound than in its absence, the candidate compound is identified as a stimulator of PYRIN-2, PYRIN-3, PYRIN-5, PYRIN-6, PYRIN-7, PYRIN-8, PYRIN-10, or PYRIN-11 mRNA or protein expression. Alternatively, when expression of PYRIN-2, PYRIN-3, PYRIN-5, PYRIN-6, PYRIN-7, PYRIN-8, PYRIN-10, or PYRIN-11 mRNA or protein is less (statistically significantly less) in the presence of the candidate compound than in its absence, the candidate compound is identified as an inhibitor of PYRIN-2, PYRIN-3, PYRIN-5, PYRIN-6, PYRIN-7, PYRIN-8, PYRIN-10, or PYRIN-11 mRNA or protein expression. The level of PYRIN-2, PYRIN-3, PYRIN-5, PYRIN-6, PYRIN-7, PYRIN-8, PYRIN-10, or PYRIN-11 mRNA or protein expression in the cells can be determined by methods described herein for detecting PYRIN-2, PYRIN-3, PYRIN-5, PYRIN-6, PYRIN-7, PYRIN-8, PYRIN-10, or PYRIN-11 mRNA or protein. The activity of the PYRIN-2, PYRIN-3, PYRIN-5, PYRIN-6, PYRIN-7, PYRIN-8, PYRIN-10, or PYRIN-11 promoter can be assayed by linking the PYRIN-2, PYRIN-3, PYRIN-5, PYRIN-6, PYRIN-7, PYRIN-8, PYRIN-10, or PYRIN-11 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the PYRIN-2, PYRIN-3, PYRIN-5, PYRIN-6, PYRIN-7, PYRIN-8, PYRIN-10, or PYRIN-11 proteins can be used as "bait proteins" in a two-hybrid assay (for a discussion of a mammalian two-hybrid assay, see e.g., Hosfield and Chang (1999) Strategies Newsletter 2(2):62–65) or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with PYRIN-2, PYRIN-3, PYRIN-5, PYRIN-6, PYRIN-7, PYRIN- 8, PYRIN-10, or PYRIN-11 ("PYRIN-2, PYRIN-3, PYRIN-5, PYRIN-6, PYRIN-7, PYRIN-8, PYRIN-10, or PYRIN-11-binding proteins" or "PYRIN-2, PYRIN-3, PYRIN-5, PYRIN-6, PYRIN-7, PYRIN-8, PYRIN-10, or PYRIN-11-bp") and modulate PYRIN-2, PYRIN-3, PYRIN-5, PYRIN-6, PYRIN-7, PYRIN-8, PYRIN-10, or PYRIN-11 activity. Such PYRIN-2, PYRIN-3, PYRIN-5, PYRIN-6, PYRIN-7, PYRIN-8, PYRIN-10, or PYRIN-11-binding proteins are also likely to be involved in the propagation of signals by the PYRIN-2, PYRIN-3, PYRIN-5, PYRIN-6, PYRIN-7, PYRIN-8, PYRIN-10, or PYRIN-11 proteins as, for example, upstream or downstream elements of the PYRIN-2, PYRIN-3, PYRIN-5, PYRIN-6, PYRIN-7, PYRIN-8, PYRIN-10, or PYRIN-11 pathway.

The two-hybrid system is based on the modular nature of most transcription factors, which consist of separable DNA-binding and activation domains. Briefly, the assay utilizes two different DNA constructs. In one construct, the gene that codes for PYRIN-2, PYRIN-3, PYRIN-5, PYRIN-6, PYRIN-7, PYRIN-8, PYRIN-10, or PYRIN-11 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PYRIN-2, PYRIN-3, PYRIN-5, PYRIN-6, PYRIN-7, PYRIN-8, PYRIN-10, or PYRIN-11-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with PYRIN-2, PYRIN-3, PYRIN-5, PYRIN-6, PYRIN-7, PYRIN-8, PYRIN-10, or PYRIN-11.

In an embodiment of the invention, the ability of a test compound to modulate the activity of PYRIN-2, PYRIN-3, PYRIN-5, PYRIN-6, PYRIN-7, PYRIN-8, PYRIN-10, or PYRIN-11, or a biologically active portion thereof can be determined by assaying the ability of the test compound to block the binding of PYRIN-2, PYRIN-3, PYRIN-5, PYRIN-6, PYRIN-7, PYRIN-8, PYRIN-10, or PYRIN-11 to its target proteins in a yeast or mammalian two-hybrid system assay. This assay could be automated for high throughput drug screening purposes. In another embodiment of the invention, PYRIN-2, PYRIN-3, PYRIN-5, PYRIN-6, PYRIN-7, PYRIN-8, PYRIN-10, or PYRIN-11 and a target protein could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of a PYRIN-2, PYRIN-3, PYRIN-5, PYRIN-6, PYRIN-7, PYRIN-8, PYRIN-10, or PYRIN-11 physical interaction with a target protein would result in induction of a reporter gene in contrast to the normal two-hybrid system where inhibition of PYRIN-2, PYRIN-3, PYRIN-5, PYRIN-6, PYRIN-7, PYRIN-8, PYRIN-10, or PYRIN-11 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to PYRIN-2, PYRIN-3, PYRIN-5, PYRIN-6, PYRIN-7, PYRIN-8, PYRIN-10, or PYRIN-11. PYRIN-2, PYRIN-3, PYRIN-5, PYRIN-6, PYRIN-7, PYRIN-8, PYRIN-10, or PYRIN-11 interactors could be configured into two-hybrid system baits and used in two-hybrid screens to identify additional members of the PYRIN-2, PYRIN-3, PYRIN-5, PYRIN-6, PYRIN-7, PYRIN-8, PYRIN-10, or PYRIN-11 pathway. The interactors of PYRIN-2, PYRIN-3, PYRIN-5, PYRIN-6, PYRIN-7, PYRIN-8, PYRIN-10, or PYRIN-11 interactors identified in this way could be useful targets for therapeutic intervention in PYRIN-2, PYRIN-3, PYRIN-5, PYRIN-6, PYRIN-7, PYRIN-8, PYRIN-10, or PYRIN-11 related diseases and pathologies and an assay of their enzymatic or binding activity could be useful for the identification of test compounds that modulate PYRIN-2, PYRIN-3, PYRIN-5, PYRIN-6, PYRIN-7, PYRIN-8, PYRIN-10, or PYRIN-11 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, PYRIN-2, PYRIN-3, PYRIN-5, PYRIN-6, PYRIN-7, PYRIN-8, PYRIN-10, or PYRIN-11 nucleic acid molecules described herein or fragments thereof, can be used to map the location of PYRIN-2, PYRIN-3, PYRIN-5, PYRIN-6, PYRIN-7, PYRIN-8, PYRIN-10, or PYRIN-11 genes on a chromosome. The mapping of the PYRIN-2, PYRIN-3, PYRIN-5, PYRIN-6, PYRIN-7, PYRIN-8, PYRIN-10, or PYRIN-11 sequences to chromosomes is an important first step in correlating these sequences with genes associated with disease.

Briefly, PYRIN-2, PYRIN-3, PYRIN-5, PYRIN-6, PYRIN-7, PYRIN-8, PYRIN-10, or PYRIN-11 genes can be mapped to chromosomes by preparing PCR primers (preferably 15–25 bp in length) from the PYRIN-2, PYRIN-3, PYRIN-5, PYRIN-6, PYRIN-7, PYRIN-8, PYRIN-10, or PYRIN-11 sequences. Computer analysis of PYRIN-2, PYRIN-3, PYRIN-5, PYRIN-6, PYRIN-7, PYRIN-8, PYRIN-10, or PYRIN-11 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the PYRIN-2, PYRIN-3, PYRIN-5, PYRIN-6, PYRIN-7, PYRIN-8, PYRIN-10, or PYRIN-11 sequences will yield an amplified fragment. Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced using human chromosomes with translocations and deletions.

PCR mapping of somatic cell hybrids is a rapid procedure for assigning a particular sequence to a particular chromosome. Three or more sequences can be assigned per day using a single thermal cycler. Using the PYRIN-2, PYRIN-3, PYRIN-5, PYRIN-6, PYRIN-7, PYRIN-8, PYRIN-10, or PYRIN-11 sequences to design oligonucleotide primers, sublocalization can be achieved with panels of fragments from specific chromosomes. Other mapping strategies which can similarly be used to map a PYRIN-2, PYRIN-3, PYRIN-5, PYRIN-6, PYRIN-7, PYRIN-8, PYRIN-10, or PYRIN-11 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the PYRIN-2, PYRIN-3, PYRIN-5, PYRIN-6, PYRIN-7, PYRIN-8, PYRIN-10, or PYRIN-11 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

A PYRIN-2, PYRIN-3, PYRIN-5, PYRIN-6, PYRIN-7, PYRIN-8, PYRIN-10, or PYRIN-11 polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37–41 and Van Keuren et al. (1986) *Hum. Genet.* 74:34–40. Alternatively, the presence of the PYRIN-2, PYRIN-3, PYRIN-5, PYRIN-6, PYRIN-7, PYRIN-8, PYRIN-10, or PYRIN-11 polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

2. Tissue Typing

The PYRIN-2, PYRIN-3, PYRIN-5, PYRIN-6, PYRIN-7, PYRIN-8, PYRIN-10, or PYRIN-11 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PYRIN-2, PYRIN-3, PYRIN-5, PYRIN-6, PYRIN-7, PYRIN-8, PYRIN-10, or PYRIN-11 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PYRIN-2, PYRIN-3, PYRIN-5, PYRIN-6, PYRIN-7, PYRIN-8, PYRIN-10, or PYRIN-11 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of PYRIN-2, PYRIN-3, PYRIN-5, PYRIN-6, PYRIN-7, PYRIN-8, PYRIN-10, or PYRIN-11 can comfortably provide positive individual identification with a panel of perhaps 10 to 1,000 primers which each yield a noncoding amplified sequence of 100 bases. If predicted coding sequences, such as those in SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25 are used, a more appropriate number of primers for positive individual identification would be 500–2,000.

If a panel of reagents from PYRIN-2, PYRIN-3, PYRIN-5, PYRIN-6, PYRIN-7, PYRIN-8, PYRIN-10, or PYRIN-11 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of PYRIN-2, PYRIN-3, PYRIN-5, PYRIN-6, PYRIN-7, PYRIN-8, PYRIN-10, or PYRIN-11 are particularly appropriate for this use as greater numbers of polymorphisms occur in the noncoding regions, making it easier to differentiate individuals using this technique. Examples of polynucleotide reagents include the PYRIN-2, PYRIN-3, PYRIN-5, PYRIN-6, PYRIN-7, PYRIN-8, PYRIN-10, or PYRIN-11 sequences or portions thereof, e.g., fragments derived from the noncoding regions of PYRIN-2, PYRIN-3, PYRIN-5, PYRIN-6, PYRIN-7, PYRIN-8, PYRIN-10, or PYRIN-11 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such PYRIN-2, PYRIN-3, PYRIN-5, PYRIN-6, PYRIN-7, PYRIN-8, PYRIN-10, or PYRIN-11 probes can be used to identify tissue by species and/or by organ type.

In a similar fashion, these reagents, e.g., PYRIN-2, PYRIN-3, PYRIN-5, PYRIN-6, PYRIN-7, PYRIN-8, PYRIN-10, or PYRIN-11 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic predictive) purposes to thereby treat an individual prophylactically. Accordingly, one aspect of the present invention relates to diagnostic assays for determining PYRIN-2, PYRIN-3, PYRIN-5, PYRIN-6, PYRIN-7, PYRIN-8, PYRIN-10, or PYRIN-11 protein and/or nucleic acid expression as well as PYRIN-2, PYRIN-3, PYRIN-5, PYRIN-6, PYRIN-7, PYRIN-8, PYRIN-10, or PYRIN-11 activity, in the context of a biological sample (e.g., blood, serum, cells, tissue) to thereby determine whether an individual is afflicted with a disease or disorder, or is at risk of developing a disorder, associated with aberrant PYRIN-2, PYRIN-3, PYRIN-5, PYRIN-6, PYRIN-7, PYRIN-8, PYRIN-10, or PYRIN-11 expression or activity. The invention also provides for prognostic (or predictive) assays for determining whether an individual is at risk of developing a disorder associated with PYRIN-2, PYRIN-3, PYRIN-5, PYRIN-6, PYRIN-7, PYRIN-8, PYRIN-10, or PYRIN-11 protein, nucleic acid expression or activity. For example, mutations in a PYRIN-2, PYRIN-3, PYRIN-5, PYRIN-6, PYRIN-7, PYRIN-8, PYRIN-10, or PYRIN-11 gene can be assayed in a biological sample. Such assays can be used for prognostic or predictive purpose to thereby prophylactically treat an individual prior to the onset of a disorder characterized by or associated with PYRIN-2, PYRIN-3, PYRIN-5, PYRIN-6, PYRIN-7, PYRIN-8, PYRIN-10, or PYRIN-11 protein, nucleic acid expression or activity.

Another aspect of the invention provides methods for determining PYRIN-2, PYRIN-3, PYRIN-5, PYRIN-6, PYRIN-7, PYRIN-8, PYRIN-10, or PYRIN-11 protein, nucleic acid expression or PYRIN-2, PYRIN-3, PYRIN-5, PYRIN-6, PYRIN-7, PYRIN-8, PYRIN-10, or PYRIN-11 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of PYRIN-2, PYRIN-3, PYRIN-5, PYRIN-6, PYRIN-7, PYRIN-8, PYRIN-10, or PYRIN-11 in clinical trials.

These and other agents are described in further detail in the following sections.

1. Diagnostic Assays

An exemplary method for detecting the presence or absence of PYRIN-2, PYRIN-3, PYRIN-5, PYRIN-6, PYRIN-7, PYRIN-8, PYRIN-10, or PYRIN-11 in a biological sample involves obtaining a biological sample from a test subject and contacting the biological sample with a compound or an agent capable of detecting PYRIN-2, PYRIN-3, PYRIN-5, PYRIN-6, PYRIN-7, PYRIN-8, PYRIN-10, or PYRIN-11 protein or nucleic acid (e.g., mRNA, genomic DNA) that encodes PYRIN-2, PYRIN-3, PYRIN-5, PYRIN-6, PYRIN-7, PYRIN-8, PYRIN-10, or PYRIN-11 protein such that the presence of PYRIN-2, PYRIN-3, PYRIN-5, PYRIN-6, PYRIN-7, PYRIN-8, PYRIN-10, or PYRIN-11 is detected in the biological sample. An agent for detecting PYRIN-2, PYRIN-3, PYRIN-5, PYRIN-6, PYRIN-7, PYRIN-8, PYRIN-10, or PYRIN-11 mRNA or genomic DNA is a labeled nucleic acid probe capable of hybridizing to PYRIN-2, PYRIN-3, PYRIN-5, PYRIN-6, PYRIN-7, PYRIN-8, PYRIN-10, or PYRIN-11 mRNA or genomic DNA. The nucleic acid probe can be, for example, the nucleic acid of SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, SEQ ID NO:25, or a portion thereof, such as an oligonucleotide of at least 15, 30, 50, 100, 250, 500, 750, 1000, 1250, or 1500 nucleotides in length and sufficient to specifically hybridize under stringent conditions to mRNA or genomic DNA. Other suitable probes for use in the diagnostic assays of the invention are described herein.

An agent for detecting PYRIN-2, PYRIN-3, PYRIN-5, PYRIN-6, PYRIN-7, PYRIN-8, PYRIN-10, or PYRIN-11 protein can be an antibody capable of binding to PYRIN-2, PYRIN-3, PYRIN-5, PYRIN-6, PYRIN-7, PYRIN-8, PYRIN-10, or PYRIN-11 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, biological fluids, and stool samples isolated from a subject, as well as tissues, cells and fluids present within a subject. That is, the detection method of the invention can be used to detect PYRIN-2, PYRIN-3, PYRIN-5, PYRIN-6, PYRIN-7, PYRIN-8, PYRIN-10, or PYRIN-11 mRNA, protein, or genomic DNA in a biological sample in vitro as well as in vivo. For example, in vitro techniques for detection of PYRIN-2, PYRIN-3, PYRIN-5, PYRIN-6, PYRIN-7, PYRIN-8, PYRIN-10, or PYRIN-11 mRNA include Northern hybridizations and in situ hybridizations. In vitro techniques for detection of PYRIN-2, PYRIN-3, PYRIN-5, PYRIN-6, PYRIN-7, PYRIN-8, PYRIN-10, or PYRIN-11 protein include enzyme linked immunosorbent assays (ELISAs), Western blots, immunoprecipitations and immunofluorescence. In vitro techniques for detection of PYRIN-2, PYRIN-3, PYRIN-5, PYRIN-6, PYRIN-7, PYRIN-8, PYRIN-10, or PYRIN-11 genomic DNA include Southern hybridizations. Furthermore, in vivo techniques for detection of PYRIN-2, PYRIN-3, PYRIN-5, PYRIN-6, PYRIN-7, PYRIN-8, PYRIN-10, or PYRIN-11 protein include introducing into a subject a labeled anti-PYRIN-2, PYRIN-3, PYRIN-5, PYRIN-6, PYRIN-7, PYRIN-8, PYRIN-10, or PYRIN-11 antibody. For example, the antibody can be labeled with a radioactive marker whose presence and location in a subject can be detected by standard imaging techniques.

Stool samples may be analyzed using various in vitro techniques, including techniques directed to analysis of DNA, RNA, or protein in the sample (Machiels et al. (2000) BioTechniques 28:286–290).

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting PYRIN-2, PYRIN-3, PYRIN-5, PYRIN-6, PYRIN-7, PYRIN-8, PYRIN-10, or PYRIN-11 protein, mRNA, or genomic DNA, such that the presence of PYRIN-2, PYRIN-3, PYRIN-5, PYRIN-6, PYRIN-7, PYRIN-8, PYRIN-10, or PYRIN-11 protein, mRNA or genomic DNA is detected in the biological sample, and comparing the presence of PYRIN-2, PYRIN-3, PYRIN-5, PYRIN-6, PYRIN-7, PYRIN-8, PYRIN-10, or PYRIN-11 protein, mRNA or genomic DNA in the control sample with the presence of PYRIN-2, PYRIN-3, PYRIN-5, PYRIN-6, PYRIN-7, PYRIN-8, PYRIN-10, or PYRIN-11 protein, mRNA or genomic DNA in the test sample.

The invention also encompasses kits for detecting the presence of PYRIN-2, PYRIN-3, PYRIN-5, PYRIN-6, PYRIN-7, PYRIN-8, PYRIN-10, or PYRIN-11 in a biological sample (a test sample). Such kits can be used to determine if a subject is suffering from or is at increased risk of developing a disorder associated with aberrant expression of PYRIN-2, PYRIN-3, PYRIN-5, PYRIN-6, PYRIN-7, PYRIN-8, PYRIN-10, or PYRIN-11 (e.g., an immunological disorder). For example, the kit can comprise a labeled compound or agent capable of detecting PYRIN-2, PYRIN-3, PYRIN-5, PYRIN-6, PYRIN-7, PYRIN-8, PYRIN-10, or PYRIN-11 protein or mRNA in a biological sample and means for determining the amount of PYRIN-2, PYRIN-3, PYRIN-5, PYRIN-6, PYRIN-7, PYRIN-8, PYRIN-10, or PYRIN-11 in the sample (e.g., an anti-PYRIN-2, PYRIN-3, PYRIN-5, PYRIN-6, PYRIN-7, PYRIN-8, PYRIN-10, or PYRIN-11 antibody or an oligonucleotide probe which binds to DNA encoding PYRIN-2, PYRIN-3, PYRIN-5, PYRIN-6, PYRIN-7, PYRIN-8, PYRIN-10, or PYRIN-11, e.g., SEQ ID NO:1, SEQ ID NO:3, SEQ ID NO:5, SEQ ID NO:7, SEQ ID NO:9, SEQ ID NO:11, SEQ ID NO:12, SEQ ID NO:14, SEQ ID NO:16, SEQ ID NO:17, SEQ ID NO:19, SEQ ID NO:21, SEQ ID NO:23, or SEQ ID NO:25). Kits may also include instruction for observing that the tested subject is suffering from or is at risk of developing a disorder associated with aberrant expression of PYRIN-2, PYRIN-3, PYRIN-5, PYRIN-6, PYRIN-7, PYRIN-8, PYRIN-10, or PYRIN-11 if the amount of PYRIN-2, PYRIN-3, PYRIN-5, PYRIN-6, PYRIN-7, PYRIN-8, PYRIN-10, or PYRIN-11 protein or mRNA is above or below a normal level.

For antibody-based kits, the kit may comprise, for example: (1) a first antibody (e.g., attached to a solid support) which binds to PYRIN-2, PYRIN-3, PYRIN-5, PYRIN-6, PYRIN-7, PYRIN-8, PYRIN-10, or PYRIN-11 protein; and, optionally, (2) a second, different antibody which binds to PYRIN-2, PYRIN-3, PYRIN-5, PYRIN-6, PYRIN-7, PYRIN-8, PYRIN-10, or PYRIN-11 protein or the first antibody and is conjugated to a detectable agent. For oligonucleotide-based kits, the kit may comprise, for example: (1) a oligonucleotide, e.g., a detectably labeled oligonucleotide, which hybridizes to a PYRIN-2, PYRIN-3, PYRIN-5, PYRIN-6, PYRIN-7, PYRIN-8, PYRIN-10, or PYRIN-11 nucleic acid sequence or (2) a pair of primers useful for amplifying a PYRIN-2, PYRIN-3, PYRIN-5, PYRIN-6, PYRIN-7, PYRIN-8, PYRIN-10, or PYRIN-11 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of PYRIN-2, PYRIN-3, PYRIN-5, PYRIN-6, PYRIN-7, PYRIN-8, PYRIN-10, or PYRIN-11.

2. Prognostic Assays

The methods described herein can furthermore be utilized as diagnostic or prognostic assays to identify subjects having or at risk of developing a disease or disorder associated with aberrant PYRIN-2, PYRIN-3, PYRIN-5, PYRIN-6, PYRIN-7, PYRIN-8, PYRIN-10, or PYRIN-11 expression or activity. For example, the assays described herein, such as the preceding diagnostic assays or the following assays, can be utilized to identify a subject having or at risk of developing a disorder associated with PYRIN-2, PYRIN-3, PYRIN-5, PYRIN-6, PYRIN-7, PYRIN-8, PYRIN-10, or PYRIN-11 protein, nucleic acid expression or activity. Alternatively, the prognostic assays can be utilized to identify a subject having or at risk for developing such a disease or disorder. Thus, the present invention provides a method in which a test sample is obtained from a subject and PYRIN-2, PYRIN-3, PYRIN-5, PYRIN-6, PYRIN-7, PYRIN-8, PYRIN-10, or PYRIN-11 protein or nucleic acid (e.g., mRNA, genomic DNA) is detected, wherein the presence of PYRIN-2, PYRIN-3, PYRIN-5, PYRIN-6, PYRIN-7, PYRIN-8, PYRIN-10, or PYRIN-11 protein or nucleic acid is diagnostic for a subject having or at risk of developing a disease or disorder associated with aberrant PYRIN-2, PYRIN-3, PYRIN-5, PYRIN-6, PYRIN-7, PYRIN-8, PYRIN-10, or PYRIN-11 expression or activity. As used herein, a "test sample" refers to a biological sample obtained from a subject of interest. For example, a test sample can be a biological fluid (e.g., serum), cell sample, tissue, or stool sample. Stool samples may be analyzed using various in vitro techniques, including techniques directed to analysis of DNA, RNA, or protein in the sample (Machiels et al. (2000) BioTechniques 28:286–290). Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant PYRIN-2, PYRIN-3, PYRIN-5, PYRIN-6, PYRIN-7, PYRIN-8, PYRIN-10, or PYRIN-11 expression or activity. For example, such methods can be used to determine whether a subject can be effectively treated with a specific agent or class of agents (e.g., agents of a type which decrease PYRIN-2, PYRIN-3, PYRIN-5, PYRIN-6, PYRIN-7, PYRIN-8, PYRIN-10, or PYRIN-11 activity). Thus, the present invention provides methods for determining whether a subject can be effectively treated with an agent for a disorder associated with aberrant PYRIN-2, PYRIN-3, PYRIN-5, PYRIN-6, PYRIN-7, PYRIN-8, PYRIN-10, or PYRIN-11 expression or activity in which a test sample is obtained and PYRIN-2, PYRIN-3, PYRIN-5, PYRIN-6, PYRIN-7, PYRIN-8, PYRIN-10, or PYRIN-11 protein or nucleic acid is detected (e.g., wherein the presence of PYRIN-2, PYRIN-3, PYRIN-5, PYRIN-6, PYRIN-7, PYRIN-8, PYRIN-10, or PYRIN-11 protein or nucleic acid is diagnostic for a subject that can be administered the agent to treat a disorder associated with aberrant PYRIN-2, PYRIN-3, PYRIN-5, PYRIN-6, PYRIN-7, PYRIN-8, PYRIN-10, or PYRIN-11 expression or activity).

The methods of the invention can also be used to detect genetic lesions or mutations in a PYRIN-2, PYRIN-3, PYRIN-5, PYRIN-6, PYRIN-7, PYRIN-8, PYRIN-10, or PYRIN-11 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a PYRIN-2, PYRIN-3, PYRIN-5, PYRIN-6, PYRIN-7, PYRIN-8, PYRIN-10, or PYRIN-11-protein, or the mis-expression of the PYRIN-2, PYRIN-3, PYRIN-5, PYRIN-6, PYRIN-7, PYRIN-8, PYRIN-10, or PYRIN-11 gene. For example, such genetic lesions can be detected by ascertaining the existence of at least one of 1) a deletion of one or more nucleotides from a PYRIN-2, PYRIN-3, PYRIN-5, PYRIN-6, PYRIN-7, PYRIN-8, PYRIN-10, or PYRIN-11 gene; 2) an addition of one or more nucleotides to a PYRIN-2, PYRIN-3, PYRIN-5, PYRIN-6, PYRIN-7, PYRIN-8, PYRIN-10, or PYRIN-11 gene; 3) a substitution of one or more nucleotides of a PYRIN-2, PYRIN-3, PYRIN-5, PYRIN-6, PYRIN-7, PYRIN-8, PYRIN-10, or PYRIN-11 gene; 4) a chromosomal rearrangement of a PYRIN-2, PYRIN-3, PYRIN-5, PYRIN-6, PYRIN-7, PYRIN-8, PYRIN-10, or PYRIN-11 gene; 5) an alteration in the level of a messenger RNA transcript of a PYRIN-2, PYRIN-3, PYRIN-5, PYRIN-6, PYRIN-7, PYRIN-8, PYRIN-10, or PYRIN-11 gene; 6) aberrant modification of a PYRIN-2, PYRIN-3, PYRIN-5, PYRIN-6, PYRIN-7, PYRIN-8, PYRIN-10, or PYRIN-11 gene, such as of the methylation pattern of the genomic DNA; 7) the presence of a non-wild type splicing pattern of a messenger RNA transcript of a PYRIN-2, PYRIN-3, PYRIN-5, PYRIN-6, PYRIN-7, PYRIN-8, PYRIN-10, or PYRIN-11 gene (e.g., caused by a mutation in a splice donor or splice acceptor site); 8) a non-wild type level of a PYRIN-2, PYRIN-3, PYRIN-5, PYRIN-6, PYRIN-7, PYRIN-8, PYRIN-10, or PYRIN-11-protein; 9) allelic loss of a PYRIN-2, PYRIN-3, PYRIN-5, PYRIN-6, PYRIN-7, PYRIN-8, PYRIN-10, or PYRIN-11 gene; and 10) inappropriate post-translational modification of a PYRIN-2, PYRIN-3, PYRIN-5, PYRIN-6, PYRIN-7, PYRIN-8, PYRIN-10, or PYRIN-11-protein. As described herein, there are a large number of assay techniques known in the art which can be used for detecting lesions in a PYRIN-2, PYRIN-3, PYRIN-5, PYRIN-6, PYRIN-7, PYRIN-8, PYRIN-10, or PYRIN-11 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the PYRIN-2, PYRIN-3, PYRIN-5, PYRIN-6, PYRIN-7, PYRIN-8, PYRIN-10, or PYRIN-11 gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a PYRIN-2, PYRIN-3, PYRIN-5, PYRIN-6, PYRIN-7, PYRIN-8, PYRIN-10, or PYRIN-11 gene under conditions such that hybridization and amplification of the PYRIN-2, PYRIN-3, PYRIN-5, PYRIN-6, PYRIN-7, PYRIN-8, PYRIN-10, or PYRIN-11-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PYRIN-2, PYRIN-3, PYRIN-5, PYRIN-6, PYRIN-7, PYRIN-8, PYRIN-10, or PYRIN-11 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in PYRIN-2, PYRIN-3, PYRIN-5, PYRIN-6, PYRIN-7, PYRIN-8, PYRIN-10, or PYRIN-11 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in PYRIN-2, PYRIN-3, PYRIN-5, PYRIN-6, PYRIN-7, PYRIN-8, PYRIN-10, or PYRIN-11 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PYRIN-2, PYRIN-3, PYRIN-5, PYRIN-6, PYRIN-7, PYRIN-8, PYRIN-10, or PYRIN-11 gene and detect mutations by comparing the sequence of the sample PYRIN-2, PYRIN-3, PYRIN-5, PYRIN-6, PYRIN-7, PYRIN-8, PYRIN-10, or PYRIN-11 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the PYRIN-2, PYRIN-3, PYRIN-5, PYRIN-6, PYRIN-7, PYRIN-8, PYRIN-10, or PYRIN-11 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type PYRIN-2, PYRIN-3, PYRIN-5, PYRIN-6, PYRIN-7, PYRIN-8, PYRIN-10, or PYRIN-11 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl. Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PYRIN-2, PYRIN-3, PYRIN-5, PYRIN-6, PYRIN-7, PYRIN-8, PYRIN-10, or PYRIN-11 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a PYRIN-2, PYRIN-3, PYRIN-5, PYRIN-6, PYRIN-7, PYRIN-8, PYRIN-10, or PYRIN-11 sequence, e.g., a wild-type PYRIN-2, PYRIN-3, PYRIN-5, PYRIN-6, PYRIN-7, PYRIN-8, PYRIN-10, or PYRIN-11 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in PYRIN-2, PYRIN-3, PYRIN-5, PYRIN-6, PYRIN-7, PYRIN-8, PYRIN-10, or PYRIN-11 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control PYRIN-2, PYRIN-3, PYRIN-5, PYRIN-6, PYRIN-7, PYRIN-8, PYRIN-10, or PYRIN-11 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PYRIN-2, PYRIN-3, PYRIN-5, PYRIN-6, PYRIN-7, PYRIN-8, PYRIN-10, or PYRIN-11 gene.

Furthermore, any cell type or tissue, preferably peripheral blood leukocytes, in which PYRIN-2, PYRIN-3, PYRIN-5, PYRIN-6, PYRIN-7, PYRIN-8, PYRIN-10, or PYRIN-11 is expressed may be utilized in the prognostic assays described herein.

3. Pharmacogenomics

Agents, or modulators which have a stimulatory or inhibitory effect on PYRIN-2, PYRIN-3, PYRIN-5, PYRIN-6, PYRIN-7, PYRIN-8, PYRIN-10, or PYRIN-11 activity (e.g., PYRIN-2, PYRIN-3, PYRIN-5, PYRIN-6, PYRIN-7, PYRIN-8, PYRIN-10, or PYRIN-11 gene expression) as identified by a screening assay described herein can be administered to individuals to treat (prophylactically or therapeutically) disorders (e.g., a neurodegenerative disease such as Alzheimer's disease) associated with aberrant PYRIN-2, PYRIN-3, PYRIN- 5, PYRIN-6, PYRIN-7, PYRIN-8, PYRIN-10, or PYRIN-11 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of PYRIN-2, PYRIN-3, PYRIN-5, PYRIN-6, PYRIN-7, PYRIN-8, PYRIN-10, or PYRIN-11 protein, expression of PYRIN-2, PYRIN-3, PYRIN-5, PYRIN-6, PYRIN-7, PYRIN-8, PYRIN-10, or PYRIN-11 nucleic acid, or mutation content of PYRIN-2, PYRIN-3, PYRIN-5, PYRIN-6, PYRIN-7, PYRIN-8, PYRIN-10, or PYRIN-11 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM exhibit no therapeutic response, as demonstrated for the analgesic effect of codeine mediated by its CYP2D6-formed metabolite morphine. The other extreme are the so-called ultra-rapid metabolizers who do not respond to standard doses. Recently, the molecular basis of ultra-rapid metabolism has been identified to be due to CYP2D6 gene amplification.

Thus, the activity of PYRIN-2, PYRIN-3, PYRIN-5, PYRIN-6, PYRIN-7, PYRIN-8, PYRIN-10, or PYRIN-11 protein, expression of PYRIN-2, PYRIN-3, PYRIN-5, PYRIN-6, PYRIN-7, PYRIN-8, PYRIN-10, or PYRIN-11 nucleic acid, or mutation content of PYRIN-2, PYRIN-3, PYRIN-5, PYRIN-6, PYRIN-7, PYRIN-8, PYRIN-10, or PYRIN-11 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a PYRIN-2, PYRIN-3, PYRIN-5, PYRIN-6, PYRIN-7, PYRIN-8, PYRIN-10, or PYRIN-11 modulator, such as a modulator identified by one of the exemplary screening assays described herein.

4. Monitoring of Effects During Clinical Trials

Monitoring the influence of agents (e.g., drugs, compounds) on the expression or activity of PYRIN-2, PYRIN-3, PYRIN-5, PYRIN-6, PYRIN-7, PYRIN-8, PYRIN-10, or PYRIN-11 (e.g., the ability to modulate aberrant cell proliferation and/or differentiation) can be applied not only in basic drug screening, but also in clinical trials. For example, the effectiveness of an agent determined by a screening assay as described herein to increase PYRIN-2, PYRIN-3, PYRIN-5, PYRIN-6, PYRIN-7, PYRIN-8, PYRIN-10, or PYRIN-11 gene expression, protein levels, or upregulate PYRIN-2, PYRIN-3, PYRIN-5, PYRIN-6, PYRIN-7, PYRIN-8, PYRIN-10, or PYRIN-11 activity, can be monitored in clinical trails of subjects exhibiting decreased PYRIN-2, PYRIN-3, PYRIN-5, PYRIN-6, PYRIN-7, PYRIN-8, PYRIN-10, or PYRIN-11 gene expression, protein levels, or downregulated PYRIN-2, PYRIN-3, PYRIN-5, PYRIN-6, PYRIN-7, PYRIN-8, PYRIN-10, or PYRIN-11 activity. Alternatively, the effectiveness of an agent determined by a screening assay to decrease PYRIN-2, PYRIN-3, PYRIN-5, PYRIN-6, PYRIN-7, PYRIN-8, PYRIN-10, or PYRIN-11 gene expression, protein levels, or downregulated PYRIN-2, PYRIN-3, PYRIN-5, PYRIN-6, PYRIN-7, PYRIN-8, PYRIN-10, or PYRIN-11 activity, can be monitored in clinical trials of subjects exhibiting increased PYRIN-2, PYRIN-3, PYRIN-5, PYRIN-6, PYRIN-7, PYRIN-8, PYRIN-10, or PYRIN-11 gene expression, protein levels, or upregulated PYRIN-2, PYRIN-3, PYRIN-5, PYRIN-6, PYRIN-7, PYRIN-8, PYRIN-10, or PYRIN-11 activity. In such clinical trials, the expression or activity of PYRIN-2, PYRIN-3, PYRIN-5, PYRIN-6, PYRIN-7, PYRIN-8, PYRIN-10, or PYRIN-11 and, preferably, other genes that have been implicated in, for example, a cellular proliferation disorder can be used as a "read out" or markers of the immune responsiveness of a particular cell.

For example, and not by way of limitation, genes, including PYRIN-2, PYRIN-3, PYRIN-5, PYRIN-6, PYRIN-7, PYRIN-8, PYRIN-10, or PYRIN-11, that are modulated in cells by treatment with an agent (e.g., compound, drug or small molecule) which modulates PYRIN-2, PYRIN-3, PYRIN-5, PYRIN-6, PYRIN-7, PYRIN-8, PYRIN-10, or PYRIN-11 activity (e.g., identified in a screening assay as described herein) can be identified. Thus, to study the effect of agents on cellular proliferation disorders, for example, in a clinical trial, cells can be isolated and RNA prepared and analyzed for the levels of expression of PYRIN-2, PYRIN-3, PYRIN-5, PYRIN-6, PYRIN-7, PYRIN-8, PYRIN-10, or PYRIN-11 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of PYRIN-2, PYRIN-3, PYRIN-5, PYRIN-6, PYRIN-7, PYRIN-8, PYRIN-10, or PYRIN-11 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a PYRIN-2, PYRIN-3, PYRIN-5, PYRIN-6, PYRIN-7, PYRIN-8, PYRIN-10, or PYRIN-11 protein, mRNA, or genomic DNA in the preadministration sample; (iii) obtaining one or more post-administration samples from the subject; (iv) detecting the level of expression or activity of the PYRIN-2, PYRIN-3, PYRIN-5, PYRIN-6, PYRIN-7, PYRIN-8, PYRIN-10, or PYRIN-11 protein, mRNA, or genomic DNA in the post-administration samples; (v) comparing the level of expression or activity of the PYRIN-2, PYRIN-3, PYRIN-5, PYRIN-6, PYRIN-7, PYRIN-8, PYRIN-10, or PYRIN-11 protein, mRNA, or genomic DNA in the pre-administration sample with the PYRIN-2, PYRIN-3, PYRIN-5, PYRIN-6, PYRIN-7, PYRIN-8, PYRIN-10, or PYRIN-11 protein, mRNA, or genomic DNA in the post administration sample or samples; and (vi) altering the administration of the agent to the subject accordingly. For example, increased administration of the agent may be desirable to increase the expression or activity of PYRIN-2, PYRIN-3, PYRIN-5, PYRIN-6, PYRIN-7, PYRIN-8, PYRIN-10, or PYRIN-11 to higher levels than detected, i.e., to increase the effectiveness of the agent. Alternatively, decreased administration of the agent may be desirable to decrease expression or activity of PYRIN-2, PYRIN-3, PYRIN-5, PYRIN-6, PYRIN-7, PYRIN-8, PYRIN-10, or PYRIN-11 to lower levels than detected, i.e., to decrease the effectiveness of the agent.

5. Transcriptional Profiling

The PYRIN-2, PYRIN-3, PYRIN-5, PYRIN-6, PYRIN-7, PYRIN-8, PYRIN-10, or PYRIN-11 nucleic acid molecules described herein, including small oligonucleotides, can be used in transcriptionally profiling. For example, these nucleic acids can be used to examine the expression of PYRIN-2, PYRIN-3, PYRIN-5, PYRIN-6, PYRIN-7, PYRIN-8, PYRIN-10, or PYRIN-11 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of PYRIN-2, PYRIN-3, PYRIN-5, PYRIN-6, PYRIN-7, PYRIN-8, PYRIN-10, or PYRIN-11, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant PYRIN-2,PYRIN-3,PYRIN-5,PYRIN-6,PYRIN-7,PYRIN-8,PYRIN-10, or PYRIN-11 expression or activity, examples of which are provided herein.

1. Prophylactic Methods

In one aspect, the invention provides a method for preventing in a subject, a disease or condition associated with an aberrant PYRIN-2, PYRIN-3, PYRIN-5, PYRIN-6, PYRIN-7, PYRIN-8, PYRIN-10, or PYRIN-11 expression or activity, by administering to the subject an agent which modulates PYRIN-2, PYRIN-3, PYRIN-5, PYRIN-6, PYRIN-7, PYRIN-8, PYRIN-10, or PYRIN-11 expression or at least one PYRIN-2, PYRIN-3, PYRIN-5, PYRIN-6, PYRIN-7, PYRIN-8, PYRIN-10, or PYRIN-11 activity. Subjects at risk for a disease which is caused or contributed to by aberrant PYRIN-2, PYRIN-3, PYRIN-5, PYRIN-6, PYRIN-7, PYRIN-8, PYRIN-10, or PYRIN-11 expression or activity can be identified by, for example, any or a combination of diagnostic or prognostic assays as described herein. Administration of a prophylactic agent can occur prior to the manifestation of symptoms characteristic of the PYRIN-2, PYRIN-3, PYRIN-5, PYRIN-6, PYRIN-7, PYRIN-8, PYRIN-10, or PYRIN-11 aberrancy, such that a disease or disorder is prevented or, alternatively, delayed in its progression. Depending on the type of PYRIN-2, PYRIN-3, PYRIN-5, PYRIN-6, PYRIN-7, PYRIN-8, PYRIN-10, or PYRIN-11 aberrancy, for example, a PYRIN-2, PYRIN-3, PYRIN-5, PYRIN-6, PYRIN-7, PYRIN-8, PYRIN-10, or PYRIN-11 agonist or PYRIN-2, PYRIN-3, PYRIN-5, PYRIN-6, PYRIN-7, PYRIN-8, PYRIN-10, or PYRIN-11 antagonist agent can be used for treating the subject. The appropriate agent can be determined based on screening assays described herein.

2. Therapeutic Methods

Another aspect of the invention pertains to methods of modulating PYRIN-2, PYRIN-3, PYRIN-5, PYRIN-6, PYRIN-7, PYRIN-8, PYRIN-10, or PYRIN-11 expression or activity for therapeutic purposes. The modulatory method of the invention involves contacting a cell with an agent that modulates one or more of the activities of PYRIN-2, PYRIN-3, PYRIN-5, PYRIN-6, PYRIN-7, PYRIN-8, PYRIN-10, or PYRIN-11 protein activity associated with the cell. An agent that modulates PYRIN-2, PYRIN-3, PYRIN-5, PYRIN-6, PYRIN-7, PYRIN-8, PYRIN-10, or PYRIN-11 protein activity can be an agent as described herein, such as a nucleic acid or a protein, a naturally-occurring cognate ligand of a PYRIN-2, PYRIN-3, PYRIN-5, PYRIN-6, PYRIN-7, PYRIN-8, PYRIN-10, or PYRIN-11 protein, a peptide, a PYRIN-2,PYRIN-3,PYRIN-5,PYRIN-6,PYRIN-7,PYRIN-8,PYRIN-10, or PYRIN-11 peptidomimetic, or other small molecule. In one embodiment, the agent stimulates one or more of the biological activities of PYRIN-2, PYRIN-3, PYRIN-5, PYRIN-6, PYRIN-7, PYRIN-8, PYRIN-10, or PYRIN-11 protein. Examples of such stimulatory agents include active PYRIN-2, PYRIN-3, PYRIN-5, PYRIN-6, PYRIN-7, PYRIN-8, PYRIN-10, or PYRIN-11 protein and a nucleic acid molecule encoding PYRIN-2, PYRIN-3, PYRIN-5, PYRIN-6, PYRIN-7, PYRIN-8, PYRIN-10, or PYRIN-11 that has been introduced into the cell. In another embodiment, the agent inhibits one or more of the biological activities of PYRIN-2, PYRIN-3, PYRIN-5, PYRIN-6, PYRIN-7, PYRIN-8, PYRIN-10, or PYRIN-11 protein. Examples of such inhibitory agents include antisense PYRIN-2, PYRIN-3, PYRIN- 5, PYRIN-6, PYRIN-7, PYRIN-8, PYRIN-10, or PYRIN-11 nucleic acid molecules and anti-PYRIN-2, PYRIN-3, PYRIN-5, PYRIN-6, PYRIN-7, PYRIN-8, PYRIN-10, or PYRIN-11 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a PYRIN-2, PYRIN-3, PYRIN-5, PYRIN-6, PYRIN-7, PYRIN-8, PYRIN-10, or PYRIN-11 protein or nucleic acid molecule or a disorder related to PYRIN-2, PYRIN-3, PYRIN-5, PYRIN-6, PYRIN-7, PYRIN-8, PYRIN-10, or PYRIN-11 expression or activity. In one embodiment, the method involves administering an agent (e.g., an agent identified by a screening assay described herein), or combination of agents that modulates (e.g., upregulates or downregulates) PYRIN-2, PYRIN-3, PYRIN-5, PYRIN-6, PYRIN-7, PYRIN-8, PYRIN-10, or PYRIN-11 expression or activity. In another embodiment, the method involves administering a PYRIN-2, PYRIN-3, PYRIN-5, PYRIN-6, PYRIN-7, PYRIN-8, PYRIN-10, or PYRIN-11 protein or nucleic acid molecule as therapy to compensate for reduced or aberrant PYRIN-2, PYRIN-3, PYRIN-5, PYRIN-6, PYRIN-7, PYRIN-8, PYRIN-10, or PYRIN-11 expression or activity. Stimulation of PYRIN-2, PYRIN-3, PYRIN-5, PYRIN-6, PYRIN-7, PYRIN-8, PYRIN-10, or PYRIN-11 activity is desirable in situations in which PYRIN-2, PYRIN-3, PYRIN-5, PYRIN-6, PYRIN-7, PYRIN-8, PYRIN-10, or PYRIN-11 is abnormally downregulated and/or in which increased PYRIN-2, PYRIN-3, PYRIN-5, PYRIN-6, PYRIN-7, PYRIN-8, PYRIN-10, or PYRIN-11 activity is likely to have a beneficial effect. Conversely, inhibition of PYRIN-2,PYRIN-3,PYRIN-5,PYRIN-6,PYRIN-7,PYRIN-8,PYRIN-10, or PYRIN-11 activity is desirable in situations in which PYRIN-2, PYRIN-3, PYRIN-5, PYRIN-6, PYRIN-7, PYRIN-8, PYRIN-10, or PYRIN-11 is abnormally upregulated, e.g., in myocardial infarction, and/or in which decreased PYRIN-2, PYRIN-3, PYRIN-5, PYRIN-6, PYRIN-7, PYRIN-8, PYRIN-10, or PYRIN-11 activity is likely to have a beneficial effect.

This invention is further illustrated by the following examples which should not be construed as limiting. The contents of all references, patents and published patent applications cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated polypeptide comprising the amino acid sequence of SEQ ID NO:6.

2. The polypeptide of claim 1, wherein the polypeptide consists of the amino acid sequence of SEQ ID NO:6.

3. An isolated polypeptide comprising an amino acid sequence that is at least 95% identical to the sequence of SEQ ID NO:6, wherein the polypeptide stimulates apoptosis.

4. The polypeptide of claim 3, wherein the amino acid sequence is at least 98% identical to the sequence of SEQ ID NO:6.

5. An isolated polypeptide consisting of amino acid residues 1–91, 188–506, or 688–1056 of SEQ ID NO:6.

6. The polypeptide of claim 5, wherein the polypeptide consists of amino acid residues 1–91 of SEQ ID NO:6.

7. The polypeptide of claim 5, wherein the polypeptide consists of amino acid residues 188–506 of SEQ ID NO:6.

8. The polypeptide of claim 5, wherein the polypeptide consists of amino acid residues 688–1056 of SEQ ID NO:6.

9. A fusion protein comprising the polypeptide of claim 1 and a heterologous polypeptide.

10. A fusion protein comprising the polypeptide of claim 3 and a heterologous polypeptide.

11. A fusion protein comprising the polypeptide of claim 5 and a heterologous polypeptide.

12. A fusion protein comprising the polypeptide of claim 4 and a heterologous polypeptide.

* * * * *